US012370352B2

(12) United States Patent
Pipkin et al.

(10) Patent No.: US 12,370,352 B2
(45) Date of Patent: Jul. 29, 2025

(54) NASAL AND OPHTHALMIC DELIVERY OF AQUEOUS CORTICOSTEROID SOLUTIONS

(71) Applicant: CyDex Pharmaceuticals, Inc., San Diego, CA (US)

(72) Inventors: James D. Pipkin, Lawrence, KS (US); Rupert O. Zimmerer, Jr., Lawrence, KS (US); John M. Siebert, Olathe, KS (US)

(73) Assignee: CyDex Pharmaceuticals, Inc., San Diego, CA (US)

( * ) Notice: Subject to any disclaimer, the term of this patent is extended or adjusted under 35 U.S.C. 154(b) by 219 days.

(21) Appl. No.: 17/387,929

(22) Filed: Jul. 28, 2021

(65) Prior Publication Data
US 2022/0339414 A1    Oct. 27, 2022

Related U.S. Application Data

(63) Continuation of application No. 12/479,576, filed on Jun. 5, 2009, now abandoned, which is a continuation-in-part of application No. PCT/US2008/068872, filed on Jun. 30, 2008, which is a continuation-in-part of application No. PCT/US2007/072387, filed on Jun. 28, 2007, and a continuation-in-part of application No. PCT/US2007/072442, filed on Jun. 29, 2007.

(51) Int. Cl.
| A61M 31/00 | (2006.01) |
| A61K 9/00 | (2006.01) |
| A61K 9/08 | (2006.01) |
| A61K 31/335 | (2006.01) |
| A61K 31/506 | (2006.01) |
| A61K 31/55 | (2006.01) |
| A61K 31/56 | (2006.01) |
| A61K 31/57 | (2006.01) |
| A61K 31/58 | (2006.01) |
| A61K 31/724 | (2006.01) |
| A61K 45/06 | (2006.01) |
| A61K 47/40 | (2006.01) |

(52) U.S. Cl.
CPC .......... *A61M 31/00* (2013.01); *A61K 9/0043* (2013.01); *A61K 9/0048* (2013.01); *A61K 9/08* (2013.01); *A61K 31/335* (2013.01); *A61K 31/506* (2013.01); *A61K 31/55* (2013.01); *A61K 31/56* (2013.01); *A61K 31/57* (2013.01); *A61K 31/58* (2013.01); *A61K 31/724* (2013.01); *A61K 45/06* (2013.01); *A61K 47/40* (2013.01)

(58) Field of Classification Search
None
See application file for complete search history.

(56) References Cited

U.S. PATENT DOCUMENTS

| 3,008,875 A | 11/1961 | Dale |
| 3,219,533 A | 11/1965 | Mullins |
| 3,426,011 A | 2/1969 | Parmerter et al. |
| 4,383,992 A | 5/1983 | Lipari |
| 4,642,305 A | 2/1987 | Johansson |
| 5,024,998 A | 6/1991 | Boder |
| 5,134,127 A | 7/1992 | Stella et al. |
| 5,164,194 A | 11/1992 | Hettche |
| 5,192,528 A | 3/1993 | Radhakrishnan et al. |
| 5,216,151 A | 6/1993 | Murikami |
| 5,318,780 A | 6/1994 | Viegas et al. |
| 5,324,718 A | 6/1994 | Loftsson |
| 5,376,645 A | 12/1994 | Stella et al. |
| 5,472,954 A | 12/1995 | Loftsson |
| 5,510,339 A | 4/1996 | Gleich et al. |
| 5,525,623 A | 6/1996 | Spear |
| 5,556,964 A | 9/1996 | Hofstraat et al. |
| 5,576,311 A | 11/1996 | Guy |
| 5,576,645 A | 11/1996 | Farwell |
| 5,587,175 A | 12/1996 | Viegas et al. |
| 5,631,267 A | 5/1997 | Gleich et al. |
| 5,654,276 A | 8/1997 | Barrett et al. |
| 5,668,110 A | 9/1997 | Barrett et al. |
| 5,677,280 A | 10/1997 | Barrett et al. |
| 5,683,983 A | 11/1997 | Barrett et al. |
| 5,691,336 A | 11/1997 | Dorn et al. |
| 5,750,549 A | 5/1998 | Caldwell et al. |
| 5,756,483 A | 5/1998 | Merkus |

(Continued)

FOREIGN PATENT DOCUMENTS

| AU | 2006200277 | 2/2006 |
| CA | 2484835 | 11/2003 |

(Continued)

OTHER PUBLICATIONS

Adjei et al., Feb. 1992, Bioavailability of leuprolide acetate following nasal and inhalation delivery to rats and healthy humans, Pharm, Res. 9(2):244-249.

(Continued)

*Primary Examiner* — Celeste A Roney
*Assistant Examiner* — Ashlee E Wertz
(74) *Attorney, Agent, or Firm* — Knobbe, Martens, Olson & Bear, LLP

(57) ABSTRACT

The present invention is directed to methods of treating nasal and/or ophthalmic diseases, symptoms, or disorders that are therapeutically responsive to corticosteroid therapy by delivering aqueous solution formulations comprising a corticosteroid to nasal and ophthalmic tissues. The invention is also directed to methods, systems, devices, and compositions for delivering aqueous solution formulations comprising a corticosteroid and an antihistamine to nasal and ophthalmic tissues.

9 Claims, 40 Drawing Sheets

(56) References Cited

U.S. PATENT DOCUMENTS

| | | |
|---|---|---|
| 5,780,467 A | 7/1998 | Dorn et al. |
| 5,824,668 A | 10/1998 | Rubinfeld et al. |
| 5,837,713 A | 11/1998 | Gleich |
| 5,840,881 A | 11/1998 | Uda et al. |
| 5,855,916 A | 1/1999 | Chiesi et al. |
| 5,874,418 A | 2/1999 | Stella et al. |
| 5,877,191 A | 3/1999 | Caldwell et al. |
| 5,914,122 A | 6/1999 | Otterbeck et al. |
| 5,929,094 A | 7/1999 | Durrette et al. |
| 5,935,941 A | 8/1999 | Pitha |
| 5,942,251 A | 8/1999 | Merkus |
| 5,955,454 A | 9/1999 | Merkus |
| 5,958,443 A | 9/1999 | Viegas et al. |
| 5,977,070 A | 11/1999 | Piazza et al. |
| 6,027,714 A | 2/2000 | Trofast |
| 6,046,177 A | 4/2000 | Stella et al. |
| 6,071,910 A | 6/2000 | Gleich et al. |
| 6,136,603 A | 10/2000 | Dean et al. |
| 6,153,746 A | 11/2000 | Shah et al. |
| 6,218,375 B1 | 4/2001 | Raghavan |
| 6,241,969 B1 | 6/2001 | Saidi et al. |
| 6,267,985 B1 | 7/2001 | Chen et al. |
| 6,284,287 B1 | 9/2001 | Sarlikiotis et al. |
| 6,287,540 B1 | 9/2001 | Trofast |
| 6,291,445 B1 | 9/2001 | Nilsson et al. |
| 6,297,227 B1 | 10/2001 | Johnson |
| 6,346,523 B1 | 2/2002 | Bisrat et al. |
| 6,358,935 B1 | 3/2002 | Beck et al. |
| 6,407,079 B1 | 6/2002 | Muller et al. |
| 6,436,902 B1 | 8/2002 | Backstrom et al. |
| 6,468,994 B2 | 10/2002 | Bisrat et al. |
| 6,479,467 B1 | 11/2002 | Buchanan et al. |
| 6,509,323 B1 | 1/2003 | Davis et al. |
| 6,518,239 B1 | 2/2003 | Kuo et al. |
| 6,598,603 B1 | 7/2003 | Andersson et al. |
| 6,610,671 B2 | 8/2003 | Buchanan et al. |
| 6,660,804 B1 | 12/2003 | Weltrowski et al. |
| 6,686,346 B2 | 2/2004 | Nilsson et al. |
| 6,761,903 B2 | 7/2004 | Chen et al. |
| 6,899,099 B2 | 5/2005 | Andersson et al. |
| 6,962,151 B1 | 11/2005 | Knoch et al. |
| 6,969,706 B1 | 11/2005 | Chang |
| 6,986,904 B2 | 1/2006 | Nilsson et al. |
| 7,034,013 B2 | 4/2006 | Thompson et al. |
| 7,115,586 B2 | 10/2006 | Loftsson |
| 7,128,928 B2 | 10/2006 | Singh et al. |
| 7,625,878 B2 | 12/2009 | Stella et al. |
| 7,829,114 B2 | 11/2010 | Thompson et al. |
| 7,893,040 B2 | 2/2011 | Loftsson et al. |
| 8,114,438 B2 | 2/2012 | Pipkin et al. |
| 9,827,324 B2 | 11/2017 | Pipkin et al. |
| 10,159,752 B2 | 12/2018 | Pipkin et al. |
| 10,207,008 B2 | 2/2019 | Pipkin et al. |
| 10,799,599 B2 | 10/2020 | Pipkin et al. |
| 2002/0022629 A1 | 2/2002 | Cagle et al. |
| 2002/0035264 A1 | 3/2002 | Kararli et al. |
| 2002/0055496 A1 | 5/2002 | McCoy et al. |
| 2002/0128468 A1 | 9/2002 | Buchanan et al. |
| 2002/0150616 A1 | 10/2002 | Vandecruys |
| 2002/0151597 A1 | 10/2002 | Banerjee et al. |
| 2002/0183293 A1 | 12/2002 | Banerjee et al. |
| 2002/0198174 A1 | 12/2002 | Lyons |
| 2003/0055023 A1 | 3/2003 | Rajewski et al. |
| 2003/0069253 A1 | 4/2003 | Cagle et al. |
| 2003/0091513 A1 | 5/2003 | Mohsen et al. |
| 2003/0103864 A1 | 6/2003 | McAffer et al. |
| 2003/0113367 A1 | 6/2003 | Penkler |
| 2003/0118512 A1 | 6/2003 | Shen et al. |
| 2003/0129242 A1 | 7/2003 | Bosch et al. |
| 2003/0143274 A1 | 7/2003 | Viegas et al. |
| 2003/0175313 A1 | 9/2003 | Garrec et al. |
| 2003/0194378 A1 | 10/2003 | Rogueda |
| 2004/0022738 A1 | 2/2004 | Pike et al. |
| 2004/0045546 A1 | 3/2004 | Hirsh et al. |
| 2004/0063663 A1 | 4/2004 | Buchanan et al. |
| 2004/0091546 A1 | 5/2004 | Johnson et al. |
| 2004/0106575 A1 | 6/2004 | Zhana et al. |
| 2004/0109888 A1 | 6/2004 | Pun et al. |
| 2004/0204394 A1 | 10/2004 | Minaskanian |
| 2004/0220153 A1 | 11/2004 | Jost-Price et al. |
| 2004/0224876 A1 | 11/2004 | Jost-Price et al. |
| 2005/0048127 A1 | 3/2005 | Brown et al. |
| 2005/0112199 A1 | 5/2005 | Padval et al. |
| 2005/0119160 A1 | 6/2005 | Keith et al. |
| 2005/0175546 A1 | 8/2005 | Sambuco et al. |
| 2005/0186267 A1 | 8/2005 | Thompson et al. |
| 2005/0222111 A1 | 10/2005 | Andersson et al. |
| 2005/0234018 A1 | 10/2005 | Lyons et al. |
| 2005/0244339 A1 | 11/2005 | Jauernig et al. |
| 2005/0244472 A1 | 11/2005 | Hughes et al. |
| 2005/0250737 A1 | 11/2005 | Hughes et al. |
| 2006/0025391 A1 | 2/2006 | Lulla et al. |
| 2006/0035874 A1 | 2/2006 | Lulla et al. |
| 2006/0045850 A1 | 3/2006 | Namburi et al. |
| 2006/0078505 A1 | 4/2006 | McAffer et al. |
| 2006/0105045 A1 | 5/2006 | Buchanan et al. |
| 2006/0110331 A1 | 5/2006 | Dang et al. |
| 2006/0120967 A1 | 6/2006 | Namburi et al. |
| 2006/0193783 A1 | 8/2006 | Bhowmick et al. |
| 2006/0194840 A1 | 8/2006 | Gozal |
| 2006/0258537 A1 | 11/2006 | Stella et al. |
| 2006/0263350 A1 | 11/2006 | Lane |
| 2007/0020196 A1 | 1/2007 | Pipkin et al. |
| 2007/0020298 A1 | 1/2007 | Pipkin et al. |
| 2007/0020299 A1 | 1/2007 | Pipkin et al. |
| 2007/0020330 A1 | 1/2007 | Dang et al. |
| 2007/0020336 A1 | 1/2007 | Loftsson |
| 2007/0148192 A1 | 6/2007 | Laddha et al. |
| 2007/0160542 A1 | 7/2007 | Hill |
| 2007/0178049 A1 | 8/2007 | Hill |
| 2007/0178050 A1 | 8/2007 | Hill |
| 2007/0185066 A1 | 8/2007 | Hill |
| 2007/0191323 A1 | 8/2007 | Hill et al. |
| 2007/0191327 A1 | 8/2007 | Hill et al. |
| 2007/0191599 A1 | 8/2007 | Hill et al. |
| 2007/0197486 A1 | 8/2007 | Hill |
| 2007/0197487 A1 | 8/2007 | Hill |
| 2007/0202051 A1 | 8/2007 | Schuschnig |
| 2007/0202054 A1 | 8/2007 | Pipkin et al. |
| 2007/0249572 A1 | 10/2007 | Hill |
| 2009/0253745 A1 | 10/2009 | Mata et al. |
| 2011/0008325 A1 | 1/2011 | Pipkin et al. |
| 2011/0123518 A1 | 5/2011 | Pipkin et al. |
| 2011/0251157 A1 | 10/2011 | Pipkin et al. |
| 2011/0281901 A1 | 11/2011 | Gupta |
| 2015/0202308 A1 | 7/2015 | Webb et al. |
| 2019/0192684 A1 | 6/2019 | Pipkin et al. |

FOREIGN PATENT DOCUMENTS

| | | |
|---|---|---|
| CN | 101199855 | 6/2008 |
| CN | 101273993 | 10/2008 |
| DE | 4207922 | 9/1993 |
| EP | 0 579 435 | 1/1994 |
| EP | 0 709 099 | 5/1996 |
| EP | 0 605 203 | 3/1998 |
| EP | 1 894 559 | 3/2008 |
| GB | 2109381 | 6/1983 |
| JP | 58225010 | 12/1983 |
| JP | 61221120 | 10/1986 |
| JP | 02-167228 | 6/1990 |
| RU | 2157214 | 10/2000 |
| RU | 2180217 | 3/2002 |
| WO | WO 91/04026 | 4/1991 |
| WO | WO 91/04984 | 4/1991 |
| WO | WO 91/11172 | 8/1991 |
| WO | WO 91/13100 | 9/1991 |
| WO | WO 94/02518 | 2/1994 |
| WO | WO 96/16659 | 6/1996 |
| WO | WO 97/11090 | 3/1997 |
| WO | WO 97/46243 | 12/1997 |
| WO | WO 98/18827 | 5/1998 |
| WO | WO 98/50077 | 11/1998 |
| WO | WO 98/55148 | 12/1998 |

(56) References Cited

FOREIGN PATENT DOCUMENTS

| WO | WO 99/42111  | 8/1999  |
|----|--------------|---------|
| WO | WO 00/015262 | 3/2000  |
| WO | WO 00/041704 | 7/2000  |
| WO | WO 01/85137  | 11/2001 |
| WO | WO 02/39993  | 5/2002  |
| WO | WO 02/089815 | 11/2002 |
| WO | WO 03/035030 | 5/2003  |
| WO | WO 03/43602  | 5/2003  |
| WO | WO 03/070194 | 8/2003  |
| WO | WO 03/080079 | 10/2003 |
| WO | WO 04/069280 | 8/2004  |
| WO | WO 04/082590 | 9/2004  |
| WO | WO 04/087043 | 10/2004 |
| WO | WO 05/060945 | 7/2005  |
| WO | WO 05/065435 | 7/2005  |
| WO | WO 05/065649 | 7/2005  |
| WO | WO 05/065651 | 7/2005  |
| WO | WO 06/058022 | 6/2006  |
| WO | WO 06/102494 | 9/2006  |
| WO | WO 07/054974 | 5/2007  |
| WO | WO 07/075798 | 7/2007  |
| WO | WO 07/075799 | 7/2007  |
| WO | WO 07/075800 | 7/2007  |
| WO | WO 07/075801 | 7/2007  |
| WO | WO 07/075859 | 7/2007  |
| WO | WO 07/075963 | 7/2007  |
| WO | WO 07/095339 | 8/2007  |
| WO | WO 07/095341 | 8/2007  |
| WO | WO 07/095342 | 8/2007  |
| WO | WO 08/005692 | 1/2008  |
| WO | WO 08/005802 | 1/2008  |
| WO | WO 08/005819 | 1/2008  |

OTHER PUBLICATIONS

AstraZeneca, Aug. 4, 2000, Pulmicort Respules (budesonide inhalation suspension 0.25 mg and 0.5 mg, package insert for Pulmicort Respules, 17 pp.

Azelastine Nasal Spray press release, MEDA AB, Accessed Jul. 9, 2014 at www.azelastine.info/src/azelastin/pdf/press/Sardana_PP_EN.pdf; 4 pages.

Bandi et al., 2004, Preparation of budesonide-and indomethacin-hydroxypropyl-β-cyclodextrin (HPBCD) complexes using a single-step, organic-solvent-free supercritical fluid process, European Journal of Pharmaceutical Sciences, 23(2):159-168.

Barnes et al., 1998, Efficacy and safety of inhaled cortocosterioids, Am. J. Respir. Care Med. 157:S1-S53.

Barry et al., Aug. 1998, The output of budesonide from nebulizers; J. Allergy Clin. Immunol., 102:321-322.

Berg et al., 1998, Pulmicort® suspension for nebulizing tested with different jet nebulizers, J. Aerosol Sci., 19(7):1101-1104.

Bosco et al., A Submicron Suspension of Budesonide Improves the Mass of ICS Delivered During Early Nebulization, 1 pp.

Bosley et al., 1994, Patient Compliance with Inhaled Medication: Does Combining Beta-Agonists with Corticosteroids Improve Compliance?, Eur. Respir. J., 7:504-509.

Brain et al., 2002, 53. Aerosols: basics and clinical considerations, in Bronchial Asthma, 2nd ed., E.B. Weis et al., eds., Little Brown & Co., pp. 594-603.

Budesonide, in Martindale: The Complete Drug Reference, pp. 1034-1035.

Challa et al., 2005, Cyclodextrins in drug delivery: an updated review, AAPS PharmaSciTech, 6(2) Article 43, E329-E357.

CyDex Announces Multiple Agreements: Cydex Press release Apr. 2002, 5(1):3.

CyDex, Inc., Aug. 8, 2007, Captisol-Enabled Budesonide Solution for Nebulization, http//www.cydexinc.com/captisol-enabledbudesonide.asp, 12 pp.

CyDex, Inc., Captisol: Sulfobutylether β-Cyclodextrin: Frequently Ased Questions, http://www.cydexinc.com. 14 pp.

CyDex, Inc., Oct. 31, 2004, Innovative Drug Delivery Technology for Enhanced Solubility and Stability, product brochure, 8 pp.

Davies et al., 1997, Evaluation of a hydrocortisone/hydroxypropyl-β-cyclodextrin solution for ocular drug delivery, Intl J. Pharmaceutics, 156(2):201-209.

Day et al., 1999, Onset of action of intranasal budesonide (Rhinocort Aqua) in seasonal allergic rhinitis studied in a controlled exposure model, J. Allerg. Clin. Immunol., 105(3):489-494.

Djupesland, 2013, Nasal drug delivery devices: characteristics and performance in a clinical perspective—a review, Drug Deliv. and Transl. Res. 3:42-62.

Dorow et al., 1993, Efficacy and tolerability of azelastine nasal spray in patients with allergic rhinitis compared to placebo and budesonide, Arzneimmittelforschung, 43(8):909-912.

Drugs in Japan, 2009, pp. 2161-2162.

Eccleston et al., 2000, Rheological behavior of nasal sprays in shear and extension, Drug Dev Ind Pharm 26(9):975-983 (abstract).

Edsbacker, 2002, Uptake, retention and biotransformation of corticosteroids in the lung and airways, in. Schleimer et al. eds., Inhaled Steroids in Asthma: Optimizing Effects in the Airways, Marcel Dekker, New York, pp. 213-246.

Evrard et al., 1999, Influence of cyclodextrins on the solubility and the pharmacokinetics of albendazole, Proceedings of the Ninth International Symposium on Cyclodextrins, Torres Labandeira et al. eds., Kluwer Academic Publishers, NL, pp. 223-226.

Evrard et al., 2004, Cyclodextrins as potential carrier in drug nebulization, Journal of Controlled Release, 96:403-410.

Flood et al., 2000, Characterization of inclusion complexes of betamethasone related steroids with cyclodextrins using high-performance liquid chromatography.; Journal of Chromatography, 903:49-65.

Frank et al., 2012, Effects of Anatomy and Particle Size on Nasal Sprays and Nebulizers, Otolaryngol Head Neck Surg 146(2):311-319.

Fridriksdottir et al., 1997, Formulation and testing of methazolamide cyclodextrin eye drop solutions, Journal of Controlled Release, 44(1):95-99.

Fridriksdottir et al., Jan. 1996, Design and in vivo testing of 17β-estradiol HPBCD sublingual tablets, Die Pharmazie, 51(1):39-42.

Fridriksdottir et al., Mar. 31-Apr. 2, 1996, Solubilization of β-cyclodextrin: the effect of polymers and various drugs on the solubility of -cyclodextrin, Proceedings of the Eighth International Symposium on Cyclodextrins, eds. Szejtli et al., Budapest, 373-376.

Friedrich et al., Dec. 7-9, 2005, Colloidal formulations to improve drug delivery by eFlow a new electronic nebuliser; Drug Delivery to the Lungs XVI Proceedings, pp. 125-128.

FrymaKoruma Dinex Vacuum Processing Unit for Liquids and Semi Solids, Product Brochure, Romaco, 2005, Romaco Ag, 4 pp.

Furubayashi et al., 2007, Infuence of Formulation Viscosity on Dru_g Absorption Followin_g Nasal Annlication in Rats, Drug Metab. Pharmacokinet 22(3):206-21.

Golden S.J. et al. "Efficacy and safety of azelastine nasal spray for the treatment of allergic rhinitis", J. Am. Osteopath. Assoc. (1999) 99(7 Suppl):S7-12.

Gudmundsdottir et al., Dec. 2001, Intranasal administration of midazolam in a cyclodextrin based formulation: bioavailability and clinical evaluation in humans, Pharmazie, 56(12):963-966.

Harris et al., 1988, Effect of Viscosity on Particle Size, Deposition, and Clearance of Nasal Delivery Systems Containing Desmopressin, Journal Pharm Sciences 77(5):405-408.

Higuchi et al., 1965, Phase-Solubility Techniques, in Advances in Analytical Chemistry and Instrumentation, vol. 4, Reilly ed., John Wiley & Sons, Inc., pp. 117-212.

Hou, 2001, Kinetics and mechanisms of budesonide degradation in propylene glycol solutions; File 35: Dissertation Abs Online Jul. 1861-2007/, 2 pp.

Ilangovan et al., 1993, Treatment of severe steroid dependent preschool asthma with nebulised budesonide suspension; Archives of Disease in Childhood, 68:356-359.

Ito (ed.), Mar. 1, 2003, Igaku-Shoin's Medical Dictionary, pub. Igaku-Shoin Ltd., p. 75.

(56) References Cited

OTHER PUBLICATIONS

Jackson, 1995, Nebulised Budesonide Therapy in Asthma: A Scientific and Practical Review, Clinical Vision Ltd, Harwell, UK.
Jain et al.., 2001, Hygroscopicity, phase solubility and dissolution of variosubstituted sulfobutylether beta-cyclodextrins (SBE) and danazol-SBE inclusion complexes; International Journal of Pharmaceutics, 212:177-186.
Jarvinen et al., 1995, Sulfobutyl ether β-cyclodextrin (SBE-β-CD) in eyedrops improves the tolerability of a topically applied pilocarpine prodrug in rabbits, Journal of Ocular Pharmacology and Therapeutics, 11(2):95-106.
Jauernig et al., 2004, Effects of the test set-up, formulation, and nebulizer type on aerodynamic droplet characteristics; Respiratory Drug Delivery IX, pp. 609-612.
Jauernig et al., Dec. 12, 2003, Assessment of the next generation impactor (NGI) for the use in the nebuliser CEN standard EN-13544-1, Drug Delivery to the Lungs XIV, 20 pp.
Jauernig et al., May 20-25, 2004, A novel budesonide formulation (BUDeFlow) to improve Asthma Treatment in babies using a new electronic inhaler, American Thoracic Society, Orlando Florida, 1 p.
Jodal et al., Apr. 20-22, 1988, Investigation of the hemolytic effect of the cyclodextrin derivatives, Proceedings of the Fourth International Symposium on Cyclodextrins, Munich, West Germany, pp. 421-425.
Johansson et al., 1992, Efficacy of a topical nasal decongestant in different formulations: the effect of viscosity, Acta Otolaryngol 112:1032-1037.
Keller et al., May 12-16, 2002, Nebulizer nanosuspensions: important device and formulation interactions, Respiratory Drug Delivery VIII, Tuscon, AZ, pp. 197-206.
Keller et al., Sep. 4-8, 2004, Prediction of the lung dose in young children by cascade impaction methods alternatively to the SAINT Model; European Respiratory Society Annual Congress, Glasgow, UK, 1 pp.
Keller, Jan. 30, 2003, The PARI eFlow: a sophisticated electronic nebuliser for improved pulmonary drug delivery; Pharmapack Conference Presentation, 22 pp.
Kilian et al., 1998, The effect of a viscosity and an absorption enhancer on the intra nasal absorption of metoprolol in rats, International Journal of Pharmaceutics 163(1-2):211-217 (abstract).
Kinnarinen et al., 2002, The in vitro pulmonary deposition of a budesonide/γ-cyclodextrin inclusion complex, Journal of Inclusion Phenomena and Macrocyclic Chemistry, 44:97-100.
Knoch et al., Dec. 7, 2002, Testing of pharmaceutical aerosols generated by nebulizers: relevant definitions and methods; Symposium on Drug Inhalation Therapy, Tokyo, 17 pp.
Kobayashi et al., Jan. 1996, Pulmonary delivery of salmon calcitonin dry powders containing absorption enhancers in rats, Pharm. Res., 13(1):80-83.
Kraft et al., 2004, The Pharmacokinetics of Nebulized Nanocrystal Budsonide Suspension in Healthy Volunteers, J. Clin. Pharmacology, 44:67-72.
Kristinsson et al., 1996, Dexamethasone-cyclodextrin-polymer co-complexes in aqueous eye drops, Investigative Ophthalmology & Visual Science, 37(6):1199-1203.
Kulkarni et al., 2012, Formulation and characterization of nasal sprays, Inhalation 10-15.
Lammers et al., 1971, Properties of cyclodextrins: Part VI. Water-soluble cyclodextrin-derivatives. Preparation and Analysis, Die Starke, 23(5): 167-171.
Lammers et al., 1972, Properties of Cyclodextrins: Part VIII, Recueil, 91:733-742.
Lintz et al., Dec. 9-10, 2004, A novel formulation approach for improved nebulised drug delivery of poorly water soluble drugs; Drug Delivery to the Lungs XV, London, UK, 4 pp.
Liu et al., 1990, Beta-cyclodextrin/steroid complexation: effect of steroid structure on association equilibria; Pharmaceutical Research, 7(8):869-873.
Loftsson et al., 1994, The effect of polyvinylpyrrolidone and hydroxypropyl methylcellulose on HPβCD complexation of hydrocortisone and its permeability through hairless mouse skin, European Journal of Pharmaceutical Sciences, 2:297-301.
Loftsson et al., 1994, The effect of water-soluble polymers on drug-cyclodextrin complexation, International Journal of Pharmaceutics (Netherlands), 110(2):169-177.
Loftsson et al., 1996, Effects of cyclodextrins and polymers on topical drug delivery to the eye—evaluations in humans, Proceedings of the 23rd International Symposium on Controlled Release of Bioactive Materials, pp. 453-454.
Loftsson et al., 1996, The influence of water-soluble polymers and pH on hydroxypropyl-β-cyclodextrin complexation of drugs, Drug Development and Industrial Pharmacy, 22(5):401-405.
Loftsson et al., 1997, Cyclodextrins as pharmaceutical excipients, Pharm. Technol. Eur. 9(5):26-34.
Loftsson et al., 1997, Enhanced complexation efficiency of cyclodextrins, Pharmaceutical Research, 14(11):S203.
Loftsson et al., 1998, Cyclodextrin solubilization of ETH-615, a zwitterionic drug, Drug Development and Industrial Pharmacy, 24(4):365-370.
Loftsson et al., 1998, The effect of water-soluble polymers on the aqueous solubility and complexing abilities of β-cyclodextrin, International Journal of Pharmaceutics, 163(1-2):115-121.
Loftsson et al., 1999, Methods to enhance the complexation efficiency of cyclodextrins, S.T.P. Pharma Sciences, 9(3):237-242.
Loftsson et al., 2001, Cyclodextrin solubilization of benzodiazepines: formulation of midazolam nasal spray, International Journal of Pharmaceutics, 212(1):29-40.
Loftsson et al., 2002, Cyclodextrins in eye drop formulations: enhanced topical delivery of corticosteroids to the eye, Acta Ophthalmologica Scandinavica, 80(2):144-150.
Loftsson et al., 2005, Cyclodextrins in drug delivery: Expert Opin. Drug Deliv. 2(2):335-351.
Loftsson et al., 2007, Cyclodextrins and their pharmaceutical applications, International J. Pharmaceutics 329:1-11.
Loftsson et al., Apr. 11, 1994, The effect of hydroxypropyl methylcellulose on the release of dexamethasone from aqueous 2-hyroxypropyl-β-cyclodextrin formulations, International Journal of Pharmaceutics (Netherlands), 104:181-184.
Loftsson et al., Oct. 1994, Polymer-cyclodextrin-drug complexes, Pharmaceutical Research, 11(10):S225.
Loftsson et al., Oct. 1996, Pharmaceutical applications of cyclodextrins. 1. Drug solubilization and stabilization, Journal of Pharmaceutical Sciences, , 85(10):1017-1025.
Loftsson et al., Sep. 16, 1996, Drug-cyclodextrin-polymer ternary complexes, European Journal of Pharmaceutical Sciences, 4(Suppl):S144.
Loftsson et al., Sep. 1996, Solubilization of β-cyclodextrin, Eur. J. Pharm. Sci, 4(Suppl.):S143.
Loftsson et al., Sep. 2001, Sustained drug delivery system based on a cationic polymer and an anionic drug/cyclodextrin complex, Pharmazie, 56(9):746-747.
Loftsson, 1996, Topically effective acetazolamide eye-drop solution in man, Pharmaceutical Sciences, 2(6):277-279.
Loftsson, 1998, Drug-cyclodextrin complexation in the presence of water soluble polymers: enhanced solubility and percutaneous transport, Abstracts of Papers Part 1, 216th ACS National Meeting, Boston, Aug. 23-27, CELL-016.
Loftsson, Apr. 2-6, 1995, The effect of polymers on cyclodextrin complexation, Book of Abstracts, 209th ACS National Meeting, 209(1):33-CELL.
Loftsson, Nov. 1988, Increasing the cyclodextrin complexation of drugs and drug biovallability through addition of water-soluble polymers, Pharmazie, 53(11):733-740.
Luangkhot et al., Dec. 11-12, 2000, Characterisation of salbutamol solution compared to budesonide suspensions consisting of submicron and micrometer particles in the Pari LC Star and a new Pari Electronic nebuliser (eFlow); Delivery to the Lungs XI, London, 4 pp.
Luangkhot et al., Oct. 29-Nov. 2, 2000, Characterisation of salbutamol solution compared to budesonide suspensions consisting of submicron and micrometer particles in the PARI LC star and a PARI Electronic Nebuliser (eFlow) prototype; AAPS Annual Meeting, Indianapolis, 1 p.

(56) References Cited

OTHER PUBLICATIONS

Mager et al., Nov. 2002, Quantitative structure-pharmacokinetic/pharmacodynamic relationships of corticosteroids in man, J. Pharm. Sci. 91(11):2441-2451.
Malvern Instruments Ltd., 2015, Particle size analysis in pharmaceutical sprays and aerosols, Retrieved from < http://www.copybook.com/pharmaceutical/malvern-instruments-ltd/articles/pharmaceutical-aerosols> on Nov. 23, 2015.
MAP Pharmaceuticals, Inc., Unit Dose Budesonide (UDB), 2005, 2 pp.
Masson et al., 1999, Drug-cyclodextrin complexation in the presence of water-soluble polymers: enhanced solubility and percutaneous transport, ACS Symposium Series, 737 (Polysaccharide Applications), pp. 24-45.
Merkus et al., 1999, Cyclodextrins in nasal drug delivery, Advanced Drug Delivery Reviews 36:41-57.
Miles et al., Preformulation Studies on a Captisol-Enabled Budesonide Inhalation Solution; http://www.cydexinc.com; 1 pp.
Modified Cyclodextrins: Scaffolds and Templates for Supremolecular Chemistry, Easton et al., eds., Imperial College Press, London, UK, 1999.
Muller et al., 1985, Change of phase-solubility behavior by gamma-cyclodextrin derivatization; Pharmaceutical Research, pp. 309-310.
Muller et al., 1997, Budesonide microparticles for pulmonary delivery produced by supercritical carbon dioxide, Proceed. Int'l. Symp. Control. Rel. Bioact. Mater, 24:69-70.
Nagase et al., 2001, Improvement of some pharmaceutical properties of DY-9760e by sulfobutyl ether β-cyclodextrin, International Journal of Pharmaceutics, 229: 163-172.
Nakate et al., Mar. 2003, Improvement of pulmonary absorption of cyclopeptide FK224 in rats by co-formulating with Eur. J. Pharm. Biopharm., 55(2):147-154.
New Trends in Cyclodextrins and Derivatives, Duchene ed., Editions de Sante, Paris, France, 1991.
Nimbalkar et al., 2001, Activation of diacetyldapsone and a preliminary evaluation of a cyclodextrin-diacetyldapsone complex in cultured lung cells, Biotechnol. Appl. Biochem. 33:123-125.
O'Callaghan, 1990, Particle size of beclomethasone dipropionate produced by two nebulisers and two spacing devices, Thorax, 45:109-111.
O'Callaghan, 2002, The output of flunisolide from different nebulisers, J. Pharm. Pharmacol., 54:565- 569.
Okimoto et al., 1996, The Interaction of Charged and Uncharged Drugs with Neutral (HP-β-CD) and Anionically Charged (SBE7-β-CD) β-Cyclodextrins, Pharmaceutical Research, 13(2):256-264.
Ono et al., 1999, Determination of stability constant of—cyclodextrin complexes using the membrane permeation technique and the permeation behavior of drug-competing agent—cyclodextrin ternary systems, European Journal of Pharmaceutical Sciences, 8:133-139.
Ono et al., 2002, Model Analysis for Oral Absorption of a Drug/Cyclodextrin Complex Involving Competitive Inclusion Complexes, J. Inclusion Phenomena Macrocyclic Chem, 44:93-96.
O'Riordan, 2002, Formulations and nebulizer performance, Respiratory Care, 47(11):1305-1313.
Patel et al., 2007, Onset of action of azelastine nasal spray compared with mometasone nasal spray and placebo in subjects with seasonal allergic rhinitis evaluated in an environmental exposure chamber Am J. Rhinol 21(4):499-503, Abstract.
Pennington et al., 1988, The influence of solution viscosity on nasal spray deposition and clearance, InternationalJournal of Pharmaceutics 43(3):221-224 (abstract).
Pinto et al., 1999, Beclomethasone/cyclodextrin inclusion complex for dry powder inhalation, S.T.P. Pharma. Sciences, 9(3):253-256 (abstract).
Plaut et al., Nov. 3, 2005, Allergic Rhinitis, New England Journal of Medicine, 353:1934-1944, 2005.
Polymer Science, in Physical Pharmacy. Physical Chemical Principles in Pharmaceutical Sciences, 3rd edition, Martin et al., 1983, pp. 592-638.
Polymers and Macromolecules, in Physicochemical Principles of Pharmacy, 2nd edition, Florence et al., eds. pp. 281-334, 1988.
Qu et al., 2002, Sulfoalkyl ether β-cyclodextrin derivatives: synthesis and characterizations, J. Inclusion Phenom. Macro. Chem, 43:213-221.
Rajewski et al., 1996, Pharmaceutical applications of cyclodextrins. 2. In vivo drug delivery, J. Pharm. Sci. 85(11):1142-1169.
Ramjeeawon et al., Sep. 2001, Understanding The Relationship Between Formulation Viscosity and Nasal Spray Performance, Retrieved from <http://ddl-conference.com/files/54.Ramjeeawon.pdf> on Nov. 23, 2015.
Raposo et al., Nov. 6-10, 2005, Cyclodextrin nanoparticles loaded with cyclosporine A for inhalation; AAPS Annual Meeting, Nashville, TN, 1 p.
Reid et al., Apr. 1996, Linear growth of very young asthmatic children treated with high-dose nebulized budesonide; Acta Pediatrica: An International Journal of Pediatrics, 85(4):421-424.
Remington's Pharmaceutical Sciences, 18th Ed., Gennaro ed., Mack Publishing Company, Easton, PA, 1990, pp. 291-294.
Rhinocort—CMI, Aug. 6, 2007, APP Guide Online Consumer Medicine Information, http://appco.com.au/appguide/drug.asp?drug id=00071322&t=cmi Rhinocort-CMI; 6 pp.
Rhinocort Aqua product information, AstraZeneca LP, Accessed 71912014 at dailymed.nlm.nih.gov/dailymed/archives/fdaDruginfo.cfm?archiveid=12638, Nov. 2008 20 pp.
Salapatek et al., 2011, Solubilized nasal steroid (CDX-947) when combined in the same solution nasal spray with an antihistamine (CDX-313) provides improved, fast-acting symptom relief in patients with allergic rhinitis, Allergy Asthma Proc., 32:221-229.
Savolainen et al., 1998, Co-administration of a water-soluble polymer increases the usefulness of cyclodextrins in solid oral dosage forms, Pharmaceutical Research, 15(11):1696-1701.
Savolainen et al., May 31-Jun. 3, 1998, Coadministration of a water-soluble polymer increases the usefulness of cyclodextrins in solid oral dosage forms, 9th Proceedings of the International Symposium on Cyclodextrins, Santiago de Comostela, Spain, eds. Labandeira et al., pp. 261-264.
Schoni, Inhalation of aerosols by children: an ongoing controversy; Swiss Medical Weekly, 3pp.
Schueepp et al., May 16-21, 2003, Assessment of an Electronic Inhaler (eFlow) with a Budesonide Solution Utilizing a Baby Cast Model Applying Different Breathing Patterns; American Thoracic Society 99th International Conference, 1 p.
Shah et al. Merck Poster "In Vivo Nasal Deposition from Different Delivery Devices and Formulations" retrieved on Sep. 29, 2014 at http://ioacrs.org/assets/uploads/outouts/7-Shah.odf.
Shao et al., 1994, Cyclodextrins as mucosal absorption promoters of insulin: III. Pulmonary route of delivery, Eur. J. Pharm. Biopharm. 40(5):283-288.
Sharpe et al., 2003, Comparison of the flow properties of aqueous suspension corticosteroid nasal sprays under differing sampling conditions, Drug Dev. Ind. Pharm. 29(9):1005-1012.
Shrewbury et al., Tolerability of a Novel Submicron Particle Formulation of Budesonide for Nebulized Delivery in Asthma; Presentation (PP), 1 p.
Sigurdardottir et al., Dec. 29, 1995, The effect of polyvinylpyrrolidone on cyclodextrin complexation of hydrocortisone and its diffusion through hairless mouse skin, International Journal of Pharmaceutics (Netherlands), 126:73-78,.
Skoner et al., Feb. 2000, Longitudinal growth in infants and young children treated with budesonide inhalation suspension for persistent asthma; J. Allergy Clin. Immunol., 105(2, part 1):259-268.
Skoner et al., Oct. 1999, Clinical use of nebulized budesonide inhalation suspension in a child with asthma; J Allergy Clin Immunology, 104(4, part 2):S210-S214.
Smaldone et al., 1998, In vitro determination of inhaled mass and particle distribution for budesonide nebulizing suspension; Journal of Aerosol Medicine, 11(2):113-125.
Srichana et al., 2001, Cyclodextrin as a potential drug carrier in salbutamol dry powder aerosols: the in-vitro deposition and toxicity studies of the complexes; Respiratory Medicine, 95:513-519.
Stella et al., 1999, Mechanisms of drug release from cyclodextrin complexes, Advanced Drug Delivery Rviews, 36:3-16.

(56) References Cited

OTHER PUBLICATIONS

Stella, Mar. 31-Apr. 2, 1996, SBE7-B-CD, a new, novel and safe polyanionic β-cyclodextrin derivative: characterization and biomedical applications, Proceedings of the Eighth International Symposium on Cyclodextrins, Budapest, Hungary, pp. 471-476.

Stern et al., Oct. 1998, Nasal budesonide offers superior symptom relief in perennial allergic rhinitis in comparison to nasal azelastine, Ann. Allergy Asthma Immunol., 81(4):354-358.

Storr et al., 1986, Nebulised beclomethasone dipropionate in preschool asthma, Archives of Desease in Childhood, 61:270-273.

Suman et al., 1998, Nasal nebulizers Versus Aqueous Nasal Spray Pumps: A Comparison of Deposition Patterns in Human Volunteers, Respiratory Drug Delivery VI, 211-218.

Suman et al., 1999, Comparison of Nasal Deposition and Clearance of Aerosol Generated by a Nebulizer and an Aqueous Spray Pump, Pharmaceutical Research 16(10):1648-1652.

Szefler, Oct. 1999, Pharmacodynamics and pharmacokinetics of budesonide: A new nebulized corticosteroid; J Allergy Clin Immunology, 104(4, part 2):S175-S183.

Uekama et al., 1994, 14. Application of cyclodextrins, in de Boer., ed., Drug Absorption Enhancement: Concepts, Possibilities, Limitations and Trends, Harwood Academic Publishers, Switzerland, pp. 411-456.

Uekama et al., 1998, Cyclodextrin drug carrier systems, Chem. Rev., 98:2045-2076.

Unpublished Experimental Results, Oct. 2006, 4 pp.

Van der Kuy et al., Nov. 1999, Bioavailability of intranasal formulations of dihydroergotamine, Eur. J. Clin. Pharmacol., 55(9):677-680.

Vozone et al., 2002, Complexation of budesonide in cyclodextrins and particle aerodynamic characterization of the complex solid form for dry powder Inhalation, Journal of Inclusion Phenomena and Macrocyclic Chemistry, 44:111-115.

Waldrep et al., 1994, Nebulized glucocorticoids in liposomes: aerosol characteristics and human dose estimates, J. Aerosol Med., 7(2):135-145.

Waldrep et al., 1997, High dose cyclosporin A and budesonide-liposome aerosols, International Journal of Pharmaceutics, 152:27-36.

Wang et al., 1997, Effect of topical applications of budesonide and azelastine of nasal symptoms, eosinophil count and mediator release in atopic patients after nasal allergen challenge during the pollen season, Int. Arch. Allergy Immunol. 114(2):185-192.

Webb et al., 1986, Nebulised beclomethasone dipropionate suspension, Arch. Dis. Child, 61:1108-1110.

Williams et al., 1999, Influence of formulation technique for hydroxypropyl-B-cyclodextrin on the stability of aspirin in HFA 134a; European Journal of Pharmaceutics and Biopharmaceutics 47:145-152.

Williams et al., 1999, Study of Solubility of Steroids in hydrofluoroalkanes propellants; Drug Development and Industrial Pharmacy, 25(12):1227-1234.

Worth et al., 1997, Steroid/cyclodextrin complexes for pulmonary delivery, Proceedings of the International Symposium on Controlled Release of Bioactive Materials, 24:747-748.

Worth et al., Sep. 15-17, 1996, Solubility of beclomethasone dipropionate-cyclodextrin complexes, Eur. J. Pharm. Sciences, 4(Suppl.):S143.

Yoshida et al., 1988, Pharmaceutical evaluation of the hydroxyalkyl ethers of 13-cyclodextrin; International Journal of Pharmaceutics, 46:217-222.

Zannou et al., 2001, Osmotic Properties of Sulfobutylether and Hydroxypropyl Cyclodextrins, Pharmaceutical Research, 18(8):1226-1231.

Office Action issued in Japanese application serial No. 2014-096717 on Oct. 23, 2015 (English translation).

Barnes et al., 1993, Efficacy and safety of inhaled corticosteroids in asthma, American Review of Respiratory Disease, 148(4):S1-S26.

International Search Report and Written Opinion dated Oct. 9, 2008 in application No. PCT/US08/068872.

NASAL AND OPHTHALMIC DELIVERY OF AQUEOUS CORTICOSTEROID SOLUTIONS

RELATEDNESS OF THE APPLICATION

The subject application is a continuation of U.S. application Ser. No. 12/479,576, filed Jun. 5, 2009, which is a continuation-in-part of International Application No. PCT/US2008/068872, filed Jun. 30, 2008, which claims the benefit of priority from International Application No. PCT/US2007/072442, filed Jun. 29, 2007, and International Application No. PCT/US2007/072387, filed Jun. 28, 2007. All priority documents are incorporated herein in their entirety by reference.

FIELD OF THE INVENTION

The present invention is directed to methods of treating nasal and/or ophthalmic diseases, symptoms, or disorders that are therapeutically responsive to corticosteroid therapy by delivering aqueous solution formulations comprising a corticosteroid to nasal and ophthalmic tissues. The invention is also directed to methods, systems, devices, and compositions for delivering aqueous solution formulations comprising a corticosteroid and an antihistamine to nasal and ophthalmic tissues.

BACKGROUND OF THE INVENTION

The nasal administration of drugs allows for their deposition to the nose, sinuses, and other nasal cavities. Intranasal administration of drugs such as corticosteroids and antihistamines may be used to treat nasal symptoms including seasonal allergic rhinitis, perennial allergic rhinitis, perennial non-allergic rhinitis, nasal polyps, as well as prevention of post surgical polyps, chronic sinusitis, recurrent sinusitis, asthma, grass pollen rhinitis, hay fever, snoring, cluster headache, and other diseases and disorders.

The ophthalmic administration of drugs allows for their deposition to the eye, including the ocular mucosa, eye surface, cornea, conjuctiva, sclera, and posterior eye parts such as the retina, choroid, and vitreous and optic nerves, as well as tissues surrounding the eye. Ophthalmic administration of drugs such as corticosteroids and antihistamines may be used to treat ocular symptoms including conjunctivitis, inflammation of tissue(s) in the eye, dry eye, filamentary keratitis, delayed tear clearance, pain, keratoconjunctival dryness, keratoconjunctivitis sicca, lesions/tumors of the eye, infectious processes of the eye, bacterial infections, viral infections, glaucoma, uveitis, diabetic retinopathy, eye trauma, blepharitis, blepharoconjunctivitis, and other diseases or disorders.

Aqueous formulations containing a corticosteroid and a solubilizing agent have been prepared: Saidi et al. (U.S. Pat. No. 6,241,969); Keller et al. (Respiratory Drug Delivery IX (2004) 221-231); Lintz et al. (AAPS Annual Meeting and Exposition, Baltimore, Nov. 8, 2004; Poster M1128); Schueepp et al. (ATS 99$^{th}$ International Conference, Seattle, May 16-21, 2003; poster 1607); Russian Patent No. 2180217 to Chuchalin; U.S. Publication No. 2006/0045850; and Waldrep et al. (*J. Aerosol Med.* (1994), 7(2), 135-145); PCT International Publications No. WO 06/108556, No. WO 03/35030, and No. WO 06/37246 and European Publications No. EP1894559 and No. EP1712220 to PARI Pharma GmbH.

Cyclodextrins have been included in nasal or ophthalmic compositions: Kaur et al. (Curr. Drug Deliv. (2004), 1(4), 351-360); Shimpi et al. (Acta Pharm. (2005), 55(2), 139-56); Viegas et al. (U.S. Pat. Nos. 6,136,334, 5,587,175, and 5,958,443); Pate et al. (U.S. Pat. No. 5,977,180); Loftsson et al. (Acta Ophthalmol. Scand. (2002), 80(2), 144-50).

Underivatized and derivatized cyclodextrins can be used to prepare aqueous formulations containing a corticosteroid: U.S. Pat. Nos. 5,376,645 and 5,134,127 to Stella et al.; U.S. Pat. No. 5,914,122 to Otterbeck et al.; Worth et al. (24$^{th}$ International Symposium on Controlled Release of Bioactive Materials (1997)); Kinnarinen et al. (11$^{th}$ International Cyclodextrin Symposium CD, (2002)); U.S. Pat. Nos. 5,472,954; 5,089,482; Zimmerer et al. in Respiratory Drug Delivery IX (2004) 461-464); Singh et al. (U.S. Pat. Nos. 7,128,928 and 6,696,426); Loftsson (U.S. Pat. Nos. 7,115,586, 5,472,954, and 5,324,718); Chang et al. (U.S. Pat. No. 6,969,706); Beck et al. (U.S. Pat. Nos. 6,723,353 and 6,358,935); Buchanan et al. (U.S. Pat. No. 6,610,671); Pitha (U.S. Pat. Nos. 6,576,261 and 5,935,941); Kis (U.S. Pat. No. 6,468,548); Muller et al. (U.S. Pat. No. 6,407,079); Wiebe et al. (U.S. Pat. No. 5,739,121); Guy (U.S. Pat. No. 5,576,311); Babcock et al. (U.S. Pat. No. 5,538,721); Folkman et al. (U.S. Pat. No. 5,227,372); Lipari (U.S. Pat. No. 4,383,992); PCT International Publication No. WO 2004/087043 to Sun Pharmaceutical Industries Ltd.; Saari et al. (Graefes Arch. Clin. Exp. Ophthalmol. (2006), 244(5), 620-6); Kristinsson et al. (Invest. Ophthalmol. Vis. Sci. (1996), 37(6), 1199-203); Usayapant et al. (Pharm. Res. (1991), 8(12), 1495-9); Bary et al. (Eur. J. Pharm. Biopharm. (2000), 50(2), 237-244); U.S. Publication No. 2006/0193783; U.S. Publication No. 2002/0198174; European Publication No. EP 0435682; Lyons et al. (abstract in AAPS Annual Meeting and Exposition, Denver, CO USA, Oct. 1-25, 2001); Amselem et al. (U.S. Pat. No. 5,747,061).

Sulfoalkyl ether cyclodextrin derivatives can be used to prepare aqueous formulations containing a corticosteroid: U.S. Publication No. 2007/0020336; U.S. Publication No. 2006/0120967; U.S. Publication No. 2002/0150616 to Van de Cruys; U.S. Publications No. 20070249572, No. 20070197487, No. 20070197486, No. 20070191599, No. 20070191327; No. 20070191323, No. 20070185066, No. 20070178050, No. 20070178049, and No. 20070160542 and PCT International Publications No. WO 07/95342, No. WO 07/95341, No. WO 07/95339, No. WO 07/75963, No. WO 07/75859, No. WO 07/75801, No. WO 07/75800, No. WO 07/75799, and No. WO 07/75798 to Hill; U.S. Publications No. 20070202054, No. 20070020299, No. 20070020298, and No. 20070020196, and PCT International Publications No. WO 08/05692, No. WO 08/05691, No. WO 08/05053, No. WO 05/065651, No. WO 05/065649, No. WO 05/065435 to Pipkin et al.; U.S. Publication No. 20060120967 and No. 20060045850 to Namburi et al.; and U.S. Publications No. 2005085446 and No. 20070049552 to Babu. Corticosteroid-containing formulations for ophthalmic use have been described: Pflugfelder et al. (U.S. Pat. No. 6,153,607), Sackeyfio et al. (U.S. Pat. No. 6,995,815), Guo et al. (U.S. Pat. Nos. 6,548,078 and 6,217,895), Sher (U.S. Pat. No. 6,117,907), Clarke et al. (U.S. Pat. Nos. 5,358,943 and 4,945,089), Schwartz (U.S. Pat. Nos. 5,212,168 and 4,904,649), and Saidi et al. (U.S. Pat. No. 6,241,969).

The nasal and/or ophthalmic delivery of an aqueous solution formulation comprising a corticosteroid as a therapeutic agent alone or in combination with another therapeutic agent, such as an antihistamine, for the treatment of allergy-related disorders or symptoms would be useful and especially desirable if it could provide an improved clinical benefit over the delivery of other formulations, such as suspension-based formulations.

SUMMARY OF THE INVENTION

The invention provides a method of treating, preventing or ameliorating in a subject a corticosteroid-responsive disease or disorder, meaning a disease or disorder in a subject that can be treated with a therapeutically effective amount of corticosteroid to provide a clinical or therapeutic benefit to the subject. In some embodiments, the corticosteroid-responsive disease or disorder is a disease, disorder, symptom, or condition of the nose or eye.

The invention provides a method for treating an allergic symptom or disorder in a subject in need thereof, comprising:
nasally administering to the subject a corticosteroid solution comprising a therapeutically effective amount of a corticosteroid, SAE-CD, and a pharmaceutically acceptable aqueous liquid carrier,
wherein the corticosteroid solution provides more rapid relief from an allergic symptom or disorder compared to a corticosteroid suspension at the same unit dose.

In some embodiments, the allergic symptom or disorder includes a non-nasal symptom selected from the group consisting of itchy/gritty eyes, tearing/watery eyes, red/burning eyes, itchy eyes and palate, and combinations thereof.

The invention also provides a method for treating an ocular symptom or disorder in a subject in need thereof, comprising:
nasally administering to the subject a corticosteroid solution comprising a therapeutically effective amount of a corticosteroid, SAE-CD, and a pharmaceutically acceptable aqueous liquid carrier,
wherein the ocular symptom or disorder is itchy/gritty eyes, tearing/watery eyes, red/burning eyes, or a combination thereof.

The invention also provides a system for treating an allergic symptom or disorder in a subject in need thereof, comprising:
a corticosteroid solution comprising a therapeutically effective amount of a corticosteroid, a thereapeutically effective amount of an antihistamine, SAE-CD, and a pharmaceutically acceptable aqueous liquid carrier, and
a metered dose device for nasal administration of the corticosteroid solution to the subject, wherein the corticosteroid solution is provided in the device.

In some embodiments, the system is for treating an ocular symptom or disorder in a subject in need thereof.

The invention also provides a metered dose device for nasal administration comprising a corticosteroid solution comprising a therapeutically effective amount of a corticosteroid, a therapeutically effective amount of an antihistamine, SAE-CD, and a pharmaceutically acceptable aqueous liquid carrier.

In some embodiments, the invention provides a method for treating a nasal symptom or disorder in a subject in need thereof, comprising:
nasally administering to the subject a corticosteroid solution comprising a therapeutically effective amount of a corticosteroid, SAE-CD, and a pharmaceutically acceptable aqueous liquid carrier,
wherein the nasal symptom or disorder is selected from the group consisting of: acute or chronic rhinitis, nasal polyps, post surgical nasal polyps, snoring, cluster headache, and combinations thereof.

In some embodiments of the method for treating a nasal symptom or disorder in a subject in need thereof, the symptom or disorder is instead selected from the group consisting of obstructive sleep apnea, eustachian tube dysfunction, serous otitis media, sleep disturbances, daytime somnolesence, nasal furuncles, epistaxis, wounds of the nasal or sinunasal mucosa, dry nose syndrome, nasal bleeding, and combinations thereof.

The invention also provides a method for treating an allergic symptom or disorder in a subject in need thereof, comprising:
ophthalmically administering to the subject a corticosteroid solution comprising a therapeutically effective amount of a corticosteroid, SAE-CD, and a pharmaceutically acceptable aqueous liquid carrier,
wherein the corticosteroid solution provides more rapid relief from an allergic symptom or disorder compared to a corticosteroid suspension at the same unit dose.

The invention also provides a method for treating ocular inflammation in a subject in need thereof, comprising:
ophthalmically administering to the subject a corticosteroid solution comprising a therapeutically effective amount of a corticosteroid, SAE-CD, and a pharmaceutically acceptable aqueous liquid carrier,
wherein the corticosteroid solution provides a more rapid reduction in ocular inflammation compared with a corticosteroid suspension at the same unit dose.

The invention also provides a system for treating an allergic symptom or disorder in a subject in need thereof, comprising:
a corticosteroid solution comprising a therapeutically effective amount of a corticosteroid, a thereapeutically effective amount of an antihistamine, SAE-CD, and a pharmaceutically acceptable aqueous liquid carrier, and
a device for ophthalmic administration of the corticosteroid solution to the subject, wherein the corticosteroid solution is provided in the device.

The invention also provides a device for ophthalmic adminstration comprising a corticosteroid solution comprising a therapeutically effective amount of a corticosteroid, a therapeutically effective amount of an antihistamine, SAE-CD, and a pharmaceutically acceptable aqueous liquid carrier.

The administration device can be: 1) a metered dose device such as a atomizer, sprayer, pump spray, dropper, squeeze tube, squeeze bottle, pipette, ampule, nasal cannula, metered dose device, nasal spray inhaler, nasal continuous positive air pressure device, or breath actuated bi-directional delivery device; or 2) a device for ophthalmic administration such as a dropper, drop dispensing package, tube, eye spray device, or eye wash unit. The device can be adapted to to emit 10 µl to 500 µl of corticosteroid solution per unit dose. The device can also comprise a nozzle, wherein the nozzle comprises a valve, and the valve provides a release of a volume of 25 µl to 260 µl per unit dose through the nozzle upon operation of the device.

In some embodiments, the corticosteroid is beclomethasone dipropionate, beclomethasone monopropionate, betamethasone, budesonide, ciclesonide, desisobutyrylciclesonide, dexamethasone, flunisolide, fluticasone propionate, fluticasone furoate, mometasone furoate, triamcinolone acetonide, or a combination thereof.

The invention also includes embodiments wherein the corticosteroid solution further comprises one or more additional therapeutically effective agents, such as an anti-IgE antibody, antibiotic agent, anticholinergic agent, antifungal agent, anti-inflammatory agent, anti-infective agent, antihistamine agent, analgesic agent, decongestant, expectorant, antitussive agent, antimicrobial agent, leukotriene receptor antagonist, or a combination thereof. Specific embodiments of these additional therapeutically effective agents can be selected from those disclosed herein or others suitable for nasal or ophthalmic administration and for treatment of diseases, disorders or symptoms of the nose or eye.

In some embodiments, the method further comprises administering a therapeutically effective amount of an antihistamine. In some embodiments, the antihistamine is diphenhydramine, clemastine, chlorpheniramine, brompheniramine, dexchlorpheniramine, dexbrompheniramine, triprolidine, doxylamine, tripelennamine, heptadine, carbinoaxime, bromdiphenhydramine, hydroxyzine, pyrilamine, acrivastine, AHR-11325, phenindamine, astemizole, azatadine, azelastine, cetirizine, ebastine, fexofenadine, ketotifen, lodoxine, loratadine, descarboethoxyloratadine, levocabastine, mequitazine, oxatomide, setastine, tazifyline, temelastine, terfenadine, tripelennamine, terfenadine carboxylate, phenyltoloxamine, pheniramine, or a combination thereof. In some embodiments, the antihistamine is carebastine, efletirizine, mapinastine, antazoline, bilastine, bepotastine besilate, rupatadine, emedastine, tecastemizole, epinastine, levocetirizine, mizolastine, noberastine, norastemizole, olopatadine, or a combination thereof. In some embodiments the antihistamine is azelastine. In some embodiments, the antihistamine is azelastine, wherein the azelastine is present at an amount of about 30 µg to about 275 µg per unit dose. In some embodiments, the antihistamine is azelastine, wherein the azelastine is present at a concentration of 0.5 to 10 mg/mL. In some embodiments, the antihistamine is olopatadine. In some embodiments, the antihistamine is azelastine, wherein the olopatadine is present at an amount of about 330 µg to about 2660 µg per unit dose. In some embodiments, the antihistamine is azelastine, wherein the olopatadine is present at a concentration of 1 to 15 mg/mL. In some embodiments, the antihistamine is cetirizine. In some embodiments, the antihistamine is cetirizine, wherein the cetirizine is present at an amount of about 0.25 mg to about 4.4 mg per unit dose. In some embodiments, the antihistamine is cetirizine, wherein the cetirizine is present at a concentration of 0.25 to 4.4 mg/mL.

In some embodiments, the administering of the corticosteroid solution is performed once or twice daily.

In some embodiments, the allergic symptom or disorder is or further includes a nasal symptom, non-nasal symptom, allergic rhinitis, seasonal allergic rhinitis, perennial allergic rhinitis, perennial non-allergic rhinitis, grass pollen rhinitis, have fever, nasal polyps, or a combination thereof. In some embodiments, the allergic symptom or disorder is or further includes ocular symptom, bacterial rhinitis, fungal rhinitis, viral rhinitis, atrophic rhinitis, vasomotor rhinitis, blocked nose, nasal congestion, or a combination thereof.

In some embodiments, the nasal symptom is rhinorrhea, nasal congestion, nasal itchiness, sneezing, nasal obstruction, or a combination thereof.

In some embodiments, the non-nasal symptom is itchy/gritty eyes, tearing/watery eyes, red/burning eyes, itchy ears and palate, or a combination thereof.

In some embodiments, the corticosteroid is budesonide. In some embodiments, the corticosteroid is budesonide, wherein the budesonide is present at an amount of about 5 µg to about 500 µg per unit dose. In some embodiments, the corticosteroid is budesonide, wherein the budesonide is present at a concentration of 40 to 2000 µg/mL.

In some embodiments, the corticosteroid is fluticasone propionate.

In some embodiments, the corticosteroid is fluticasone furoate.

In some embodiments, the corticosteroid is mometasone furoate.

In some embodiments, the molar ratio of the SAE-CD to the corticosteroid is 1:1 or greater. In some embodiments, the molar ratio of the SAE-CD to an additional therapeutic agent is 1:1 or greater. In some embodiments, the molar ratio of the SAE-CD to an antihistamine is greater than 2:1.

Some embodiments of the invention includes those wherein the corticosteroid solution comprises: 1) a corticosteroid, such as budesonide, fluticasone propionate, fluticasone furoate, mometasone furoate, ciclesonide, or a combination thereof; and 2) another therapeutically effective agent, such as azelastine, olopatadine, cetirizine, loratadine, desloratadine, azithromycin, voriconazole, or a combination thereof. In some embodiments, the aqueous liquid carrier comprises water, buffer, alcohol, organic solvent, glycerin, propylene glycol, poly(ethylene glycol), poloxamer, surfactant or a combination thereof. In some embodiments, the aqueous liquid carrier comprises povidone, polyol or a combination thereof.

Some embodiments of the invention also provide a unit dose of a therapeutic corticosteroid solution comprising: about 32 µg of budesonide; SAE-CD; pharmaceutically acceptable aqueous liquid carrier; disodium edetate of about 0.005 to about 0.1% by weight of the unit dose; and potassium sorbate of about 0.05 to about 0.2% by weight of the unit dose, and wherein the corticosteroid solution is suitable for nasal administration to a subject in need thereof.

Some embodiments of the invention also provide a method of treating preventing or ameliorating in a subject a corticosteroid-responsive disease or disorder, the method comprising metering into the nose of the subject a therapeutically effective amount of budesonide that is less than about 320 µg per day, delivered as 8 or more unit doses, wherein each unit dose consists of about 32 µg of budesonide; SAE-CD; disodium edetate of about 0.005 to about 0.1% by weight of the unit dose; potassium sorbate of about 0.05 to about 0.2% by weight of the unit dose; and a pharmaceutically acceptable aqueous liquid carrier.

In some embodiments, the corticosteroid solution has a pH of about 3.5 to about 5 or about about 4.2 to about 4.6.

In some embodiments, the SAE-CD is a compound, or mixture of compounds, of the Formula 1:

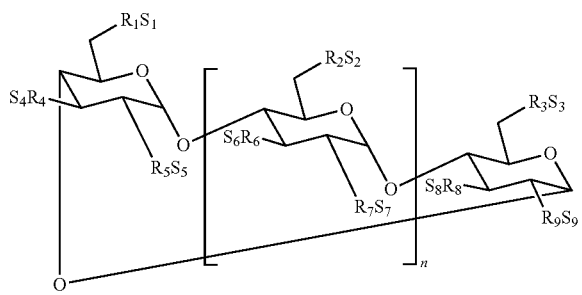

Formula 1 wherein:
n is 4, 5 or 6;
$R_1$, $R_2$, $R_3$, $R_4$, $R_5$, $R_6$, $R_7$, $R_8$ and $R_9$ are each, independently, —O— or a —O—($C_2$-$C_6$ alkylene)-$SO_3^-$ group, wherein at least one of $R_1$-$R_9$ is independently a —O—($C_2$-$C_6$ alkylene)-$SO_3^-$ group, a —O—

(CH$_2$)$_m$SO$_3^-$ group wherein m is 2 to 6, —OCH$_2$CH$_2$CH$_2$SO$_3^-$, or —OCH$_2$CH$_2$CH$_2$CH$_2$SO$_3$); and S$_1$, S$_2$, S$_3$, S$_4$, S$_5$, S$_6$, S$_7$, S$_8$ and S$_9$ are each, independently, a pharmaceutically acceptable cation.

In some embodiments, the corticosteroid solution further comprises one or more pharmaceutically acceptable excipients, such as a preservative, an antioxidant, a buffering agent, an acidifying agent, an alkalizing agent, a solubility-enhancing agent, a complexation-enhancing agent, a diluent, an electrolyte, glucose, a stabilizer, a bulking agent, an antifoaming agent, an oil, an emulsifying agent, flavor, sweetener, a taste-masking agent, a tonicity modifier, a surface tension modifier, a viscosity modifier, a density modifier, or a combination thereof.

In some embodiments, the SAE-CD is present at a concentration of about 10 to about 500 mg/mL of corticosteroid solution, and/or the SAE-CD is present in an amount of 100 μg to 1000 mg per unit dose.

The invention includes all combinations of the embodiments and aspects disclosed herein. Accordingly, the invention includes the embodiments and aspects specifically disclosed, broadly disclosed, or narrowly disclosed herein, as well as combinations thereof and subcombinations of the individual elements of said embodiments and aspects.

These and other aspects of this invention will be apparent upon reference to the following detailed description, examples, claims and attached figures.

BRIEF DESCRIPTION OF THE FIGURES

The following drawings are given by way of illustration only, and thus are not intended to limit the scope of the present invention.

FIG. 10A—Azelastine pH Rate Profile Area % (25° C.), 0.5 mg/mL azelastine HCl in 3 mM citrate@pH 4, 5, & 6; with and without 1.75% CAPTISOL, Stored in 25° C. Stability Chamber; FIG. 10B—Azelastine pH Rate Profile Area % (40° C.), 0.5 mg/mL azelastine HCl in 3 mM citrate@pH 4, 5, & 6; with and without 1.75% CAPTISOL, Stored in 40° C. Stability Chamber; FIG. 10C—Azelastine pH Rate Profile Area % (60° C.), 0.5 mg/mL azelastine HCl in 3 mM citrate@pH 4, 5, & 6; with and without 1.75% CAPTISOL, Stored in 60° C. Stability Chamber.

DETAILED DESCRIPTION OF THE INVENTION

Figure 1A:
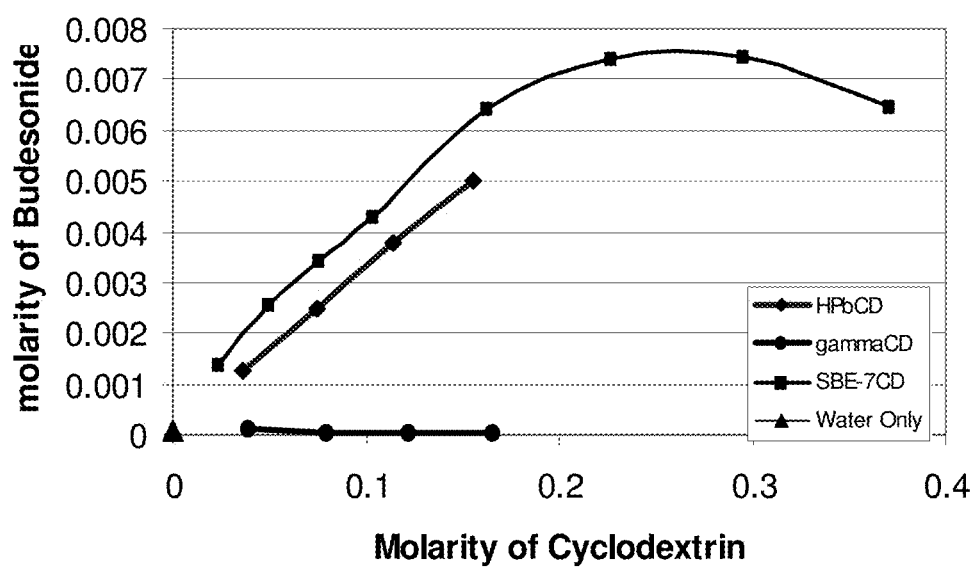
FIG. 1A depicts a phase solubility graph of the concentration (molar) of cyclodextrin versus the concentration (molar) of budesonide for γ-CD, HP-β-CD and SBE7-β-CD.

The present invention is directed to methods of treating nasal and/or ophthalmic diseases, symptoms, or disorders that are therapeutically responsive to corticosteroid therapy by delivering aqueous solution formulations comprising a corticosteroid to nasal and ophthalmic tissues. The invention is also directed to methods, systems, devices, and compositions for delivering aqueous solution formulations comprising a corticosteroid and an antihistamine to nasal and ophthalmic tissues. The systems of the invention comprise an administration device, and a composition of the invention. The composition of the invention is a corticosteroid solution comprising a corticosteroid and SAE-CD. The composition can be a nasal or non-nasal composition or an ophthalmic composition. In some embodiments, a non-nasal composition excludes an inhalable composition for pulmonary delivery.

By including SAE-CD in a liquid composition containing corticosteroid, the corticosteroid is dissolved. The corticosteroid exhibits greater stability in the presence of SAE-CD than it does in its absence. When a second active agent is present, the second active agent can also exhibit greater stability in the presence of SAE-CD than it does in its absence.

The methods, systems, devices, and compositions of the invention can provide an enhanced pharmacokinetic profile over a suspension formulation comprising approximately the same amount of a therapeutic agent and delivered under substantially the same conditions. The therapeutic agent is a corticosteroid alone or a corticosteroid combined with one or more additional therapeutic agents. As such, one or more therapeutic agents in the methods, systems, devices, and compositions of the invention can demonstrate an enhanced pharmacokinetic profile when compared with the same therapeutic agent or agents in a suspension formulation. The term "enhanced pharmacokinetic profile" is taken to mean a higher AUC (e.g. AUC$_{last}$ or AUC$_{(0 \to \infty)}$) per μg of therapeutic agent delivered or administered, a higher Cmax per μg of therapeutic agent delivered or administered, increased bioavailability, absorption or distribution of the therapeutic agent at the site of delivery, a shorter Tmax, or a longer Tmax. The methods, systems, devices, and compositions of the invention can also provide other enhancements over a suspension-based formulation, such as enhanced drug delivery, increased rate of drug administration, reduced treatment time, reduced toxicity, improved stability, enhanced bioabsorption, increased output rate, increased total output, reduced side effects associated with the therapeutic agent, increased nasal cavity deposition, increased paranasal sinus cavity deposition, increased ocular deposition, improved quality of life, reduced mucociliary clearance, reduced ocular clearance, and/or improved patient compliance.

Alternatively, the methods, systems, devices, and compositions of the invention provide substantially the same pharmacokinetic profile or an enhanced pharmacokinetic profile over a suspension formulation comprising a higher amount of therapeutic agent and delivered under substantially the same conditions. The therapeutic agent in the formulation can be present at a dose that is less than about 80%, less than about 70%, less than about 60% less than about 50%, less than about 40%, less than about 20%, or less than about 10% of that in the suspension.

The amount and/or concentration of SAE-CD in the composition can be varied as needed or as described herein to provide a composition that possesses a desired physical property, provide therapeutic effectiveness in subjects to which the composition is administered, and/or achieve a desired performance in an administration device. SAE-CD can be present in an amount sufficient to solubilize and/or stabilize the therapeutic agent when the SAE-CD and therapeutic agent are placed in the aqueous carrier. The aqueous carrier can be present in an amount sufficient to aid in dissolution of the therapeutic agent and form a solution of sufficient volume and sufficiently low viscosity to permit administration with an administration device. SAE-CD can be present in solid form or in solution in the aqueous carrier. The therapeutic agent can be present in dry powder/particle form or in suspension in the aqueous carrier. In some embodiments, SAE-CD is present at a concentration of about 10 to about 500 mg/mL of composition, and/or SAE-CD is present in an amount of 100 µg to 1000 mg per unit dose.

In some embodiments, SAE-CD is present in an amount sufficient to decrease the amount of unsolubilized therapeutic agent in the suspension-based composition and to improve the administration of the suspension-based composition. In some embodiments, SAE-CD is present in an amount sufficient to solubilize enough therapeutic agent such that the suspension-based composition to which the SAE-CD was added is converted to a solution, substantially clear solution (containing less than 5% precipitate or solid), or a clear solution. It is possible that other components of the suspension-based composition will not completely dissolve in, or may separate out from, the solution.

In some embodiments, SAE-CD is present in an amount sufficient to solubilize at least 50%, at least 75%, at least 90%, at least 95% or substantially all of the therapeutic agent. Some embodiments of the invention include those wherein at least 50% wt., at least 75% wt., at least 90% wt., at least 95% wt., at least 98% wt., or all of the therapeutic agent is dissolved in the liquid composition.

The compositions of the inventions are suitable for nasal and/or ophthalmic administration. The compositions can be administered via an administration device suitable for nasal administration or ophthalmic administration of pharmaceutical compositions. As used herein, an administration device is any pharmaceutically acceptable device adapted to deliver a composition of the invention to a subject's nose or eye(s). A nasal administration device can be a metered administration device (metered volume, metered dose, or metered-weight) or a continuous (or substantially continuous) aerosol-producing device. Suitable nasal administration devices also include devices that can be adapted or modified for nasal administration. An ophthalmic administration device can be a dropper, drop dispensing package, tube, eye spray device, eye wash unit, and other devices known to those of ordinary skill in the art. In some embodiments, the nasally or ophthalmically administered dose can be absorbed into the bloodstream of a subject.

A metered nasal administration device delivers a fixed (metered) volume or amount (dose) of a nasal composition upon each actuation. Exemplary metered dose devices for nasal administration include, by way of example and without limitation, an atomizer, sprayer, dropper, squeeze tube, squeeze-type spray bottle, pipette, ampule, nasal cannula, metered dose device, nasal spray inhaler, breath actuated bi-directional delivery device, pump spray, pre-compression metered dose spray pump, monospray pump, bispray pump, and pressurized metered dose device. The administration device can be a single-dose disposable device, single-dose reusable device, multi-dose disposable device or multi-dose reusable device.

The compositions of the invention can be used with any known metered administration device. In some embodiments, the device is a pump nasal spray or a squeeze bottle. The performance of a composition of the invention in a metered administration device is detailed in Example 35.

A continuous aerosol-producing device delivers a mist or aerosol comprising droplet of a nasal composition dispersed in a continuous gas phase (such as air). A nebulizer, pulsating aerosol nebulizer, and a nasal continuous positive air pressure device are exemplary of such a device. Suitable nebulizers include, by way of example and without limitation, an air driven jet nebulizer, ultrasonic nebulizer, capillary nebulizer, electromagnetic nebulizer, pulsating membrane nebulizer, pulsating plate (disc) nebulizer, pulsating/vibrating mesh nebulizer, vibrating plate nebulizer, a nebulizer comprising a vibration generator and an aqueous chamber, a nebulizer comprising a nozzle array, and nebulizers that extrude a liquid formulation through a self-contained nozzle array.

Commercially available administration devices that are used or can be adapted for nasal administration of a composition of the invention include the AERONEB™ (Aerogen, San Francisco, CA), AERONEB GO (Aerogen); PART LC PLUS™, PART BOY™ N, PART eflow (a nebulizer disclosed in U.S. Pat. No. 6,962,151), PART LC SINUS, PARI SINUSTAR™, PART SINUNEB, VibrENT™ and PART DURANEB™ (PARI Respiratory Equipment, Inc., Monterey, CA or Munich, Germany); MICROAIR™ (Omron Healthcare, Inc, Vernon Hills, Illinois), HALOLITE™ (Profile Therapeutics Inc, Boston, MA), RESPIMAT™ (Boehringer Ingelheim Ingelheim, Germany) AERODOSE™ (Aerogen, Inc, Mountain View, CA), OMRON ELITE™ (Omron Healthcare, Inc, Vernon Hills, Illinois), OMRON MICROAIR™ (Omron Healthcare, Inc, Vernon Hills, Illinois), MABISMIST™ II (Mabis Healthcare, Inc, Lake Forest, Illinois), LUMISCOPE™ 6610, (The Lumiscope Company, Inc, East Brunswick, New Jersey), AIRSEP MYSTIQUE™, (AirSep Corporation, Buffalo, NY), ACORN-1 and ACORN-II (Vital Signs, Inc, Totowa, New Jersey), AQUATOWER™ (Medical Industries America, Adel, Iowa), AVA-NEB (Hudson Respiratory Care Incorporated, Temecula, California), AEROCURRENT™ utilizing the AEROCELL™ disposable cartridge (AerovectRx Corporation, Atlanta, Georgia), CIRRUS (Intersurgical Incorporated, Liverpool, New York), DART (Professional Medical Products, Greenwood, South Carolina), DEVILBISS™ PULMO AIDE (DeVilbiss Corp; Somerset, Pennsylvania), DOWNDRAFT™ (Marquest, Englewood, Colorado), FAN JET (Marquest, Englewood, Colorado), MB-5 (Mefar, Bovezzo, Italy), MISTY NEB™ (Baxter, Valencia, California), SALTER 8900 (Salter Labs, Arvin, California), SIDE-STREAM™ (Medic-Aid, Sussex, UK), UPDRAFT-II™ (Hudson Respiratory Care; Temecula, California), WHISPER JET™ (Marquest Medical Products, Englewood, Colorado), AIOLOS™ (Aiolos Medicnnsk Teknik, Karlstad, Sweden), INSPIRON™ (Intertech Resources, Inc., Bannockburn, Illinois), OPTIMIST™ (Unomedical Inc., McAllen, Texas), PRODOMO™, SPIRA™ (Respiratory Care Center, Hameenlinna, Finland), AERx™ Essence™ and Ultra™ (Aradigm Corporation, Hayward, California), SONIK™ LDI Nebulizer (Evit Labs, Sacramento, California), ACCUSPRAY™ (BD Medical, Franklin Lake, NJ), ViaNase ID™ (electronic atomizer; Kurve, Bothell, WA), OptiMist device or OPTINOSE (Oslo, Norway), MAD Nasal (Wolfe Tory Medical, Inc., Salt Lake City, UT), Freepod™ (Valois, Marly le Roi, France), Dolphin™ (Valois), Monopowder™ (Valois), Equadel™ (Valois), VP3™ and VP7™ (Valois), VP6 Pump™ (Valois), Standard Systems Pumps (Ing. Erich Pfeiffer, Radolfzell, Germany), AmPump (Ing. Erich Pfeiffer), Counting Pump (Ing. Erich Pfeiffer), Advanced Preservative Free System (Ing. Erich Pfeiffer), Unit Dose System (Ing. Erich Pfeiffer), Bidose System (Ing. Erich Pfeiffer), Bidose Powder System (Ing. Erich Pfeiffer), Sinus Science™ (Aerosol Science Laboratories, Inc., Camarillo, CA), ChiSys® (Archimedes, Reading, UK), Fit-Lizer® (Bioactis, Ltd, an SNBL subsidiary (Tokyo, JP), Swordfish V™ (Mystic Pharmaceuticals, Austin, TX), DirectHaler™ Nasal (DirectHaler, Copenhagen, Denmark) and SWIRLER® Radioaerosol System (AMICI, Inc., Spring City, PA).

Particularly suitable administration devices include single dose and multi-dose embodiments of: a pump spray bottle; the PART eFlow (a nebulizer equipped with a vibrating mesh nebulizer comprising a vibration generator, an aerosol chamber, an inhalation valve, and an exhalation valve; U.S. Pat. Nos. 5,954,047, 6,026,808, 6,095,141, and 6,527,151, the entire disclosures of which are hereby incorporated by reference); AERx Essence and AERx Ultra (from ARADIGM; an aerosol generator comprising a nozzle array, whereby a liquid formulation is extruded through a self-contained nozzle array); Aeroneb Go (a nebulizer equipped with a vibrating mesh nebulizer comprising a vibration generator, an aerosol chamber, an inlet and an outlet); VibrENT™ (a nebulizer that delivers a pressure-pulsed aerosol; the delivery rate of liquid composition is about 0.160 mL/min; in PCT International Publications No. WP 2004/20029 and No. WO 2001/34232; Schuschnig et al. in European Patent Publication No. EP 1820493, and *Respiratory Drug Delivery* (2008), the entire disclosures of which are hereby incorporated by reference); PARI SINUSTAR (a nebulizer adapted for nasal administration that delivers an aqueous liquid composition at a rate of about 0.18 mL/min); and the PARI SINUS (including PARI LC Star, PARI LL and PARI Sprint).

The Aradigm AERx delivery system, the AERx Essence and AERx Ultra, is particularly suitable for use according to the invention, as it is recognized in the art as providing controlled dose expression, control of generated aerosol particle size, control of aerosol particle size, and management of the inspiration and delivery process (Farr et al., Drug Delivery Technology May 2002 Vol. 2, No. 3, 42-44). For example, the PARI eFlow vibrating plate nebulizer is particularly suitable for use according to the invention, as it is recognized in the art as providing the above-mentioned desired performance parameters (Keller et al. (ATS 99th International Conference, Seattle, May 16-21, 2003; poster 2727).

The parameters used to effect nebulization via an electronic nebulizer, such as flow rate, mesh membrane size, aerosol inhalation chamber size, mask size and materials, inlet and outlet valves, outflow tube, internal channel plurality of air outputs communicating with the internal chamber, vibration generator and power source may be varied in accordance with the principles of the present invention to maximize their use with different types of aqueous corticosteroid compositions. In some embodiments, substantially all of a dose (weight or volume) is delivered in less than 1.5 minutes or continuously delivered over 1.5 to 60 minutes.

Valves and actuators can be obtained from Bespak (Milton Keynes, UK). Actuators used in the administration device can be horizontal or vertical. The administration device can incorporate the VelocityJet™ micropump. The administration devices can be equipped with different types of baffles, valves, tubes, channels, reservoirs, mixing chambers, vortex chamber, particle dispersion chamber, nasal adapter, vibrating pulse and/or sound wave generator.

Nebulizers that nebulize liquid formulations containing no propellant are suitable for use with the compositions provided herein. Any of these and other known nebulizers can be used to deliver the formulation of the invention including but not limited to the following: nebulizers available from Pari GmbH (Starnberg, Germany), DeVilbiss Healthcare (Heston, Middlesex, UK), Healthdyne, Vital Signs, Baxter, Allied Health Care, Invacare, Hudson, Omron, Bremed, AirSep, Luminscope, Medisana, Siemens, Aerogen, Mountain Medical, Aerosol Medical Ltd. (Colchester, Essex, UK), AFP Medical (Rugby, Warwickshire, UK), Bard Ltd. (Sunderland, UK), Carri-Med Ltd. (Dorking, UK), Plaem Nuiva (Brescia, Italy), Henleys Medical Supplies (London, UK), Intersurgical (Berkshire, UK), Lifecare Hospital Supplies (Leies, UK), Medic-Aid Ltd. (West Sussex, UK), Medix Ltd. (Essex, UK), Sinclair Medical Ltd. (Surrey, UK), and many other companies. The AERx and RESPIMAT nebulizers are described by D. E. Geller (Respir. Care (2002), 47 (12), 1392-1404), the entire disclosure of which is incorporated by reference.

Nebulizers for use herein include, but are not limited to, jet nebulizers (optionally sold with compressors), ultrasonic nebulizers, vibrating membrane, vibrating mesh nebulizers, vibrating plate nebulizers, vibrating cone nebulizer, and others. Exemplary jet nebulizers for use herein include Pari LC plus/ProNeb, Pari LC plus/ProNeb Turbo, Pari LC Plus/Dura Neb 1000 & 2000 Pari LC plus/Walkhaler, Pari LC plus/Pari Master, Pari LC star, Omron CompAir XL Portable Nebulizer System (NE-C18 and JetAir Disposable nebulizer), Omron compare Elite Compressor Nebulizer System (NE-C21 and Elite Air Reusable Nebulizer, Pari LC Plus or Pari LC Star nebulizer with Proneb Ultra compressor, Pulomo-aide, Pulmo-aide LT, Pulmo-aide traveler, Invacare Passport, Inspiration Healthdyne 626, Pulmo-Neb Traverler, DeVilbiss 646, Whisper Jet, Acorn II, Misty-Neb, Allied aerosol, Schuco Home Care, Lexan Plasic Pocet Neb, SideStream Hand Held Neb, Mobil Mist, Up-Draft, Up-Draft II, T Up-Draft, ISO-NEB, Ava-Neb, Micro Mist, and PulmoMate. Exemplary ultrasonic nebulizers for use herein include MicroAir, UltraAir, Siemens Ultra Nebulizer 145, CompAir, Pulmosonic, Scout, 5003 Ultrasonic Neb, 5110 Ultrasonic Neb, 5004 Desk Ultrasonic Nebulizer, Mystique Ultrasonic, Lumiscope's Ultrasonic Nebulizer, Medisana Ultrasonic Nebulizer, Microstat Ultrasonic Nebulizer, and Mabismist Hand Held Ultrasonic Nebulizer. Other nebulizers for use herein include 5000 Electromagnetic Neb, 5001 Electromagnetic Neb 5002 Rotary Piston Neb, Lumineb I Piston Nebulizer 5500, Aeroneb Portable Nebulizer System, Aerodose™ Inhaler, and AeroEclipse Breath Actuated Nebulizer. Exemplary vibrating membrane, mesh or plate nebulizers are described by R. Dhand (*Respiratory Care*, (December 2002), 47(12), p. 1406-1418), the entire disclosure of which is hereby incorporated by reference.

The volume or amount of composition administered can vary according to the intended delivery target and administration device used. The amount of active agent in a dose or unit dose can vary according to the intended delivery target and administration device used.

During operation of a nebulizer based system, the corticosteroid can be delivered at a rate of at least about 20-50 μg/min, or 10-200 μg/min, wherein this range may increase or decrease according to the concentration of corticosteroid in the composition in the administration device.

The present invention provides SAE-CD based formulations, wherein the SAE-CD is a compound of the Formula 1:

Formula 1 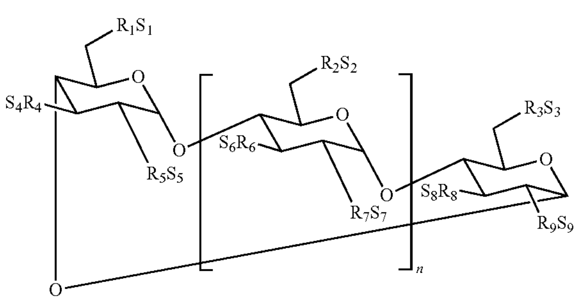 wherein:

n is 4, 5 or 6;

$R_1$, $R_2$, $R_3$, $R_4$, $R_5$, $R_6$, $R_7$, $R_8$ and $R_9$ are each, independently, —O— or a —O—($C_2$-$C_6$ alkylene)-$SO_3^-$ group, wherein at least one of $R_1$ to $R_9$ is independently a —O—($C_2$-$C_6$ alkylene)-$SO_3^-$ group, preferably a —O—$(CH_2)_m SO_3^-$ group, wherein m is 2 to 6, preferably 2 to 4, (e.g. —$OCH_2CH_2CH_2SO_3^-$ or —$OCH_2CH_2CH_2CH_2SO_3^-$); and $S_1$, $S_2$, $S_3$, $S_4$, $S_5$, $S_6$, $S_7$, $S_8$ and $S_9$ are each, independently, a pharmaceutically acceptable cation which includes, for example, $H^+$, alkali metals (e.g. $Li^+$, $Na^+$, $K^+$), alkaline earth metals (e.g., $Ca^{+2}$, $Mg^{+2}$), ammonium ions and amine cations such as the cations of ($C_1$-$C_6$)-alkylamines, piperidine, pyrazine, ($C_1$-$C_6$)-alkanolamine and ($C_4$-$C_5$)-cycloalkanolamine.

Exemplary embodiments of the SAE-CD derivative of the invention include derivatives of the Formula II (SAEx-α-CD), wherein "x" ranges from 1 to 18; of the Formula III (SAEy-β-CD), wherein"y" ranges from 1 to 21; and of the Formula IV (SAEz-γ-CD), wherein"z" ranges from 1 to 24 such as:

| SAEx-α-CD | SAEy-β-CD | SAEz-γ-CD | Name |
|---|---|---|---|
| SEEx-α-CD | SEEy-β-CD | SEEz-γ-CD | Sulfoethyl ether CD |
| SPEx-α-CD | SPEy-β-CD | SPEz-γ-CD | Sulfopropyl ether CD |
| SBEx-α-CD | SBEy-β-CD | SBEz-γ-CD | Sulfobutyl ether CD |
| SptEx-α-CD | SPtEy-β-CD | SPtEz-γ-CD | Sulfopentyl ether CD |
| SHEx-α-CD | SHEy-β-CD | SHEz-γ-CD | Sulfohexyl ether CD |

"SAE" represents a sulfoalkyl ether substituent bound to a cyclodextrin. The values "x", "y" and "z" represent the average degree of substitution as defined herein in terms of the number of sulfoalkyl ether groups per CD molecule. Some suitable SAE-CD's include, for example, sulfobutyl ether 4-β-CD or sulfobutyl ether 7-β-CD, sulfobutyl ether 6-γ-CD, sulfobutyl ether 4-γ-CD, sulfobutyl ether 3 to 8-γ-CD, or a sulfobutyl ether 5-γ-CD, or a compound of the formula 1 or a mixture thereof.

The SAE-CD used is described in U.S. Pat. Nos. 5,376,645 and 5,134,127 to Stella et al, the entire disclosures of which are hereby incorporated by reference. U.S. Pat. No. 3,426,011 to Parmerter et al. discloses anionic cyclodextrin derivatives having sulfoalkyl ether substituents. Lammers et al. (*Recl. Trav. Chim. Pays-Bas* (1972), 91(6), 733-742); *Staerke* (1971), 23(5), 167-171) and Qu et al. (*J. Inclusion Phenom. Macro. Chem.* , (2002), 43, 213-221) disclose sulfoalkyl ether derivatized cyclodextrins. U.S. Pat. No. 6,153,746 to Shah et al. discloses a process for the preparation of sulfoalkyl ether cyclodextrin derivatives. An SAE-CD can be made according to the disclosures of Stella et al., Parmerter et al., Lammers et al. or Qu et al., and if processed to remove the major portion (>50%) of the underivatized parent cyclodextrin, used according to the present invention. The SAE-CD can contain from 0% to less than 50% wt. of underivatized parent cyclodextrin.

The terms "alkylene" and "alkyl," as used herein (e.g., in the -0-($C_2$-$C_6$-alkylene)$SO_3^-$ group or in the alkylamines), include linear, cyclic, and branched, saturated and unsaturated (i.e., containing one double bond) divalent alkylene groups and monovalent alkyl groups, respectively. The term "alkanol" in this text likewise includes both linear, cyclic and branched, saturated and unsaturated alkyl components of the alkanol groups, in which the hydroxyl groups can be situated at any position on the alkyl moiety. The term "cycloalkanol" includes unsubstituted or substituted (e.g., by methyl or ethyl) cyclic alcohols.

In some embodiments of the present invention, compositions contain a mixture of cyclodextrin derivatives, having the structure set out in formula (I), where the composition overall contains on the average at least 1 and up to 3n+6 alkylsulfonic acid moieties per cyclodextrin molecule. The present invention also provides compositions containing a single type of cyclodextrin derivative, or at least 50% of a single type of cyclodextrin derivative. The invention also includes formulations containing cyclodextrin derivatives having a narrow or wide and high or low degree of substitution. These combinations can be optimized as needed to provide cyclodextrins having particular properties.

The present invention also provides compositions containing a mixture of cyclodextrin derivatives wherein two or more different types of cyclodextrin derivatives are included in the composition. By different types, is meant cyclodextrins derivatized with different types of functional groups e.g., hydroxyalkyl and sulfoalkyl. Each independent different type can contain one or more functional groups, e.g. SBE-CD where the cyclodextrin ring has only sulfobutyl functional groups, and hydroxypropyl-ethyl-β-CD where the cyclodextrin ring has both hydroxypropyl functional groups and ethyl functional groups. The amount of each type of cyclodextrin derivative present can be varied as desired to provide a mixture having the desired properties.

Exemplary SAE-CD derivatives include SBE4-β-CD, SBE7-β-CD, SBE11-β-CD, SBE3.4-γ-CD, SBE4.2-γ-CD, SBE4.9-γ-CD, SBE5.2-γ-CD, SBE6.1-γ-CD, SBE7.5-γ-CD, SBE7.8-γ-CD and SBES-γ-CD which correspond to SAE-CD derivatives of the formula I wherein n=5, 5, 5 and 6; m is 4; and there are on average 4, 7, 11 and 5 sulfoalkyl ether substituents present, respectively. These SAE-CD derivatives increase the solubility of poorly water soluble active agents to varying degrees.

Since SAE-CD is a poly-anionic cyclodextrin, it can be provided in different salt forms. Suitable counterions include cationic organic atoms or molecules and cationic inorganic atoms or molecules. The SAE-CD can include a single type of counterion or a mixture of different counterions. The properties of the SAE-CD can be modified by changing the identity of the counterion present. For example, a first salt form of SAE-CD can have a greater corticosteroid stabilizing and/or solubilizing power than a different second salt form of SAE-CD. Likewise, an SAE-CD having a first degree of substitution can have a greater corticosteroid stabilizing and/or solubilizing power than a second SAE-CD having a different degree of substitution.

The liquid compositions and systems of the invention provide an improved clinical benefit or therapeutic benefit over an otherwise similar suspension-based formulations excluding SAE-CD but comprising substantially the same dose of active agent, such as corticosteroid. Exemplary advantages may include enhanced drug delivery, increased rate of drug administration, reduced treatment time, reduced toxicity, ease of manufacture, assurance of sterility, improved stability, enhanced bioabsorption, no concern for solid particle growth, enhanced pharmacokinetic profile, reduced corticosteroid-related side effects, improved patient quality of life, and/or improved clinical or pharmaceutical performance over the suspension formulation.

Figure 2:
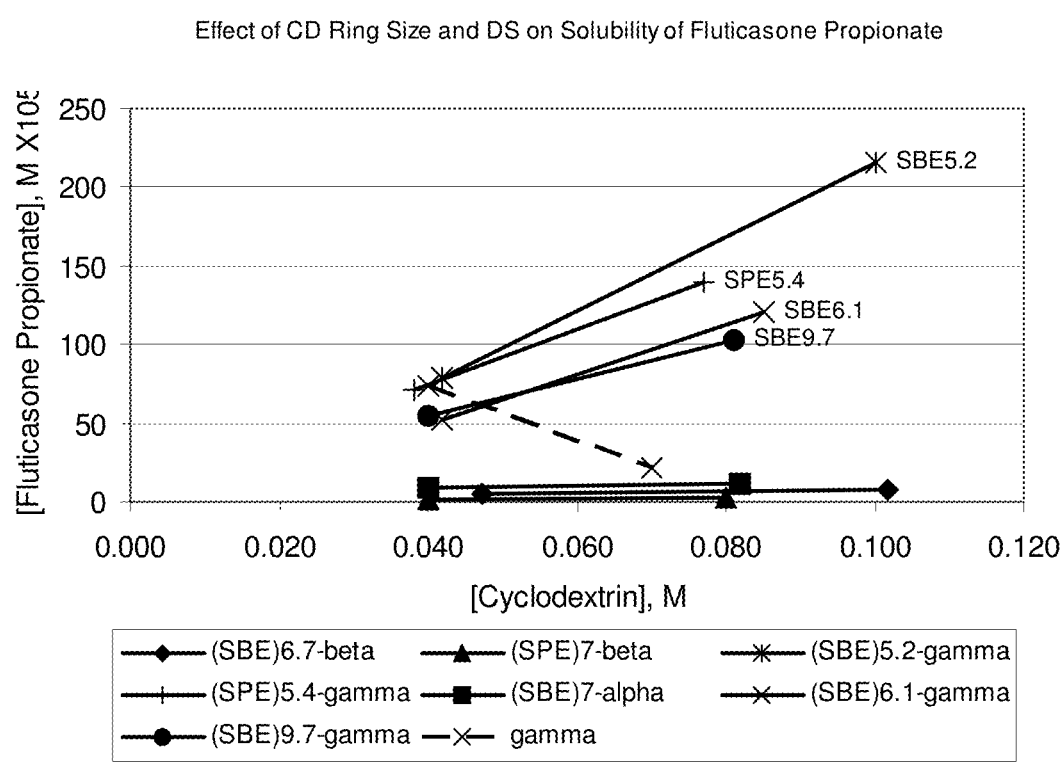
FIG. 2 depicts a phase solubility diagram for fluticasone propionate in the presence of several different cyclodextrins.
Figure 3:
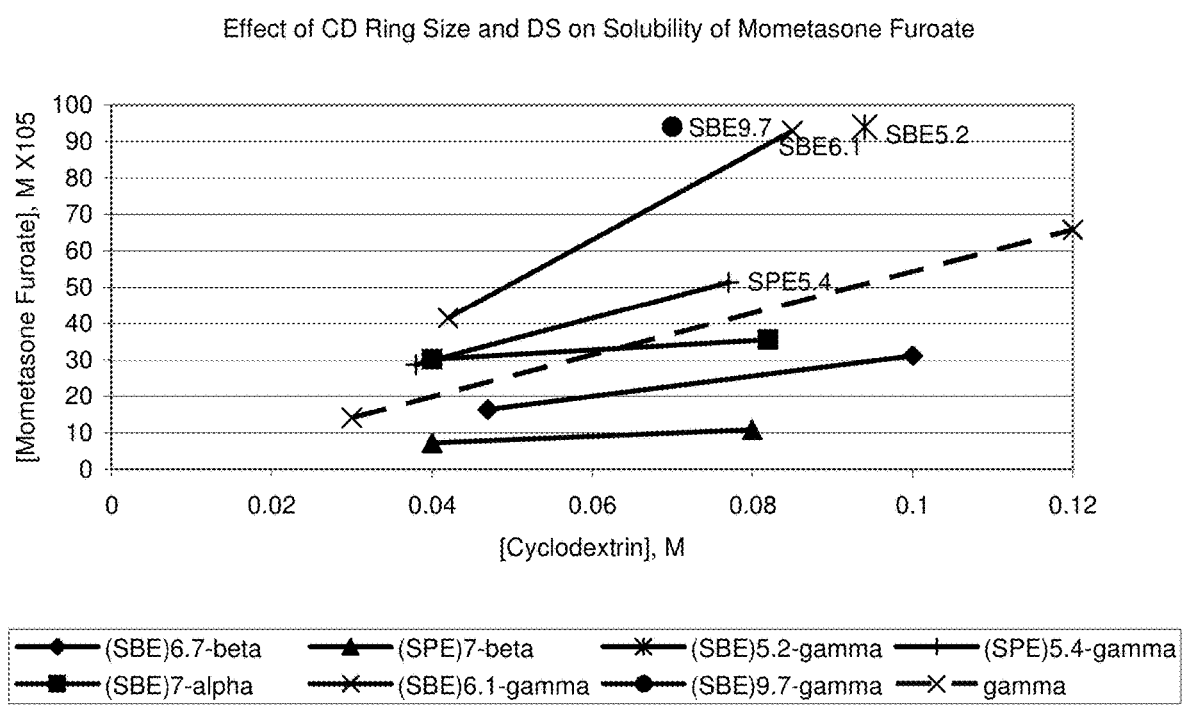
FIG. 3 depicts a phase solubility diagram for mometasone furoate in the presence of several different cyclodextrins.

The enhanced solubilization of a corticosteroid by one SAE-CD versus another is demonstrated by the data in the following tables which depict the molar solubility for fluticasone propionate with different SAE-CDs at about 0.03 to 0.12M concentrations such that the solubilizing power followed about this rank order over this concentration range of SAE-CD: SBE5.2-γ-CD>SPE5.4-γ-CD>SBE6.1-γ-CD>SBE9.7-γ-CD>>SBE7-α-CD>SBE6.7-β-CD>SPE7-β-CD. For mometasone furoate, the solubilizing power followed about this rank order over this concentration range of SAE-CD: SBE9.7-γ-CD>SBE6.1-γ-CD>SBE5.2-γ-CD>>SPE5.4-γ-CD>SBE7-α-CD>SBE6.7-β-CD>SPE7-β-CD. Differences were also observed for the binding of budesonide (and triamcinolone with specific embodiments of SAE-CD. According to the invention, a SAE-γ-CD binds a corticosteroid better than a SAE-β-CD does. Also, a SAE-β-CD binds budesonide better than a SAE-α-CD does. The phase solubility data is summarized in Example 23 and FIGS. 2-3.

Figure 4:
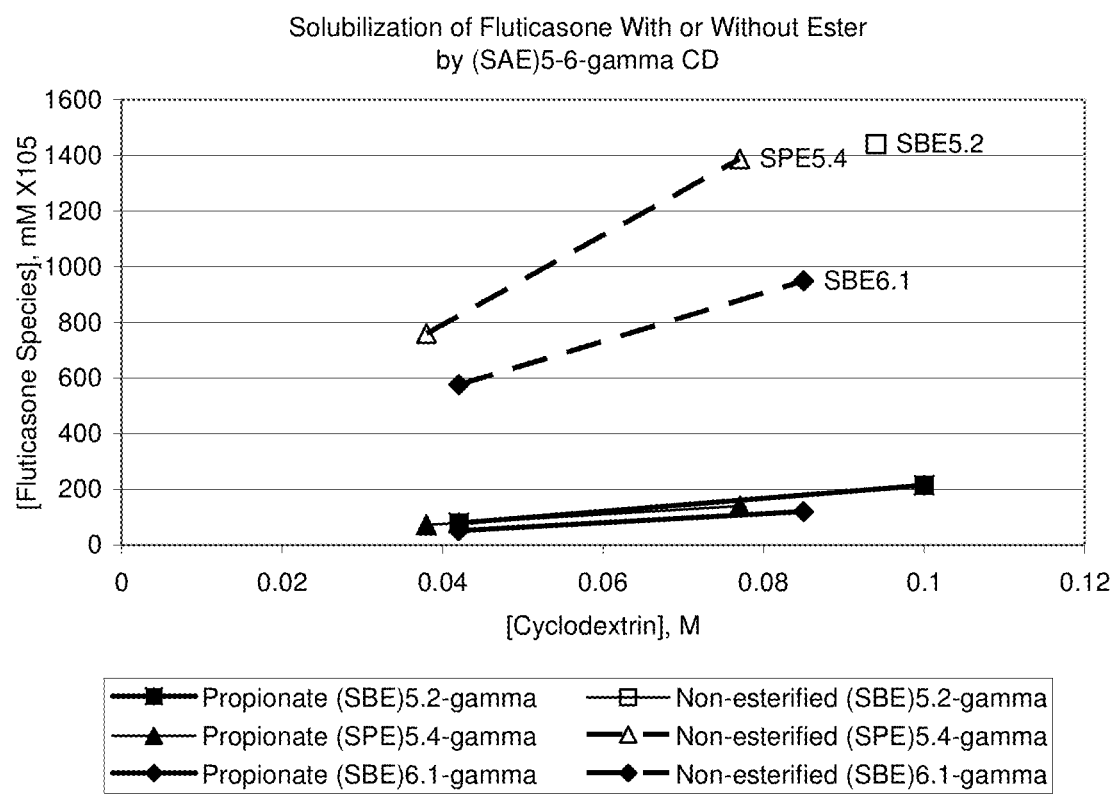
FIG. 4 depicts a phase solubility diagram for esterified and non-esterified fluticasone in the presence of SAE(5-6)-γ-CD.

The inventors have also discovered that SAE-γ-CD is particularly suitable for use in complexing esterified and non-esterified corticosteroids as compared to complexation of the same corticosteroids with SAE-γ-CD or SAE-α-CD. The table in Example 23 summarizes the phase solubility data depicted in FIG. 4 for fluticasone and fluticasone propionate with various different SAE-γ-CD species having a degree of substitution in the range of 5-10.

SAE-γ-CD is more effective at binding with a particular regioisomer of esterified corticosteroids than is SAE-β-CD or SAE-α-CD. The procedure set forth in Example 18 details the comparative evaluation of the binding of SAE-γ-CD and SAE-β-CD with a series of structurally related corticosteroid derivatives.

By "complexed" is meant "being part of a clathrate or inclusion complex with", i.e., a complexed therapeutic agent is part of a clathrate or inclusion complex with a cyclodextrin derivative. By "major portion" is meant at least about 50% by weight. Thus, a formulation according to the present invention can contain an active agent of which more than about 50% by weight is complexed with a cyclodextrin. The actual percent of active agent that is complexed will vary according to the complexation equilibrium binding constant characterizing the complexation of a specific cyclodextrin to a specific active agent. The invention also includes embodiments wherein the active agent is not complexed with the cyclodextrin or wherein a minor portion of the active agent is complexed with the derivatized cyclodextrin. It should be noted that an SAE-CD, or any other anionic derivatized cyclodextrin, can form one or more ionic bonds with a positively charged compound. This ionic association can occur regardless of whether the positively charged compound is complexed with the cyclodextrin either by inclusion in the cavity or formation of a salt bridge.

The binding of a drug to the derivatized cyclodextrin can be improved by including an acid or base along with the drug and cyclodextrin. For example, the binding of a basic drug with the cyclodextrin might be improved by including an acid along with the basic drug and cyclodextrin. Likewise, the binding of an acidic drug with the cyclodextrin might be improved by including a base (alkaline material) along with the acidic drug and cyclodextrin. The binding of a neutral drug might be improved by including a basic, acidic or other neutral compound along with the neutral drug and cyclodextrin. Suitable acidic compounds include inorganic and organic acids. Examples of inorganic acids are mineral acids, such as hydrochloric and hydrobromic acid. Other suitable acids include sulfuric acid, sulfonic acid, sulfenic acid, and phosphoric acid. Examples of organic acids are aliphatic carboxylic acids, such as acetic acid, ascorbic acid, carbonic acid, citric acid, butyric acid, fumaric acid, glutaric acid, glycolic acid, α-ketoglutaric acid, lactic acid, malic acid, mevalonic acid, maleic acid, malonic acid, oxalic acid, pimelic acid, propionic acid, succinic acid, tartaric acid, or tartronic acid. Aliphatic carboxylic acids bearing one or more oxygenated substituents in the aliphatic chain are also useful. A combination of acids can be used.

Suitable basic compounds include but are not limited to inorganic and organic bases. Suitable inorganic bases include ammonia, metal oxide and metal hydroxide. Suitable organic bases include primary amine, secondary amine, tertiary amine, imidazole, triazole, tetrazole, pyrazole, indole, diethanolamine, triethanolamine, diethylamine, methylamine, tromethamine (TRIS), aromatic amine, unsaturated amine, primary thiol, and secondary thiol. A combination of bases can be used.

An anionic derivatized cyclodextrin can complex or otherwise bind with an acid-ionizable agent. As used herein, the term acid-ionizable agent is taken to mean any compound that becomes or is ionized in the presence of an acid. An acid-ionizable agent comprises at least one acid-ionizable functional group that becomes ionized when exposed to acid or when placed in an acidic medium. Exemplary acid-ionizable functional groups include a primary amine, secondary amine, tertiary amine, quaternary amine, aromatic amine, unsaturated amine, primary thiol, secondary thiol, sulfonium, hydroxyl, enol and others known to those of ordinary skill in the chemical arts.

The degree to which an acid-ionizable agent is bound by non-covalent ionic binding versus inclusion complexation formation can be determined spectrophotometrically using methods such as $^1$HNMR, $^{13}$CNMR, or circular dichroism, for example, and by analysis of the phase solubility data for the acid-ionizable agent and anionic derivatized cyclodextrin. The artisan of ordinary skill in the art will be able to use these conventional methods to approximate the amount of each type of binding that is occurring in solution to determine whether or not binding between the species is occurring predominantly by non-covalent ionic binding or inclusion complex formation. An acid-ionizable agent that binds to derivatized cyclodextrin by both means will generally exhibit a bi-phasic phase solubility curve. Under conditions where non-covalent ionic bonding predominates over inclusion complex formation, the amount of inclusion complex formation, measured by NMR or circular dichroism, will be reduced even though the phase solubility data indicates significant binding between the species under those conditions; moreover, the intrinsic solubility of the acid-ionizable agent, as determined from the phase solubility data, will generally be higher than expected under those conditions.

As used herein, the term non-covalent ionic bond refers to a bond formed between an anionic species and a cationic species. The bond is non-covalent such that the two species together form a salt or ion pair. An anionic derivatized cyclodextrin provides the anionic species of the ion pair and the acid-ionizable agent provides the cationic species of the ion pair. Since an anionic derivatized cyclodextrin is multivalent, an SAE-CD can form an ion pair with one or more acid-ionizable agents.

The parent cyclodextrins have limited water solubility as compared to SAE-CD and HPCD. Underivatized α-CD has a water solubility of about 14.5% w/v at saturation. Underivatized β-CD has a water solubility of about 1.85% w/v at saturation. Underivatized γ-CD has a water solubility of about 23.2% w/v at saturation. Dimethyl-beta-cyclodextrin (DMCD) forms a 43% w/w aqueous solution at saturation. The SAE-CD can be combined with one or more other cyclodextrins or cyclodextrin derivatives in the composition to solubilize the corticosteroid.

Other water soluble cyclodextrin derivatives that can be used according to the invention include the hydroxyethyl, hydroxypropyl (including 2- and 3-hydroxypropyl) and dihydroxypropyl ethers, their corresponding mixed ethers and further mixed ethers with methyl or ethyl groups, such as methylhydroxyethyl, ethyl-hydroxyethyl and ethyl-hydroxypropyl ethers of alpha-, beta- and gamma-cyclodextrin; and the maltosyl, glucosyl and maltotriosyl derivatives of alpha, beta- and gamma-cyclodextrin, which can contain one or more sugar residues, e.g. glucosyl or diglucosyl, maltosyl or dimaltosyl, as well as various mixtures thereof, e.g. a mixture of maltosyl and dimaltosyl derivatives. Specific cyclodextrin derivatives for use herein include hydroxypropyl-beta-cyclodextrin, hydroxyethyl-beta-cyclodextrin, hydroxypropyl-gamma-cyclodextrin, hydroxyethyl-gamma-cyclodextrin, dihydroxypropyl-beta-cyclodextrin, glucosyl-alpha-cyclodextrin, glucosyl-beta-cyclodextrin, diglucosyl-beta-cyclodextrin, maltosyl-alpha-cyclodextrin, maltosyl-beta-cyclodextrin, maltosyl-gamma-cyclodextrin, maltotriosyl-beta-cyclodextrin, maltotriosyl-gamma-cyclodextrin and dimaltosyl-beta-cyclodextrin, and mixtures thereof such as maltosyl-beta-cyclodextrin/dimaltosyl-beta-cyclodextrin, as well as methyl-beta-cyclodextrin. Procedures for preparing such cyclodextrin derivatives are well-known, for example, from Bodor U.S. Pat. No. 5,024,998 dated Jun. 18, 1991, and references cited therein. Other cyclodextrins suitable for use in the present invention include the carboxyalkyl thioether derivatives such as ORG 26054 and ORG 25969 made by ORGANON (AKZO-NOBEL), hydroxybutenyl ether derivatives made by EASTMAN, sulfoalkyl-hydroxyalkyl ether derivatives, sulfoalkyl-alkyl ether derivatives, and other derivatives as described in US Pregrant Patent Application Publications No. 2002/0128468, No. 2004/0106575, No. 2004/0109888, and No. 2004/0063663, or U.S. Pat. Nos. 6,610,671, 6,479,467, 6,660,804, or 6,509,323.

The HP-β-CD can be obtained from Research Diagnostics Inc. (Flanders, NJ). HP-β-CD is available with different degrees of substitution. Exemplary products include ENCAPSIN™ (degree of substitution~4; HP4-β-CD) and MOLECUSOL™ (degree of substitution~8; HP8-β-CD); however, embodiments including other degrees of substitution are also available. Since HPCD is non-ionic, it is not available in salt form.

Dimethyl cyclodextrin is available from FLUKA Chemie (Buchs, CH) or Wacker (Iowa). Other derivatized cyclodextrins suitable in the invention include water soluble derivatized cyclodextrins. Exemplary water-soluble derivatized cyclodextrins include carboxylated derivatives; sulfated derivatives; alkylated derivatives; hydroxyalkylated derivatives; methylated derivatives; and carboxy-β-cyclodextrins, e.g. succinyl-β-cyclodextrin (SCD), and $6^4$-amino-$6^4$-deoxy-N-(3-carboxypropyl)-β-cyclodextrin. All of these materials can be made according to methods known in the prior art. Suitable derivatized cyclodextrins are disclosed in, e.g., *Modified Cyclodextrins: Scaffolds and Templates for Supramolecular Chemistry* (Eds. Christopher J. Easton, Stephen F. Lincoln, Imperial College Press, London, UK, 1999) and *New Trends in Cyclodextrins and Derivatives* (Ed. Dominique Duchene, Editions de Sante, Paris, France, 1991).

Sulfobutyl ether β-cyclodextrin (CAPTISOL, CyDex Inc., degree of substitution=6.6), 2-hydroxypropyl β-cyclodextrin (HP-β-CD, CERESTAR, degree of substitution=5.5), succinylated-β-cyclodextrin (S-CD, Cyclolab), and 2,6, di-o-methyl-β-cyclodextrin (DM-CD, Fluka) % w/w solutions were prepared at their native pH or buffered as needed. Sulfoalkyl ether γ-CD and sulfoalkyl ether α-CD derivatives were obtained from CyDex, Inc. (Lenexa, KS) and The University of Kansas (Lawrence, KS).

The amount of derivatized cyclodextrin required to provide the desired effect will vary according to the materials comprising the formulation.

Figure 1B:
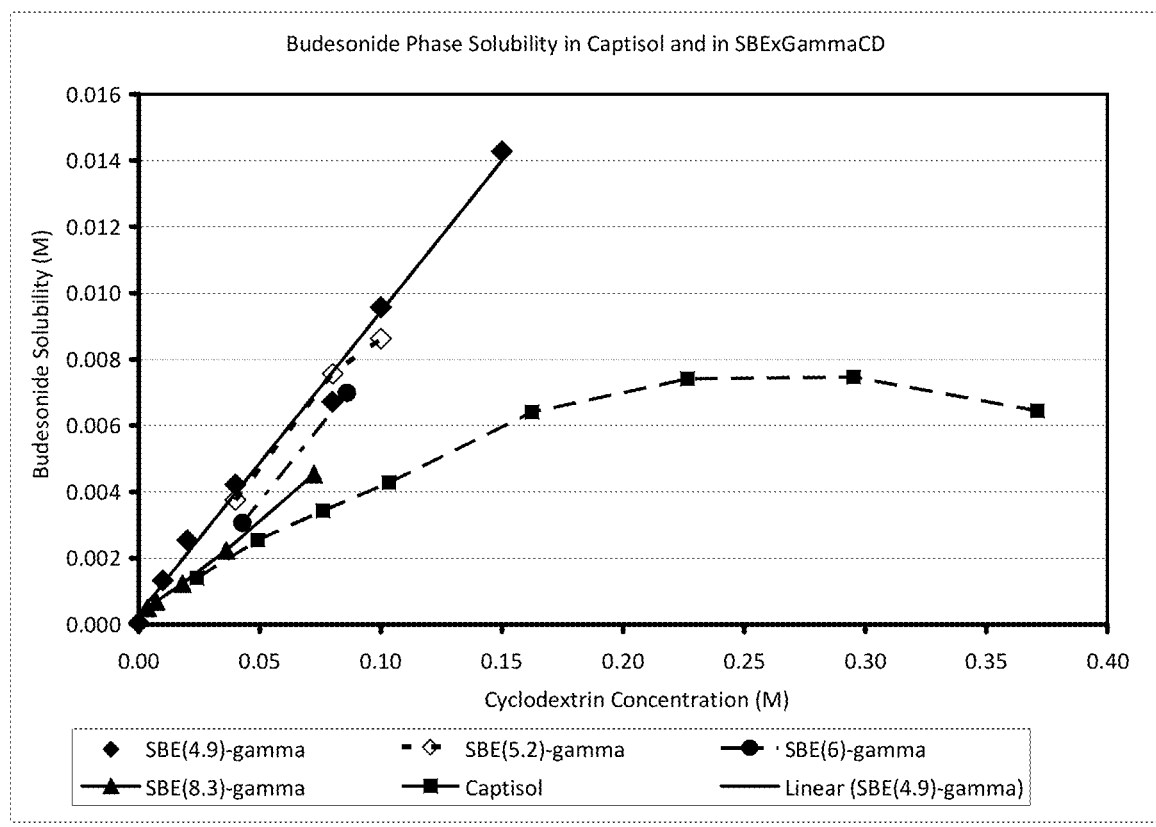
FIG. 1B depicts a phase solubility graph for budesonide concentration (M) versus cyclodextrin concentration (M) for various SBG-γ-CD species and CAPTISOL.

Different cyclodextrins are able to solubilize a corticosteroid to different extents. FIG. 1A depicts a molar phase solubility curve for budesonide with HP-β-CD, SBE7-β-CD, and γ-CD as compared to water. The inventors have found that SAE-CD is superior to other cyclodextrins and cyclodextrin derivatives at solubilizing budesonide. On a molar basis, SBE-β-CD is a better solubilizer of budesonide than HP-β-CD. In addition, the solubilizing power among the SAE-CD derivatives followed about this rank order for budesonide over a SAE-CD concentration range of 0.04 to 0.1 M: SBE5.2-γ-CD SPE5.4-γ-CD>SBE6.1-γ-CD>SBE7-α-CD>SBE9.7-γ-CD SBE6.7-β-CD>SPE7-β-CD. For example, a 0.1 M concentration of SBE7-β-CD was able to solubilize a greater amount of budesonide than either γ-CD or HP-β-CD. Moreover, SAE-CD-containing nebulizable formulations provide a greater output rate for corticosteroid by nebulization as compared to γ-CD or HP-β-CD administered under otherwise similar conditions. Additional phase solubility data is depicted in FIG. 1B for various SBE-γ-CD derivatives (SBE4.9-γ-CD, SBE5.23-γ-CD, SBE6-γ-CD, SBE9.67-γ-CD, and SBE4.9-γ-CD) and CAPTISOL. The data indicate that the SBE-γ-CD derivatives generally outperform CAPTISOL in dissolution of budesonide.

The output rate (the rate at which the dose of the therapeutically effective agent(s) in the corticosteroid solution is administered or delivered) will vary according to the performance parameters of the device used to administer the dose. The higher the output rate of a given device, the lower the amount of time required to deliver or administer the corticosteroid solution, as defined herein, or the dose of the therapeutically effective agent(s) in the corticosteroid solution.

Nebulization of CAPTISOL solutions provides several advantages with respect to other cyclodextrins. The droplets leaving the nebulizer are of a more advantageous size and the CAPTISOL solutions are nebulized faster than similar solutions of other Cyclodextrins. The smaller droplet size of aerosolized composition is favored for delivery of active agents such as a corticosteroid to the paranasal sinus cavities and/or deep nasal cavity.

CAPTISOL is emitted from a nebulizer faster and also to a greater extent than the other cyclodextrins, thus the output rate of the nebulizer is greater when CAPTISOL is nebulized. The output rate is highest for the CAPTISOL solution as compared to other cyclodextrin solutions indicating that an equivalent amount of drug can be delivered in a shorter period of time. Under the conditions used, β-CD is unable to solubilize an equivalent amount of corticosteroid due to the limited solubility of β-CD in water.

The compositions of the invention can be made from other suspension-based aqueous formulations, which formulations can be adapted for nasal delivery, by addition of SAE-CD thereto. Exemplary suspension-based aqueous formulations include the UDB formulation (Sheffield Pharmaceuticals, Inc.), VANCENASE™ AQ (beclomethasone dipropionate aqueous suspension; Schering Corporation, Kenilworth, NJ), ATOMASE™ (beclomethasone dipropionate aqueous suspension; Douglas Pharmaceuticals Ltd., Aukland, Australia), BECONASE™ (beclomethasone dipropionate aqueous suspension; Glaxo Wellcome), NASACORT AQ™ (triamcinolone acetonide nasal spray, Aventis Pharmaceuticals), TRI-NASAL™ (triamcinolone acetonide aqueous suspension; Muro Pharmacaceuticals Inc.) and AEROBID-M™ (flunisolide inhalation aerosol, Forest Pharmaceuticals), NASALIDE™ and NASAREL™ (flunisolide nasal spray, Ivax Corporation), FLONASE™ (fluticasone propionate, GlaxoSmithKline), and NASONEX™ (mometasone furoate, Schering-Plough Corporation).

The suspension formulation can comprise corticosteroid present in particulate, microparticulate, nanoparticulate or nanocrystalline form. Accordingly, an SAE-CD can be used to improve the administration of a corticosteroid suspension-based formulation. Moreover, the SAE-CD outperforms other cyclodextrin derivatives.

In some embodiments, SAE-CD (in solid or liquid form) and a suspension-based formulation comprising corticosteroid are mixed. The SAE-CD is present in an amount sufficient to increase the amount of solubilized corticosteroid, i.e. decrease the amount of unsolubilized corticosteroid, therein. Prior to administration, the liquid can be optionally aseptically filtered or terminally sterilized. The liquid is then nasally administered to a subject. As a result, the amount of drug that the subject receives is higher than the subject would have received had the unaltered suspension formulation been administered.

In some embodiments, SAE-CD (in liquid form, as ready-to-use liquid or as a concentrate) and a solid formulation comprising corticosteroid are mixed to form a liquid composition. The SAE-CD is present in an amount sufficient to solubilize a substantial portion of the corticosteroid. The liquid is then administered nasally or ophthalmically using a suitable administration device.

In other embodiments, SAE-CD (in solid form) and a solid formulation comprising corticosteroid are mixed to form a solid mixture to which is added an aqueous liquid carrier in an amount sufficient to form a nebulizable formulation. Mixing and/or heating are optionally employed upon addition of the liquid carrier to form the formulation. The SAE-CD is present in an amount sufficient to solubilize a substantial portion of the corticosteroid. The formulation is then administered nasally using an administration device as defined herein.

In some embodiments, the nasal device is a nebulizer for nasal administration. The size of the reservoir varies from one type of nebulizer to another. The volume of the liquid formulation can be adjusted as needed to provide the required volume for loading into the reservoir of a particular type or brand of nebulizer. The volume can be adjusted by adding additional liquid carrier or additional solution containing SAE-CD. In general, the reservoir volume of a nebulizer is about 10 µl to 100 mL. Low volume nebulizers, such as ultrasonic and vibrating mesh/vibrating plate/vibrating cone/vibrating membrane nebulizers, pre-filled reservoir strips inclusive of delivery nozzle typically have a reservoir volume of 10 µl to 6 mL or 10 µl to 5 mL. The low volume nebulizers provide the advantage of shorter administration times as compared to large volume nebulizers.

Example 28 details a procedure for preparation of a solution of the invention to be used with a low volume (low reservoir volume and/or low reservoir residual volume) nebulizer, such as an AERx nebulizer. The solutions of the invention can be nebulized with any nebulizer; however, with an AERx delivery system that coordinates both the nasal inspiration and delivery processes to optimize deep paranasal sinus cavity penetration, an initial sample volume of about 10 µl to 100 or 50 µl can be used to load AERx Strip multiple unit dose container. Administration of this solution with the system makes it feasible for a therapeutic dose to be administered to a subject in a single puff (a single full nasal inspiration by a subject, i.e. 3-5 seconds) via nebulization. Based on general performance expectations of such devices the corticosteroid can be expected to be delivered to the nose in a single dosing event using corticosteroid solutions prepared with SAECD.

Example 32 details a procedure for the comparison of nebulization parameters in four different nebulizers using a formulation of the invention and PULMICORT RESPULES (suspension-based formulation). In each case, the formulation of the invention out performs the suspension-based formulation. The solution of the invention provide a 1.25, 1.4, 2.1, 3.3, 3.67, 1.25 to 3.7, or 1.25 to 4 fold increase in the amount of budesonide delivered. Under the conditions tested, the AIRSEP MYSTIQUE was most efficient at emitting/nebulizing the SAE-CD/budesonide formulation.

In some embodiments, a suspension-based formulation is converted to a liquid formulation prior to administration (as a mist or aerosol) to a subject. The conversion can take place in the same container in which the suspension is provided, in a different container, or in the reservoir of an administration device. In order to form a liquid composition, a substantial portion of the corticosteroid must be dissolved. As used in reference to the amount of dissolved corticosteroid, a "substantial portion" is at least 20% wt., at least 30% wt., at least 40% wt., or at least 20% wt and less than 50% wt. of the corticosteroid. As used in reference to the amount of dissolved corticosteroid, a "major portion" is at least 50% wt. of the corticosteroid.

Pharmacists working in compounding pharmacies can and do prepare suspension-based formulations comprising corticosteroid. Such pharmacists will now be able to prepare a single use or multi-use liquid compositions by employing a method described herein. Alternatively, a subject (patient) undergoing corticosteroid treatment can convert the suspension-based formulation to a liquid formulation of the invention by employing a method described herein. Instead of preparing the liquid formulation from the suspension at the pharmacy, a kit containing the suspension formulation and SAE-CD can be prepared.

The concentration of SAE-CD in solution can be expressed on a weight to weight or weight to volume basis; however, these two units are interconvertible. When a known weight of cyclodextrin is dissolved in a known weight of water, the % w/w cyclodextrin concentration is determined by dividing the cyclodextrin weight in grams by the total weight (cyclodextrin+water weight) in like units and multiplying by 100. When a known weight of cyclodextrin is dissolved to a known total volume, the % w/v cyclodextrin concentration is determined by dividing the cyclodextrin weight in grams by the total volume in milliliters and multiplying by 100. The correlation between the two cyclodextrin concentration percentages was experimentally determined by preparing various % w/w cyclodextrin solutions and measuring the density of each with a pycnometer at 25° C. The density (g/mL) of each % w/w CAPTISOL solution is presented in the table below.

| CAPTISOL % w/w | Density (g/mL) | Viscosity (Cp, 25 C.) |
|---|---|---|
| 59.4 | 1.320 | 527.0 |
| 49.4 | 1.259 | 51.9 |
| 39.7 | 1.202 | 17.0 |
| 29.8 | 1.149 | 5.91 |
| 19.7 | 1.095 | 2.78 |
| 8.5 | 1.041 | 1.75 |
| 0.0 | 1.002 | 1 | slope = 0.0053
y-intercept = 0.995
correlation = 0.9989

The resulting linear relationship readily enables the conversion of CAPTISOL concentrations expressed in % w/w to that of % w/v by the following equation:

% w/v=((% w/w*slope)+y-intercept)*% w/w where the slope and intercept values are determined from a linear regression of the density data in the table. For example, by using the above equation, a 40% w/w CAPTISOL solution would be equivalent to a ~48.3% w/v CAPTISOL solution.

In some embodiments, the composition comprises less than or about 25% wt./wt. of SAE-CD for administration by nebulizer, or less than or about 50% wt./wt. of SAE-CD for administration with metered administration devices.

The nose comprises the nostrils, or nares, which admit and expel air for respiration, nose hairs (vibrissae), which catch airborne particulate contaminants and prevent them from reaching the lungs, olfactory mucosa, and the nasal cavity. Within the nasal cavity, target sites for delivery or active agent include the middle meatus, superior turbinate and posterior regions. The paranasal sinuses (paranasal sinus cavities) are connected to the nasal cavity by small orifices call ostia. The paranasal sinuses include the: (1) the maxillary sinuses, also called the antra, which are located under the eyes, in the upper jawbone; (2) the frontal sinuses, which lie above the eyes, in the bone of the forehead; (3) the ethmoid sinuses, positioned between the nose and the eyes, backwards into the skull; and (4) the sphenoid sinuses, which are more or less in the centre of the skull base.

The nasal cavity and the paranasal sinuses are lined with mucosa. These mucosae can be often affected by conditions such as allergies and infections. Nasal administration of the solutions of the methods, systems, devices, and compositions of the invention provide improved means to deliver therapeutically useful active agents to these mucosae and to treat diseases, disorders and/or symptoms thereof.

Anatomically, the eyes and nose are connected via the nasolacrimal duct and indirectly through local neurosensory (e.g. the trigeminal nerve) mechanisms. Allergens and allergic treatments from the ocular surface drain through the nasolcarimal duct into the inferior turbinate of the nose. Through the nasolacrimal duct, ocular treatments can affect nasal symptoms in patients suffering from allergic rhinitis. Fluids can travel from the eyes to the nose within five minutes, and topical treatments can positively affect nasal symptoms induced by a conjunctival allergen challenge (Spangler et al., *Clin Ther* 25(8): 2245-2267 (2003)). Thus, topical ocular treatments can be beneficial in treating both ocular and nasal symptoms of allergic rhinitis.

The paranasal sinuses are, under normal circumstances, poorly ventilated during breathing. Most of the air exchange of the sinuses occurs through the diffusion of air through the ostia, whereas little or no convective flow is observed. If an aerosol, such as a therapeutic aerosol generated by a conventional nebuliser, is inspired through the nose, the aerosol will flow through the nasal cavity. Since there is virtually no active flow into the paranasal sinuses, very little or almost none of the aerosol is deposited therein. However, the droplet size of the aerosol or mist administered nasally to a subject can be varied to provide preferential deposition in the nasal cavity versus paranasal sinus cavities or vice versa. The relative percentage of paranasal sinus cavity deposition can be increased by employing a nasal administration device capable of generating appropriately sized droplets and/or capable of generating a variable pressure aerosolized plume.

The mass median diameter (MMD) which will lead to the relatively largest aerosol deposition can depend on individual factors, in particular on the geometry of the paranasal sinuses including the ostia through which the aerosol reaches the sinuses. For example, the volume of the sinuses and the diameter of the ostia differ substantially between individuals. A larger diameter of the ostia is believed to favor the entrance of larger aerosol droplets into the sinuses, even though the diameters of the ostia and of the droplets are of completely different magnitudes. If the individual sinunasal anatomy, or a parameter derived therefrom, of a person to be treated with an aerosol is at least partially known, it is possible to select a particular MMD for optimised sinunasal or sinus delivery.

The target site for delivery of the formulation will depend upon the MMD of droplets (aerosol, mist, vapor, plume, or spray) administered to a subject. Generally, the smaller the droplet size the greater the percentage of paranasal sinus cavity, turbinate, and/or posterior nasal cavity deposition, and vice versa. In order to maximize nasal delivery (nose, sinus cavity, nasopharyngeal cavity, nasal vestibule, anterior region, superior turbinate, middle turbinate, inferior turbinate, and/or olfactory region), the formulation can be administered nasally and the MMAD can be at least about 3.5 microns, at least about 5 microns, at least about 10 microns, at least about 20 microns, at least about 35 microns, at least about 50 microns, at least about 100 microns, or at least about 150 microns.

In some embodiments, the MMD of the droplets in the aerosol (liquid phase dispersed within a continuous gas phase) can range from about 2 µm to about 6 µm, as measured by laser diffraction. In some embodiments, the most useful MMD for depositing the aerosol in the nasal cavity and in the paranasal sinuses can range from 3 µm to 3.5 µm. In some embodiments, the aerosol of the invention can have a MMD of about 2.5 µm to about 4.5 µm, about 3 µm to about 4 µm, or about 2.8 µm to about 3.5 µm. In further embodiments, the MMD is approximately 2.8 µm±0.2 µm, 3.0 µm±0.2 µm, 3.2 µm±0.2 µm, 3.4 µm±0.2 µm, 3.6 µm±0.2 µm, 3.8 µm±0.2 µm, or 4.0 µm±0.2 µm. Various appropriate analytical apparatuses to determine the mass median diameter are known and commercially available, such as the Malvern MasterSizer X or Malvern SprayTec. The geometric distribution of the aerosolised liquid particles or droplets can be determined simultaneously with the mass median diameter.

Delivery of active agent to the deep nasal cavity or paranasal sinus cavities can also be promoted by an aerosol generating administration device comprising a droplet dispersion chamber suitable to provide for vortical particle flow of the aerosol prior to administration to a subject, wherein the administration device is capable of producing droplets substantially having a uniform mean diameter from about 5 µm to about 30 µm, about 8 µm to about 25 µm, about 10 µm to about 20 µm, about 10 µm to about 17 µm, about 10 µm to about 15 µm, and about 12 µm to about 17 µm. In some embodiments, the aerosol comprises droplets substantially having a uniform mean diameter of about 2 µm to about 50 µm, about 5 µm to about 50 µm, about 5 µm to about 40 µm, about 5 µm to about 35 µm, about 5 µm to about 30 µm, about 5 µm to about 20 µm, about 5 µm to about 17 µm, about 5 µm to about 15 µm, about 8 µm to about 30 µm, about 8 µm to about 25 µm, about 8 µm to about 20 µm, about 10 µm to about 30 µm, about 10 µm to about 25 µm, about 11 µm to about 40 µm, about 11 µm to about 30 µm, about 11 µm to about 20 µm, about 11 µm to about 15 µm, about 15 µm to about 25 µm, about 15 µm to about 20 µm, or about 17 µm to about 23 µm. The phrase "substantially having a uniform mean diameter," as used herein with respect to the particle diameter ranges, refers to the use of particle collections, wherein at least 50%, at least 60%, at least 70%, at least 80%, at least 90%, at least 95%, or at least 98% have the preferred diameter range. In some embodiments, at least 60%, at least 70%, at least 80%, at least 90% or at least 95% of the nebulized particles are of the particle diameter range. In some embodiments, at least 70%, at least 80%, at least 90% or at least 95% of the nebulized particles are of the particle diameter range. The ViaNase ID™ (Kurve, Bothell, WA) electronic atomizer is particularly suitable for this mode of administration, and it delivers an aqueous liquid composition at a rate of about 0.1 mL/min.

Another method of promoting paranasal sinus cavity delivery of the composition is by: providing the liquid composition; and aerosolizing the liquid composition with an aerosol generator capable of emitting an aerosol whose pressure pulsates with a frequency in the range from about 10 Hz to about 90 Hz, wherein the aerosol generator is adapted to maintain an amplitude of pressure pulsation of the emitted aerosol of at least about 5 mbar. In some embodiments, the liquid composition has a volume of less than or about 5 mL. An aerosol flow which is superimposed with pressure fluctuations, or pressure pulses, creates periodic transient pressure gradients extending from the actively ventilated nasal cavity through the ostia to the paranasal sinuses, which gradients cause a short period of convective flow of air and aerosol into the sinuses until the pressure therein has become equal to the air pressure in the nasal cavity. A portion of the aerosol droplets which thus enter the paranasal sinuses are deposited therein onto the mucosa. The extent to which the aerosol is deposited depends on the droplet size. Droplets that are smaller than the preferred particle size are relatively likely to be expelled from the sinuses during the subsequent pulsation phase in which the aerosol pressure, and thus the pressure in the nasal cavity, is lower than the pressure within the sinuses, and during which a convective flow of air from the paranasal sinuses to the nasal cavity occurs. In order that an effective flow of air and aerosol into the paranasal sinuses is induced, it is important to generate the pulsating aerosol with an appropriate device which is capable of emitting such aerosol, such as the PART SINUS (including PART LC Star, PART LL and PART Sprint) or VibrENT™ (PART) nebulizer families whose compressors are adapted to generate a pulsating aerosol by employing pressure pulses of appropriate frequency and altitude.

Following administration of a dose of active agent to a subject, the relative percentage of the dose delivered to the nasal cavity versus the paranasal sinus cavities can vary such that: 1) a major portion (greater than 50% wt.) of the dose is delivered to the nasal cavity and a minor portion (less than 50% wt.) of the dose is delivered to the paranasal sinus cavities; 2) a major portion (greater than 50% wt.) of the dose is delivered to the paranasal sinus cavities and a minor portion (less than 50% wt.) of the dose is delivered to the nasal cavity; or 3) approximately 50% wt. of the dose is delivered to each the nasal cavity and the paranasal sinus cavities.

The invention can provide at least about 30% wt., at least about 40% wt., at least about 50% wt., at least about 60% wt., at least about 70% wt., at least about 80% wt., at least about 90% wt. or at least about 95% wt. for delivery of active agent into the nasal cavity and/or paranasal sinus cavities based upon the emitted dose.

As drug in solution will be distributed equally in the large and small droplets leaving the nebulizer, the fine particle fraction will contain more corticosteroid resulting in a greater inspirable dose that can reach the paranasal sinus cavities.

The in-vitro spray characteristics of the budesonide containing aqueous preparations of Example 33 were determined. The spray pattern at 3 and 6 cm, droplet size using a Malvern SprayTec, and respirable fraction using a cascade impactor were determined for Solution A and Suspension B. There were no apparent differences between Solution A and Suspension B in terms of axis lengths and ovality ratios at each spray distance. The average droplet size (D50) was 35 µm and 38 µm, respectively. The small droplets (D10) were 17 µm and 17 µm, respectively. The respirable fraction (% <9 µm) averaged less than 1% for both Solution A and Suspension B.

The performance of a solution of the invention in a nebulizer can depend upon the viscosity of the solution in its reservoir, the nebulization solution. The viscosity of an aqueous solution of SBE7-β-CD changes with respect to concentration approximately as indicated in the table above. Viscosity of the composition can have an impact on percentage of nebulization composition emitted from a nebulizer, output rate of nebulized corticosteroid and droplet size distribution.

The amount of residual composition left in the reservoir of the nebulizer may be greater for solutions containing SAE-CD than for a budesonide-containing suspension. Under similar nebulization conditions, some nebulizers more efficiently reduce the volume of nebulization suspension than of nebulization solution in the reservoir of the nebulizer; however, this does not necessarily correspond with the total amount of drug emitted by the nebulizer.

In other words, the output rate of an SAE-CD nebulization solution versus that of a suspension can differ such that the solution has a higher output rate (in terms of drug output) than does the suspension.

An SAE-CD (SBE7-β-CD) concentration of less than or about 25% wt./wt. was identified as the approximate upper acceptable level for a composition adapted for use in a nebulizer, "acceptable" being defined as the upper concentration of SAE-CD that can be used without building up excessive viscosity, which can adversely affect the nebulization time and output rate. An SAE-CD concentration of less than or about 50% wt./wt. was identified as the approximate upper acceptable level for a composition adapted for use in a metered administration device. The practical upper limit for concentration of SAE-CD will vary among the particular type of administration device used. The upper acceptable concentration of SAE-CD in a liquid composition can vary according to the DS of the derivative, the alkyl chain length of the sulfoalkyl functional group, and/or the CD ring size of the SAE-CD.

Viscosity of the liquid composition can impact droplet size and droplet size distribution of the aerosolized composition. For example, the present compositions tend to form larger droplets, in terms of Dv50, at the lower concentrations, and thereby lower viscosity, of SAE-CD in the absence of corticosteroid, e.g. budesonide. A significant portion of the aerosolized mass is of a respirable size range. Moreover, the solutions containing SAE-CD apparently form droplets that are comparable in size to those of the nebulized suspension.

A solution (aqueous liquid composition) made by mixing a suspension of corticosteroid with SAE-CD is suitable for use in a variety of different air driven jet nebulizers.

The SAE-CD containing solutions are suitable for administration with an administration device, e.g. by nebulization, across a range of concentrations. Moreover, the droplet size distribution can be partially controlled by adjusting the concentration of SAE-CD.

Depending upon the nebulizer used, the conditions under which the nebulizer is operated and the concentration of SAE-CD in solution, different maximum output rates can be achieved. Use of SAE-CD in a composition, however, can result in an increased output rate of corticosteroid, e.g. budesonide, regardless of the format of the administration device.

Accordingly, the total nebulization time of the AERONEB GO is one fourth the time to sputter for the Pari LC+ air jet nebulizer. As a result, treatment time would be reduced with the pulsating membrane nebulizer as compared to the air jet nebulizer, and the amount of budesonide emitted from the pulsating membrane nebulizer is 2 to 3 times more than from the air jet nebulizer. It was also determined that the percent of drug exiting the nebulizer (the emitted dose) was 81% of the amount initially loaded into the reservoir (the nominal dose). Hence, less drug would need to be loaded into the pulsating membrane nebulizer to treat the patient in need thereof to provide the same "dose to subject" as provided by an air jet nebulizer.

A comparison of the AUC data can be made by consideration of the dose delivered to each subject ("dose to subject") or dose delivered to the nasal or paranasal cavities of each subject ("dose to nose") or dose delivered to the ocular surface of each subject ("dose to eye") or dose emitted by the administration device ("emitted dose") or dose available for administration or delivery ("nominal dose" or "nominal available dose" or "loaded dose").

Practice of the method or system of the invention with the composition of the invention can result in differences in the amount of corticosteroid absorbed systemically when compared to administration of a suspension-based corticosteroid composition, e.g. RHINOCORT AQUA. In some embodiments, the composition, method and system of the invention provide a higher AUC ((pg*h/mL)/μg of corticosteroid administered), lower AUC, or approximately the same AUC as does a suspension-based corticosteroid composition administered under substantially the same conditions. Similarly, in some embodiments, the composition, method and system of the invention provide a higher Cmax (pg of corticosteroid/mL of plasma), lower Cmax, or approximately the same Cmax as does a suspension-based corticosteroid composition administered under substantially the same conditions.

The solutions of the invention can provide an enhanced pharmacokinetic profile over suspension-based formulations following their nasal or ophthalmic administration.

The corticosteroids that are useful in the present invention generally include any steroid produced by the adrenocortex, including glucocorticoids and mineralocorticoids, and synthetic analogs and derivatives of naturally occurring corticosteroids having anti-inflammatory activity. Suitable synthetic analogs include prodrugs and ester derivatives. Examples of corticosteroids that can be used in the compositions of the invention include aldosterone, beclomethasone, betamethasone, budesonide, ciclesonide (Altana Pharma AG), cloprednol, cortisone, cortivazol, deoxycortone, desonide, desoximetasone, dexamethasone, difluorocortolone, fluclorolone, flumethasone, flunisolide, fluocinolone, fluocinolone acetonide, fluocinonide, fluocortin butyl, fluorocortisone, fluorocortolone, fluorometholone, flurandrenolone, fluticasone, fluticasone valerate, halcinonide, hydrocortisone, icomethasone, loteprednol etabonate, meprednisone, methylprednisolone, mometasone, paramethasone, prednisolone, prednisone, rofleponide, RPR 106541, tixocortol, triamcinolone, and their respective pharmaceutically acceptable derivatives, such as beclomethasone dipropionate (anhydrous or monohydrate), beclomethasone monopropionate, dexamethasone 21-isonicotinate, fluticasone propionate, icomethasone enbutate, tixocortol 21-pivalate, and triamcinolone acetonide. In some embodiments, the corticosteroid is beclomethasone dipropionate, budesonide, flunisolide, fluticasone propionate, mometasone furoate, triamcinolone acetonide, or a combination thereof. Other corticosteroids not yet commercialized, but that are commercialized subsequent to the filing of this application, are considered useful in the present invention unless it is otherwise established experimentally that they are not suitable.

Corticosteroids can be provided as the UDB (unit dose budesonide) formulation (Sheffield Pharmaceuticals, Inc.), VANCENASE AQ (beclomethasone dipropionate aqueous suspension; Schering Corporation, Kenilworth, NJ), ATOMASE (beclomethasone dipropionate aqueous suspension; Douglas Pharmaceuticals Ltd., Aukland, Australia), BECONASE (beclomethasone dipropionate aqueous suspension; Glaxo Wellcome, NASACORT AQ (triamcinolone acetonide nasal spray, Aventis Pharmaceuticals), TRI-NASAL (triamcinolone acetonide aqueous suspension; Muro Pharmacaceuticals Inc.) and AEROBID-M, (flunisolide inhalation aerosol, Forest Pharmaceuticals), NASALIDE and NASAREL (flunisolide nasal spray, Ivax Corporation), FLONASE (fluticasone propionate, GlaxoSmithKline), VERAMYST (fluticasone furoate, GSK) and NASONEX (mometasone furoate, Schering-Plough Corporation). Corticosteroids commercially available for ophthalmic administration include perdnisolone sodium phosphate ophthalmic solution (INFLAMASE) and prednisolone acetate opthalmic solution (PRED FORTE). SAE-CD can be added to all such commercial formulations to provide a composition of the invention.

Corticosteroids can be grouped according to their relative lipophilicity as described by Barnes et al. (*Am. J. Respir. Care Med*. (1998), 157, p. S1-S53), Miller-Larsson et al. (*Am J. Respir. Crit. Care Med*. (2003), 167, A773), D. E. Mager et al. (*J. Pharm. Sci*. (November 2002), 91(11), 2441-2451) or S. Edsbäcker (Uptake, retention, and biotransformation of corticosteroids in the lung and airways. In: Schleimer R P, O'Byrne P M O, Szefler S J, Brattsand R, editor(s). Inhaled steroids in asthma: optimizing effects in the airways. New York: Marcel Dekker, 2002: 213-246). Generally, the less lipophilic a corticosteroid is, the lower the amount of SAE-CD required to dissolve it in an aqueous medium and vice versa.

Some embodiments of the invention comprise a corticosteroid having a lipophilicity approximating or exceeding that of flunisolide. Some embodiments of the invention comprise a corticosteroid having a lipophilicity less than that of flunisolide. Some embodiments of the invention exclude a corticosteroid having a lipophilicity less than flunisolide, i.e., embodiments excluding hydrocortisone, prednisolone, prednisone, dexamethasone, betamethasone, methylprednisolone, triamcinolone, and fluocortolone.

Corticosteroids that are less lipophilic than flunisolide generally require a SAE-CD to corticosteroid molar ratio of less than 10:1 to dissolve the corticosteroid in an aqueous medium. Exemplary corticosteroids of this group include hydrocortisone, prednisolone, prednisone, dexamethasone, betamethasone, methylprednisolone, triamcinolone, and fluocortolone. Some embodiments of the invention exclude corticosteroids that are less lipophilic than flunisolide. Other embodiments of the invention include corticosteroids that are more lipophilic than flunisolide.

Corticosteroids that are at least as lipophilic as or more lipophilic than flunisolide generally require a SAE-CD to corticosteroid molar ratio of more than 10:1 to dissolve the corticosteroid in an aqueous medium. In some embodiments, the corticosteroid used in the invention is at least as lipophilic as or more lipophilic than flunisolide. Exemplary corticosteroids of this group include beclomethasone, beclomethasone dipropionate, beclomethasone monopropionate, budesonide, ciclesonide, desisobutyryl-ciclesonide, flunisolide, fluticasone, fluticasone propionate, mometasone, mometasone furoate, and triamcinolone acetonide.

Budesonide ((R,S)-11β, 16α, 17, 21-tetrahydroxypregna-1, 4-diene-3, 20-dione cyclic 16, 17-acetal with butyraldehyde; $C_{25}H_{34}O_6$; Mw: 430.5) is an anti-inflammatory corticosteroid that exhibits potent glucocorticoid activity.

Commercial formulations of budesonide are sold by AstraZeneca LP (Wilmington, DE) under the trademarks ENTOCORT EC, PULMICORT RESPULES, RHINOCORT AQUA, RHINOCORT NASAL INHALER and PULMICORT TURBOHALER, and under its generic name. PULMICORT RESPULES suspension, which is a sterile aqueous suspension of micronized budesonide, is administered by inhalation using a nebulizer. The general formulation for a unit dose of the PULMICORT RESPULES is set forth in U.S. Pat. No. 6,598,603, and it is an aqueous suspension in which budesonide is suspended in an aqueous medium comprising about 0.05 to 1.0 mg of budesonide, 0.05 to 0.15 mg of NaEDTA, 8.0 to 9.0 mg of NaCl, 0.15 to 0.25 mg of polysorbate, 0.25 to 0.30 mg of anhydrous citric acid, and 0.45 to 0.55 mg of sodium citrate per one mL of water. RHINOCORT NASAL INHALER is a metered-dose pressurized aerosol unit containing a suspension of micronized budesonide in a mixture of propellants. RHINOCORT® AQUA™ (U.S. Pat. Nos. 6,986,904, 6,565,832, and 5,976,573; the entire disclosures of which are hereby incorporated by reference) is an unscented metered-dose manual-pump spray formulation (for nasal administration) containing a suspension of micronized budesonide in an aqueous medium. A unit dose of the formulation consists of: (a) about 32 μg budesonide; and (b) a mixture consisting of (1) microcrystalline cellulose and sodium carboxymethyl cellulose, the mixture present at about 0.5 to 2.5% by weight of the therapeutic composition, (2) dextrose, (3) Polysorbate 80 present at about 0.005 to 0.5% by weight of the therapeutic composition, (4) disodium edetate present at about 0.005 to 0.1% by weight of the therapeutic composition, (5) and potassium sorbate present at about 0.05 to 0.2% by weight of the therapeutic composition, wherein the budesonide is in the form of finely divided particles, at least 90% of which have a mass equivalent sphere diameter of less than 20 μm, suspended in an aqueous medium. Budesonide is commercially available as a mixture of two isomers (22R and 22S) and can also be prepared as a single isomer 22R-budesonide.

The invention also provides compositions comprising a water soluble γ-CD derivative, a corticosteroid (either esterified or unesterified) and an aqueous liquid medium. In certain embodiments, the invention also provides compositions comprising a water soluble β-CD derivative, and an aqueous liquid carrier.

The suitability of a corticosteroid for use in the liquid composition/formulation can be determined by performing a phase solubility binding study as detailed in Example 23. Phase solubility binding data is used to determine the saturated solubility of a corticosteroid in the presence of varying amounts of SAE-CD in an aqueous liquid carrier. The phase solubility binding curve depicted in FIG. 3 demonstrates the saturated solubility of budesonide in an aqueous liquid carrier comprising γ-CD, HP-β-CD or SBE7-β-CD. A phase solubility curve in the graph defines the boundary for the saturated solubility the corticosteroid in solutions containing various different concentrations of cyclodextrin. A molar phase solubility curve can be used to determine the molar ratio of SAE-CD to corticosteroid or of corticosteroid to SAE-CD at various concentrations of corticosteroid. The area below the phase solubility curve, e.g. of FIG. 3, denotes the region where the corticosteroid is solubilized in an aqueous liquid medium to provide a substantially clear aqueous solution. In this region, the SAE-CD is present in molar excess of the corticosteroid and in an amount sufficient to solubilize the corticosteroid present in the liquid carrier. The boundary defined by the phase solubility curve will vary according to the corticosteroid and SAE-CD within a composition or formulation of the invention. The data detailed in Example 23 provides a summary of the minimum molar ratio of SAE-CD to corticosteroid required to achieve the saturated solubility of the corticosteroid in the composition or formulation of the invention under the conditions studied.

Depending upon the corticosteroid used in the formulation, the molar ratio of corticosteroid to SAE-CD (or of SAE-CD to corticosteroid) can vary in order to obtain a solution suitable for administration. Some embodiments of the invention include those wherein the corticosteroid to SAE-CD molar ratio is 0.5 to 0.0001 (1:2 to 1:10,000), 1:1 to 1:100, 1:1 to 1:10,000, 0.1 (1:10) to 0.03 (1:33.33), about 0.072 (1:13.89 or about 1:14) to 0.0001 (1:10,000), or 0.063 (1:15.873 or about 1:16) to 0.003 (1:333.33 or about 1:333). In some embodiments, the corticosteroid is budesonide and the molar ratio of SAE-CD to budesonide is greater than 10:1, or at least 14:1.

In some embodiments, the minimum molar ratio of SAE-CD to corticosteroid is about 1:1 or greater, about 1.5:1 or greater, about 1.6:1 or greater, about 1.8:1 or greater, about 2:1 or greater, about 2.2:1 or greater, about 3:1 or greater, about 3.4:1 or greater, about 3.8:1 or greater, about 4:1 or greater, about 5:1 or greater, about 5.7:1 or greater, about 6:1 or greater, about 7:1 or greater, about 8:1 or greater, about 8.8:1 or greater, about 9:1 or greater, greater than about 10:1, about 12:1 or greater, greater than about 11:1, greater than about 13:1, greater than about 14:1, about 16:1 or greater, about 20:1 or greater, about 25:1 or greater, about 30:1 or greater, about 40:1 or greater. In some embodiments, the molar ratio of SAE-CD to corticosteroid ranges about from >10:1 to about 1000:1, about from >10:1 to about 100:1, about from >10:1 to about 50:1, about from >10:1 to about 30:1, about from >10:1 to about 500:1. In some embodiments, the maximum molar ratio of SAE-CD to corticosteroid can be about 4,000:1 or less, about 3,000:1 or less, about 2,000:1 or less, about 1,500:1 or less, about 1,400:1 or less, about 1,200:1 or less, about 1,000:1 or less, about 900:1 or less, about 800:1 or less, about 600:1 or less, about 500:1 or less, about 400:1 or less, about 360:1 or less, about 300:1 or less, about 275:1 or less, about 250:1 or less, about 200:1 or less, about 150:1 or less, about 100:1 or less, about 80:1 or less, or about 60:1 or less. Combinations of the upper and lower molar ratios are useful.

The solubility of a corticosteroid in a composition is affected by its intrinsic solubility in the aqueous medium and its binding constant with SAE-CD. The higher the intrinsic solubility of the corticosteroid, the lesser the amount of SAE-CD required to solubilize a dose of it in the composition. The maximum concentration of corticosteroid in an aqueous solution containing SAE-CD is known as its concentration at saturated solubility. The saturated solubility of a corticosteroid in the presence of a fixed amount of SAE-CD will vary according to the identity of the corticosteroid and the SAE-CD. The higher the concentration at saturated solubility, the more soluble the corticosteroid is in the presence of SAE-CD. Example 45 summarizes saturated solubility data for some corticosteroids in the absence (intrinsic solubility of corticosteroid in the aqueous test medium) and in the presence of two different SAE-CD's as determined herein.

The binding of a corticosteroid to the SAE-CD can be characterized by its equilibrium binding constant. The higher the binding constant, the more tightly the corticosteroid is bound to the SAE-CD. Example 46 summarizes the equilibrium binding constants (K) for some corticosteroids in the presence of CAPTISOL or SBE6.1-γ-CD (0.04 M).

The equilibrium binding constant data can be used in combination with the phase solubility data (saturated solubility data) to prepare compositions according to the invention having a target concentration of corticosteroid and SAE-CD. Accordingly, some embodiments of the invention comprise a corticosteroid having an intrinsic solubility in water that approximates or is less than the intrinsic solubility of flunisolide (less than about $11 \times 10^{-5}$ M or less than about $11.3 \times 10^{-5}$ M) in water as determined herein. In some embodiments, the invention comprises a corticosteroid having an intrinsic solubility in water that is greater than that of flunisolide.

Even though a composition or formulation of the invention can comprise the corticosteroid present in an aqueous medium at a concentration up to its saturated solubility in the presence of a particular concentration of SAE-CD, some embodiments of the invention include those wherein the corticosteroid is present at a concentration that is less than its saturated solubility in the presence of that concentration of SAE-CD. The corticosteroid can be present at a concentration that is 95% or less, 90% or less, 85% or less, 80% or less, or 50% or less of its saturated solubility as determined in the presence of SAE-CD. It is generally easier to prepare solutions that comprise the corticosteroid at a concentration that is less than its saturated solubility in the presence of SAE-CD.

Therefore, the molar ratio of SAE-CD to corticosteroid in a formulation or composition of the invention can exceed the molar ratio obtained at the saturated solubility of the corticosteroid in the presence of SAE-CD, such as defined by the phase solubility binding curve for the corticosteroid. In such a case, the molar ratio of SAE-CD to corticosteroid in the composition or formulation can be at least about 1%, at least about 2%, at least about 5%, at least about 7.5%, at least about 10%, at least about 15%, at least about 20%, at least about 25%, at least about 50%, at least about 75%, at least about 100%, or at least about 200% greater than the molar ratio at the saturated solubility of the corticosteroid in the presence of SAE-CD. For example, if the molar ratio at the saturated solubility is about 14:1, then the molar ratio in the composition or formulation can be at least about 14.1:1 (for at least 1% higher), at least about 14.3:1 (for at least 2% higher), at least about 14.7:1 (for at least 5% higher), at least about 15.4:1 (for at least 10% higher), at least about 16.1:1 (for at least 15% higher), at least about 16.8:1 (for at least 20% higher), at least about 17.5:1 (for at least 25% higher), at least about 21:1 (for at least 50% higher), at least about 24.5:1 (for at least 75% higher), at least about 28:1 (for at least 100% higher), or at least about 42:1 (for at least 100% higher).

Changes in the molar ratio of SAE-CD to corticosteroid can also have an impact upon the dissolution rate of corticosteroid in an aqueous medium. Generally, increasing the molar ratio results in an increase in the rate of dissolution of the corticosteroid. The corticosteroid compound can be present in the final, diluted corticosteroid nebulizable composition in an amount from about 1 μg/mL to about 10 mg/mL, about 10 μg/mL to about 1 mg/mL, or about 20 μg/mL to about 500 μg/mL. For example, the drug concentration can be between about 30 and 1000 μg/mL for triamcinolone acetonide, and between about 50 and 2000 μg/mL for budesonide, depending on the volume to be administered. By following the preferred methods of the present invention, relatively high concentrations of the corticosteroid can be achieved in an aqueous-based composition.

Similarly, the corticosteroid compound is present in the final, diluted corticosteroid composition designed for nasal administration in an amount from about 10 µg/mL to 6 mg/mL, 50 µg/mL to about 10 mg/mL, about 100 µg/mL to about 2 mg/mL, or about 300 µg/mL to about 1 mg/mL. For example, the drug concentration can range from about 250 µg/mL and about 1 mg/mL or about 250 µg/mL and about 6 mg/mL for triamcinolone acetonide, and range from about 400 µg/mL to about 1.6 mg/mL, 40 µg/mL to about 6 mg/mL, 40 µg/mL to about 3 mg/Ml, 250 µg/mL to about 6 mg/mL, or about 250 µg/mL to about 3 mg/mL for budesonide, depending on the volume to be administered.

For the treatment of nasal cavity, paranasal sinus cavity, and/or ophthalmic disease, symptoms or disorders, the corticosteroid composition is prepared as described herein. The corticosteroid for such treatment can be, beclomethasone dipropionate, beclomethasone monopropionate, betamethasone, budesonide, ciclesonide, desisobutyryl-ciclesonide, flunisolide, fluticasone, fluticasone propionate, fluticasone furoate, mometasone, mometasone furoate, or triamcinolone acetonide, and can be formulated in the concentrations set forth herein.

The corticosteroid or any other therapeutic (active) agent herein can be present in its neutral, ionic, salt, basic, acidic, natural, synthetic, diastereomeric, isomeric, enantiomerically pure, enantiomerically enriched, racemic, solvate, anhydrous, hydrate, hemi-hydrate, sesqui-hydrate, chelate, derivative, analog, esterified, non-esterfied, polymorph, co-crystal, other common form, or a combination thereof. When used in reference to a therapeutic agent, "combination thereof" is taken to mean a combination of any two or more of the forms of the therapeutic agent defined herein. Accordingly, whenever a therapeutic agent is named herein, all such forms available are included. For example, all known forms of budesonide are considered within the scope of the invention.

As used herein, a dose includes a unit dose, a nominal dose, emitted dose, nominal available dose, dose to subject, dose to nose, dose to eye, or other such term of art. Unless otherwise specified, the term a "unit dose" is a single dose, such as a single spray from a metered spray device. An administration of an effective amount, effective dose, or therapeutically effective amount to a subject can comprise one or more unit doses. In certain embodiments, the effective dose can be a single unit dose administered to one nostril or one eye. In certain embodiments, the therapeutically effective amount can be two unit doses administered to one nostril or one eye. In certain embodiments, the effective dose can be two unit doses, with one unit dose administered to each eye or each nostril. In some embodiments, the therapeutically effective amount can be more than two unit doses, with more than one dose administered to a nostril(s) or eye(s). The term "effective amount" or "effective dose" or "therapeutically effective amount" is the amount or quantity of active agent that is sufficient to elicit the required or desired therapeutic effect, or the amount that is sufficient to elicit an appreciable biological response when administered to a subject when given at one event or period of administration. A single period of administration can comprise administration of 1, 2, 3, 4, 5, 6, 7, 8, or more unit doses. For administration with a nebulizer, or any other device that continuously generates an aerosol over a period of time, the "period of administration" is that period of time required to deliver a therapeutically effective amount of an active agent to one or both nostrils of a subject. For administration with a nebulizer, or any other device that continuously generates an aerosol over a period of time, the unit dose is an amount contained in the reservoir of the device that is delivered in one period of administration, i.e., for a nebulizer, the unit dose is the therapeutically effective dose delivered in one period of administration. A nebulizer can contain a single unit dose that is administered over a single period of administration. Alternatively, a nebulizer can contain multiple unit doses that are administered in multiple periods of administration, for example, 1 to 8 unit doses administered in 1 to 8 periods of administration. A nebulizer can also contain multiple reservoirs containing single or multiple unit doses. For administration with a metered administration device, i.e., a device that provides a fixed volume or amount of composition upon actuation, e.g., pump nasal spray, squeeze bottle, atomizer, dropper, and other similar devices, the event of administration, for delivery of an effective dose, is a predetermined number of actuations of the device which releases a corresponding predetermined number of unit doses, e.g., 1 to 8 actuations of the administration device releases 1 to 8 unit doses in one or both nostrils of a subject. The unit dose of active agent delivered is assumed to be the amount of active agent emitted from the administration device, i.e., the emitted dose.

The term "nominal dose" refers to an amount of active agent placed in the reservoir of a nebulizer, wherein the volume of liquid in the reservoir is determined according the size of the reservoir. The term "nominal available dose" refers to the amount of active agent that is determined could be or should have been available to a subject when administered a formulation of the invention by nebulization but formulation is/was not administered in its entirety. The term "emitted dose" refers to the amount of active agent emitted from a nebulizer. The term "dose to subject" refers to the amount of active agent delivered to and retained by a subject following administration of a formulation of the invention by nebulization. The term "dose to nose" refers to the amount of active agent delivered to and retained by the nose (nasal cavity and/or paranasal sinus cavities) of a subject following administration of a formulation of the invention by nebulization.

The daily dose of the corticosteroid is generally about 0.05 mg to 10 mg, depending on the drug and the disease, in accordance with the 2006 *Physician's Desk Reference* (*PDR*). However, in view of the improved bioavailability of a corticosteroid when administered as a solution of the invention, the dose required to achieve a desired clinical endpoint, clinical benefit or therapeutic benefit can be lower than the corresponding dose indicated in the PDR.

The following table provides exemplary dosing regimens for various corticosteroids as included in the commercially available branded nasal administration products in particular dosage strengths. The composition of the invention can be dosed according to these same dosing regimens or other dosing regimens herein.

| Generic Name/ Brand Name | Dosing Regimen | Drug Amount per unit dose (Total Dose Range per day) | Total Weight/ Volume administered |
| --- | --- | --- | --- |
| Beclomethasone Dipropionate Beconase ® AQ (GSK) | 1-2 sprays in each nostril twice daily | 42 mcg (168-336 mcg/day) | 100 mg |
| Ciclesonide Omnaris ® (Sepracor) | 2 sprays in each nostril once daily | 50 mcg (200 mcg/day) | 70 µL |
| Fluticasone Propionate Flonase ® (GSK) | Starting: 2 sprays in each nostril once daily or 1 spray twice daily Maintenance: 1 spray in each nostril once daily | 50 mcg Starting: (200 mcg/day) Maintenance: (100 mcg/day) | 100 mg |
| Fluticasone Furoate Veramyst ® (GSK) | Starting: 2 sprays in each nostril once daily Maintenance: 1 spray in each nostril once daily | 27.5 mcg Starting: (110 mcg/day) Maintenance: (55 mcg/day) | 50 µL |
| Budesonide Rhinocort ® Aqua (AZ) | 1-2 sprays in each nostril once or twice daily | 32 mcg (64 mcg in Canada) (64-320 mcg/day) | 51 mg |
| Triamcinolone Acetonide Nasacort ® AQ (Sanofi-Aventis) | 2 sprays in each nostril once daily | 55 mcg (220 mcg/day) | 100 mg |
| Mometasone Furoate Nasonex ® (Schering-Plough) | 2 sprays in each nostril once daily | 50 mcg (200 mcg/day) | 100 mg |
| Flunisolide Nasarel ® (Ivax) | 2 sprays in each nostril twice daily Titrate: 2 sprays per nostril three times daily | 29 mcg-Nasarel (232-464 mcg/day) | 100 mg |
| Dexamethasone Dexacort ® Turbinaire (USB) | | 84 mcg (inhalation vapor) | |
| Betamethasone + Neomycin sulphate Betnesol-N ® Nasal Drops (GSK) | 2-3 drops instilled in each nostril 2-3 times daily | Strength: 1 mg/mL (1.04 mg-3.6 mg/day) | 0.13-0.20 mL |
| Fluticasone Propionate Flixonase ® Nasule Drops (Allen & Hanbury/GSK) | 1 nasule contents instilled in each nostril 1-2 times daily | 400 mcg/Nasule (400-800 mcg/day) | 400 µL |
| Dexamethasone + tramazoline HCl (Dexa-Rhinapray ® Duo | 1 spray per nostril up to 6 times daily; not for use for more than 14 consecutive days | Dexamethasone: 20 mcg; (40-240 mcg/day)_Tramazoline: 120 mcg (240-1440 mcg/day) | |

| Generic Name | Brand Name | Drug Strength | Dosing Regimen per Affected Eye | Total Drug Delivered Per Day* |
| --- | --- | --- | --- | --- |
| Dexamethasone (susp) | Maxidex ® (Alcon) | 0.1% w/v | 1-2 drops every 4-6 hours | 0.16-0.48 mg* |
| Dexamethasone Sodium phosphate (soln) | Decadron ® (Merck) | 0.1% w/v | 1-2 drops every hour while awake & every 12 hours at night | 0.8-1.6 mg* Also assumes 20 drops/day |

-continued

| Generic Name | Brand Name | Drug Strength | Dosing Regimen per Affected Eye | Total Drug Delivered Per Day* |
|---|---|---|---|---|
| Fluorometholone | Fluor-Op ® (Novartis) | 0.1%, 0.25% w/v | 1 drop 2-4 times a day | 0.06-0.24 mg |
| Loteprednol etabonate | Alrex ® (Bausch & Lomb) | 0.2% w/v | 1 drop 4 times a day | 0.32 mg* |
| Prednisolone Acetate (susp) | Pred-Forte ® (Allergan) | 0.12%, 0.125, 1% w/v | 1-2 drops 2 to 4 times a day | 1.2-9.4 mg (for the 1% susp) |
| Prednisolone Sodium Phosphate (soln) | Inflamase Forte ® (Novartis) | 0.125%, 0.1% w/v | 1-2 drops every hour while awake & every 12 hours at night | 0.8-2 mg* Also assumes 20 drops/day |

The following table provides exemplary dosing regimens for various corticosteroids as included in the commercially available branded ocular administration products in particular dosage strengths. The composition of the invention can be dosed according to these same dosing regimens or other dosing regimens herein.

*A typical volume of an eye drop has been found to range from 25 to 50 mcL. So if the volume is not specified in the product label, it was assumed for the purposes of this chart that the volume is 40 mcL as indicated by a asterisk.

A dose of corticosteroid, such as budesonide, can also be administered once daily, once every two days, seven days per week, once every week, once every month, for an extended period of time, such as several days, weeks, or even longer, or even less frequently. A dose of budesonide, or corticosteroid, can be administered twice, thrice or more times per day or on an as-needed basis. Administration can be during the daytime and/or nighttime. In some embodiments, such as set forth in U.S. Pat. Nos. 6,598,603 and 6,899,099, a dose comprises 0.05 to 2.0 mg or 0.25 to 1.0 mg of budesonide.

In some embodiments, a dose comprises about 1 µg to about 20 mg, about 1 µg to about 10 mg, about 0.01 mg to about 10 mg, about 0.025 mg to about 10 mg, about 0.05 mg to about 5 mg, about 0.1 mg to about 5 mg, about 0.125 mg to about 5 mg, about 0.25 mg to about 5 mg, about 0.5 mg to about 5 mg, about 0.05 mg to about 2 mg, about 0.1 mg to about 2 mg, about 0.125 mg to about 2 mg, about 0.25 mg to about 2 mg, about 0.5 mg to about 2 mg, about 10 µg to about 2.5 mg, about 5 µg to about 500 µg, about 5 µg to about 250 µg, about 5 µg to about 130 µg, about 45 µg to about 1000 µg, about 1 µg, about 10 µg, about 16 µg, about 25 µg, about 27.5 µg, about 29 µg, about 32 µg, at least about 25 µg, about 40 µg, about 42 µg, about 45 µg, about 48 µg, about 50 µg, about 55 µg, about 64 µg, about 84 µg, about 96 µg, about 100 µg, about 125 µg, about 128 µg, about 200 µg, about 250 µg, about 400 µg, about 800 µg, about 25 µg to about 66 µg, about 48 µg to about 81 µg, about 73 µg to about 125 µg, about 95 µg, about 35 µg to about 95 µg, about 25 µg to about 125 µg, about 60 µg to about 170 µg, about 110 µg, about 170 µg, about 45 µg to about 220 µg, about 45 µg to about 85 µg, about 48 µg to about 82 µg, about 85 µg to about 160 µg, about 140 µg to about 220 µg, about 120 µg to about 325 µg, about 205 µg to about 320 µg, about 325 µg, about 90 µg to about 400 µg, about 95 µg to about 170 µg, about 165 µg to about 275 µg, or about 275 µg to about 400 µg of corticosteroid, such as budesonide, said dose being a unit dose, nominal dose, nominal available dose, emitted dose, delivered dose, dose to subject, dose to eye, or dose to nose.

Some embodiments of the invention also provide a unit dose of a therapeutic corticosteroid solution comprising: about 32 µg to 64 µg of budesonide; SAE-CD; pharmaceutically acceptable aqueous liquid carrier; disodium edetate present at of about 0.005 to about 0.1% by weight of the therapeutic composition unit dose; and potassium sorbate present at of about 0.05 to about 0.2% by weight of the therapeutic composition unit dose, and wherein the corticosteroid solution is suitable for nasal administration to a mammal as a unit dose. subject in need thereof.

Some embodiments of the invention also provide a method of treating, preventing or ameliorating in a subject a corticosteroid-responsive disease or disorder, the method comprising:

metering into the nose of a mammal a the subject a therapeutically effective amount of budesonide that is less than about 320 µg per day, delivered as 8 or more unit doses, wherein each unit dose consists of: about 32 µg of budesonide; SAE-CD; disodium edetate present at of about 0.005 to about 0.1% by weight of the therapeutic composition unit dose; potassium sorbate present at of about 0.05 to about 0.2% by weight of the therapeutic composition unit dose; and a pharmaceutically acceptable aqueous liquid carrier. In some embodiments, the therapeutically effective amount of budesonide is delivered as 7 unit doses, 6 unit doses, 5 unit doses, 4 unit doses, 3 unit doses, 2 unit doses or as one unit dose. In some embodiments, the unit dose comprises 64 µg, 96 µg, 128 µg, 160 µg, 192 µg, 224 µg, 256 µg, 288 µg, or 320 µg of budesonide.

In some embodiments, the corticosteroid solution has a pH of about 3.5 to about 5 or about 4.2 to about 4.6.

The corticosteroid can be present at a concentration of about 20 µg to about 30 mg of corticosteroid per mL of solution. As a result, about 10 mg to 500 mg of SAE-CD, or 10 mg to 250 mg of SAE-CD, or 10 mg to 300 mg of SAE-CD per mL or per g of solution in order to dissolve a substantial portion of the corticosteroid.

Due to the wide range of reservoir volumes available for administration devices and of varying dose requirements among the corticosteroids, a formulation of the invention can comprise 1 µg to 20 mg of corticosteroid in 0.01 mL to 100 mL of solution volume. The compositions of the invention can comprises a dose or unit dose of corticosteroid in an approximate solution volume of 10 µl to 100 mL, 10 µl to 5000 µl, 10 µl to 2.5 mL, 20 µl to 5 mL, 10 µl to 500 µl, 10 µl to 200 µl, 10 µl to 400 µl, 50 µl to 50 mL, 50 µl to 10 mL, 50 µl to 5 mL, 0.1 to 10 mL, 0.1 mL to less than 10 mL, 0.1 mL to 7.5 mL, 0.1 mL to 5 mL, 0.1 mL to 3 mL, 0.1 mL to 2 mL, 0.1 mL to 1 mL, 0.05 mL to 7.5 mL, 0.05 mL to 5 mL, 0.05 mL to 3 mL, 0.05 mL to 2 mL, 0.05 mL to 1 mL, 50 µl to 137 µl, 50 µl to 70 µl, 137 µl to 400 µl, 50 µl to 200 µl, 25 µl, 50 µl, 75 µl, 100 µl, 150 µl, 200 µl, 250 µl, 500 µl, 750 µl, 1 mL, 2 mL, 5 mL, or 10 mL.

An administration device can be adapted to emit about 10 to about 500 µl, about 0.2 to about 5 mL, or about 0.5 to about 100 mL of a liquid composition per actuation or per dose. In some embodiments, the administration device comprises a nozzle which comprises a valve. Together, the nozzle and valve can be adapted to release 25 µl to 260 µl, 50 µl to 137 µl, 50 µl to 70 µl, 137 µl to 400 µl, or 51 to 100 mg of a liquid composition of the invention.

The composition of the invention can be packaged for single-use or multi-use. A single use package comprises a single dose of corticosteroid and a multi-use package comprises two or more doses of corticosteroid. The packaging can comprise one or more containers. A container can comprise one or more doses. A single use container comprises a single dose, and a multi-use container comprises two or more doses. Suitable packaging and containers include, by way of example and without limitation, a bottle, vial, ampoule, syringe, blister, capsule, or blow/fill/seal container, or other devices such as those detailed in the examples. The packaging can in a preservative free system such as the Advanced Preservative Free system from Pfeiffer, or the Freepod from Valois, or in a single use spray device such as the Pfeiffer Bidose System or Unitdose System.

The composition can exit the device as a liquid, gel, vapor, fine aerosol, mist, cloud or plume. Depending upon the mode of administration, the composition can be delivered to the nasal cavity, paranasal sinus cavities, or delivered topically to the eye(s) of a subject.

The administration device can employ single use (single dose) or multi-use (multi-dose) packaging. An administration device can be used repeatedly with single use or multi-use packages and/or containers.

The fill volume for the reservoir of a multi-dose, metered dose nasal spray must be sufficient to provide for the number of actuations required to initially prime the spray pump, periodically reprime the pump, and to provide the desired number of doses in a consistent manor. Since the tail-off characteristics (performance when container is nearly empty) can vary as a function of pump design, container geometry and formulation, the fill volume should be sufficient to compensate for all these variables. As such, the reservoir in an administration device can comprise an overfill. As used herein, "overfill" is the amount or percentage of extra composition (either in terms of the volume or weight of the composition or the amount of drug in the composition) added to the composition in the reservoir to compensate for the tail-off characteristics of the device. In some embodiments, the overfill is at least about 1%, at least about 2.5%, at least about 5%, at least about 7.5%, at least about 10%, at least about 15%, at least about 25%, at least about 35%, at least about 45%, at least about 50% of the target volume or weight of composition in a unit dose or dose of the composition.

The time required to administer or deliver a dose of the invention will depend upon its mode of administration, i.e., the administration device used. For administration with an administration device that substantially continuously emits an aerosol over a period of time, e.g. nebulizer, the time required to administer or deliver a dose of corticosteroid is less than 30 min, less than 20 min, less than 10 min, less than 7 min, less than 5 min, less than 3 min, or less than 2 min, or the time is about 0.05 min to 10 min, about 0.1 min to 5 min, about 0.1 min to 3 min, about 0.1 min to 2 min, about 0.1 min to 1.5 min, about 0.5 min to about 1.5 min, or about 1 min. The time will vary according to the dose of active agent in, the concentration of active agent in, and the volume of the composition in the reservoir of an administration device, and it will also depend upon the format of the administration device, aerosolization efficiency, and reservoir volume. In a given administration device, the lower the volume of the liquid composition, the more quickly a corresponding dose of active agent is administered or delivered. The higher the concentration of active agent in the composition, the faster a dose of the active agent can be administered or delivered.

For metered volume (or metered weight) administration devices that generate a plume or aerosol by actuation, e.g., squeeze bottle pump spray, pump spray, atomizer, the time for administration of a dose is merely the time it takes to affect one, two or more actuations of the device in one or both nostrils of a subject or about the time it takes for a subject to take a single breath (about 1 sec to 3 sec, or 1 sec to 5 sec).

The formulation of the invention can be used to deliver two or more different active agents (active ingredients, therapeutic agents, etc.). Particular combinations of active agents can be provided by the present formulation. Some combinations of active agents include: 1) a first drug from a first therapeutic class and a different second drug from the same therapeutic class; 2) a first drug from a first therapeutic class and a different second drug from a different therapeutic class; 3) a first drug having a first type of biological activity and a different second drug having about the same biological activity; 4) a first drug having a first type of biological activity and a different second drug having a different second type of biological activity. Exemplary combinations of active agents are described herein.

A corticosteroid, such as budesonide, can be administered as its isomeric pair or single isomer and in combination with one or more other drugs (active ingredients, therapeutic agents, active agents, etc., the terms being used interchangeably herein unless otherwise specified). Such other drugs include: $B_2$ adrenoreceptor agonist, topical anesthetic, $D_2$ receptor agonist, anticholinergic agent, anti-infective agent, antibiotic, antifungal agent; hormones such as insulin, growth hormone, growth hormone releasing factor, glucagon, somatostatin, chorionic gonadotropin, adrenocorticotropic hormone (ACTH), and interferon; anti-inflammatory agents such as aspirin, aminopyrine, acetaminophen, ibufenac, ibuprofen, indomethacin, colchicine, sulpyrine, mefenamic acid, phenacetin, phenylbutazone, flufenamic acid and probenecid; antibiotics such as penicillin or its derivatives, cephalosporin or its derivatives; erythromycin, tetracycline, furadiomycin, leucomycin; chemotherapeutic agents such as sulfathiazole and nitrofurazone; cardiac agents such as digitalis and digoxin; blood vein dilating agents such as nitroglycerin and papaverine hydrochloride; cough curing agents such as codeine; azulen; phenovalin; pepsin; enzymes such as lysozyme hydrochloride; other systemic agents such as antihypertensives and diuretic; tranquilizers; sex hormone; vitamin; ulcer medication; analgesic; decongestant; expectorant; antitussive; antihistamine agent; bronchodilator; topical anesthetic; sensory agents; oral care agents; miscellaneous respiratory agent; gastrointestinal agent; and combinations thereof.

B2-Adrenoreceptor agonists for use in combination with the compositions provided herein include, but are not limited to, Albuterol (alpha$^1$-(((1,1-dimethylethyl)amino) methyl)-4-hydroxy-1,3-benzenedimethanol); Bambuterol (dimethylcarbamic acid 5-(2-((1,1-dimethylethyl)amino)-1-hydroxyethyl)-1,3-phenylene ester); Bitolterol (4-methylbenzoic acid 4-(2-((1,1-dimethylethyl)amino)-1-hydroxyethyl)-1,2-phenyleneester); Broxaterol (3-bromo-alpha-(((1,1-dimethylethyl)amino)methyl)-5-isoxazolemethanol); Isoproterenol (4-(1-hydroxy-2-((1-methylethyl-)amino) ethyl)-1,2-benzene-diol); Trimetoquinol (1,2,3,4-tetra-hydro-1-((3,4-,5-trimethoxyphenyl)-methyl)-6,7-isoquinolinediol); Clenbuterol (4-amino-3,5-dichloro-alpha-(((1,1-dimethylethyl)amino)methyl)benzenemethanol); Fenoterol (5-(1-hydroxy-2-((2-(4-hydroxyphenyl)-1-methylethyl) amino)ethyl)-1,3-benzenediol); Formoterol (2-hydroxy-5-((1RS)-1-hydroxy-2-(((1RS)-2-(p-methoxyphenyl)-1-methylethyl)amino)ethyl) formanilide); (R,R)-Formoterol; Desformoterol ((R,R) or (S,S)-3-amino-4-hydroxy-alpha-(((2-(4-methoxyphenyl)-1-methyl-ethyl)amino)methy enzenemethanol); Hexoprenaline (4,4'-(1,6-hexane-diyl)-bis (imino(1-hydroxy-2,1-ethanediyl)))bis-1,2-benzenediol); Isoetharine (4-(1-hydroxy-2-((1-methylethyl)amino)butyl)-1,2-benzenediol); Isoprenaline (4-(1-hydroxy-2-((1-methylethyl)amino)ethyl)-1,2-benzenediol); Meta-proterenol (5-(1-hydroxy-2-((1-methylethyl)amino)ethyl)-1,3-benzenediol); Picumeterol (4-amino-3,5-dichloro-alpha-(((6-(2-(2-pyridinyl)ethoxy)hexyl)-amino)methyl) benzenemethanol); Pirbuterol (.alpha.$^6$-(((1,1-dimethylethyl)-amino)methyl)-3-hydroxy-2,6-pyridinemethanol); Procaterol (((R*,S*)-(.+-.)-8-hydroxy-5-(1-hydroxy-2-((1-methylethyl)amino)butyl)-2(1H)-quinolin-one); Reproterol ((7-(3-((2-(3,5-dihydroxyphenyl)-2-hydroxyethyl)amino)-propyl)-3,7-dihydro-1,3-dimethyl-1H-purine-2,6-dione); Rimiterol (4-(hydroxy-2-piperidinylmethyl)-1,2-benzenediol); Salbutamol ((.+-.)-alpha$^1$-(((1,1-dimethylethyl) amino)methyl)-4-hydroxy-1,3-benzenedimethanol); (R)-Salbutamol; Salmeterol ((.+-.)-4-hydroxy-.alpha$^1$-(((6-(4-phenylbutoxy)hexyl)-amino)methyl)-1,3-benzenedimethanol); (R)-Salmeterol; Terbutaline (5-(2-((1,1-dimethylethyl)amino)-1-hydroxyethyl)-1,3-benzenediol); Tulobuterol (2-chloro-.alpha.-(((1,1-dimethylethyl)amino) methyl)benzenemethanol); and TA-2005 (8-hydroxy-5-((1R)-1-hydroxy-2-(N-((1R)-2-(4-methoxyphenyl)-1-methylethyl)amino)ethyl)carbostyril hydrochloride).

Dopamine (D2) receptor agonists include, but are not limited to, Apomorphine ((r)-5,6,6a,7-tetrahydro-6-methyl-4H-dibenzo[de,g]quinoline-10,11-diol); Bromocriptine ((5'.alpha.)-2-bromo-12'-hydroxy-2'-(1-methylethyl)-5'-(2-methylpropyl)ergotaman-3',6', 18-trione); Cabergoline ((8.beta.)-N-(3-(dimethylamino)propyl)-N-((ethylamino)carbony-1)-6-(2-propenyl)ergoline-8-carboxamide); Lisuride (N'-((8-alpha-)-9,10-didehydro-6-methylergolin-8-yl)-N,N-diethylurea); Pergolide ((8-beta-)-8-((methylthio)methyl)-6-propylergoline); Levodopa (3-hydroxy-L-tryrosine); Pramipexole ((s)-4,5,6,7-tetrahydro-N$^6$-prop-yl-2,6-benzothiazolediamine); Quinpirole hydrochloride (trans-(-)-4aR-4,4a,5,6,7,8,8a,9-octahydro-5-propyl-1H-pyrazolo[3,4-g] quinoline hydrochloride); Ropinirole (4-(2-(dipropylamino) ethyl)-1,3-dihydro-2H-indol-2-one); and Talipexole (5,6,7,8-tetrahydro-6-(2-propenyl)-4H-thia-zolo[4,5-d]azepin-2-amine). Other dopamine D$_2$ receptor agonists for use herein are disclosed in International Patent Application Publication No. WO 99/36095, the relevant disclosure of which is hereby incorporated by reference.

Anticholinergic agents for use herein include, but are not limited to, ipratropium bromide, oxitropium bromide, atropine methyl nitrate, atropine sulfate, ipratropium, belladonna extract, scopolamine, scopolamine methobromide, homatropine methobromide, hyoscyamine, isopriopramide, orphenadrine, benzalkonium chloride, tiotropium bromide and glycopyrronium bromide. In certain embodiments, the compositions contain an anticholinergic agent, such as ipratropium bromide or tiotropium bromide, at a concentration of about 5 µg/mL to about 5 mg/mL, or about 50 µg/mL to about 200 µg/mL. In other embodiments, the compositions for use in the methods herein contain an anticholinergic agent, including ipratropium bromide and tiotropium bromide, at a concentration of about 83 µg/mL or about 167 µg/mL.

Other active ingredients for use herein in combination therapy, include, but are not limited to, IL-5 inhibitors such as those disclosed in U.S. Pat. Nos. 5,668,110, 5,683,983, 5,677,280, 6,071,910 and 5,654,276, the relevant disclosures of which are hereby incorporated by reference; antisense modulators of IL-5 such as those disclosed in U.S. Pat. No. 6,136,603, the relevant disclosure of which is hereby incorporated by reference; milrinone (1,6-dihydro-2-methyl-6-oxo-[3,4'-bipyridine]-5-carbonitrile); milrinone lactate; tryptase inhibitors such as those disclosed in U.S. Pat. No. 5,525,623, the relevant disclosure of which is hereby incorporated by reference; tachykinin receptor antagonists such as those disclosed in U.S. Pat. Nos. 5,691,336, 5,877,191, 5,929,094, 5,750,549 and 5,780,467, the relevant disclosures of which are hereby incorporated by reference; leukotriene receptor antagonists such as montelukast sodium (Singular™, R-(E)]-1-[[[1-[3-[2-(7-chloro-2-quinolinyl)ethenyl-]phenyl]-3-[2-(1-hydroxy-1-methylethyl)phenyl]-propyl]thio]methyl] cyclopro-paneacetic acid, monosodium salt), 5-lypoxygenase inhibitors such as zileuton (Zyflo™, Abbott Laboratories, Abbott Park, Ill.), and anti-IgE antibodies such as Xolair™ (recombinant humanized anti-IgE monoclonal antibody (CGP 51901; IGE 025A; rhuMAb-E25), Genentech, Inc., South San Francisco, Calif.), and topical anesthetics such as lidocaine, N-arylamide, aminoalkylbenzoate, prilocaine, etidocaine (U.S. Pat. Nos. 5,510,339, 5,631,267, and 5,837,713, the relevant disclosures of which are hereby incorporated by reference).

Analgesics useful for this invention include any narcotic and non-narcotic analgesics, such as menthol, acetaminophen, NSAIDs, salicylates including aspirin (acetylsalicylic acid), salsalate, sodium salicylate, diflunisal, etc. and mixtures thereof, indomethacin and optically active isomers or racemates or active metabolites of NSAIDs (NSAIDs include propionic acid derivatives, acetic acid derivatives, fenamic acid derivatives, biphenylcarboxylic acid derivatives and oxicams) including fenoprofen, flurbiprofen, ibuprofen, ketoprofen, naproxen, oxaprozin, etodolac, indomethacin, ketorolac, nabumetone, sulindac, tolmetin, meclofenamate, mefenamic acid, piroxicam, bromfenac, carprofen, tiaprofenic acid, cicloprofen, diclofenac, benzydomine, their pharmaceutically acceptable salts and mixtures thereof. All of these, as well as acceptable dosage ranges, are described in the following: U.S. Pat. No. 4,749,720 to Sunshine et al. issued Jun. 7, 1988; U.S. Pat. No. 4,749,721 to Sunshine et al. issued Jun. 7, 1988; U.S. Pat. No. 4,749,722 to Sunshine et al. issued Jun. 7, 1988; U.S. Pat. No. 4,749,723 to Sunshine et al. issued Jun. 7, 1988; U.S. Pat. No. 4,749,711 to Sunshine et al. issued Jun. 7, 1988, U.S. Pat. No. 4,749,697 to Sunshine et al. issued Jun. 7, 1988, U.S. Pat. No. 4,783,465 to Sunshine et al., issued Nov. 8, 1988, U.S. Pat. No. 4,619,934 to Sunshine et al., issued Oct. 28, 1986, U.S. Pat. No. 4,840,962 to Sunshine et al. issued Jun. 20, 1989; U.S. Pat. No. 4,906,625 to Sunshine et al. issued Mar. 6, 1990; U.S. Pat. No. 5,025,019 to Sunshine et al. issued Jun. 18, 1991; U.S. Pat. No. 4,552,899 to Sunshine et al. issued Nov. 12, 1985, Facts and Comparisons, 1998, p. 242-260, all of which are incorporated by reference herein, in their entirety.

The decongestants used in the compositions of the present invention include, for example, pseudoephedrine, phenylpropanolamine, phenylephrine, epinephrine, ephedrine, naphazoline, xylometazoline, oxymetazoline, propylhexedrine, tetrahydrozoline, their pharmaceutically acceptable salts, and mixtures thereof.

The expectorants (also known as mucolytic agents) used in the present invention include, for example, guaifenesin, iodinated glycerol, glyceryl guaiacolate, terpin hydrate, ammonium chloride, N-acetylcysteine and bromhexine, ambroxol, iodide, their pharmaceutically acceptable salts, and mixtures thereof.

The antitussives used in the present invention include, for example, menthol (can also be used as an analgesic), dextromethorphan, chlophedianol, car-betapentane, caramiphen, noscapine, diphenhydramine, codeine, hydrocodone, hydromorphone, fominoben, benzonatate, their pharmaceutically-acceptable salts, and mixtures thereof.

Examples of antihistamine agent used in the present invention include both sedating and non-sedating antihistamines, such as diphenhydramine, clemastine, chlorpheniramine, brompheniramine, dexchlorpheniramine, dexbrompheniramine, triprolidine, doxylamine, tripelennamine, heptadine, carbinoaxime, bromdiphenhydramine, hydroxyzine, pyrilamine, acrivastine, AHR-11325, phenindamine, astemizole, azatadine, azelastine, cetirizine, carebastine, efletirizine, mapinastine, ebastine, fexofenadine, ketotifen, lodoxine, loratadine, descarboethoxyloratadine, levocabastine, mequitazine, oxatomide, setastine, tazifyline, temelastine, terfenadine, tripelennamine, terfenadine carboxylate, phenyltoloxamine, pheniramine, antazoline, bilastine, bepotastine besilate, rupatadine, emedastine, tecastemizole, epinastine, levocetirizine, mizolastine, noberastine, norastemizole, olopatadine, pharmaceutically acceptable salts thereof, pharmaceutically active metabolites thereof, optically active isomers or racemates, and mixtures thereof. All of these antihistamines, as well as their acceptable dosage ranges, are described in: U.S. Patents to Sunshine et al. listed above under analgesics; Facts and Comparisons, 1998, p. 188-195, which is incorporated by reference herein in its entirety.

Antihistamines are commercially widely available. The invention includes embodiments wherein the antihistamine is azelastine, olopatadine, cetirizine, or loratadine. Azelastine (4-[(4-chlorophenyl)methyl]-2-(1-methylazepan-4-yl)-phthalazin-1-one) is an antihistamine and mast cell stabilizer commercially available as ASTELIN (MedPointe Inc., Cranbury, NJ; MEDA Pharmaceuticals, Solna, Sweden) and indicated for the treatment of hay fever, seasonal allergies, and allergic conjunctivitis. Olopatadine is also an antihistamine and is commercially available as PATANASE® (Alcon. Ft. Worth, TX). These drugs are administered as follows. The compositions of the invention comprising these drugs can be administered according to the dosing regimens below or other dosing regimens disclosed herein.

| Generic Name | Brand Name | Drug Strength | Dosing Regimen per Affected Eye | Total Drug Delivered per Day* |
| --- | --- | --- | --- | --- |
| Ketotifen Fumerate | Zaditor ® (Novartis) | 0.025% w/v | 1 drop every 12 hours | 0.02-0.04 mg |
| Olopatadine HCl | Patanol ®; Pataday ™ (Alcon) | 0.1%; 0.2% w/v | 1-2 drops twice daily; 1 drop once daily | 0.08-0.16 mg |
| Azelastine HCl | Optivar ® (Meda) | 0.05% w/v | 1 drop twice daily | 0.03-0.06 mg |
| Epinastine HCl | Elestat ® (Allergan) | 0.05% w/v | 1 drop twice daily | 0.04 mg* |
| Emadastine Difumerate | Emadine ® (Alcon) | 0.05% w/v | 1 drop four times daily | 0.08 mg* |
| Levocabastine HCl | Livostin ® (Novartis) | 0.05% w/v | 1 drop four times daily | 0.06-0.12 mg |

*A typical volume of an eye drop has been found to range from 25 to 50 mcL. So if the volume is not specified in the product label, it was assumed for the purposes of this chart that the volume is 40 mcL as indicated by a asterisk.

In some embodiments, the composition of the invention comprises a dose or unit dose of azelastine present at an amount of about 30 μg to about 275 μg, about 65 mcg to about 1100 mcg, about 130 mcg to about 650 mcg, about 30 μg, about 65 μg, about 137 mcg, about 274 mcg, about 548 mcg, or about 1096 mcg.

In some embodiments, the composition of the invention comprises a dose or unit dose of olopatadine present at an amount of about 330 mcg to about 5500 mcg, about 330 mcg to about 2660 mcg, about 660 mcg to about 5320 mcg, about 660 mcg to about 2660 mcg, about 550 mcg to about 1330 mcg, about 665 mcg, about 1330 mcg, about 1995 mcg, about 2660 mcg, about 3325 mcg, about 3990 mcg, about 4655 mcg, or about 5320 mcg.

In some embodiments, the composition of the invention comprises a dose or unit dose of cetirizine present at an amount of about 0.25 mg to 5.55 mg, 0.25 mg to about 4.4 mg, 0.55 mg to 4.4 mg, 0.55 mg to 3.3 mg, 0.55 mg to 2.2 mg, about 0.55 mg, about 1.1 mg, about 2.2 mg, about 3.3 mg, about 4.4 mg, or about 5.5 mg per unit dose.

Bronchodilators used in the invention include, for example, terbutaline sulfate, isoetharine, aminophylline, oxtriphylline, dyphylline, ethylnorepinephrine, isoproterenol, epinephrine, isoprenaline, metaproterenol, bitoterol, theophylline, albuterol, isoproterenol and phenylephrine bitartrate, bitolterol, ephedrine sulfate, pirbuterol acetate, pharmaceutically acceptable salts thereof, and mixtures thereof. All of these bronchodilators, as well as their acceptable dosage ranges, are described in Facts and Comparisons, 1998, p. 173b-179e, which is incorporated by reference herein in its entirety.

Topical anesthetics include, for example, lidocaine, dibucaine, dyclonine, benzocaine, butamben, tetracaine, pramoxine, their pharmaceutically-acceptable salts, and mixtures thereof. All of these agents, as well as their acceptable dosage ranges, are described in Facts and Comparisons, 1998, p. 601-607, which is incorporated by reference herein in its entirety.

Sensory agents include, for example, coolants, salivating agents, and warming agents. These agents are present in the compositions at a level of from about 0.001% to about 10%, preferably from about 0.1% to about 1%, by weight of the composition. Suitable cooling agents include carboxamides, menthols, thymol, camphor, capsicum, phenol, eucalyptus oil, benzyl alcohol, salicyl alcohol, ethanol, clove bud oil, and hexylresorcinol, ketals, diols, and mixtures thereof. Coolants can be paramenthan carboxyamide agents such as N-ethyl-p-menthan-3-carboxamide (WS-3 supplied by Sterling Organics), taught by U.S. Pat. No. 4,136,163, issued Jan. 23, 1979, to Watson et al., which is incorporated herein by reference in its entirety. Another paramenthan carboxyamide agent is N,2,3-trimethyl-2-isopropylbutanamide, known as "WS-23", and mixtures of WS-3 and WS-23. Additional coolants are selected from menthol, 3-1-menthoxypropane-1,2-diol, known as TK-10 supplied by Takasago Perfumery Co., Ltd., Tokyo, Japan, menthone glycerol acetal known as MGA, manufactured by Haarmann and Reimer, menthyl lactate known as Frescolat™ manufactured by Haarmann and Reimer, and mixtures thereof. Additional cooling agents include cyclic sulphones and sulphoxides and others, all of which are described in U.S. Pat. No. 4,032,661, to Rowsell et al., which is herein incorporated by reference. The terms "menthol" and "menthyl" as used herein include dextro- and levoratotory isomers of these compounds and racemic mixtures thereof. TK-10 is described in detail in U.S. Pat. No. 4,459,425, to Amano et al. and incorporated herein by reference.

Salivating agents include Jambu™ manufactured by Takasago Perfumery Co., Ltd., Tokyo, Japan. Warming agents include capsicum and nicotinate esters, such as benzyl nicotinate.

Miscellaneous respiratory agents include, for example, leukotriene receptor antagonists such as zafirlukast, zileuton; nasal inhalant products such as corticosteroids, other steroids, beclomethasone, flunisolide, triamcinolone; mucolytics such as acetylcysteine; anticholinergics such as ipratropium bromide; cromolyn sodium, nedocromil sodium; surfactants; and mixtures thereof. These agents can be present in the compositions at a level of from about 0.001% to about 10%, or from about 0.1% to about 5% by weight of the composition.

Antimicrobial agents can also be present. Such agents can include, but are not limited to, triclosan, 5-chloro-2-(2,4-dichlorophenoxy)-phenol, as described in The Merck Index, 11th ed. (1989), pp. 1529 (entry no. 9573) in U.S. Pat. No. 3,506,720, and in European Patent Application No. 0,251, 591 of Beecham Group, PLC, published Jan. 7, 1988; chlorhexidine (Merck Index, no. 2090), alexidine (Merck Index, no. 222; hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; nystatin, tannic acid (forms protective film over cold sores, fever blisters, and canker sores), clotrimazole, carbamide peroxide, amlexanox (indicated for treatment of aphthous ulcers); and analogs and salts of the above antimicrobial antiplaque agents. The antimicrobial agents generally comprise from about 0.1% to about 5% by weight of the compositions of the present invention.

Exemplary suitable antiinfective, antibiotic and antifungal compounds for use in combination in a formulation of the invention are listed in the table below. A combination composition of the invention can comprise one or more corticosteroids and one or more other therapeutic agents and can be administered according to the dosing regimens below or other dosing regimens herein.

| Generic Name | Brand Name | Class | Dosing Range |
| --- | --- | --- | --- |
| Amikacin | Amikin | Aminoglycoside | 50-500 mg |
| Amphotericin B | Fungizone | Antifungal | 2.5-45 mg |
| Azithromycin | Zithromax | Macrolide | 50-400 mg |
| Aztreonam | Azactam | Monobactam | 250-1000 mg |
| Cefazolin | Ancef, Kefzol | Cephlasporin (Gen I) | 250-1000 mg |
| Cefepime | Maxipime | Cephlasporin (Gen IV) | 125-1000 mg |
| Cefonicid | Moniacid | Cephlasporin (Gen II) | 250-1000 mg |
| Cefoperazone | Cefobid | Cephlasporin (Gen III) | 250-1000 mg |
| Cefotaxime | Claforan | Cephlasporin (Gen III) | 250-1000 mg |
| Cefotetan | Cefotan | Cephlasporin (Cephamycin) | 250-1000 mg |
| Cefoxitin | Mefoxin | Cephlasporin (Cephamycin) | 250-1000 mg |
| Ceftazidime | Fortaz, Ceptaz | Cephlasporin (Gen III) | 250-1000 mg |
| Ceftizoxime | Cefizox | Cephlasporin (Gen III) | 250-1000 mg |
| Ceftriaxone | Rocephin | Cephlasporin (Gen III) | 250-1000 mg |
| Cefuroxime | Ceftin | Cephlasporin (Gen II) | 100-600 mg |
| Cephapirin | Cefadyl | Cephlasporin (Gen I) | 250-1000 mg |
| Ciprofloxacin | Cipro | Quinolone | 25-200 mg |
| Clindamycin | Cleocin | Lincosamide | 50-600 mg |
| Doxycycline | Vibramycin | Tetracycline | 10-100 mg |
| Fluconazole | Diflucan | Antifungal | 12.5-150 mg |
| Gentamycin | Garamycin | Aminoglycoside | 10-200 mg |
| Itraconazole | Sporanox | Antifungal | 12.5-150 mg |
| Levofloxacin | Levaquin | Quinolone | 40-200 mg |
| Meropenem | Merrin | Carbapenem | 200-750 mg |
| Mezlocillin | Mezlin | Penicillin | 300-1500 mg |
| Miconazole | Monistat | Antifungal | 12.5-300 mg |
| Nafcilin | Nafcil | Penicillin | 100-1000 mg |
| Ofloxacin | Floxin | Quinolone | 25-200 mg |
| Piperacillin | Pipracil | Penicillin | 100-1000 mg |
| Rifampin | Rifadin | Miscellaneous | 500-5000 mg |
| Ticarcillin + Clavulanate | Timentin | Penicillin | 500-5000 mg |
| Tobramycin | Nebcin | Aminoglycoside | 10-200 mg |
| Vancomycin | Vancocin | Antifungal | 50-400 mg |

Other suitable antifungal agents include butoconazole, econazole, oxiconazole, sulconazole, tioconazole, posaconazole, terconazole, tiniconazole, voriconazole, anidulafungin (LY303366, VER-002), micafungin (FK463), Echinocandins, Cyclic Peptide Antifungals, Triazoles, genaconazole, ravuconazole, TAK-456 and TAK-457, ZD0870, UR-9625, UR-9746, UR-975 1 and UR-9825, T-8581, CS-758, SS-750, Echinocandin B (A30912A), Cilofungin (LY 121 01 9), FR901379 (echinocandin-type peptide, WF11899A), FR901469 (lipopeptidolactone), FR131535, FR203903, Aculeacin A-G, Mulundocandin, Sporiofungin, Pneumocandin A, S3 17941F1, Corynecandin, Mer-WF3010, Fusacandin, Arthrichitin, Furanocandin, Azalomycins, LY 329960, DB 289, aminocandin, naftifine, terbinafine, caspofungin, nystatin, flucytosine, griseofulvin, and mixtures thereof.

The amount and/or concentration of corticosteroid and/or other therapeutically effective agent in a unit dose or dose of the composition can be as specified herein or as customarily present in known dosage forms comprising the same drugs.

The corticosteroid and/or other therapeutically effective agent, if present, can be administered to a subject in need thereof according to a dosing regimen as described herein or as recognized in the art as being suitable for the treatment of a disease, disorder or symptom therapeutically responsive to the corticosteroid and/or other therapeutically effective agent.

Methods of the invention can further comprise administering an additional therapeutically effective agent. In some embodiments, the corticosteroid and additional therapeutically effective agent are administered simultaneously, sequentially, or separately.

Dosing, use and administration of the therapeutic agents disclosed herein is generally intended to follow the guidelines set forth in the Physician's Desk Reference, 55$^{th}$ Edition (Thompson Healthcare, Montvale, NJ, 2005) the relevant disclosure of which is hereby incorporated by reference. The amount of drug included in the compositions of the present invention will be whatever amount is therapeutically effective and will depend upon a number of factors, including the identity and potency of the chosen drug, the disorder being treated, the health of the subject being treated and other such factors common to the pharmaceutical industry for prescription of drugs to a subject. The drugs will generally be administered according to their known dosing regimens such as those disclosed in the Pharmaceutical Desk Reference or those recognized as suitable by the Food and Drug Administration (USA), European Medicines Agency (Europe), National Institute of Health Sciences (Japan), and National Administration of Drugs, Food, and Medical Technology (Administración Nacional de Medicamentos, Alimentos y Tecnologia Medica, Argentina).

Non-limiting exemplary compositions of the invention comprising a corticosteroid and another active agent can comprise the following components.

| FORM. | Corticosteroid (A) | Other Active Ingredient (B) |
|---|---|---|
| I | Budesonide | Olopatadine* |
| II | Budesonide | Azelastine* |
| III | Budesonide | Azithromycin |
| IV | Budesonide | Voriconazole |
| V | Budesonide | Azithromycin and voriconazole |
| VI | Mometasone furoate | Azelastine* |
| VII | Mometasone furoate | Olopatadine* |
| VIII | Mometasone furoate | Azithromycin |
| IX | Fluticasone proprionate | Loratadine |
| X | Fluticasone proprionate | Desloratadine |
| XI | Fluticasone propionate | Cetirizine* |
| XII | Fluticasone propionate | Azelastine* |
| XIII | Fluticasone propionate | Olopatadine* |
| XIV | Fluticasone furoate | Azelastine* |
| XV | Fluticasone furoate | Olopatadine* |

-continued

| FORM. | Corticosteroid (A) | Other Active Ingredient (B) |
|---|---|---|
| XVI | Ciclesonide | Azelastine* |
| XVII | Ciclesonide | Olopatadine* |

*denotes use as its salt, e.g. hydrochloride salt, or free base

A combination formulation of the invention can comprise one or more corticosteroids and one or more second therapeutic (active) agents selected from azithromycin, clinafloxacin, gemifloxacin (Factive®), moxifloxacin (Avelox®), gatifloxacin (Tequin®, Zymar®), sitafloxacin, roxithromycin, norfloxacin, cetirizine hydrochloride, desloratadine, fexofenadine hydrochloride, natamycin, fluconazole itraconazole ketoconazole, capsaicin, benzocaine, tetrahydrozoline hydrochloride, oxymetazoline HCl, epinephrine, zileuton, cromolyn sodium, triazolam, a pharmaceutically acceptable salt thereof, and an isomer thereof.

A composition comprising a corticosteroid and another active agent can be prepared according to the examples below. In some embodiments, the SAE-CD is present in an amount sufficient to solubilize the corticosteroid and the other active agent. In other embodiments, the SAE-CD is present in an amount sufficient to solubilize the corticosteroid or the other active agent.

Depending upon the other active agent used, it may or may not bind competitively against the corticosteroid with the SAE-CD. In some embodiments, the SAE-CD has a higher equilibrium binding constant for the other active agent than it has for the corticosteroid. In some embodiments, the SAE-CD has a higher equilibrium binding constant for the corticosteroid than it has for the other active agent. In some embodiments, the SAE-CD has approximately the same equilibrium binding constant for the other active agent as it has for the corticosteroid. Alternatively, the other active agent does not bind with the SAE-CD even though the corticosteroid does. Accordingly, the invention provides embodiments wherein, the SAE-CD solubilizes the corticosteroid, the other active agent, or a combination thereof. The invention also provides embodiments wherein, the SAE-CD solubilizes at least a major portion of the corticosteroid, the other active agent, or of each. The invention also provides embodiments wherein, the SAE-CD does not solubilize the other active agent.

The molar ratio of SAE-CD to corticosteroid and SAE-CD to other active agent can vary as needed to provide a combination formulation as described herein. The SAE-CD is generally present in molar excess over the corticosteroid, the other active agent, or both.

A composition of the invention can comprise SAE-CD, corticosteroid, aqueous liquid carrier, and an antihistamine. In some embodiments, the composition contains SAE-CD, budesonide, water (or aqueous buffer) and azelastine. Example 14 details the preparation of such a composition. Other solutions of azelastine in buffer with varying amounts of SAE-CD, in the absence of budesonide, were prepared and scanned by UV Spectrometer. The change in absorption as a function of SAE-CD concentration was plotted and used to determine the equilibrium binding constant of azelastine with SAE-CD, according to the Benesi-Hildebrand equation. The equilibrium binding constant of azelastine with CAPTISOL was found to be approximately 10,000 at pH 4.5. The binding constant for budesonide under similar conditions was determined to be about 1000; therefore, azelastine will compete with budesonide, or another corticosteroid, for binding to SAE-CD. Accordingly, the amount of SAE-CD present can be increased to permit complete dissolution of both drugs.

Figure 11A:
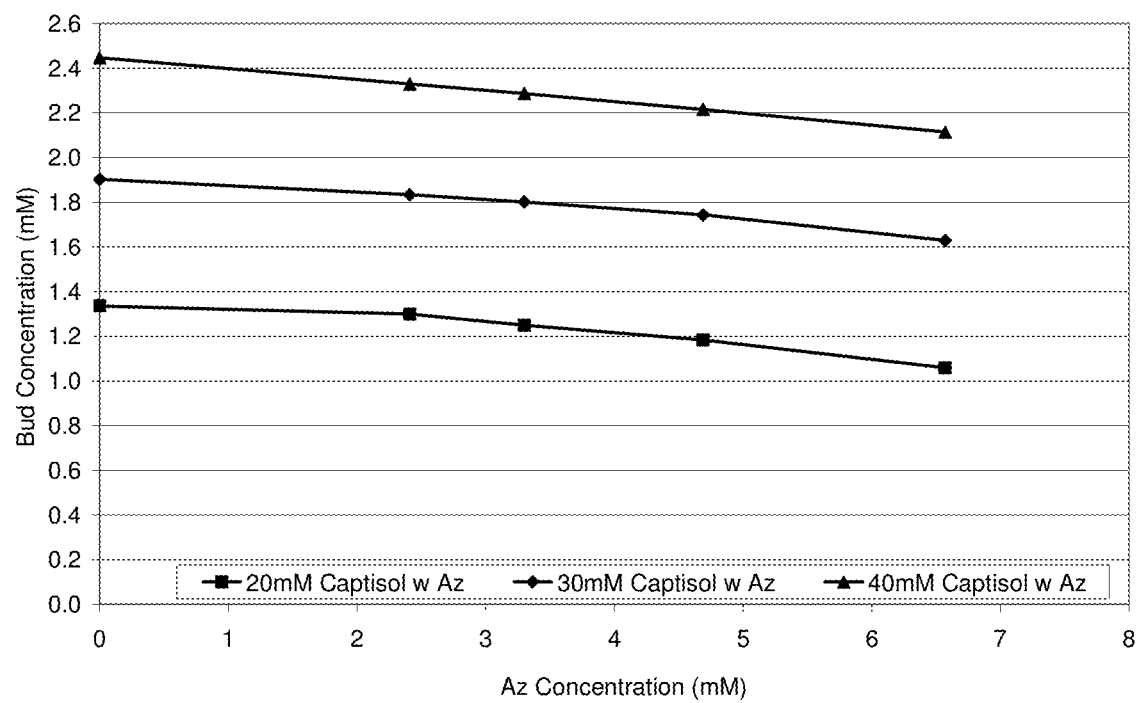
FIGS. 11A and 11B depict phase solubility diagrams for budesonide in the presence of varying amounts of azelastine hydrochloride and fixed amounts of SBE-β-CD or SBE-γ-CD.
Figure 11B:
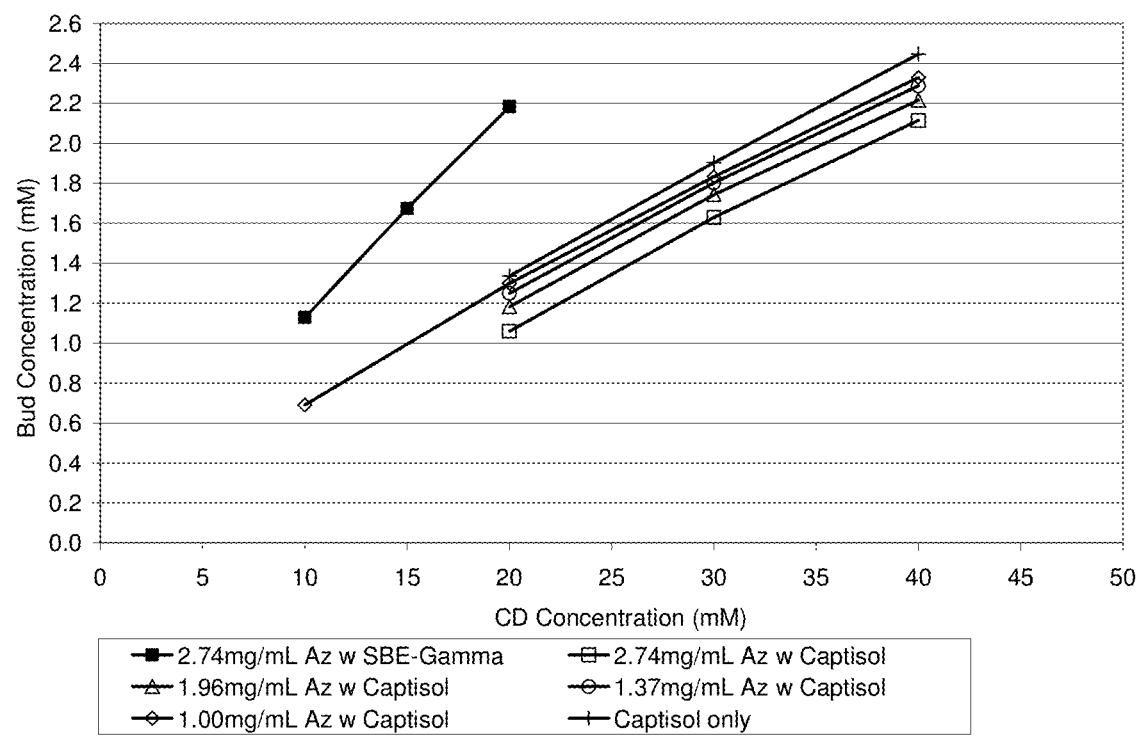

The equilibrium binding constant of the corticosteroid can change when a second active agent is present in a composition of the invention. Since azelastine hydrochloride (AZ-HCl) has an approximately 10-fold higher binding constant for SBE-β-CD than does budesonide (BUD), the amount of SBE-β-CD present in an aqueous composition of the three needs to be sufficient to solubilize both drugs. Example 19 details a procedure for determination of the phase solubility of budesonide in the presence of varying amounts of azelastine. The results are depicted in FIGS. 11A (for SBE-β-CD) and 11B (for SBE-β-CD and SBE-γ-CD). FIG. 11A is a chart of the phase solubility of BUD as a function of AZ-HCl concentration in solution in the presence of 20-40 mM CAPTISOL. The data indicate that the concentration of BUD at saturated solubility decreases as the concentration of AZ-HCl increases. FIG. 11B is a chart of the phase solubility of BUD as a function of SBE-β-CD or SBE-γ-CD concentration in solution using various different concentrations of AZ-HCl (1.00-2.75 mg.mL). The data indicate that the concentration of BUD at saturated solubility increases as the concentration of AZ-HCl increases and that higher concentrations of SBE-CD are required in order to dissolve the BUD as the concentration of AZ-HCl increases. Thus, increasing the amount of AZ-HCl in the solution decreases the overall solubility of BUD. The equilibrium complex stability constant between azelastine and SBE-β-CD is surprisingly about 5-times greater than that between azelastine and SBE-γ-CD (~10000 M−1 versus 2200 M$^{-1}$) while the equilibrium complex stability constant for budesonide with SBE-β-CD is half that of the equilibrium complex stability constant for budesonide with SBE-γ-CD (i.e.1000 M$^{-1}$ versus 2000 M$^{-1}$). Surprisingly, the nominal amount of SBE-β-CD required to solubilize a similar dose of budesonide in the presence of azelastine is greater than in the absence of azelastine as well as greater than the increase required if the cyclodextrin was SBE-γ-CD. Therefore, it is advantageous to prepare solution compositions of these combinations using SBE-γ-CD due to the efficiency of interaction so as to require less of one SAExCD versus another different SAEyCD to solubilize similar amounts of actives in the presence of each other.

In some embodiments of the invention, the concentrations of budesonide, azelastine (free base or HCl salt), and SAE-CD (e.g. SBE-CD) in the composition are as follows:
 a) budesonide is present at a concentration of about 0.627 mg/g (32 mcg/51 mg), about 0.457 mg/mL (32 mcg/70 mcL), 0.320 mg/mL (32 mcg/100 mcL), about 0.320 mg/g (32 mcg/100 mg), from 0.04 mg/mL to 2 mg/mL, or from 0.04 mg/mL to 1 mg/mL;
 b) azelastine is present at a concentration of about 0.5 to about 10 mg/mL, about 0.5 to about 6 mg/mL, about 1 to about 5 mg/mL, about 1 to about 3 mg/mL, about 2 to about 3 mg/mL, about 2.5 to about 3 mg/mL, about 2.75 mg/mL about 0.137 mg/51 mg, about 0.137 mg/0.137 mL, about 0.137 mg/0.050 mL, about 0.137 mg/0.070 mL, about 0.137 mg/0.1 mL, or about 1 mg/mL to 10 mg/mL (0.137 mg/0.020 mL); and/or
 c) SAE-CD is present at a concentration of about 100 mg/mL, about 10 to about 500 mg/mL, or about 10 to about 500 mg/g.

In some embodiments, the concentrations of budesonide, azelasatine and SAE-CD in the composition are as set forth in the table below.

| [budesonide] | [azelastine] | [SBE-CD] |
|---|---|---|
| 32 mcg/51 mg of composition | 137 mcg/51 mg of composition | 7 mg/51 mg |
| 32 mcg/70 mcL of composition | 137 mcg/70 mcL of composition | 7 mg/70 mcL |
| 32 mcg/100 mg of composition | 137 mcg/100 mg of composition | 7 mg/100 mg |
| 0.04 to 2 mg/mL of composition | 1 to 10 mg/mL of composition | 10 to 500 mg/mL of composition (or per g of composition) |

In some embodiments of the invention, the concentrations of budesonide, olopatadine (free base or HCl salt), and SAE-CD (e.g. SBE-CD) in the composition are as follows:
 a) budesonide is present at a concentration of about 0.627 mg/g (32 mcg/51 mg), about 0.457 mg/mL (32 mcg/70 mcL), 0.320 mg/mL (32 mcg/100 mcL), about 0.320 mg/g (32 mcg/100 mg), from 0.04 mg/mL to 2 mg/mL, or from 0.04 mg/mL to 1 mg/mL;
 b) olopatadine is present at a concentration of about 0.5 to about 15 mg/mL, about 1 to about 10 mg/mL, about 1 to about 15 mg/mL, about 5 to about 10 mg/mL, about 6 to about 7 mg/mL, about 0.665 mg/0.10 mL, about 0.665 mg/0.70 mL, about 0.665 mg/0.50 mL, 5.32 mg/0.2 mL, or about 6.5 mg/5 mL; and/or
 c) SAE-CD is present at a concentration of about 100 mg/mL, about 10 to about 500 mg/mL, or about 10 to about 500 mg/g.

In some embodiments of the invention, the concentrations of budesonide, cetirizine (free base or HCl salt), and SAE-CD (e.g. SBE-CD) in the composition are as follows:
 a) budesonide is present at a concentration of about 0.627 mg/g (32 mcg/51 mg), about 0.457 mg/mL (32 mcg/70 mcL), 0.320 mg/mL (32 mcg/100 mcL), about 0.320 mg/g (32 mcg/100 mg), from 0.04 mg/mL to 2 mg/mL, or from 0.04 mg/mL to 1 mg/mL;
 b) cetirizine is present at a concentration of about 0.25 to about 4.4 mg/mL, about 0.55 to about 4.4 mg/mL, about 1.1 to about 4.4 mg/mL, about 1.1 to about 2.2 mg/mL, about 1 to about 25 mg/mL, about 2 to about 24 mg/mL, about 5 to about 20 mg/mL, about 7 to about 15 mg/mL, about 10 to about 12 mg/mL, about 1.1 mg/0.1 mL, about 1.1 mg/0.05 mL, about 1.1 mg/0.70 mL, about 1.1 mg/0.2 mL, or about 2.2 mg/5 mL; and/or
 c) SAE-CD is present at a concentration of about 100 mg/mL, about 10 to about 500 mg/mL, or about 10 to about 500 mg/g.

In some embodiments of the invention, the concentrations of mometasone furoate, olopatadine (free base or HCl salt), and SAE-CD (e.g. SBE-CD) in the composition are as follows:
 a) mometasone furoate is present at a concentration of about 0.5 mg/mL (50 mcg/100 mcL), about 0.71 mg/mL (50 mcg/70 mcL), about 1.0 mg/mL (50 mcg/100 mcL), about 1.0 mg/mL (200 mcg/200 mcL), or about 0.1 mg/mL (500 mcg/5000 mcL);
 b) olopatadine is present at a concentration of about 0.5 to about 15 mg/mL, about 1 to about 10 mg/mL, about 1 to about 15 mg/mL, about 5 to about 10 mg/mL, about 6 to about 7 mg/mL, about 0.665 mg/0.10 mL, about 0.665 mg/0.70 mL, about 0.665 mg/0.50 mL, 5.32 mg/0.2 mL, or about 6.5 mg/5 mL; and/or
 c) SAE-CD is present at a concentration of about 300 mg/mL, about 10 to about 500 mg/mL, or about 10 to about 500 mg/g.

In some embodiments of the invention, the concentrations of fluticasone propionate, cetirizine (free base or HCl salt), and SAE-CD (e.g. SBE-CD) in the composition are as follows:
  a) fluticasone propionate is present at a concentration of about 0.5 mg/mL (50 mcg/100 mcL), about 0.71 mg/mL (50 mcg/70 mcL), about 1.0 mg/mL (50 mcg/100 mcL), about 1.0 mg/mL (200 mcg/200 mcL), or about 0.1 mg/mL (500 mcg/5000 mcL);
  b) cetirizine is present at a concentration of about 0.55 to about 4.4 mg/mL, about 1.1 to about 4.4 mg/mL, about 1.1 to about 2.2 mg/mL, about 1 to about 25 mg/mL, about 2 to about 24 mg/mL, about 5 to about 20 mg/mL, about 7 to about 15 mg/mL, about 10 to about 12 mg/mL, about 1.1 mg/0.1 mL, about 1.1 mg/0.05 mL, about 1.1 mg/0.70 mL, about 1.1 mg/0.2 mL, or about 2.2 mg/5 mL; and/or
  c) SAE-CD is present at a concentration of about 300 mg/mL, about 10 to about 500 mg/mL, or about 10 to about 500 mg/g.

Embodiments of the present invention allow for combination compositions (those containing two or more active agents (therapeutic agents)) to be prepared in a variety of ways:
  1) Mixing ready to use solutions of a second therapeutic agent with a ready to use solution of a corticosteroid in SAE-CD;
  2) Mixing ready to use solutions of a second therapeutic agent with a concentrated solution of a corticosteroid dissolved using SAE-CD;
  3) Mixing a ready to use solution of a second therapeutic agent with substantially dry SAE-CD and a substantially dry corticosteroid;
  4) Mixing a ready to use solution of a second therapeutic agent with a substantially dry mixture of SAE-CD and a corticosteroid or more conveniently a pre-measured amount of the mixture in a unit container such as a capsule (empty a capsule into ready to use solution);
  5) Mixing a ready to use solution of a corticosteroid such as budesonide with a substantially dry second therapeutic agent; or
  6) Dissolving a substantially dry second therapeutic agent and a substantially dry SAE-CD plus a substantially dry corticosteroid.

The materials used herein can be used in micronized or non-micronized form and crystalline, polymorphic or amorphous form. This is particularly true of the corticosteroids and other active ingredients.

It is well understood by those of ordinary skill in the art that the above solutions or powders can optionally contain other ingredients such as buffers and/or tonicity adjusters and/or antimicrobials and/or additives or other such excipients as set forth herein or as presently used in nasally administered liquid formulations.

A corticosteroid-responsive disease, symptom or disorder is one wherein a subject suffering from such will receive a clinical benefit after administration of a corticosteroid according to the invention. A type of corticosteroid-responsive disease, symptom or disorder is any allergic and/or inflammatory disease, symptom or disorder. Exemplary ones include nasal symptom, non-nasal symptom, ocular symptom, acute or chronic rhinitis, nasal polyps, post surgical polyps, obstructive sleep apnea, Eustachian tube dysfunction, serous otitis media, sleep disturbances, daytime somnolence, snoring, cluster headache, nasal furuncles, epistaxis, wounds of the nasal or sinunasal mucosa, dry nose syndrome, nasal bleeding, herpes, sarcoidosis, fibrosis, cancer, autoimmune reaction, or a combination thereof.

In some embodiments, acute or chronic rhinitis is selected from the group consisting of allergic rhinitis, seasonal allergic rhinitis, perennial allergic rhinitis, perennial non-allergic rhinitis, bacterial rhinitis, fungal rhinitis, viral rhinitis, atrophic rhinitis, grass pollen rhinitis, have fever, blocked nose, nasal congestion, vasomotor rhinitis, or a combination thereof.

In some embodiments, the nasal symptom is rhinorrhea, nasal congestion, nasal itchiness, sneezing, nasal obstruction or a combination thereof. In some embodiments, the non-nasal symptom is itchy/gritty eyes, tearing/watery eyes, red/burning eyes, itchy ears and palate, or a combination thereof.

In some embodiments, the invention excludes a method of or system for treating asthma, allergic asthma, rhinosinusitis, and/or sinusitis.

Conjunctivitis is an inflammation of the conjunctiva, the membrane lining the external surface of the eye, and is most often caused by an allergic reaction. Allergic conjuctivitis is one of the most common eye conditions in children and adults with symptoms including itching, stinging, burning, redness, tearing and swelling of the eyelids and the whites of the eye. Allergic conjunctivitis is most often associated with allergic rhinitis (Hay Fever) and can be associated with asthma.

Allergic rhinitis is one of the most chronic atopic diseases that is associated with considerable cost and co-morbidity. Allergic rhinitis is initiated by an IgE-mediated response to allergens and results in a consequent release of preformed mediators and cytokines, which induce inflammatory cell recruitment and their activation at the target organ. Seasonal allergic rhinitis (SAR), triggered by pollen from trees, grasses and weeds, is characterized by sneezing, nasal congestion, nasal itching, rhinorrhea, and pruritic, watery red eyes.

Animal dander, mold, dust, and dust mites can also trigger symptoms of rhinitis. Non-allergic rhinitis can also be induced by viruses, and environmental factors such as toxins and tobacco smoke.

Corticosteroids can also be used to treat ocular conditions such as: (1) inflammatory conditions including conditions of the palpebral and bulbar conjunctiva, cornea, and anterior segment of the globe such as allergic conjunctivitis, acne rosacea, superficial punctate keratitis, herpes zoster keratitis, iritis, cyclitis, selected infective conjunctivitis; (2) corneal injuries including injury from chemical, radiation, or thermal burns or penetration by foreign bodies; and (3) ocular pain and burning/stinging following ocular surgery such as corneal refractive surgery.

The compositions of the invention can generally have a storage shelf life of 6 months. In this case, shelf life is determined only as regards the increase in the amount of corticosteroid degradation by-products or a reduction in the amount of corticosteroid remaining in the composition. For example, for a composition having a shelf life of at least six months, the composition will not demonstrate an unacceptable and substantial increase in the amount of degradants during the storage period of at least six months. The criteria for acceptable shelf-life are set as needed according to a given product and its storage stability requirements. In other words, the amount of degradants in a composition having an acceptable shelf-life will not increase beyond a predetermined value during the intended period of storage. On the other hand, the amount of degradants of a composition having an unacceptable shelf-life will increase beyond the predetermined value during the intended period of storage.

The method of Example 3 can be followed to determine the stability of the active agent in solution. The shelf-life can be defined as the time to loss of less than about 10%, less than about 5%, less than about 3%, less than about 2% or less than about 1% potency. Under the conditions tested, the loss of potency was first order. The shelf life of a CAPTISOL-ENABLED Budesonide Nasal Solution (a solution comprising budesonide and SBE7-β-CD) is greater than about 3 years at a pH between 4 and 5, i.e. about 90 months at pH 4.0 and about 108 months at pH 5.0 without the need to add any other stabilizers, such as EDTA, in water in the presence of about 5% wt./vol. SAE-CD.

SAE-CD is also capable of stabilizing the isomers of budesonide to different extents. SBE7-β-CD stabilized both R- and S-isomers of budesonide in solutions at both pH 4 and 6. The with/without CAPTISOL ratio of rate constants was much less than 1 at all temperatures. SBE7-β-CD had a greater effect on the stability of both the R and S-isomer at pH 6 than at pH 4. At a given temperature the ratio of rate constants with/without SBE7-β-CD was less at pH 6 than at pH 4. Although SBE7-β-CD stabilized both isomers, the S-isomer appears to be stabilized to an even greater extent than the R. At all temperatures and pHs tested, the ratio of rate constants with/without SBE7-β-CD was lower for the S isomer. The degree of stabilization affected by SBE7-β-CD at 60° C. is greater than at 80° C. An even greater degree of stabilization would be expected at 40° C. and/or room temperature (20-30° C.). Accordingly a solution comprising SAE-CD and budesonide is stable at a pH from 4 to 6, from 4 to 5, or about 4.5.

SBE7-β-CD also significantly reduced the photodecomposition of budesonide. The loss of budesonide was first order and independent of pH.

Figure 10A:
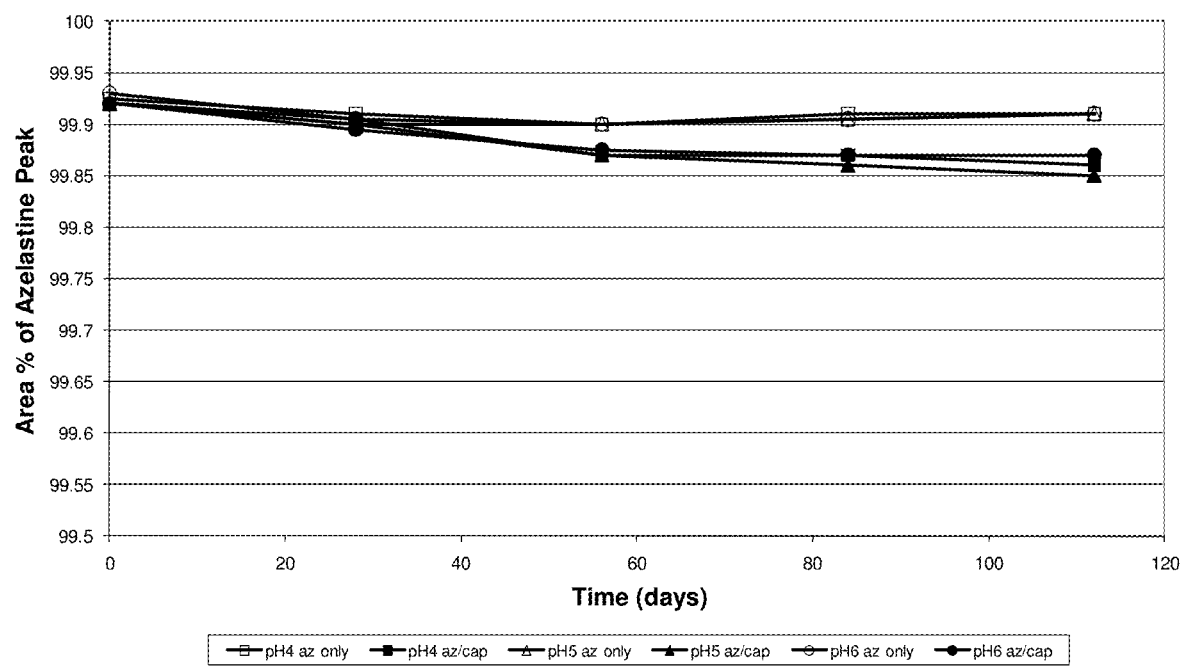
FIGS. 10A-10C depict charts of the pH rate profile for degradation of azelastine in the presence or absence of SAE-CD at varying temperatures and pH's.
Figure 10B:
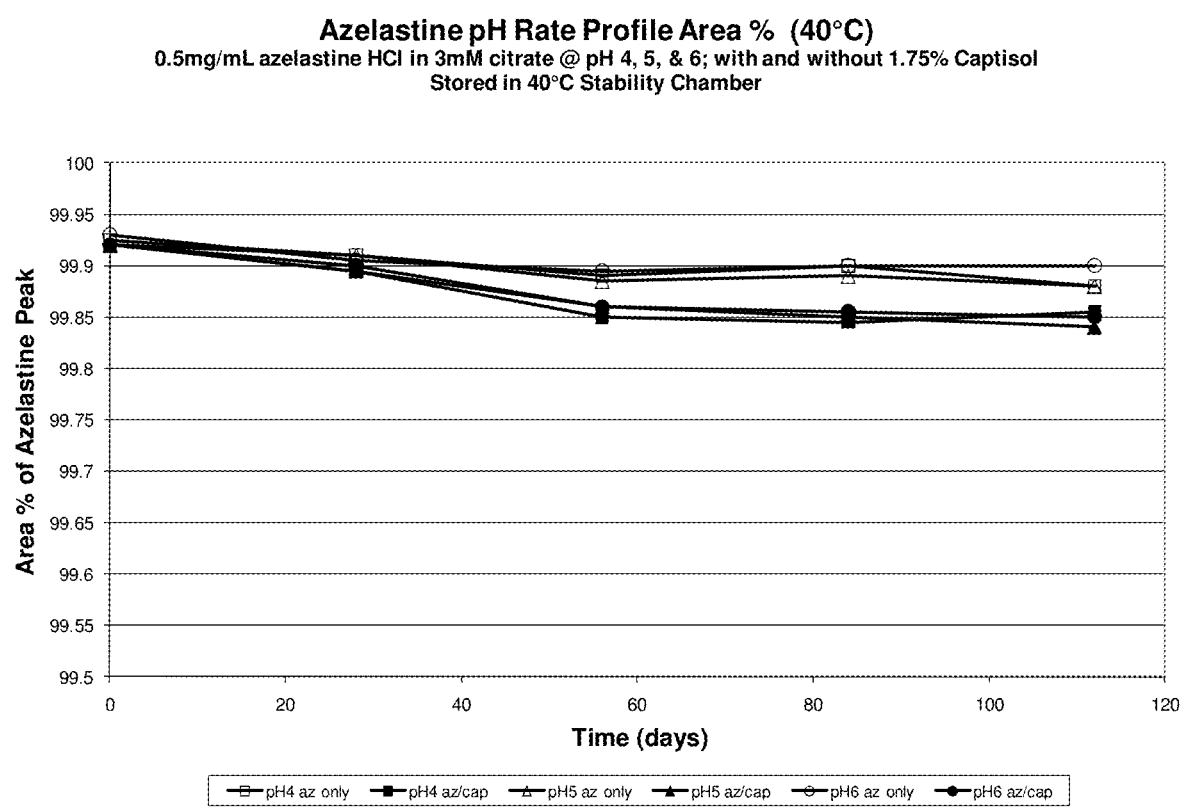
Figure 10C:
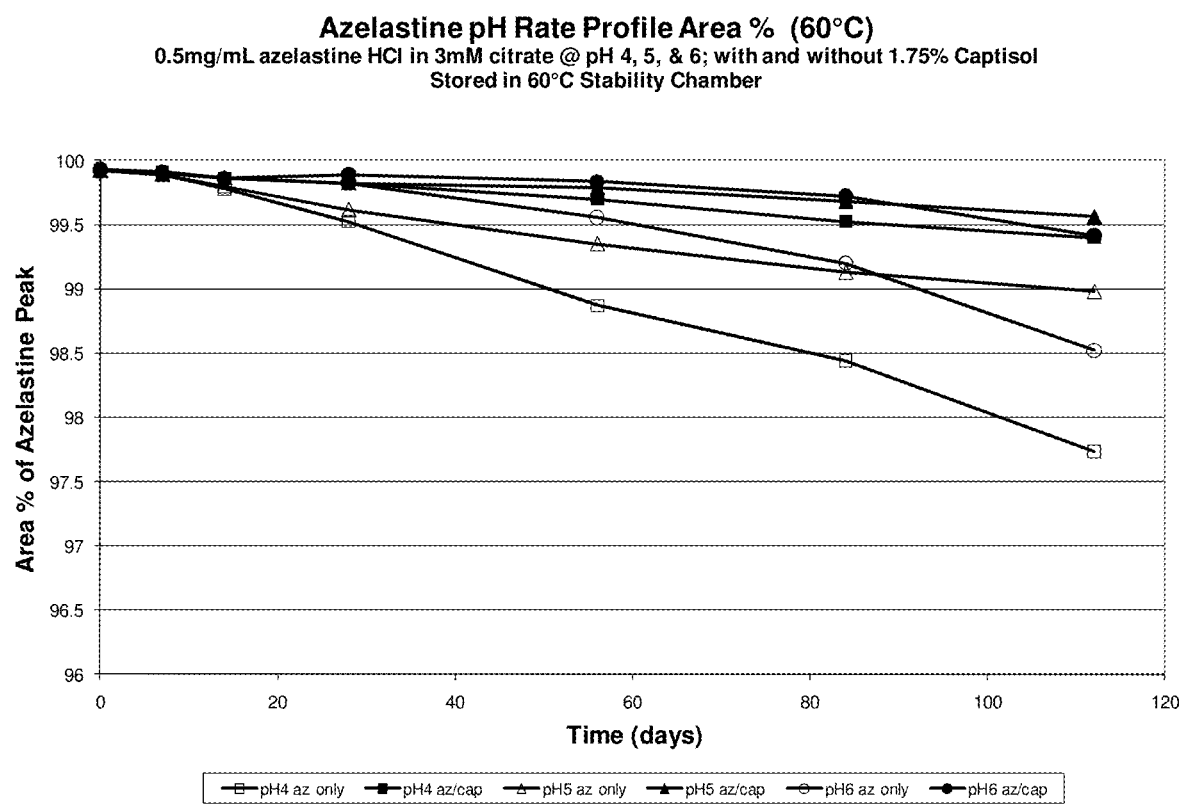

SAE-CD is also capable of stabilizing a second active agent included in the composition. Example 16 details a procedure for evaluating the stability of azelastine in the presence of SAE-CD at varying temperatures and in solutions of different pH's. The results are depicted in FIGS. 10A to 10C. The SAE-CD stabilized the azelastine for the period of sixteen weeks regardless of the temperature or pH of the solution. The lower the temperature, the greater the stabilization. Of the three pH values evaluated, the greatest stabilization was observed at pH 5. Accordingly, a solution comprising SAE-CD and azelastine is most stable at a pH from 4 to 6 or from 4.5 to 5.5.

The composition of the invention can be provided as a powder adapted to form an aqueous solution for nasal, non-nasal and/or ophthalmic administration. The powder can also be adapted for administration with a powder-administering device. The powder can instead comprise an admixture of a solid derivatized cyclodextrin and solid corticosteroid and, optionally, at least one solid pharmaceutical excipient, such that a major portion of the active agent is not complexed with the derivatized cyclodextrin prior to reconstitution of the admixture with an aqueous carrier. Alternatively, the composition can comprise a solid mixture comprising the inclusion complex of a derivatized cyclodextrin and an active agent, wherein a major portion of the active agent is complexed with the derivatized cyclodextrin prior to reconstitution of the solid mixture with an aqueous carrier.

A powder composition of the invention can be prepared according to any of the following processes. A liquid composition of the invention is first prepared, then a solid is formed by lyophilization (freeze-drying), spray-drying, spray freeze-drying, antisolvent precipitation, various processes utilizing supercritical or near supercritical fluids, or other methods known to those of ordinary skill in the art to make a solid for reconstitution. Examples 25, 26, 27, 29 details a method for the preparation of a lyophilized solid composition comprising corticosteroid and SAE-CD by lyophilization of a liquid composition or formulation of the invention.

A liquid vehicle (carrier) included in a formulation of the invention comprises a pharmaceutically acceptable aqueous liquid carrier, such as water or buffer, aqueous alcohol, propylene glycol, glycerin, poly(ethylene glycol), poloxamer, povidone, polyol (such as sorbitol), aqueous organic solvent or a combination thereof. Example 30 details the preparation of a liquid formulation comprising 20% w/v SAE-CD, corticosteroid, water and ethanol (0-5%). Increasing the concentration of the ethanol in the liquid resulted in a decrease in the maximum saturated solubility of the corticosteroid. For nasal administration, an aqueous liquid carrier can be aqueous saline (which generally contains sodium chloride as the salt, and is fully described in Remington's Pharmaceutical Sciences, 19. sup.th edition (1995) p. 1502, which is herein incorporated by reference). The salt can be present in the solution at a level of about 0.01% to about 2%, preferably from about 0.5% to about 1.0% by weight of solution. Suitable nontoxic pharmaceutically acceptable nasal carriers are known to those skilled in the art. The choice of a suitable carrier will depend on the exact nature of the particular nasal dosage form required, e.g., whether the active agent is to be formulated into a nasal solution (for use as drops or as a spray), a nasal ointment, a nasal gel or another nasal form.

The compositions of the invention can include a preservative, antioxidant, buffering agent, acidifying agent, alkalizing agent, colorant, solubilizing agent, solubility-enhancing agent, complexation-enhancing agent, diluent, electrolyte, glucose, stabilizer, bulking agent, antifoaming agent, oil, emulsifying agent, cryoprotectant, plasticizer, flavors, sweeteners, taste-masking agent, tonicity modifier, surface tension modifier, surfactant, viscosity modifier, density modifier, volatility modifier, saline, other excipients known by those of ordinary skill in the art for use in preserved formulations, or a combination thereof.

As used herein, the term "alkalizing agent" is intended to mean a compound used to provide alkaline medium, such as for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, diethanolamine, organic amine base, alkaline amino acids and trolamine and others known to those of ordinary skill in the art.

As used herein, the term "acidifying agent" is intended to mean a compound used to provide an acidic medium for product stability. Such compounds include, by way of example and without limitation, acetic acid, acidic amino acids, citric acid, fumaric acid and other alpha hydroxy acids, hydrochloric acid, ascorbic acid, phosphoric acid, sulfuric acid, tartaric acid and nitric acid and others known to those of ordinary skill in the art.

Inclusion of a preservative in the solution is optional, since the formulation is self-preserved by SAE-CD depending upon its concentration in solution. If a conventional preservative is included in the composition, the corticosteroid, such as budesonide, can have a greater binding with the SAE-CD than does a conventional preservative. Nonetheless, a preservative can be further included in the formulation if desired. Preservatives can be used to inhibit microbial growth in the compositions. The amount of preservative is generally that which is necessary to prevent microbial growth in the composition for a storage period of at least six months. As used herein, a preservative is a compound used to at least reduce the rate at which bioburden increases, but preferably maintains bioburden steady or reduces bioburden after contamination has occurred. Such compounds include, by way of example and without limitation, 3-(trimethoxysilyl)propyldimethyloctadecylammonium chloride, stearyldimethylbenzyl-ammonium chloride, 6-acetoxy-2,4-dimethyl-metadioxane, alkali metal sorbates and mixtures, ammonium sorbate, BAC, benzalkonium chloride, benzethonium chloride, benzoic acid (and salts), benzyl alcohol, boric acid, bronopol, butyl parabens, C.sub.16 benzalkonium halide compounds, cetrimide, cetyldimethylbenzylammonium chloride, cetylpyridinium bromide, cetylpyridinium chloride, chlorbutanol, chlorhexidine, chlorine dioxide, chlorite components, Chlorobutanol, chlorocresol, chlorohexidine gluconate, chlorohexidine hydrochloride, cresol, distearyldimethylammonium chloride, dodecylguanidine, dodecylguanidine hydrochloride, domiphen bromide, ethanol, ethyl parabens, guanidines, lauroylisoquinolium bromide, Methylparaben, myristylgamma picolinium chloride, paraben mixtures, phenol, phenol derivative, phenoxyethanol, phenylethanol, phenylmercuric acetate, phenylmercuric nitrate, phenylmercuric salts, polyhexmethylenebiguanidine hydrochloride, polymeric quaternary ammonium compounds, potassium sorbate, propylparaben, quaternary ammonium alkylene glycol phospholipid derivatives, quaternary ammonium salts, propyl parabens, sodium sorbate, sorbic acid (and salts), stearylpentaethoxyammonium chloride, stearyltolylmethyl-ammonium chloride, sulfites inorganic, thiomersal, thymol, and others known to those of ordinary skill in the art.

As used herein, the term "antioxidant" is intended to mean an agent that inhibits oxidation and thus is used to prevent the deterioration of preparations by the oxidative process. Such compounds include, by way of example and without limitation, acetone, potassium metabisulfite, potassium sulfite, ascorbic acid, ascorbyl palmitate, citric acid, butylated hydroxyanisole, butylated hydroxytoluene, hypophosphorous acid, monothioglycerol, propyl gallate, sodium ascorbate, sodium citrate, sodium sulfide, sodium sulfite, sodium bisulfate, sodium formaldehyde sulfoxylate, thioglycolic acid, EDTA, pentetate, sodium metabisulfite, and others known to those of ordinary skill in the art.

As used herein, the term "buffering agent" is intended to mean a compound used to resist change in pH upon dilution or addition of acid or alkali. Buffers are used in the present compositions to adjust the pH to a range of between about 2 and about 8, about 3 to about 7, or about 4 to about 5. Such compounds include, by way of example and without limitation, acetic acid, sodium acetate, adipic acid, benzoic acid, sodium benzoate, boric acid, sodium borate, citric acid, glycine, maleic acid, monobasic sodium phosphate, dibasic sodium phosphate, HEPES, lactic acid, tartaric acid, potassium metaphosphate, potassium phosphate, monobasic sodium acetate, sodium bicarbonate, tris, sodium tartrate and sodium citrate anhydrous and dihydrate and others known to those of ordinary skill in the art. Other buffers include citric acid/phosphate mixture, acetate, barbital, borate, Britton-Robinson, cacodylate, citrate, collidine, formate, maleate, McIlvaine, phosphate, Prideaux-Ward, succinate, citrate-phosphate-borate (Teorell-Stanhagen), veronal acetate, MES (2-(N-morpholino)ethanesulfonic acid), BIS-TRIS (bis(2-hydroxyethyl)imino-tris(hydroxymethyl)methane), ADA (N-(2-acetamido)-2-iminodiacetic acid), ACES (N-(carbamoylmethyl)-2-aminoethanesulfonaic acid), PIPES (piperazine-N,N'-bis(2-ethanesulfonic acid)), MOPSO (3-(N-morpholino)-2-hydroxypropanesulfonic acid), BIS-TRIS PROPANE (1,3-bis(tris(hydroxymethyl)methylamino)propane), BES (N,N-bis(2-hydroxyethyl)-2-aminoethanesulfonaic acid), MOPS (3-(N-morpholino)propanesulfonic acid), TES (N-tris(hydroxymethyOmethyl-2-aminoethanesulfonic acid), HEPES (N-(2-hydroxyethyl)piperazine-N'-(2-ethanesulfonic acid), DIPSO (3-(N,N-bis(2-hydroxyethyl)amino)-2-hydroxypropanesulfonic acid), MOBS (4-(N-morpholino)-butanesulfonic acid), TAPSO (3-(N-tris(hydroxymethyl)methylamino)-2-hydroxypropanesulfonic acid), TRIZMA™ (tris(hydroxymethylaminomethane), HEPPSO (N-(2-hydroxyethyl)piperazine-N'-(2-hydroxypropanesulfonic acid), POP SO (piperazine-N,N'-bis(2-hydroxypropanesulfonic acid)), TEA (triethanolamine), EPPS (N-(2-hydroxyethyl)piperazine-N'-(3-propanesulfonic acid), TRICINE (N-tris(hydroxymethyl)methylglycine), GLY-GLY (glycylglycine), BICINE (N,N-bis(2-hydroxyethyl)glycine), HEPBS (N-(2-hydroxyethyl)piperazine-N'-(4-butanesulfonic acid)), TAPS (N-tris(hydroxymethyl)methyl-3-aminopropanesulfonic acid), AMPD (2-amino-2-methyl-1,3-propanediol), and/or any other buffers known to those of skill in the art.

A complexation-enhancing agent can be added to the compositions of the invention. When such an agent is present, the ratio of cyclodextrin/active agent can be changed. A complexation-enhancing agent is a compound, or compounds, that enhance(s) the complexation of the active agent with the cyclodextrin. Suitable complexation enhancing agents include one or more pharmacologically inert water soluble polymers, hydroxy acids, and other organic compounds typically used in liquid formulations to enhance the complexation of a particular agent with cyclodextrins.

Hydrophilic polymers can be used as complexation-enhancing, solubility-enhancing and/or water activity reducing agents to improve the performance of formulations containing a cyclodextrin. Suitable polymers are disclosed in *Pharmazie* (2001), 56(9), 746-747; *International Journal of Pharmaceutics* (2001), 212(1), 29-40; Cyclodextrin: From Basic Research to Market, International Cyclodextrin Symposium, 10th, Ann Arbor, MI, United States, May 21-24, 2000 (2000), 10-15 (Wacker Biochem Corp.: Adrian, Mich.); PCT International Publication No. WO 9942111; *Pharmazie*, 53(11), 733-740 (1998); *Pharm. Technol. Eur.*, 9(5), 26-34 (1997); *J. Pharm. Sci.* 85(10), 1017-1025 (1996); European Patent Application EP0579435; Proceedings of the International Symposium on Cyclodextrins, 9th, Santiago de Comostela, Spain, May 31-Jun. 3, 1998 (1999), 261-264 (Editor(s): Labandeira, J. J. Torres; Vila-Jato, J. L. Kluwer Academic Publishers, Dordrecht, Neth); *S. T. P. Pharma Sciences* (1999), 9(3), 237-242; ACS Symposium Series (1999), 737(Polysaccharide Applications), 24-45; *Pharmaceutical Research* (1998), 15(11), 1696-1701; *Drug Development and Industrial Pharmacy* (1998), 24(4), 365-370; *International Journal of Pharmaceutics* (1998), 163(1-2), 115-121; Book of Abstracts, 216th ACS National Meeting, Boston, August 23-27 (1998), CELL-016, American Chemical Society; *Journal of Controlled Release*, (1997), 44/1 (95-99); *Pharm. Res.* (1997) 14(11), S203; *Investigative Ophthalmology & Visual Science*, (1996), 37(6), 1199-1203; Proceedings of the International Symposium on Controlled Release of Bioactive Materials (1996), 23rd, 453-454; Drug Development and Industrial Pharmacy (1996), 22(5), 401-405; Proceedings of the International Symposium on Cyclodextrins, 8th, Budapest, March 31-April 2, (1996), 373-376. (Editor(s): Szejtli, J.; Szente, L. Kluwer: Dordrecht, Neth.); *Pharmaceutical Sciences* (1996), 2(6), 277-279; *European Journal of Pharmaceutical Sciences*, (1996) 4(SUPPL.), 5144; Third European Congress of Pharmaceutical Sciences Edinburgh, Scotland, UK September 15-17, 1996; *Pharmazie*, (1996), 51(1), 39-42; *Eur. J. Pharm. Sci.* (1996), 4(Suppl.), 5143; U.S. Pat. Nos. 5,472, 954 and 5,324,718; *International Journal of Pharmaceutics* (Netherlands), (Dec. 29, 1995) 126, 73-78; Abstracts of Papers of the American Chemical Society, (02 APR 1995) 209(1), 33-CELL; *European Journal of Pharmaceutical Sciences*, (1994) 2, 297-301; *Pharmaceutical Research* (New York), (1994) 11(10), 5225; *International Journal of Pharmaceutics* (Netherlands), (Apr. 11, 1994) 104, 181-184; and *International Journal of Pharmaceutics* (1994), 110(2), 169-77, the entire disclosures of which are hereby incorporated by reference.

Other suitable polymers are well-known excipients commonly used in the field of pharmaceutical formulations and are included in, for example, *Remington's Pharmaceutical Sciences*, 18th *Edition*, Alfonso R. Gennaro (editor), Mack Publishing Company, Easton, PA, 1990, pp. 291-294; Alfred Martin, James Swarbrick and Arthur Commarata, *Physical Pharmacy. Physical Chemical Principles in Pharmaceutical Sciences*, 3rd *edition* (Lea & Febinger, Philadelphia, PA, 1983, pp. 592-638); A. T. Florence and D. Altwood, (*Physicochemical Principles of Pharmacy*, 2nd *Edition*, MacMillan Press, London, 1988, pp. 281-334. The entire disclosures of the references cited herein are hereby incorporated by references. Still other suitable polymers include water-soluble natural polymers, water-soluble semi-synthetic polymers (such as the water-soluble derivatives of cellulose) and water-soluble synthetic polymers. The natural polymers include polysaccharides such as insulin, pectin, algin derivatives (e.g. sodium alginate) and agar, and poly-peptides such as casein and gelatin. The semi-synthetic polymers include cellulose derivatives such as methylcellulose, hydroxyethylcellulose, hydroxypropyl cellulose, their mixed ethers such as hydroxypropyl methylcellulose and other mixed ethers such as hydroxyethyl ethylcellulose and hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g. carbomer). Other natural, semi-synthetic and synthetic polymers not named here which meet the criteria of water solubility, pharmaceutical acceptability and pharmacological inactivity are likewise considered to be within the ambit of the present invention.

An emulsifying agent is intended to mean a compound that aids the formation of an emulsion. An emulsifier can be used to wet the corticosteroid and make it more amenable to dissolution. Emulsifiers for use herein include, but are not limited to, polyoxyethylene sorbitan fatty esters or polysorbates, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan mono-oleate, polyoxyethylene (20) sorbitan monopalmitate, polyoxyethylene (20) sorbitan monostearate; lecithins; alginic acid; sodium alginate; potassium alginate; ammonium alginate; calcium alginate; propane-1,2-diol alginate; agar; carrageenan; locust bean gum; guar gum; tragacanth; acacia; xanthan gum; karaya gum; pectin; amidated pectin; ammonium phosphatides; microcrystalline cellulose; methylcellulose; hydroxypropylcellulose; hydroxypropylmethylcellulose; ethylmethylcellulose; carboxymethylcellulose; sodium, potassium and calcium salts of fatty acids; mono- and di-glycerides of fatty acids; acetic acid esters of mono- and di-glycerides of fatty acids; lactic acid esters of mono- and di-glycerides of fatty acids; citric acid esters of mono- and di-glycerides of fatty acids; tartaric acid esters of mono- and di-glycerides of fatty acids; mono- and diacetyltartaric acid esters of mono- and di-glycerides of fatty acids; mixed acetic and tartaric acid esters of mono- and di-glycerides of fatty acids; sucrose esters of fatty acids; sucroglycerides; polyglycerol esters of fatty acids; polyglycerol esters of polycondensed fatty acids of castor oil; propane-1,2-diol esters of fatty acids; sodium stearoyl-2-lactylate; calcium stearoyl-2-lactylate; stearoyl tartrate; sorbitan monostearate; sorbitan tristearate; sorbitan monolaurate; sorbitan monooleate; sorbitan monopalmitate; extract of quillaia; polyglycerol esters of dimerised fatty acids of soya bean oil; oxidatively polymerised soya bean oil; and pectin extract.

As used herein, the term "stabilizer" is intended to mean a compound used to stabilize the therapeutic agent against physical, chemical, or biochemical process that would reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate, sodium saccharin and other known to those of ordinary skill in the art.

As used herein, the term "viscosity modifier" is intended to mean a compound or mixture of compounds that can be used to adjust the viscosity of an aqueous liquid composition of the invention. The viscosity modifier can increase or decrease the viscosity. Suitable viscosity modifiers include HPMC, CMC (sodium carboxymethylcellulose), glycerin, PEG and others recognized by artisans in the field. In some embodiments, the composition excludes HPMC.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those of ordinary skill in the art. Other tonicity modifiers include both inorganic and organic tonicity adjusting agents. Tonicity modifiers include, but are not limited to, ammonium carbonate, ammonium chloride, ammonium lactate, ammonium nitrate, ammonium phosphate, ammonium sulfate, ascorbic acid, bismuth sodium tartrate, boric acid, calcium chloride, calcium disodium edetate, calcium gluconate, calcium lactate, citric acid, dextrose, diethanolamine, dimethylsulfoxide, edetate disodium, edetate trisodium monohydrate, fluorescein sodium, fructose, galactose, glycerin, lactic acid, lactose, magnesium chloride, magnesium sulfate, mannitol, polyethylene glycol, potassium acetate, potassium chlorate, potassium chloride, potassium iodide, potassium nitrate, potassium phosphate, potassium sulfate, proplyene glycol, silver nitrate, sodium acetate, sodium bicarbonate, sodium biphosphate, sodium bisulfite, sodium borate, sodium bromide, sodium cacodylate, sodium carbonate, sodium chloride, sodium citrate, sodium iodide, sodium lactate, sodium metabisulfite, sodium nitrate, sodium nitrite, sodium phosphate, sodium propionate, sodium succinate, sodium sulfate, sodium sulfite, sodium tartrate, sodium thiosulfate, sorbitol, sucrose, tartaric acid, triethanolamine, urea, urethan, uridine and zinc sulfate. In some embodiments, the tonicity of the liquid formulation approximates the tonicity of the tissues in the respiratory tract.

An osmotic agent can be used in the compositions to enhance the overall comfort to the patient upon delivery of the corticosteroid composition. Osmotic agents can be added to adjust the tonicity of SAE-CD containing solutions. Osmolality is related to concentration of SAE-CD in water. At SBE7-β-CD concentrations below about 11-13% w/v, the solutions are hypotonic or hypoosmotic with respect to blood and at SBE7-β-CD concentrations above about 11-13% w/v the SBE7-β-CD containing solutions are hypertonic or hyperosmotic with respect to blood. When red blood cells are exposed to solutions that are hypo- or hypertonic, they can shrink or swell in size, which can lead to hemolysis. SBE-CD is less prone to induce hemolysis than other derivatized cyclodextrins. Suitable osmotic agents include any low molecular weight water-soluble species pharmaceutically approved for nasal delivery such as sodium chloride, lactose and glucose. The formulation of the invention can also include biological salt(s), potassium chloride, or other electrolyte(s).

As used herein, the term "antifoaming agent" is intended to mean a compound or compounds that prevents or reduces the amount of foaming that forms on the surface of the liquid formulation. Suitable antifoaming agents include dimethicone, simethicone, octoxynol, ethanol and others known to those of ordinary skill in the art.

As used herein, the term "bulking agent" is intended to mean a compound used to add bulk to the lyophilized product and/or assist in the control of the properties of the formulation during lyophilization. Such compounds include, by way of example and without limitation, dextran, trehalose, sucrose, polyvinylpyrrolidone, lactose, inositol, sorbitol, dimethylsulfoxide, glycerol, albumin, calcium lactobionate, and others known to those of ordinary skill in the art.

A solubility-enhancing agent or solubility enhancer can be added to the formulation of the invention. A solubility-enhancing agent is a compound, or compounds, that enhance (s) the solubility of the corticosteroid when in an aqueous liquid carrier. When another solubility enhancing agent is present, the ratio of SAE-CD to corticosteroid can be changed, thereby reducing the amount of SAE-CD required to dissolve the corticosteroid. Suitable solubility enhancing agents include one or more cyclodextrins, cyclodextrin derivatives, SAE-CD, organic solvents, detergents, soaps, surfactant and other organic compounds typically used in parenteral formulations to enhance the solubility of a particular agent. Exemplary solubility enhancers are disclosed in U.S. Pat. No. 6,451,339; however, other surfactants used in the pharmaceutical industry can be used in the formulation of the invention. Some suitable cyclodextrin include underivatized cyclodextrins and cyclodextrin derivatives, such as SAE-CD, SAE-CD derivatives, hydroxyalkyl ether cyclodextrin and derivatives, alkyl ether cyclodextrin and derivatives, sulfated cyclodextrin and derivatives, hydroxypropyl-β-cyclodextrin, 2-HP-β-CD, methyl-β-cyclodextrin, carboxyalkyl thioether derivatives, succinyl cyclodextrin and derivatives, and other cyclodextrin suitable for pharmaceutical use. SAE-CD cyclodextrins are particularly advantageous.

Suitable surfactants include phospholipids, among other compounds, which include for example phosphocholines or phosphatidylcholines, in which the phosphate group is additionally esterified with choline, furthermore phosphatidyl ethanolamines, phosphatidyl inositols, lecithins. Other ionic surfactants which can serve as solubility-enhancing agents are, for example, sodium lauryl sulfate, sodium cetylstearyl sulfate, sodium (or calcium or potassium) docusate, medium and long chain fatty acids.

SAE-CD can serve as a taste-masking agent by complexation with poor-tasting molecule. For example, SAE-CD can complex with a bitter or sour tasting active agent in a composition of the invention to reduce the bitterness or sourness of the agent as compared to the uncomplexed active agent. Accordingly, "improved taste" or "taste-masking" is taken to mean a reduction in the bitterness or sourness of a composition or active agent. Active agents can differ in the native bitterness or sourness. For example, olopatadine is known to have reduced bitterness as compared to azelastine. The invention includes taste-masked embodiments, wherein the SAE-CD is complexed with an active agent having reduced bitterness or reduced sourness as compared to another active agent.

In some embodiments, the methods, systems, devices, and compositions of the invention are associated with improved taste of a therapeutic agent as compared to the therapeutic agent alone or in existing formulations. In some embodiments, the improved taste is associated with administration of an antihistamine. In some embodiments, the improved taste is associated with administration of azelastine. The effectiveness of SAE-CD at masking the taste of a drug can be determined, for example, according to Example 31, which details the procedure used to conduct an electronic tongue study on a composition comprising SBE-β-CD and azelastine.

If desired, the composition further comprises an aqueous liquid carrier other than water. Suitable organic solvents that can be used in the formulation include, for example, ethanol, glycerin, poly(ethylene glycol), propylene glycol, poloxamer, aqueous forms thereof, others known to those of ordinary skill in the art and combinations thereof.

It should be understood that compounds used in the art of pharmaceutical formulations generally serve a variety of functions or purposes. Thus, if a compound named herein is mentioned only once or is used to define more than one term herein, its purpose or function should not be construed as being limited solely to that named purpose(s) or function(s).

A composition can be purged with an inert gas prior to storage to remove substantially all of the oxygen contained in the formulation. In general, the formulation or composition of the invention has a shelf-life of at least 6 months depending upon the intended use.

If needed, the SAE-CD-containing formulation can be prepared as a clear aqueous solution that can be sterile filtered through a filter having a pore size of 0.45 μm or less and that is stable and preserved under a variety of storage conditions. The invention thus provides a filtration-sterilized liquid formulation comprising a solution of the invention and a method of sterilizing a solution of the invention by sterile filtration through a filter. Sterile filtration can be done without substantial mass loss of solubilized corticosteroid, meaning less than 5% mass loss.

The formulation can be prepared at a temperature at or above 5° C., at or above 25° C., at or above 35° C., at or above 45° C. or at or above 50° C. Specific embodiments of the methods of preparing a liquid formulation include those wherein: 1) the method further comprises sterile filtering the formulation through a filtration medium having a pore size of 0.1 microns or larger; 2) the liquid formulation is sterilized by irradiation or autoclaving; and/or 3) the nebulization solution is purged with nitrogen or argon or other inert pharmaceutically acceptable gas prior to storage such that a substantial portion of the oxygen dissolved in, and/or in surface contact with the solution is removed.

An active agent contained within the present formulation can be present as its pharmaceutically acceptable salt. As used herein, "pharmaceutically acceptable salt" refers to derivatives of the disclosed compounds wherein the active agent is modified by reacting it with an acid or base as needed to form an ionically bound pair. Examples of pharmaceutically acceptable salts include conventional non-toxic salts or the quaternary ammonium salts of the parent compound formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. The pharmaceutically acceptable salts of the present invention can be synthesized from the parent active agent which contains a basic or acidic moiety by conventional chemical methods. Lists of other suitable salts are found in Remington's Pharmaceutical Sciences, 17$^{th}$. ed., Mack Publishing Company, Easton, PA, 2005, the relevant disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "patient" or "subject" are taken to mean humans and non-humans, such as mammals, for example, cats, dogs, mice, guinea pigs, horses, bovine cows, and sheep.

The utility and therapeutic efficacy of a nasal aqueous liquid composition according to the invention for the treatment of seasonal allergic rhinitis (SAR)/conjunctivitis (SARC) was demonstrated in a clinical trial conducted according to Example 33.

The time to target or peak therapeutic effect is the period of time after administration of a dose that it takes for the active agent to achieve the target or peak therapeutic effect, respectively, in a subject. The onset of a target or desired therapeutic effect is the point in time that the beginning of the target or desired therapeutic effect is first observed in the subject after administration of a composition.

In some embodiments, the compositions, methods, and systems of the invention relieve non-nasal symptoms sooner and to a greater degree than an aqueous suspension-based formulation comprising the same unit dose of corticosteroid and administered under substantially the same conditions but excluding SAE-CD. In some embodiments, the compositions and systems provide more rapid relief of nasal symptoms than the aqueous suspension based formulation. The compositions and systems of the invention also provide simplified manufacture, improved administered-dose uniformity, and improved taste-masking and odor-masking as compared to the aqueous suspension-based formulation. In some embodiments, the compositions, methods, and systems of the invention provide an enhanced and/or more rapid onset of a target or desired therapeutic effect and/or a more rapid time to target, desired or peak therapeutic effect as compared to the aqueous suspension-based compositions, methods, or systems excluding SAE-CD.

A therapeutic effect will be observed following administration of a composition. The onset of a target or desired therapeutic effect is the point in time that the beginning of the target or desired therapeutic effect is first observed in the subject after administration of a composition. In some embodiments, the onset of a target or desired therapeutic effect generally occurs within 0.1 min to 120 min, 1 min to 90 min, 1 min to 60 min, 1 min to 30 min, 1 min to 20 min, 1 min to 15 min, or 1 min to 10 min after nasal or ophthalmic administration of the composition.

In some embodiments, the time to a target or peak therapeutic effect can occur from minutes to hours after administration. In some embodiments, the time to target can occur from 8 to 10 hours, within 1 to 2 days, or within 1 to 2 weeks after nasal or ophthalmic administration of the composition, said administration being conducted according to a dosing regimen as detailed herein.

In some embodiments, the methods, systems, devices, and compositions of the invention comprise a combination of corticosteroid and azelastine with SAE-CD in a solution that is useful for treating nasal, non-nasal, and ocular symptoms. In some embodiments, the symptoms are allergic symptoms resulting from exposure of a subject to an airborne allergen.

A clinical study according to Example 34 was conducted to demonstrate the therapeutic efficacy of a nasal composition comprising budesonide, azelastine hydrochloride, CAPTISOL and buffer as compared to the sequential administration of RHINOCORT AQUA (RA) and ASTELIN (AST).

In some embodiments, the nasal compositions, systems, and methods of the invention comprising a corticosteroid, SAE-CD and an antihistamine provides a therapeutic effect (clinical benefit) that approximates or is enhanced over the therapeutic effect provided by the separate and sequential nasal administration of: a) an aqueous suspension composition comprising the same unit dose of corticosteroid; and b) an aqueous composition comprising the same unit dose of antihistamine. In some embodiments, the therapeutic effect is relief of nasal, non-nasal and ocular allergic symptoms. In some embodiments, the nasal composition, system and method of the invention provide an improved quality of life in subjects suffering from an allergic disorder, such as SAR and/or SARC.

The compositions, methods, and systems of the invention can provide an enhanced therapeutic effect as compared to a suspension-based aqueous formulation of corticosteroid. The enhanced therapeutic effect can be: 1) enhanced or better relief of non-nasal symptoms (especially ocular symptoms); 2) a more rapid onset of therapeutic effect; 3) a more rapid time to peak or target therapeutic effect; 4) more rapid relief of nasal symptoms; 5) enhanced or better relief of nasal symptoms; 6) more rapid relief of non-nasal symptoms; 7) enhanced quality of life, especially emotional status or practical problems; and/or 8) reduced corticosteroid-related side effects, such as epistaxis, dryness, or burning.

In some embodiments, the corticosteroid solutions of the invention provide more rapid relief of a symptom or disorder, such as an allergic symptom or disorder, when compared with a corticosteroid suspension at the same unit dose and under substantially similar conditions. In some embodiments, the corticosteroid solutions of the invention provide a rate of relief that is about 25%, about 35%, about 45%, about 50%, about 60%, or about 75% more rapid when compared with a corticosteroid suspension at the same unit dose and under substantially similar conditions. In some embodiments, the corticosteroid solutions of the invention provide a rate of relief that is about 1.2-fold greater, about 1.5-fold greater, about 2-fold greater, about 2.5-fold greater, about 3-fold greater, about 4-fold greater, or about 5-fold greater than a corticosteroid suspension at the same unit dose and under substantially similar conditions.

An in vivo study according to Example 41 was conducted in rabbits to compare the ability of budesonide to provide an anti-inflammatory therapeutic effect or other clinical benefit.

In some embodiments, the corticosteroid solutions of the methods, systems, devices, and compositions of the present inventions are administered ophthalmically for the treatment of ocular symptoms. In some embodiments, the corticosteroid solutions of the inventions are administered for the treatment of nasal symptoms when administered ophthalmically.

In some embodiments, the corticosteroid solutions of the invention provide more rapid relief in the treatment of ocular and nasal symptoms compared to other corticosteroid solutions or suspensions at the same unit dose when administered ophthalmically. In some embodiments, the ocular symptom is inflammation. In some embodiments, the corticosteroid solutions of the invention allow for a more rapid reduction in ocular inflammation compared to other corticosteroid solutions or suspensions when administered ophthalmically. In some embodiments, the corticosteroid solutions of the invention provide more rapid relief of total ocular symptoms based on a Total Ocular Symptom Score (TOSS) using a visual analogue scale (TOSS-VAS) of subjects or a five point scale (0-4) of subjects with allergic conjunctivitis exposed to controlled ragweed pollen using an EEC model compared with other corticosteroid solutions or suspensions at the same unit dose when administered ophthalmically. In some embodiments, the corticosteroid solutions of the invention provide a greater relief of TNSS compared with other corticosteroid solutions or suspensions at the same unit dose when administered ophthalmically. In some embodiments, the corticosteroid solutions of the invention provide more rapid onset of action in the treatment of allergic rhinitis compared with other corticosteroid solutions or suspensions at the same unit dose when administered ophthalmically. In some embodiments, the corticosteroid solutions of the invention provide a reduced dose of corticosteroid to elicit an equivalent or greater therapeutic effect as provided by other corticosteroid solutions or suspensions at higher unit doses when administered ophthalmically. In some embodiments, the corticosteroid solutions of the invention provide improved dose uniformity among separate unit doses compared to unit doses provided by other corticosteroid solutions or suspensions when administered ophthalmically. In some embodiments, the corticosteroid solutions of the invention are more easily manufactured than other corticosteroid solutions or suspensions for ophthalmic administration. In some embodiments the corticosteroid solution for ophthalmic administration comprises one or more additional therapeutic agents, such as an antihistamine. In some embodiments, the corticosteroid solution additionally comprises azelastine.

When comparing the performance of a liquid composition of the invention to the performance of a suspension-based composition, it is assumed that administration of the two compositions will be conducted using the same administration device, the same unit dose or total dose, substantially the same dosing regimen, and/or substantially the same administration procedure.

All the various embodiments or options described herein can be combined in any and all variations. In some embodiments, the subject invention comprises combinations of SAE-CD, corticosteroid and a pharmaceutically acceptable aqueous liquid carrier, which specifically exclude one or more (but not all) of the SAE-CDs and one or more (but not all) of the corticosteroids described herein. In additional embodiments, the subject invention may comprise combinations of SAE-CDs, corticosteroids, antihistamines and an aqueous liquid carrier, said combinations specifically excluding one or more of the antihistamines described herein.

The following examples should not be considered exhaustive, but merely illustrative of only a few of the many embodiments contemplated by the present invention.

Example 1

Exemplary formulations according to the invention were made according to the following general procedures.

Method A

Cyclodextrin is dissolved in water (or buffer) to form a solution containing a known concentration of cyclodextrin. This solution is mixed with an active agent in solid, suspension, gel, liquid, paste, powder or other form while mixing, optionally while heating to form a solution.

Method B

A known amount of substantially dry cyclodextrin is mixed with a known amount of substantially dry active agent. A liquid is added to the mixture to form a suspension, gel, solution, syrup or paste while mixing, optionally while heating and optionally in the presence of one or more other excipients, to form a solution.

Method C

A known amount of substantially dry cyclodextrin is added to a suspension, gel, solution, syrup or paste comprising a known amount of active agent while mixing, optionally while heating and optionally in the presence of one or more other excipients, to form a solution.

The methods of this example can be modified by the inclusion of a wetting agent in the composition in order to facilitate dissolution and subsequent inclusion complexation of the corticosteroid. A surfactant, soap, detergent or emulsifying agent can be used as a wetting agent.

Method D

To a solution comprising a known concentration or amount of SAE-CD, aqueous liquid carrier, and optionally one or more other excipients, is added a molar excess of the corticosteroid based upon the molar ratio of SAE-CD to corticosteroid at the point of saturated solubility of the corticosteroid, in the presence of the SAE-CD, as determined herein. For example, corticosteroid would be added at a 5%, 10%, 15%, 20%, 25%, 30% or greater molar excess. The components are mixed until equilibration, the point at which there is only a minor change in the concentration of budesonide over a one-hour period of time. Then, the excess corticosteroid is removed leaving behind the target solution of the invention.

The budesonide is added to the SAE-CD-containing solution as either a solid or suspension in an aqueous liquid carrier, which can be water, buffer, aqueous alcohol, aqueous organic solvent or a combination thereof. The alcohol and organic solvent are of a pharmaceutically acceptable grade, such as ethanol, propylene glycol, and others as described herein.

Method E

The SAE-CD and corticosteroid are triturated to form a mixture. Then, an aqueous liquid carrier is added to the mixture form the target solution of the invention.

The trituration can be conducted dry or in the presence of moisture, water, buffer, alcohol, surfactant, organic solvent, glycerin, poly(ethylene glycol), poloxamer, or a combination thereof.

Method F

Any of the methods herein are conducted in the presence of heat, e.g. at a temperature of least 40° C.

Method G

Any of the methods herein are conducted with cooling, e.g. at a temperature of less than 20° C. or less than 10° C. or less than 5° C.

Method H

Any of the methods herein are conducted in the presence of high shear mixing such as with a sonicator, narrow gauge syringe(s), mixer/homogenizer (POLYTRON from KINEMATICA, Europe; FLUKO, Shanghai, China; ULTIMA-GRAL from GEA Niro, Inc., Columbia, MD), rotor-stator mixer, or saw tooth mixer.

Method I

Any of the methods herein are conducted under reduced pressure.

Method J

The aqueous corticosteroid solution can be prepared by diluting a concentrated corticosteroid solution with water, buffer, or other aqueous liquid carrier.

Example 2

The MMD of nebulized solutions containing SBE7-β-CD and budesonide was determined as follows.

Placebo solutions of three different cyclodextrins were prepared at different concentrations. Two mL of the solutions were added to the cup of a Pari LC Plus nebulizer supplied with air from a Pari Proneb Ultra compressor. The particle size of the emitted droplets was determined using a Malvern Mastersizer S laser light scattering instrument.

Example 3

The content of corticosteroid in aqueous solutions containing SAE-CD was determined by HPLC chromatography of aliquots periodically drawn from the liquid in storage.

Citrate-phosphate (McIlvaines) buffer solutions at a pH of 4, 5, 6, 7, or 8 were prepared by mixing various portions of 0.01M citric acid with 0.02 M $Na_2HPO_4$. These stock solutions contained 5% w/w CAPTISOL. Approximately 250 μg/mL of budesonide was dissolved in each buffer solution. Aliquots of the solutions were stored at 40° C., 50° C. and 60° C. Control samples were stored at 5° C. but are not reported here. HPLC analysis of the samples was performed initially and after 1, 2, and 3 months storage.

The HPLC conditions included:

| | |
|---|---|
| Instrument: | PE Series 200 |
| Column: | Phenomenex Luna C18(2) 4.6 × 150 mm 3 um |
| Mobile Phase: | 58% Phosphate Buffer pH 3.4/39.5% ACN/ 2.5% MeOH |
| Mobile Phase Program: | 100% A (isocratic) |
| Wavelength | 240 |
| Flow Rate: | 0.6 mL/min |
| Standard Range: | Seven standards - 1 to 500 μg/mL |

Example 4

The viscosity of aqueous solutions containing SAE-CD was measured using a cone and plate viscometer.

A Brookfield Programmable DV-III+ Rheometer, CPE-40 cone and CPE 40Y plate (Brookfield Engineering Laboratories, Middleboro, MA) was used to make measurements on 0.5 mL samples at 1, 2, 3, 5 and 10 rpm. Samples were sheared for approximately 5 revolutions prior to each measurement. This allowed accurate rheological characterization of the samples. The temperature of all samples was equilibrated to 25+/−1 degree centigrade using a double wall viscometer cone supplied with water from an electronically controlled thermostatic circulating water bath (Model, 8001, Fisher Scientific, Pittsburgh, PA). The viscometer was calibrated using 5 and 50 centipoise using silicon oil calibration standards. Viscosity measurements were made at 5 or more rotation speeds to look for sheer thinning behavior (viscosities that decrease as the rate of sheer increases). Higher rotation speeds result in increased rates of shear.

Example 5

Nebulizer output rate as a function of SAE-CD concentration was measured according to the following general procedure.

Nebulizer Output was tested using Pari LC Plus Nebulizer with a Pari ProNeb Ultra Air Compressor (Minimum Nebulizer Volume=2 mL, Maximum Nebulizer Volume=8 mL) for solutions containing 43%, 21.5%, 10.75% and 5.15% w/w SBE7-β-CD. Percentage of sample emitted was estimated gravimetrically. The nebulizer cup was weighed before and after nebulization was complete. Nebulization Time was defined as the duration of time when nebulizer run was started until the time of first sputter. Nebulizer Output Rate was calculated by dividing % Emitted with Nebulization Time.

Example 6

Preparation of a solution containing budesonide.

A buffer solution containing 3 mM Citrate Buffer and 82 mM NaCl at pH 4.45 is prepared. ~12.5 grams of CAPTISOL was placed into a 250 mL volumetric flask. ~62.5 mg of budesonide was placed into the same flask. Flask was made to volume with the 3 mM citrate buffer/82 mM NaCl solution. The flask was well-mixed on a vortexer for 10 minutes and sonicated for 10 minutes. The flask was stirred over weekend with magnetic stirrer. Stirring was stopped after ~62 hours and flask was revortexed and resonicated again for 10 minutes each. The solution was filtered through a 0.22 μm Durapore Millex-GV Millipore syringe filter unit. The first few drops were discarded before filter rest of solution into an amber glass jar with a Teflon-lined screw cap. Sample concentration was ~237 μg/mL.

Example 7

Preparation of a solution containing budesonide.

Approximately 5 grams of CAPTISOL was placed into a 100 mL volumetric flask. ~26.3 mg of budesonide was placed into the same flask. The flask was made to volume with the 3 mM citrate buffer/82 mM NaCl solution. The mixture was well-mixed on a vortexer for 10 minutes and sonicated for 10 minutes. The mixture was stirred overnight with a magnetic stirrer. Stirring was stopped after ~16 hours and flask was revortexed and resonicated again for 10 minutes each. The solution was filtered through 0.22 μm Durapore Millex-GV Millipore syringe filter unit. The first 5 drops were discarded before filter rest of solution into an amber glass jar with a Teflon-lined screw cap. Sample was analyzed to be 233 µg budesonide/mL.

Example 8

Preparation of a solution containing budesonide.

The procedure of Example 7 was followed except that 12.5 g of CAPTISOL, 62.5 mg of budesonide and about 250 mL of buffer were used. Sufficient disodium EDTA was added to prepare a solution having an EDTA concentration of about 0.01 or 0.05% wt/v EDTA.

Example 9

Preparation of a solution containing SAE-CD and budesonide as prepared from a PULMICORT RESPULES suspension.
Method A To the contents of one or more containers of the PULMICORT RESPULES (nominally 2 mL of the suspension), about 50 mg (corrected for water content) of CAPTISOL was added per mL of Respule and mixed or shaken well for several minutes. After standing from about 30 minutes to several hours, the solution was used as is for in vitro characterization. In addition to budesonide and water, the PULMICORT RESPULE (suspension) also contains the following inactive ingredients per the label: citric acid, sodium citrate, sodium chloride, disodium EDTA and polysorbate 80.
Method B Weigh approximately 200 mg amounts of CAPTISOL (corrected for water content) into 2-dram amber vials. Into each vial containing the weighed amount of CAPTISOL empty the contents of two PULMICORT RESPULES containers (0.5 mg/2 mL, Lot #308016 Feb05) by gently squeezing the deformable plastic container to the last possible drop. The Respules were previously swirled to re-suspend the budesonide particles. The vials are screw capped, mixed vigorously by vortex and then foil wrapped. The material can be kept refrigerated until use.

The liquid composition prepared according to any of these methods can be used in any known administration device. By converting the suspension to a liquid, an improvement in delivery of budesonide (a corticosteroid) is observed.

Example 10

Other solutions according to the invention can be prepared as detailed below.

| Component | Mg per mL (as prepared) Concentrate A | Mg per mL (as prepared) Concentrate B | Mg per mL (per target) Final Solution |
|---|---|---|---|
| Budesonide EP | 1 | ~1.6 (sat'd) | 0.250 |
| CAPTISOL | 200 | 200 | 50 |
| Sodium Citrate tribasic dihydrate | 0 | 0 | 0.44 |
| Citric Acid | 0 | 0 | 0.32 |
| Sodium Chloride | 0 | 0 | 4.8 |
| Disodium EDTA | 0 | 0 | 0-0.5 |
| Polysorbate 80 (TWEEN 80) | 0 | 0 | 0-1 |
| Water | Qs | Qs | QS with buffer containing CAPTISOL or budesonide |

Dilute Concentrate A at a ratio of 1 to 4 with pH 4.5 salinated citrate buffer (4 mM containing 109 mM sodium chloride) to contain 5% w/v CAPTISOL on an anhydrous basis. Filter the diluted concentrate through a 0.22 µm Millipore Durapore Millex-GV syringe filter unit. Assay the filtered solution by HPLC then add supplemental budesonide as needed to give a solution final concentration of about 250 µg/mL (±<5%).

Dilute Concentrate B at a ratio of 1 to 4 with pH 4.5 salinated citrate buffer (4 mM containing 109 mM sodium chloride) to contain 5% w/v CAPTISOL on an anhydrous basis. Filter the diluted concentrate through a 0.22 µm Millipore Durapore Millex-GV syringe filter unit. Assay the filtered solution by HPLC then dilute further with pH 4.5 salinated citrate buffer (3 mM containing 82 mM sodium chloride containing 5% w/v CAPTISOL) as required to give a final solution concentration of about 250 µg/mL (±<5%). This technique takes advantage of the excess solid budesonide used to saturate the solution.

Example 11

Clarity of solutions was determined by visual inspection or instrumentally. A clear solution is at least clear by visual inspection with the unaided eye.

Example 12

The following method was used to determine the performance of nebulization compositions emitted from a nebulizer.

Two mL of the test CD solution or Pulmicort suspension was accurately pipetted by volumetric pipettes into a clean nebulizer cup prior to starting each experiment. The test nebulizer was assembled and charged with the test solution or suspension according to the manufacturer instructions. The end of the mouthpiece was placed at a height of approximately 18 cm from the platform of the MALVERN MASTERSIZER to the middle point of tip of the nebulizer mouthpiece. A vacuum source was positioned opposite the mouthpiece approximately 6 cm away to scavenge aerosol after sizing. The distance between the mouthpiece and the detector was approximately 8 cm. The center of the mouthpiece was level with the laser beam (or adjusted as appropriate, depending on the individual design of each nebulizer). The laser passed through the center of the emitted cloud when the nebulizer was running. Measurements were manually started 15 seconds into nebulization. Data collection started when beam obscuration reached 10% and was averaged over 15,000 sweeps (30 seconds). Scattered light intensity data on the detector rings was modeled using the "Standard-Wet" model. Channels 1 and 2 were killed due to low relative humidity during measurement to prevent beam steering. The volume diameter of droplets defining 10, 50 (volume median), and 90% of the cumulative volume undersize was determined. (Dv10 is the size below which 10% of the volume of material exists, Dv50 is the size below which 50% of the volume of material exists and Dv90 is the size below which 90% of the volume of material exists.

The procedure above can be practiced with slight modification on a MALVERN SPRAYTEC to determine the particle size of droplets emitted by a nebulizer.

Example 13

Solutions of budesonide with and without SBE7-β-CD were prepared at two different pHs (4 and 6) and stored at 2 different temperatures (60° C. and 80° C.). Citrate buffers (50 mM) at each pH value were prepared by mixing differing portions of 50 mM citric acid and 50 mM sodium citrate (tribasic, dihydrate) solutions. To achieve a concentration of budesonide in the buffers without SBE7-β-CD sufficient for accurate measurement, the budesonide was dissolved first in 100% ethyl alcohol. An aliquot of the ethanol/budesonide solution was then added drop-wise with stirring to each buffer solution. The theoretical budesonide concentration was 100 μg/mL with a final ethanolic content of 5% in each buffer. All solution preps and procedures involving budesonide were done in a darkened room under red light. After shaking solutions for 24 hours, both buffer solutions were filtered through Millipore Millex-GV 0.22 μm syringe filters to remove any solid that had precipitated (no significant amounts observed) from the solutions. The final budesonide concentration was about 50 μg/mL. Both the pH 4 and 6 solutions were split in two, and solid SBE7-β-CD was added to one of the portions to create solutions with and without 1% w/v SBE7-β-CD at each pH. Each solution was aliquoted into individual amber vials. They were then placed in ovens at 60° C. and 80° C. Sample vials were removed from the ovens and analyzed by HPLC at 0, 96, 164, and 288 hours. The HPLC assay conditions are summarized below.

Chromatographic Conditions
(Adapted from Hou, S., Hindle, M., and Byron, P. R. A. Stability-Indicating HPLC Assay Method for Budesonide. *Journal of Pharmaceutical and Biomedical Analysis*, 2001; 24: 371-380.)

| Instrument: | PE Series 200 |
|---|---|
| Column: | Phenomenex Luna C18(2) 4.6 × 150 mm 3 um |
| Mobile Phase: | 58% Phosphate Buffer pH 3.4/39.5% ACN/2.5% MeOH |
| Mobile Phase Program: | 100% A (isocratic) |
| Wavelength | 240 nm |
| Flow Rate: | 0.6 mL/min |
| Standard Range: | Seven standards - 1 to 500 μg/mL |

Example 14

Preparation of solution comprising SAE-CD (10% wt.), budesonide (500 μg/mL), and azelastine hydrochloride (0.2% wt.).

CAPTISOL (2.37 g) was weight into an amber vial. Azelastine hydrochloride (43.8 mg) was weighed into the same vial. PULMICORT NEBUAMPs (10) were mixed vigorously for 1 min. The contents of each NEBUAMP were dispensed into the amber vial containing CAPTISOL and azelastine and mixed by vortexing, shaking, sonication and overnight mixing on a roller mixer to permit equilibration. The resulting solution was clear.

Example 15

The temperature stability of the composition of Example 14 was determined as follows.

The solution of Example 14 was divided into vials and grouped and stored at 25° C., 40° C., or 60° C. A control sample was stored at 5° C. The samples were stored for 10 days and two vials were removed for analysis at 0, 3, and 10 days. Assay samples were prepared by drawing one aliquot from each vial, diluting 2004 with 8004 of mobile phase (see below), and assaying the samples by HPLC according to the European Pharmacopeia, Monograph 1633E for "azelastine hydrochloride" (version 5.0 corrected 01/2005).

Example 16

The pH and temperature stability of an aqueous liquid composition comprising SAE-CD, azelastine, and buffer were determined as follows.

Aqueous solutions comprising azelastine HCl (0.5 mg/mL) with and without CAPTISOL (1.75% wt.) were prepared. Stock citrate solutions (sodium citrate (3 mM) and citric acid solution (3 mM); 500 mL each) were prepared. The citrate solutions were combined and titrated to prepare stock buffered solutions (at least 150 mL each) having a pH of 4, 5, or 6. A stock solution of azelastine hydrochloride (5 mg/mL) in water was prepared. Assay solutions comprising CAPTISOL, azelastine and buffer were prepared by mixing CAPTISOL (1.4 g) and stock solution of azelastine (7.5 mL) in stock buffered solution (QS to final volume of 75 mL for each different pH). Assay solutions comprising azelastine and buffer were prepared by mixing stock solution of azelastine (7.5 mL) and stock buffered solution (67.5 mL, or QS to final volume of 75 mL). Six assay solutions were prepared as follows: 1) pH 4-azelastine only; 2) pH 4-azelastine+CAPTISOL; 3) pH 5-azelastine only; 4) pH 5-azelastine+CAPTISOL; 5) pH 6-azelastine only; 6) pH 6-azelastine+CAPTISOL. Portions of each assay solution were stored at 25° C., 40° C., and 60° C. for a period of sixteen weeks. Aliquots of the assay solutions were taken at 0, 1, 2, 4, 8, 12, and 16 weeks. The aliquots were assayed by HPLC as described herein. Control samples for each assay solution were stored at 5° C. to provide reference points.

Example 17

Exemplary compositions of the invention packaged in various multi-dose volume metered dose pump spray devices are made to include the following ingredients in the amounts specified according to the procedure below.

| Ingredient | Function | 50 μL Spray (mg/mL) | 70 μL Spray (mg/mL) | 100 μL Spray (mg/mL) | 137 μL Spray (mg/mL) |
|---|---|---|---|---|---|
| Budesonide | Active Substance | 0.64 | 0.46 | 0.32 | 0.234 |
| CAPTISOL | Solubilizer/Stabilizer | 96 | 68 | 48 | 36 |
| Disodium edetate, | Antioxidant | 0.1 | 0.1 | 0.1 | 0.1 |
| Sodium chloride, | Tonicity modifier | 0 | 27 | 45 | 56 |
| Citric acid, | Buffer | 0.3 | 0.3 | 0.3 | 0.3 |
| Sodium citrate dihydrate | Buffer | 0.5 | 0.5 | 0.5 | 0.5 |
| Polysorbate 80 0.05 mg/mL | Surfactant | optional | optional | optional | optional |

| Ingredient | Function | 50 µL Spray (mg/mL) | 70 µL Spray (mg/mL) | 100 µL Spray (mg/mL) | 137 µL Spray (mg/mL) |
|---|---|---|---|---|---|
| Potassium Sorbate 1 mg/mL | Antimicrobial | optional | optional | optional | optional |
| Sterile water for injection, | Solvent | q.s. to 1.0 mL | q.s. to 1.0 mL | q.s. to 1.0 mL | q.s. to 1.0 mL |

| Ingredient | Function | 50 µL Spray (mg/mL) | 70 µL Spray (mg/mL) | 100 µL Spray (mg/mL) | 137 µL Spray (mg/mL) |
|---|---|---|---|---|---|
| Budesonide | Active Substance | 0.64 | 0.46 | 0.32 | 0.234 |
| Azelastine HCl | Active Substance | 2.74 | 1.96 | 1.37 | 1.00 |
| CAPTISOL | Solubilizer/Stabilizer | 128 | 91 | 64 | 48 |
| Disodium edetate, | Antioxidant | 0.1 | 0.1 | 0.1 | 0.1 |
| Sodium chloride, | Tonicity modifier | 0 | 27 | 45 | 56 |
| Citric acid, | Buffer | 0.3 | 0.3 | 0.3 | 0.3 |
| Sodium citrate dihydrate | Buffer | 0.5 | 0.5 | 0.5 | 0.5 |
| Polysorbate 80 0.05 mg/mL | Surfactant | optional | optional | optional | optional |
| Potassium Sorbate 1 mg/mL | Antimicrobial | optional | optional | optional | optional |
| Sterile water for injection, | Solvent | q.s. to 1.0 mL | q.s. to 1.0 mL | q.s. to 1.0 mL | q.s. to 1.0 mL |

Compositions comprising the specified concentrations of ingredients are prepared and packaged into multi-dose metered volume pump spray devices. The compositions optionally comprise potassium sorbate at a concentration of about 1 mg/mL and/or polysorbate 80 at a concentration of about 0.005%. Each package contains approximately 120 doses plus an overfill of the composition. Suitable packages for the specified spray volumes include:
1. 50 µL Spray volume: 9 mL of composition in a 10 mL bottle; for example 20242 02 001 diagnostic 6/8 amber glass type 1 400 20 neck finish bottle fitted with Nasal Spray Pump having a 50 µL dose volume, 20/400 screw closure, and 42.0 mm dip tube length;
2. 70 µL Spray volume: 13 mL of composition in a 15 mL amber glass bottle;
3. 100 µL Spray volume: 17 mL of composition in a 20 mL amber glass vial;
4. 137 µL Spray volume: 24 mL of composition in a 24 mL amber glass vial.

Example 18

Comparative evaluation of various forms of SAE-CD in the solubilization of corticosteroid derivatives.

The solubility of beclomethasone dipropionate (BDP), beclomethasone 17-monopropionate (B17P), beclomethasone 21-monopropionate (B21P) and beclomethasone (unesterified) in solutions containing CAPTISOL and various $SBE_n\gamma$-CD was evaluated. BDP, B17P and B21P were obtained from Hovione. Beclomethasone was obtained from Spectrum Chemicals. CAPTISOL, SBE(3.4) γ-CD, SBE (5.23) γ-CD and SBE(6.1) γ-CD were provided by CyDex, Inc. (Lenexa, KS). γ-CD was obtained from Wacker Chemical Co. SBE(5.24) γ-CD and SBE(7.5) γ-CD were provided by the University of Kansas.

A 0.04M solution of each selected CD was prepared. Each form of beclomethasone required 2 mL of CD solution, therefore the 0.04M solutions were prepared in 20 or 25 mL volumetric flasks in duplicate (N=2). The following table indicates the amount of each CD used after accounting for the content of water in each CD.

| CD | MW (g/mole) | mg of CD (volume) |
|---|---|---|
| SBE(6.7) β-CD | 2194.6 | 2297.0 (25 mL) |
| γ-CD | 1297 | 1433.0 (25 mL) |
| SBE(3.4) γ-CD | 1834.9 | 1891.6 (25 mL) |
| SBE(5.24) γ-CD | 2119.5 | 1745.7 (20 mL) |
| SBE(6.1) γ-CD | 2261.9 | 1866.8 (20 mL) |
| SBE(7.5) γ-CD | 2483.3 | 2560.0 (25 mL) |

Beclomethasone forms were weighed in amounts in excess of the anticipated solubilities directly into 2-dram Teflon-lined screw-capped vials. These amounts typically provided approximately 6 mg/mL of solids. Each vial then received 2 mL of the appropriate CD solution. The vials were vortexed and sonicated for about 10 minutes to aid in wetting the solids with the fluid. The vials were then wrapped in aluminum foil to protect from light and placed on a lab quake for equilibration. The vials were visually inspected periodically to assure that the solids were adequately being wetted and in contact with the fluid. The time points for sampling were at 24 hrs for all samples and 72 hours for BDP only.

Solutions of SBE(6.1) γ-CD were prepared at 0.04, 0.08, and 0.1M and solutions of SBE (5.23) γ-CD were prepared at only 0.04 and 0.08M. Beclomethasone dipropionate was weighed in amounts in excess of the anticipated solubilities directly into 2-dram teflon-lined screw-capped vials. These amounts typically provided approximately 2 mg/mL of solids. Each vial then received 2 mL of the appropriate CD solution (N=1). The vials were vortexed and sonicated for about 10 minutes to aid in wetting the solids with the fluid. The vials were then wrapped in aluminum foil to protect from light and placed on a lab quake for a five-day equilibration.

Solutions of γ-CD were prepared at 0.01 and 0.02M. Beclomethasone dipropionate was weighed in amounts in excess of the anticipated solubilities directly into 2-dram teflon-lined screw-capped vials. These amounts typically provided approximately 2 mg/mL of solids. Each vial then received 2 mLs of the γ-CD solution (N=2). A solution was also prepared to measure the intrinsic solubility of BDP using HPLC grade water in place of the CD. The samples were wrapped in foil and placed on a lab quake for five days.

At the end of the equilibration time for each stage, the vials were centrifuged and 1 mL of the supernatant removed. The removed supernatant was then filtered using the Durapore PVDF 0.22 μm syringe filter (discarded first few drops), and diluted with the mobile phase to an appropriate concentration within the standard curve. The samples were then analyzed by HPLC to determine concentration of solubilized corticosteroid. The data are detailed below.

| CD | Beclomethasone dipropionate (μg/mL) | Beclomethasone 17-mono-propionate (μg/mL) | Beclomethasone 21-mono-propionate (μg/mL) | Beclomethasone (unesterified) (μg/mL) |
|---|---|---|---|---|
| $SBE_{3.4}$ γ-CD | 0.04M → 336.8 | 0.04M → 10621.6 | 0.04M → 172.6 | 0.04M → 11360.2 |
| $SBE_{5.24}$ γ-CD | 0.04M → 267.0 | 0.04M → 9500.8 | 0.04M → 139.8 | 0.04M → 10949.9 |
| $SBE_{6.1}$ γ-CD | 0.04M → 243.8 | 0.04M → 11666.9 | 0.04M → 153.8 | 0.04M → 11007.0 |
| $SBE_{7.5}$ γ-CD | 00.04M → 168.5 | 0.04M → 8539.1 | 0.04M → 122.4 | 0.04M → 9635.2 |
| $SBE_{6.7}$ β-CD | 0.04M → 60.4 | 0.04M → 6799.6 | 0.04M → 50.6 | 0.04M → 6927.0 |
| γ-CD | 0.04M → 105.8 | 0.04M → 136.9 | 0.04M → 9.4 | 0.04M → 114.8 |

Figure 5:
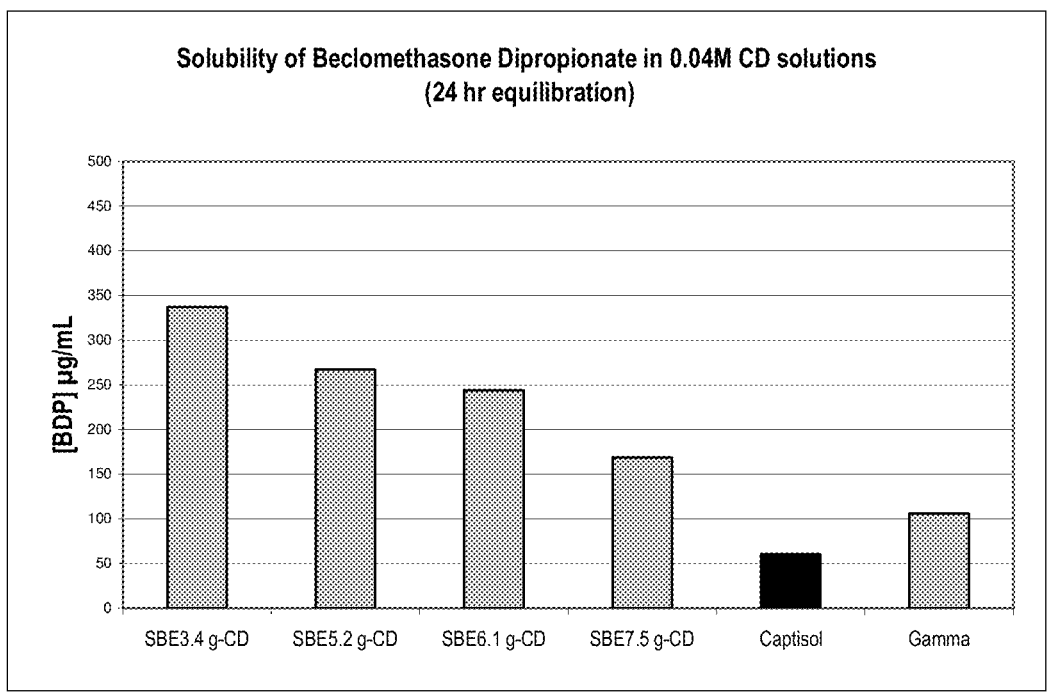
FIG. 5 depicts a bar chart summarizing the aqueous solubility of beclomethasone dipropionate in the presence of various SAE-CD derivatives.

The survey study shows that in the presence of SBE(3.4) γ-CD (0.04M), all of the forms of beclomethasone were at or near their highest solubilities. B17P, the active metabolite of BDP, has the highest solubility of the esterified beclomethasone forms in any of the derivatized CDs. The results indicate that SBE-γ-CD complexes with beclomethasone dipropionate better than CAPTISOL or γ-CD alone. Of the SAE-CD derivatives evaluated, the optimal degree of substitution of the SBE γ-CD that provides the greatest enhancement in solubility of BDP is DS=3.4, and solubility decreases almost linearly as the degree of substitution increases. This is true for both the 24 hr and 5 day equilibration times. In terms of BDP solubilization with SAE-CD: SBE(3.4)γ-CD>SBE(5.2)γ-CD>SBE(6.1)γ-CD>SBE(7.5)γ-CD>γ-CD>CAPTISOL (SBE7-β-CD). The data is summarized in FIG. 5. Therefore, it has been determined that SAE-γ-CD cyclodextrin derivatives are unexpectedly better at solubilizing corticosteroids than are SAE-β-CD derivatives. Formulations based upon SAE-γ-CD are suitable for use in the compositions of the invention.

Example 19

Determination of the phase solubility of budesonide in the presence of SAE-CD and azelastine hydrochloride.

A stock solution of citrate buffer (3 mM, pH 4.5) was prepared. Stock solutions of CAPTISOL in buffer having CAPTISOL present in the varying concentrations (10 mM, 20 mM, 30 mM, and 40 mM) were prepared by mixing appropriate amounts of CAPTISOL and the buffer stock solution. The stock solutions of CAPTISOL in buffer were used to prepare stock solutions of azelastine HCl/CAPTISOL/buffer having 1mg/mL, 1.37 mg/mL, 1.96 mg/mL, or 2.74 mg/mL azelastine HCl. Budesonide (at a concentration of 2 mg/mL) was added to the various stock solutions of azelastine HCl/CAPTISOL/buffer and mixed and allowed to equilibrate at ambient temperature for a period of four days. Any budesonide remaining suspended in the solutions was removed by filtration and the concentration of budesonide in each solution measured by HPLC as described herein. The results are depicted in FIG. 11A.

The above procedure was repeated with 10 mM, 15 mM and 20 mM solutions of SBE-γ-CD and only one concentration of azelastine HCl (2.74 mg/mL). The data are summarized in FIG. 11B.

Example 20

Exemplary compositions of the invention packaged in various multi-dose volume metered dose pump spray devices and nebulizers are made to include the following ingredients in the amounts specified according to the procedure below.

| Ingredient[1] | Function | For a 50 μL Spray (mg/mL) | For a 70 μL Spray (mg/mL) | For a 100 μL Spray (mg/mL) | 200 μL Ampoule (mg/mL) | 5000 μL Ampoule (mg/mL) |
|---|---|---|---|---|---|---|
| Mometasone Furoate | Active Substance | 1.0 | 0.71 | 0.50 | 1.00 | 0.1 |
| Olopatadine HCl | Active Substance | 13.3 | 9.5 | 6.65 | 26.6 | 1.3 |
| SBE γ-CD | Solubilizer-Stabilizer Nominal/Practical amts | 452/500 | 323/429 | 226/300 | 452/500 | 45.2/60 |
| Disodium edetate, dihydrate | Antioxidant | 0.1 | 0.1 | 0.1 | 0.1 | 0.1 |

-continued

| Ingredient[1] | Function | For a 50 µL Spray (mg/mL) | For a 70 µL Spray (mg/mL) | For a 100 µL Spray (mg/mL) | 200 µL Ampoule (mg/mL) | 5000 µL Ampoule (mg/mL) |
|---|---|---|---|---|---|---|
| Citric acid, | Buffer | 0.3 | 0.3 | 0.3 | 0.3 | 0.3 |
| Sodium citrate dihydrate | Buffer | 0.5 | 0.5 | 0.5 | 0.5 | 0.5 |
| Sterile water for injection, | Solvent | q.s. to 1.0 mL | q.s. to 1.0 mL | q.s. to 1.0 mL | q.s. to 1.0 mL | q.s. to 1.0 mL |

To prepare the above formulation, the mometasone furoate and olopatadine HCl are dissolved using SBE(6.1) γ-CD and citrate buffer at about pH 4.5. Vigorous mixing and sonication may be required for a day or more under an inert atmosphere to effect total dissolution. If after assaying the solution it is determined to be below the desired target for the active ingredients, additional active ingredient can be added to the solution and stirring continued. Once both drugs have dissolved completely in the CD solution, confirmed by assay, the product is filtered using a 0.22 µm PVDF filter. The solution is then dispensed under an inert atmosphere into a preservative free multidose container fitted with a suitable pump spray or filled into blow-fill-seal LDPE containers for use in a suitable nebulizer or as a drop. Optionally, compositions could contain potassium sorbate present at a concentration of about 1 mg/mL and or polysorbate 80 present at a concentration of about 0.005% and be filled in suitable multi dose containers and fitted with a suitable metering pump spray device.

Each package contains approximately 120 doses plus an overfill as defined herein. Suitable packages for the specified spray volumes include:

1. 50 µL Spray volume: 9 mL of composition in a 10 mL bottle; for example 20242 02 001 diagnostic 6/8 amber glass type 1 400 20 neck finish bottle fitted with Nasal Spray Pump having a 50 µL dose volume, 20/400 screw closure, and 42.0 mm dip tube length;
2. 70 µL Spray volume: 13 mL of composition in a 15 mL amber glass bottle;
3. 100 µL Spray volume: 17 mL of composition in a 20 mL amber glass vial;
4. 200 µL ampoule: a single blow-fill-seal LDPE (or comparable substance ampoule used for nebulization;
5. 5000 µL ampoule: a single blow-fill-seal LDPE (or comparable substance ampoule used for nebulization.

Example 21

Evaluation of the AERONEB GO nebulizer versus a RAINDROP nebulizer with a solution comprising budesonide, aqueous liquid carrier and SAE-CD.

The AERONEB GO nebulizer (AEROGEN Inc., Mountainview, California) is detailed in U.S. Pregrant Publication No. 2005-011514 to Power et al. (Application U.S. Ser. No. 10/833,932 filed Apr. 27, 2004), PCT International Publication No. WO 2005/009323 to Aerogen, Inc. et al. (PCT Application No. PCT/US2004/021268 filed Jul. 6, 2004), and European Application No. EP 16426276, the entire disclosures of which are hereby incorporated by reference.

The RAINDROP nebulizer is available from Nellcor (Tyco Healthcare).

The solution of the invention used for this study was prepared according to Example 28.

Characterization of droplet size distribution of an aerosolized solution using a cascade impactor was determined according to Example 26.

Determination of total drug output and drug output rate from a nebulizer containing a liquid of the invention was determined according to Example 27.

Example 22

Evaluation of the pulsating membrane nebulizer of U.S. Pat. No. 6,962,151 with a solution comprising budesonide, aqueous liquid carrier and SAE-CD. Inertial Impaction Characterization of $Tc^{99m}$-DTPA Labelled CAPTISOL-ENABLED Budesonide Aerosols Generated via a Pari Electronic Nebulizer The nebulizer detailed in U.S. Pat. No. 6,962,151, is also described in PCT International Application No. PCT/US00/29541 filed Oct. 27, 2000, and U.S. application Ser. No. 11/269,783 filed Nov. 7, 2005.

Aerosol characterization was conducted by standard in vitro inertial impaction tests using an Andersen Cascade Impactor (ACI). Technetium-99m ($^{99m}Tc$), in the form of diethylenetriaminepenta-acetic acid (DTPA, GE Healthcare), was added to the CAPTISOL-ENABLED Budesonide Nasal Solution (CEBUD). The suitability of $^{99m}Tc$-DTPA to function as a surrogate for budesonide in CEBUD preparations was validated in the course of an earlier clinical trial. Preparation of the budesonide solution formulation for testing was conducted as per the description below. It was calculated that approximately 10MBq of $^{99m}Tc$ should be added to the budesonide formulation (11.05 g) on the day of testing, in order to provide sufficient activity for in vitro imaging.

Two Pari electronic vibrating membrane nebulizers were used. At the core of this electronic nebulizer is a stainless steel membrane with thousands of laser drilled holes. Laser drilling allows flexibility to customize particle size, ensure reproducibility, and maintain a high output rate with smaller particles. The perforated membrane is vibrated at high frequencies in a resonant "bending" mode which yields high particle output rates. The nebulizer provides rapid drug delivery, efficiency, ideal particle sizing, low residual volume, and optimal performance matched to the drug formulation (See Rajiv Dhand, *Respiratory Care* 2002; (12): 1406-1416). Approximately 0.5 mL of drug solution was loaded and subsequently delivered via each nebulizer on 3 separate occasions. Runs 1, 3 and 5 were conducted with Device 1 and runs 2, 4 and 6 were conducted with Device 2.

Pre-Dose

On each occasion, prior to dose delivery, the filled nebulizer was imaged for 60 seconds on Head I of the dual head gamma camera (Axis, Philips Medical Systems). Also, the nebulizers were weighed before and after addition of the budesonide formulation.

Inertial Impaction Testing

The nebulizer was positioned at the USP (United States Pharmacopoeia) inlet of the ACI and a flow rate of 28.3 L/min was drawn through the impactor using a vacuum pump. Flow through the impactor was started prior to activation of the electronic nebulizer. A stopwatch was used in order to measure the duration of dose delivery.

The ACI test conditions were the same as those used for Pari LC Plus air-jet nebulizer evaluation in the course of the earlier clinical study.

Following deposition the USP throat was removed from the ACI and imaged for 120 seconds. The collection plates were removed from the impactor and placed on Head I of the gamma camera and imaged for 120 seconds. The plates were subsequently washed and dried before conduct of further impaction tests.

Post-Dose

On each occasion, the nebulizer weight was recorded after delivery of the dose. The nebulizer was imaged as described below.

Image Processing

A rectangular ROI was applied to image to the nebulizer pre-dose. This ROI was then re-applied to image the nebulizer after dose delivery.

A rectangular ROI was also applied to the USP Inlet image.

A circular ROI was drawn around collection plate 0, copied and placed around plate 1. This was repeated for plates 2-7 and the filter. A rectangular ROI was also drawn to assess the background counts. Raw counts were corrected for background activity and adjusted to counts per minute (cpm).

Aerosol performance is characterized in the table, in terms of the fine particle fraction (FPF) i.e. % emitted dose with a particle size<5.8 μm, mass median aerodynamic diameter (MMAD), geometric standard deviation (GSD) and the nebulization delivery time.

CEBUD Preparation

The expelled contents of five PULMICORT RESPULES (1 mg/mL) were combined together. CAPTISOL (165 mg) on a dried basis was added per Respule used to the combined contents of the commercial suspension to provide a CAPTISOL concentration of about 7.5% w/v.

The mixture was vortexed briefly to disperse and dissolve the CAPTISOL. Then placed on a roller-bed mixer and allowed to mix for two-four or several hours. Aliquots of the equilibrated mixture were used to recover any budesonide retained in the original Respule container, and the recombined together. The mixture was then further equilibrated overnight (~20 hours) on the roller-bed mixer. After visually checking that all the suspended solids had dissolved, the required volume of 99m Tc-DSPA/saline solution (provided by Medical Physical Department, UHW) was added. So about 180 μl of the Radiolabel solution was added to the CAPTISOL-ENABLED Budesonide Nasal Solution and vortexed briefly.

Example 23

Determination of the phase solubility curve for corticosteroid dissolution with SAE-CD.

The solubility of corticosteroid solutions containing SAE-CD was determined by HPLC chromatography of aliquots from equilibrated filtered or centrifuged corticosteroid solutions as follows.

SAE-CD/steroid solutions were prepared by weighing dry solids of SAE-CD (to provide 0.04 molar) and excess steroid drug (6 mg/mL) together into a screw-capped vial. A volume of water was aliquoted to each vial (separate vial for each steroid). Intrinsic solubility was determined by weighing excess steroid (6 mg/mL) and adding a volume of water in the absence of CD. Vials were capped, initially vortexed and sonicated. Vials were then placed on a roller-mixer (model: SRT2; Manufacturer: Stuart Scientific; Serial number: R000100052) or rocker/mixer (Model: LabQuake; Manufacturer: Barnstead/Thermolyne; Serial number: 1104010438202). Higher excesses of solid steroid (up to 10 mg/mL) were then added to any vial where the liquid contents clarified overnight (e.g. prednisolone, hydrocortisone, and prednisone). Samples were rolled and mixed on the roller or rocker for 72 hours. At various times during the equilibration, samples were additionally vortexed or sonicated briefly (up to 30 minutes). After the designated equilibration time, samples were filtered (0.22 μm, 25 mm, Duropore—PVDF, manufacturer: Millipore) into clean vials except for the intrinsic solubility sample for Beclomethasone Dipropionate which was centrifuged and the supernatant transferred to a clean vial. Samples were analyzed by conventional HPLC methods. The results are detailed below.

| | | [Fluticasone] $\times 10^5$M | | [Mometasone] $\times 10^5$M | | | [Triamcinolone |
|---|---|---|---|---|---|---|---|
| –CD | [CD] M | as propionate | non esterified | As furoate | non esterified | [Budesonide] $\times 10^5$M | acetonide] $\times 10^5$M |
| $H_2O$ | NA | 0.39 | 0.16 | 1.82 | 0.00 | 6.59 | 3.56 |
| β | 0.015M | | | 1.36 | 12.9 | 81.3 | |
| $(SBE)_{6.7}$ | 0.0465 | 5.41 | 126.4 | 16.4 | 121.7 | 254.8 | 457.0 |
| β | 0.0950 | 7.99 | 215.9 | 31.1 | 226.1 | 428.1 | 1023.3 |
| $(SBE)_{2.4}$ | 0.04 | 1.70 | 12.8 | | | | |
| β | 0.08 | 2.46 | | | | | |
| $(SPE)_7$ β | 0.04 | 1.05 | 93.9 | 7.23 | 122.4 | | |
| | 0.08 | 2.12 | 151.2 | 10.8 | 223.3 | 241.6 | |

Solubility of Selected Steroids Enhanced by Alpha-Cyclodextrins

| -CD | [CD] M | [Fluticasone] $\times 10^5$M as propionate | [Fluticasone] $\times 10^5$M non esterified | [Mometasone] $\times 10^5$M as furoate | [Mometasone] $\times 10^5$M non esterified | [Budesonide] $\times 10^5$M | [Triamcinolone acetonide] $\times 10^5$M |
|---|---|---|---|---|---|---|---|
| H$_2$O | NA | 0.39 | 0.16 | 1.82 | 0.00 | 6.59 | 3.56 |
| A | 0.04 | | | 0.00 | 8.4 | | |
| | 0.08 | | | 0.27 | 28.5 | | |
| (SBE)$_7$ | 0.04 | 8.37 | | 30.1 | 55.0 | 348.1 | |
| α | 0.08 | 11.4 | | 35.5 | 116.9 | 597.9 | |

Solubility of Selected Steroids Enhanced by Gamma-Cyclodextrins

| -CD | [CD] M | [Fluticasone] $\times 10^5$M as propionate | [Fluticasone] $\times 10^5$M non esterified | [Mometasone] $\times 10^5$M as furoate | [Mometasone] $\times 10^5$M non esterified | [Budesonide] $\times 10^5$M | [Triamcinolone acetonide] $\times 10^5$M |
|---|---|---|---|---|---|---|---|
| H$_2$O | NA | 0.39 | 0.16 | 1.82 | 0.00 | 6.59 | 3.56 |
| Γ | 0.035 | 73.5 | | 14.1 | 2.71 | 10.1 | 197.8 |
| | 0.1 | 22.1 | 82.2 | 65.8 | 0.09 | 4.1 | 138.6 |
| (SBE)$_{5.2}$ | 0.04 | 79.12 | | | | 375.8 | |
| γ | 0.1 | 215.3 | 1440.4 | 93.9 | 889.2 | 861.6 | |
| (SBE)$_{6.1}$ | 0.04 | 51.82 | 575.6 | 41.5 | 841.1 | 306.6 | 1059.5 |
| γ | 0.08 | 120.8 | 949.0 | 92.9 | 1423.1 | 698.8 | 2386.1 |
| (SBE)$_{9.7}$ | 0.04 | 54.5 | | | | | |
| γ | 0.075 | 103.1 | 895.0 | 94.0 | 889.6 | 453.4 | |
| (SPE)$_{5.4}$ | 0.04 | 71.7 | 759.5 | 28.7 | | 400.9 | |
| γ | 0.08 | 140.1 | 1387.8 | 51.3 | 1467.1 | 774.2 | |

The phase solubility data, determined according to this example or Example 18, can be used to determine the molar ratio of SAE-CD to corticosteroid necessary to dissolve the corticosteroid in an aqueous medium. The table below details relevant molar ratio data.

| Corticosteroid | SAE-CD | Approximate Molar Ratio at Saturated Solubility of Corticosteroid* (SAE-CD:corticosteroid) |
|---|---|---|
| Beclomethasone dipropionate | SAE-β-CD | 358 |
| Beclomethasone dipropionate | SAE-γ-CD | 86 |
| Budesonide | SAE-β-CD | 16 |
| Budesonide | SAE-γ-CD | 13 (SBE6.1), 10.8 (SBE5.2), 10.1 (SPE5.4) |
| Budesonide | SAE-α-CD | 12 |
| X-1 corticosteroid | SAE-β-CD | 190 |
| X-1 corticosteroid | SAE-γ-CD | 1390 |
| Flunisolide | SAE-β-CD | 16 |
| Flunisolide | SAE-γ-CD | 9 |
| Fluticasone | SAE-β-CD | 32 |
| Fluticasone Propionate | SAE-β-CD | 797 |
| Fluticasone Propionate | SAE-γ-CD | 78 |
| Fluticasone Propionate | SAE-α-CD | 501 |
| Hydrocortisone | SAE-β-CD | 1.6 |
| Hydrocortisone | SAE-γ-CD | 1.8 |
| Methylprednisolone | SAE-β-CD | 5.7 |
| Methylprednisolone | SAE-γ-CD | 3.4 |
| Mometasone | SAE-α-CD | 73 |
| Mometasone | SAE-β-CD | 33 |
| Mometasone furoate | SAE-α-CD | 141 |
| Mometasone furoate | SAE-β-CD | 274 |
| Mometasone furoate | SAE-γ-CD | 101 |
| Prednisolone | SAE-β-CD | 2.2 |
| Prednisolone | SAE-γ-CD | 2 |
| Prednisone | SAE-β-CD | 2.2 |
| Prednisone | SAE-γ-CD | 3.2 |
| Triamcinolone acetonide | SAE-β-CD | 8.8 |
| Triamcinolone acetonide | SAE-γ-CD | 3.8 |

*This value was determined in the presence of SAE-CD under the conditions detailed in Example 18 or this example.

Example 24

Exemplary compositions of the invention packaged in various multi-dose volume metered dose pump spray devices are made to include the following ingredients in the amounts specified according to the procedure below.

| Ingredient[1] | Function | 50 μL Spray (mg/mL) | 70 μL Spray (mg/mL) | 100 μL Spray (mg/mL) | 200 μL Ampoule (mg/mL) | 5000 μL Ampoule (mg/mL) |
|---|---|---|---|---|---|---|
| Fluticasone Propionate | Active Substance | 1.0 | 0.71 | 0.50 | 1.00 | 0.1 |
| Cetirizine HCl | Active Substance | 22 | 15.7 | 11 | 11 | 0.22 |
| SBE γ-CD | Solubilizer-Stabilizer nominal/practical | 452/500 | 323/429 | 226/300 | 452/500 | 45.2/60.0 |
| Disodium edetate, dihydrate | Antioxidant | 0.1 | 0.1 | 0.1 | 0.1 | 0.1 |
| Citric acid, | Buffer | 0.3 | 0.3 | 0.3 | 0.3 | 0.3 |
| Sodium citrate dihydrate | Buffer | 0.5 | 0.5 | 0.5 | 0.5 | 0.5 |
| Sterile water for injection, | Solvent | q.s. to 1.0 mL | q.s. to 1.0 mL | q.s. to 1.0 mL | q.s. to 1.0 mL | q.s. to 1.0 mL |

To prepare the above formulation, the fluticasone propionate and cetirizine HCl are dissolved using SBE γ-CD and citrate buffer at about pH 4.5 to 5. Vigorous mixing and sonication may be required for a day or more under an inert atmosphere to effect total dissolution. If after assaying the solution it is determined to be below the desired target for the active ingredients, additional active ingredient can be added to the solution and stirring continued. Once both drugs have dissolved completely in the CD solution, confirmed by assay, the product is filtered using a 0.22 μm PVDF filter. The solution is then dispensed under an inert atmosphere into a preservative free multidose container fitted with a suitable pump spray or filled into blow-fill-seal LDPE containers for use in a suitable nebulizer or as drops. Optionally, compositions can contain potassium sorbate present at a concentration of about 1 mg/mL and/or polysorbate 80 present at a concentration of about 0.005% and be filled in suitable multi-dose containers and fitted with a suitable metering pump spray device.

Suitable packaging is detailed in Example 20. The packaging can be in a preservative free pump spray system such as the Advanced Preservative Free system from Pfeiffer, or the Freepod from Valois, or in a single use pump spray device such as the Pfeiffer Bidose System or Unitdose System. For the nebulized solutions the Kurve ViaNase™ or another comparable nasal nebulizer device could be used.

Example 25

A composition comprising a corticosteroid and antifungal agent is prepared as follows.

The following ingredients are combined in the amounts indicated.

| Ingredient | Function | 1 mL vial (mg/mL) | 2 mL vial (mg/2 mL) | 5 mL vial (mg/5 mL) |
|---|---|---|---|---|
| Budesonide | Active Substance | 0.05 | 0.1 | 0.25 |
| Voriconazole | Active Substance | 10 | 20 | 50 |
| CAPTISOL | Solubilizer/Stabilizer | 165 | 330 | 825 |
| Disodium edetate dehydrate | Antioxidant | 0.1 | 0.2 | 0.5 |
| Citric acid, | Buffer | 0.3 | 0.6 | 1.5 |
| Sodium citrate dihydrate | Buffer | 0.5 | 1.0 | 2.5 |
| Sterile water for injection* | Solvent | q.s. to 1.0 mL | q.s. to 2.0 mL | q.s. to 5.0 mL |

*The water is removed during processing by lyophilization or spray drying or other suitable drying technique to form a powdered composition. Hence the contents are reconstituted just prior to use.

Example 26

A composition comprising a corticosteroid and antimicrobial agent is prepared as follows.
Method A.

| Ingredient | Function | 50 μL Spray (mg/mL) | 70 μL Spray (mg/mL) | 100 μL Spray (mg/mL) | 200 μL Ampoule (mg/mL) | 5000 μL Ampoule (mg/mL) |
|---|---|---|---|---|---|---|
| Budesonide | Active Substance | 0.64 | 0.46 | 0.32 | 0.16 | 0.0064 |
| Azithromycin | Active Substance | 0.4 | 0.29 | 0.2 | 0.1 | 0.004 |
| CAPTISOL | Solubilizer/Stabilizer | 64 | 46 | 32 | 16 | 0.64 |
| Disodium edetate dihydrate | Antioxidant | 0.1 | 0.1 | 0.1 | 0.1 | 0.1 |

-continued

| Ingredient | Function | 50 μL Spray (mg/mL) | 70 μL Spray (mg/mL) | 100 μL Spray (mg/mL) | 200 μL Ampoule (mg/mL) | 5000 μL Ampoule (mg/mL) |
|---|---|---|---|---|---|---|
| Citric acid, | Buffer | 0.3 | 0.3 | 0.3 | 0.3 | 0.3 |
| Sodium citrate dehydrate | Buffer | 0.5 | 0.5 | 0.5 | 0.5 | 0.5 |
| Sterile water for injection | Solvent | q.s. to 1.0 mL | q.s. to 1.0 mL | q.s. to 1.0 mL | q.s. to 1.0 mL | q.s. to 1.0 mL |

To prepare the above formulation the budesonide and azithromycin is dissolved using CAPTISOL and citrate buffer at about pH 4.5. Vigorous mixing and sonication may be required for a day or more under an inert atmosphere to effect total dissolution. If after assaying the solution it is determined to be below the desired target for the active ingredients, additional active ingredient can be added to the solution and stirring continued. Once both drugs have dissolved completely in the CD solution, confirmed by assay, the product is filtered using a 0.22 μm PVDF filter. The solution can then be dispensed under an inert atmosphere into a preservative free multidose container fitted with a suitable pump spray or filled into blow-fill-seal LDPE containers for use in a suitable nebulizer or as a drop. Optionally, compositions can contain potassium sorbate present at a concentration of about 1 mg/mL and/or polysorbate 80 present at a concentration of about 0.005% and be filled in suitable multi-dose containers and fitted with a suitable metering pump spray device. Suitable packaging is detailed in Example 24.

Method B.

| Ingredient | Function | 1 mL vial (mg/mL) | 2 mL vial (mg/mL) | 5 mL vial (mg/mL) |
|---|---|---|---|---|
| Budesonide | Active Substance | 0.05 | 0.1 | 0.25 |
| Azithromycin | Active Substance | 10 | 20 | 100 |
| CAPTISOL | Solubilizer/Stabilizer | 7.5 | 15 | 37.5 |
| Disodium edetate dihydrate | Antioxidant | 0.1 | 0.2 | 0.5 |
| Citric acid, | Buffer | 0.3 | 0.6 | 1.5 |
| Sodium citrate dihydrate | Buffer | 0.5 | 1.0 | 2.5 |
| Sterile water for injection* | Solvent | q.s. to 1.0 mL | q.s. to 2.0 mL | q.s. to 5.0 mL |

*The water is removed during processing by lyophilization or spray drying or other suitable drying technique to prepare a powdered composition. Hence the contents are reconstituted just prior to use.

Example 27

A powdered composition of budesonide and azelastine can be prepared as follows.

The following ingredients are combined in the amounts indicated to prepare an active composition.

| Ingredient | Function | Amount needed (mg/mL) |
|---|---|---|
| Budesonide | Active Substance | 0.457 |
| Azelastine HCL | Active Substance | 1.96 |
| CAPTISOL | Solubilizer/Stabilizer | 100 |
| Disodium edetate, dihydrate | Antioxidant | 0.1 (0.05 to 0.15) |
| Citric acid | Buffer | 0.3 |

-continued

| Ingredient | Function | Amount needed (mg/mL) |
|---|---|---|
| Sodium citrate dihydrate | Buffer | 0.5 (0.45 to 0.55) |
| Sterile water for injection,* | Solvent | q.s. to 1 mL |

*Water is removed during processing by lyophilization or spray drying or other suitable technique. If necessary, the concentration used for the processing method can be adjusted to assist in achieving the desired particle size.

The budesonide and azelastine HCL are dissolved in the CAPTISOL and citrate buffer (about pH 4.5) using a vigorous stirring method. During processing and packaging the liquid product is further protected using an inert atmosphere. In addition the water used for the process may be sparged with nitrogen to reduce oxygen. Once both drugs are dissolved, the solution is lyophilized using a suitable method that will produce a stable, uniform cake. The lyophilized product is then sized to obtain an average particle size of Dv(50) between 10-100 μm or about 65 μm as the active composition.

The active composition can be mixed with a bulking agent to prepare a powder formulation for administration with an administration device capable of emitting and nasally delivering the powder. The powder formulation can be prepared according to the table below.

| Ingredient | Function | 20 mg Powder Nasal Aerosol | 50 mg Powder Nasal Aerosol |
|---|---|---|---|
| Actives Composition (see below) | Active Substances (Includes: budesonide, azelastine) | 7.225 mg (0.032 mg, 0.137 mg) | 7.225 mg (0.032 mg, 0.137 mg) |
| Lactose | Diluent/Bulking Agent | 12.775 mg | 42.775 mg |

The following procedure can be used. A bulking agent, such as lactose suitable for inhalation (Lactohale®), is dry

Example 28

Preparation of a liquid formulation comprising SAE-CD and budesonide, optionally containing TWEEN.

A 3 mM citrate buffer at pH 4.5 was added to 2 grams of CAPTISOL and 25 mg of budesonide in a serum vial to make the final volume 10 mL. The suspension was well mixed by vortexing and sonication. A 20% stock solution of CAPTISOL without budesonide was also prepared in 3 mM citrate buffer. These mixtures, along with the buffer were sealed in separate vials and autoclaved using the 20-minute hold at 121° C. cycle. HPLC analysis of the clear budesonide solution showed the concentration was 2100 μg/mL. The 20% CAPTISOL stock solution was used to dilute the sample to 2000 μg/mL. A portion of the above resulting solution was optionally diluted with an equal volume of the 3 mM citrate buffer. HPLC analysis showed the final concentration was 990 μg of budesonide/mL.

The TWEEN could be added to the above solution as follows. A solution of 0.02% TWEEN was prepared with the autoclaved buffer only solution to form a TWEEN stock solution for use as a diluent for the above solutions. The dilutions for the 10% CAPTISOL/1 mg/mL budesonide were done by weight. Approximately 9 grams of the 20% captsiol/2000 μg/mL was mixed with ~9 grams of either the autoclaved buffer only solution or the autoclaved buffer/ 0.02% TWEEN solution. These solutions were well-mixed, filtered and reassayed by HPLC.

The budesonide concentrations of the above formulations were found to be 986 μg/mL for the solution without TWEEN and 962 μg/mL for the solution with TWEEN.

The solutions can be nebulized with any nebulizer; however, with an AERx nebulizer, an initial sample volume of 50 μl can be used. Administration of this solution with the nebulizer makes it feasible for a therapeutic dose to be administered to a subject in a single puff (a single full inspiration by a subject) via nebulization.

Example 29

Preparation and dissolution of a lyophilized formulation comprising SAE-CD and budesonide.

An excess of budesonide, 3.5 mg/mL, was added to 3 L of 30% CAPTISOL in 3 mM citrate buffer containing 0.1 mg/mL EDTA. After mixing for 2 days, an additional 1 mg/mL budesonide was added and equilibrated an additional 4 days. The preparation was filtered through a 0.22μ Durapore filter and placed in three stainless steel trays in a freeze dryer. The solution was frozen at −30° C. for one hour and lyophilized over 30 hours to remove essentially all the water. The lyophile was powdered, screened and the powder transferred to a plastic bottle. The final composition contained 8.2 mg budesonide per gram of powder.

When approximately 65 mg of powder was added to 2 mL of water, an essentially clear solution containing the same amount of budesonide as in the reference suspension product was rapidly obtained.

mixed with the sized lyophilized product to provide a total administered amount of 20 to 50 mg as needed for a unit dose powder nasal spray such as the Monopowder (Valois) or DirectHaler™ (DirectHaler).

Example 30

Preparation of an aqueous liquid formulation comprising SAE-CD, ethanol and budesonide.

CAPTISOL/Ethanol solutions were prepared by making a stock CAPTISOL solution at 22.2% (~0.1 M) w/v which was diluted with either ethanol or water in varying amounts to create four solutions of 0, 1, 2, 5% ethanol and about 20% w/v CAPTISOL. CAPTISOL/Ethanol/Budesonide solutions were prepared by adding dry budesonide (2.5 mg/mL) to a volume of the prepared CAPTISOL/ethanol solutions and then these were equilibrated on a Labquake for 72 hours. These solutions were filtered (Duropore syringe filters) and analyzed by HPLC to determine the concentration (μg/mL) of budesonide dissolved in the formulation.

Example 31

An electronic tongue study can be conducted as follows to determine the effectiveness of SAE-CD at masking the bitter taste of an active agent, such as azelastine.

The e-tongue (Astree II, Alpha M.O.S., Toulouse, France) has been used to demonstrate an increasing change in the taste of azelastine HCl solution upon the addition of increasing amounts of CAPTISOL. Solutions containing 2 mg/mL azelastine HCL in 3 mM, pH=4 citrate buffer, with different amounts of CAPTISOL were prepared. The e-tongue uses a seven-sensor probe assembly to detect dissolved organic and inorganic compounds. The probes consist of a silicon transistor with proprietary organic coatings, which govern the probe's sensitivity and selectivity. Measurement is potentiometric, with readings taken against an Ag/AgCl reference electrode. Samples are placed in an autosampler carrousel where the electrodes are introduced into each sample. Each probe is cross-selective to allow coverage of full taste profile. The system samples, quantifies, digitizes, and records potentiometer readings. Taste cognition happens not in the probe, but in the computer, where the e-tongue's statistical software interprets the sensor data into taste patterns. The distance from the azelastine HCL in buffer to the solutions containing 5%, 10% or 15% CAPTISOL were 334.03, 418.96, and 491.76 respectively indicating a large change in taste.

Example 32

To investigate how the incorporation of CAPTISOL at 5% w/v into PULMICORT RESPULES impact performance of different types of nebulizers.

The emitted dose of budesonide from four different nebulizers (PART LC PLUS (air jet), OMRON MICROAIR NE-U22, AIRSEP MYSTIQUE(ultrasonic), AEROGEN AERONEB) was determined. The package insert-approved Pari air jet system was used as the benchmark to judge performance of the other nebulizers. The emitted dose was from 1.25 to 3.7 times higher when CAPTISOL was added to the budesonide suspension. The Emitted dose (ED) was determined by:

1) Drawing the nebulized formulations through a 300 mL glass filter apparatus at 15 l/min, and collecting drug on double or triple layers of glass fiber depth filter and the interior walls. Collection was stopped every two minutes, the budesonide quantitatively recovered, and filters were changed to prevent filter saturation or alterations in airflow. Budesonide recovery was quantified by HPLC; and/or
2) Summing the amount of budesonide on the cascade impactor stages after nebulization.

The results are detailed below. (ND means "not determined.")

| Formulation | Total Delivered (ED) (μg, mean & SD), Filter[1] | Total Delivered (ED) (μg, mean & SD), Impactor[2] |
|---|---|---|
| Pari LC Plus (Air Jet) Listed in the Pulmicort package insert | | |
| Pulmicort | 171.5 ± 6.3 | 137.8 ± 14.9 |
| Pulmicort + 5% CAPTISOL | 247.4 ± 11.3 | 172.4 ± 6.6 |
| Omron MicroAir NE-U22 | | |
| Pulmicort | 179.9 ± 17.2 | 168.8 ± 30.1 |
| Pulmicort + 5% CAPTISOL | 380.1 ± 8.5 | 349.6 ± 10.0 |
| AirSep Mystique (Ultrasonic) | | |
| Pulmicort | 32.9 ± 6.4 | ND* |
| Pulmicort + 5% CAPTISOL | 120.8 ± 19.6 | ND* |
| Aerogen AeroNeb | | |
| Pulmicort | 90.7 ± 4.5 | ND* |
| Pulmicort + 5% CAPTISOL | 301.2 ± 19.5 | ND* |

Example 33

A clinical trial was conducted to evaluate the performance of a formulation of the invention in the treatment of nasal symptoms and non-nasal symptoms caused by exposure of subjects to an allergen.

Three aqueous based formulations were made: Solution A—comprising CAPTISOL, budesonide and aqueous liquid carrier; Suspension B—comprising RHINOCORT AQUA suspension of budesonide in aqueous liquid carrier; and Solution C (placebo)—comprising buffered saline. Solution A was made by mixing two NEBUAMPS (500 μg/mL nominal) to a bottle containing 348 mg CAPTISOL, followed by mixing overnight to form a solution containing 424 μg/mL of budesonide and 75 mg/mL of CAPTISOL in a total volume of 4.4 mL. Solution B was purchased and used as is (32 μg of budesonide per spray) using a spray volume of 50 μl with the supplied valve. Bottles containing Solutions A and C were equipped with a 70 μl Pfeiffer spray valve. Bottles were masked prior to use. Solutions A and B were administered at a dose of 32 μg per spray. Dosing of Solutions A or C or Suspension B was as a single spray in each nostril.

The bulk solution concentration of budesonide in Solution A ranged from 418-439 μg/mL with an average of 432±6 μg/mL. Based upon HPLC analysis, each spray of Solution A contained about 31 μg of budesonide.

Clinical Protocol.

Figure 7:
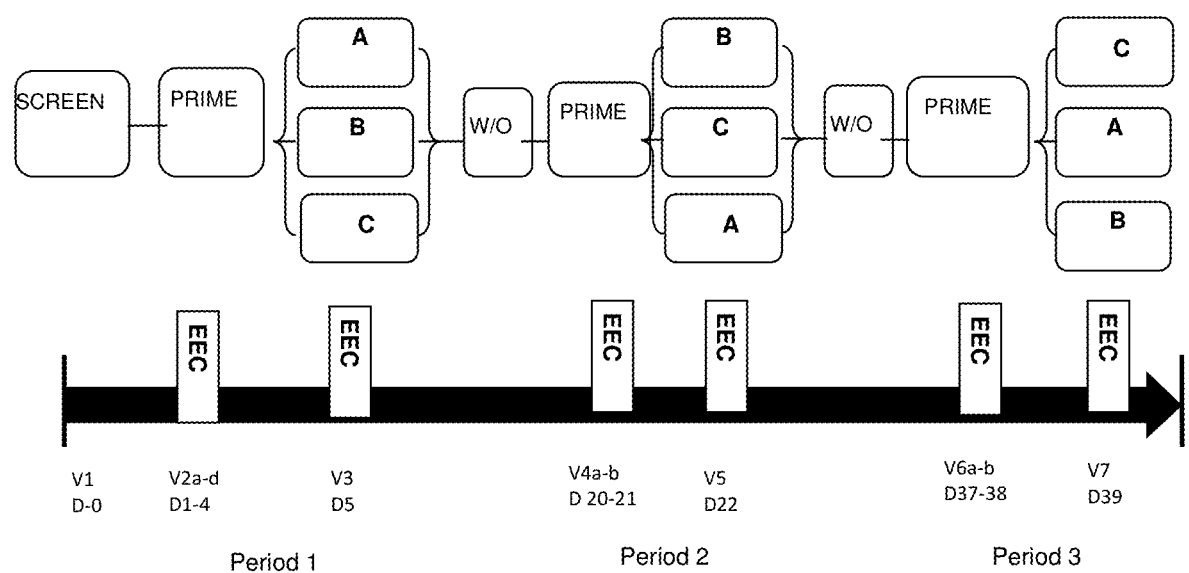
FIG. 7 depicts a graphical summary of the study protocol of Example 33.

A randomized, double-blind, placebo-controlled, single-center, three-way cross-over study was conducted to compare the relative efficacy of budesonide, administered via nasal spray using Solution A and Solution B, with Solution C as the placebo control, in the treatment of SAR in an environmental exposure chamber. Sixty five subjects were enrolled in the study and exposed to ragweed pollen using an EEC model. The total nasal symptom score (TNSS) and total non-nasal symptom score (TNNSS) for each subject was determined. A graphical summary of the study protocol is depicted in FIG. 7. Patients were exposed to 3000 to 4000 particles per cubic meter of ragweed pollen using an Environmental Exposure Chamber model of the disease. After the initial exposure to pollen, patients were then treated with Solution A (CAPTISOL, budesonide, aqueous carrier solution), Suspension B (RHINOCORT AQUA: budesonide, aqueous carrier suspension), or Solution C (saline placebo) in a crossover design. Each patient remained in the chamber exposed to pollen and rated their nasal symptom and their non-nasal symptoms over a period of 10 hours.

The primary objective of the study was to compare the relative efficacy of budesonide administered via CAPTISOL-ENABLED Budesonide nasal solution and RHINOCORT AQUA in patients with SAR exposed to controlled ragweed pollen using an EEC model. Secondary objectives of the study were to: 1) assess the onset of action of Solution A and Solution B as compared to placebo; 2) compare the tolerance of each as determined by patient questionnaire and adverse events recorded; and 3) compare the effect of the three solutions on the EEC-specific Quality of Life Questionnaire (EEC-QOLQ).

This was a randomized, double-blind, placebo-controlled, single-center, 3-way cross-over study with three periods of two-four 3 h priming visits followed by a 12 h treatment visit. Following an initial 30-minute exposure to ragweed pollen in the EEC, the patients evaluated four nasal symptoms (itchy nose, runny nose, congestion and sneezing) and four non-nasal symptoms (itchy/gritty eyes, tearing/watery eyes, red/burning eyes, and itchy ears/palate) every 30 minutes for 1.5 hours to determine adequate baseline symptoms. Each symptom was rated on a scale of 0 to 3 (none, mild, moderate, and severe). Patients who met the predetermined minimum TNSS score of 6 out of a maximum of 12, including a minimum score of 2 out of 3 for runny nose on the last two diary cards prior to treatment, were randomized to receive one of three treatments in a double-blind manner. Patients who did not meet the predetermined TNSS were not dosed and were withdrawn from the study.

Following administration of the study drug, the patients were asked to assess their NSS (nasal symptom score), OSS (ocular symptom score), and NNSS (non-nasal symptom score) at 15, 30, 45, 60, 90 and 120 minutes post dosing; then every hour up to 10 hours post-dose. TSS was the sum score of 4 nasal symptoms: runny-, itchy-, stuffy-nose and sneezing; and 4 non-nasal symptoms: 3 ocular symptoms (TOSS): redness, itching, tearing and 1 non-nasal, non-ocular: itchy ears/palate. During the entire time the patients were in the EEC, they were exposed to ragweed pollen at a concentration of 3500±500 particles per $m^3$.

Figure 6A:
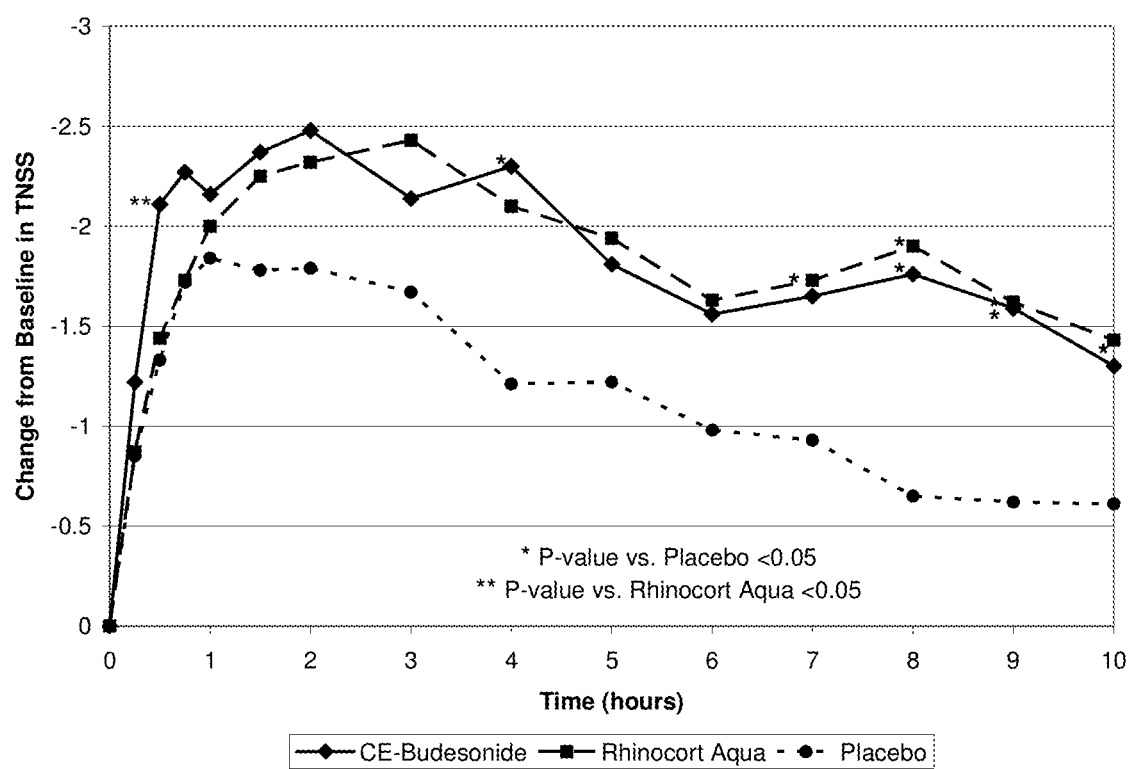
FIGS. 6A to 6I depict charts detailing the results of a clinical study conducted according to Example 33.
Figure 6B:
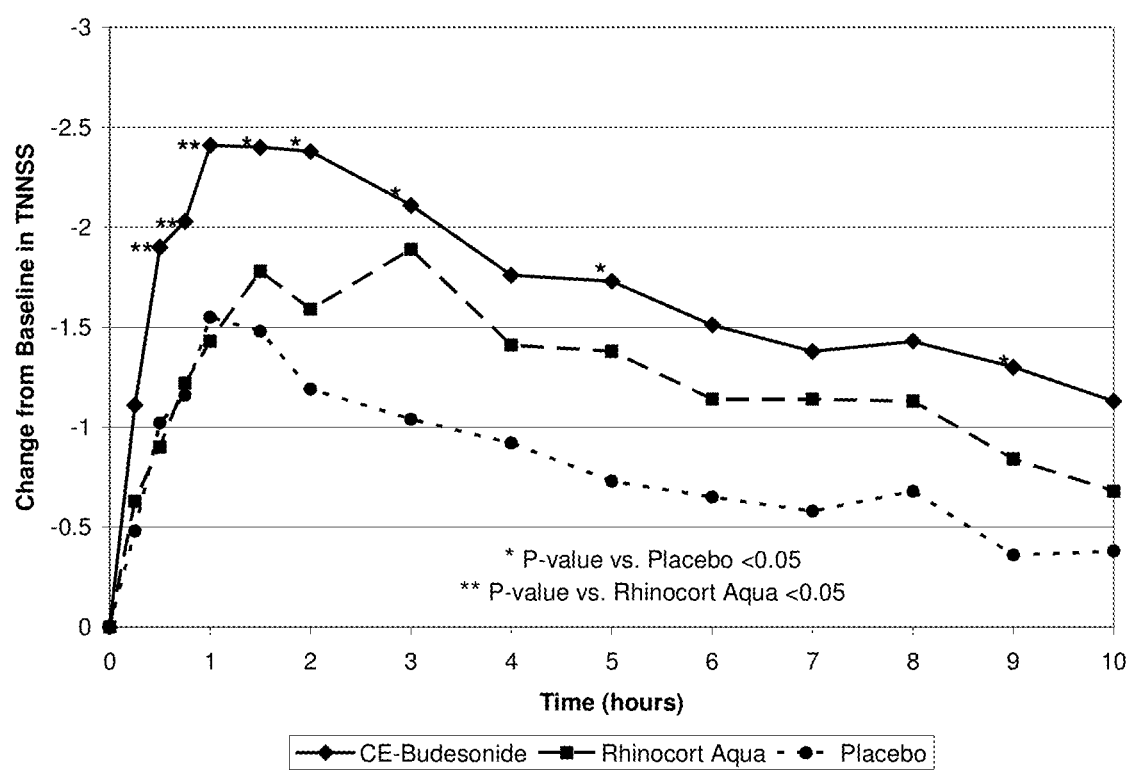
Figure 6C:
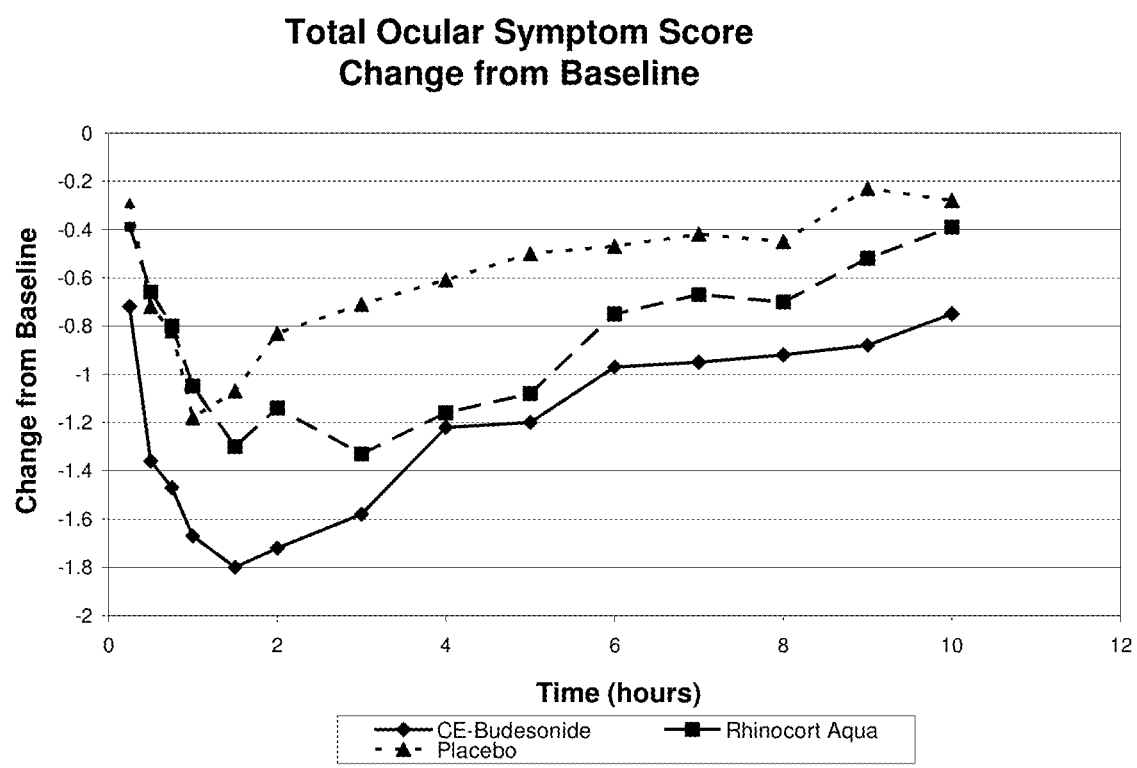
Figure 6D:
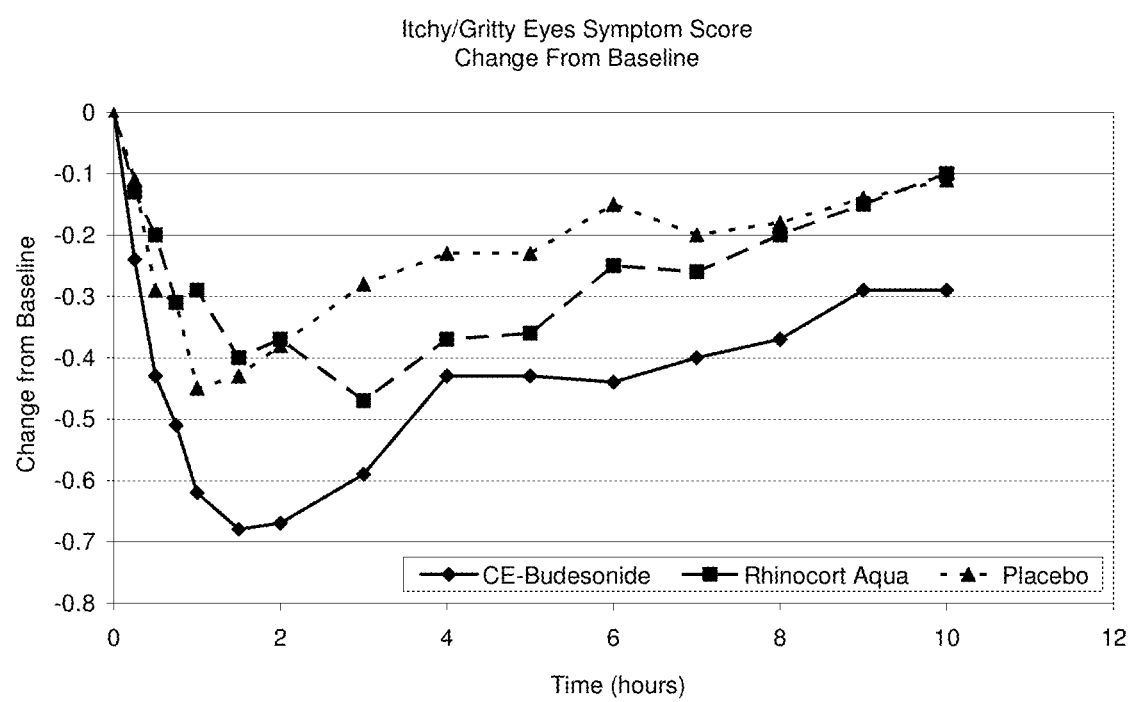
Figure 6E:
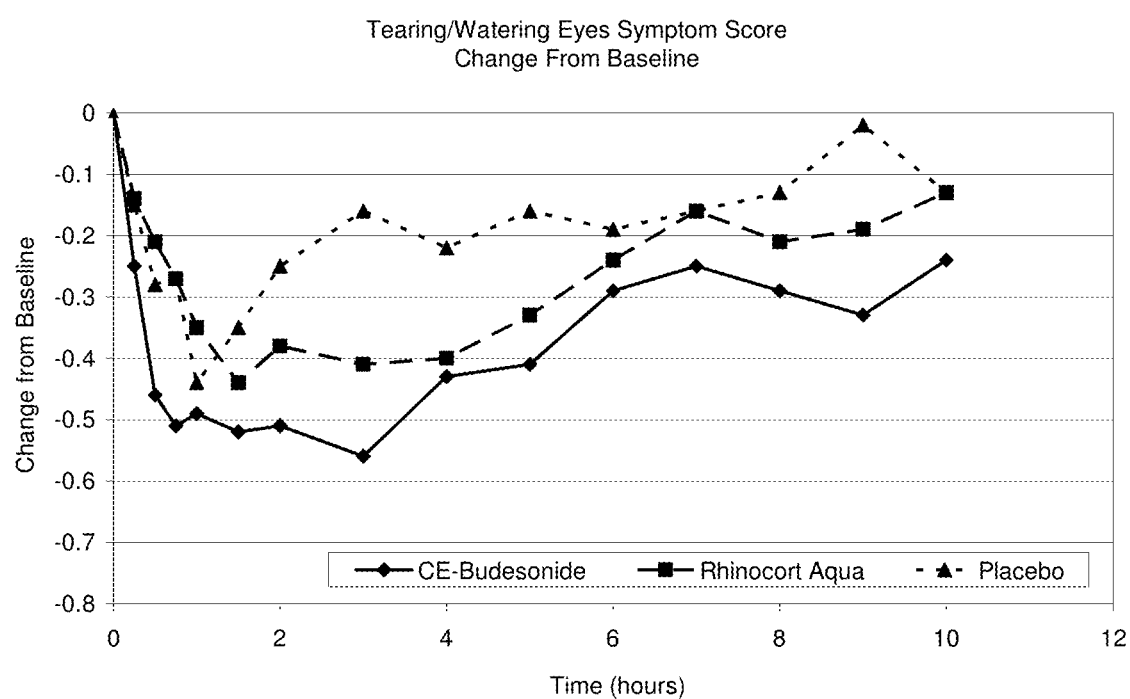

Patients rated nasal symptoms (rhinorrhea, nasal congestion, nasal itchiness, and sneezing) and non-nasal symptoms (itchy/gritty eyes, tearing/watery eyes, red/burning eyes, itchy ears and palate). See FIGS. 6A-6C and 6F. Area under the curve (AUC) was calculated based on the mean change from baseline for TNSS, TNNSS and TSS and was compared using analysis of covariance. See FIGS. 6G, 6H and 6I. Secondary efficacy assessed the onset of action of CAPTISOL-ENABLED Budesonide compared to RHINOCORT AQUA and placebo. The TNSS and TNNSS scores were then totaled. This data was evaluated to determine efficacy and speed of action.

The effect of CAPTISOL-ENABLED Budesonide compared to placebo on ocular symptoms was determined. The mean AUC for itchy/gritty eyes demonstrated significant efficacy of CAPTISOL-ENABLED Budesonide (−4.21±7.00) over placebo (−2.10±6.62) (p=0.042). The mean AUC for tearing/watery eyes also demonstrated significant efficacy of CAPTISOL-ENABLED Budesonide (−3.05±7.08) over placebo (−1.67±6.66) (p=0.047). Unlike CAPTISOL-ENABLED Budesonide, micronized suspension (RHINOCORT AQUA) did not demonstrate significant efficacy compared to placebo in ocular symptoms. The effect of CAPTISOL-ENABLED Budesonide compared to placebo on itchy/gritty eyes was greatest at timepoints 1.5, 2 and 3 hr post-dose with changes from baseline of −0.70±0.84 (p=0.031), −0.67±0.83 (p=0.020) and −0.58±0.83 (p=0.044), respectively. Similarly, the effect on tearing/watery eyes was greatest at 3 hr with changes from baseline of −0.55±0.89 (p=0.004) and the effect on red/burning eyes was greatest at 0.5, 1 and 2 hr with changes from baseline of −0.47±0.74 (p=0.010), −0.58±0.88 (p=0.030) and −0.55±0.97 (p=0.022), respectively. Based on the mean change from baseline, the onset of action for CAPTISOL-ENABLED Budesonide for improvement in itchy/gritty eyes was 1.5 hr. CAPTISOL-ENABLED Budesonide also demonstrated significance on itchy/gritty eyes over RHINOCORT AQUA at 0.5 hr (p=0.008) and 0.75 hr (p=0.014). The data for these symptoms is summarized in FIGS. 6D-6E.

Figure 6F:
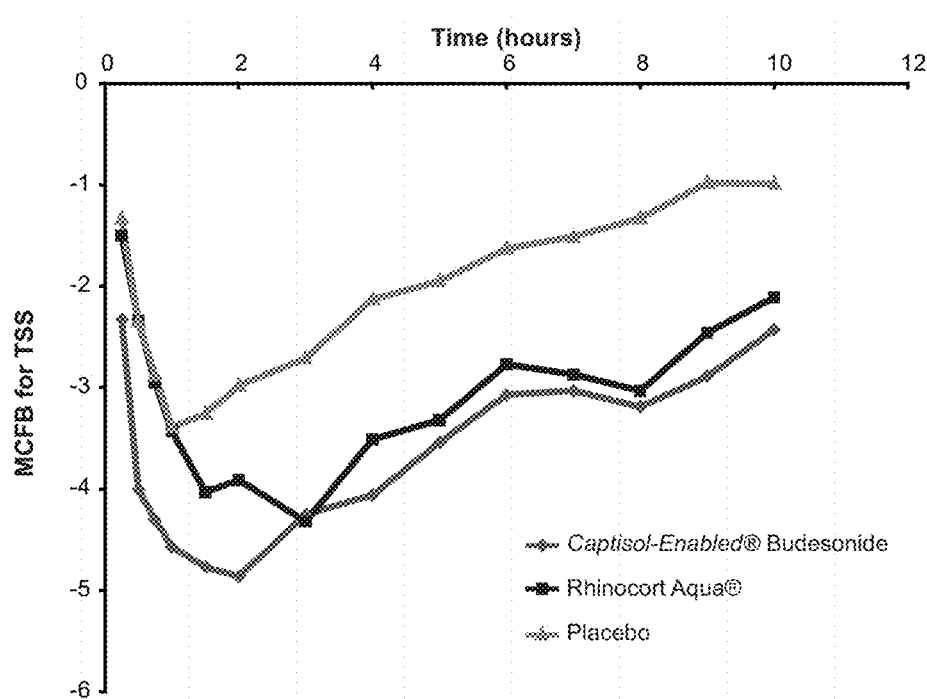
Figure 6G:
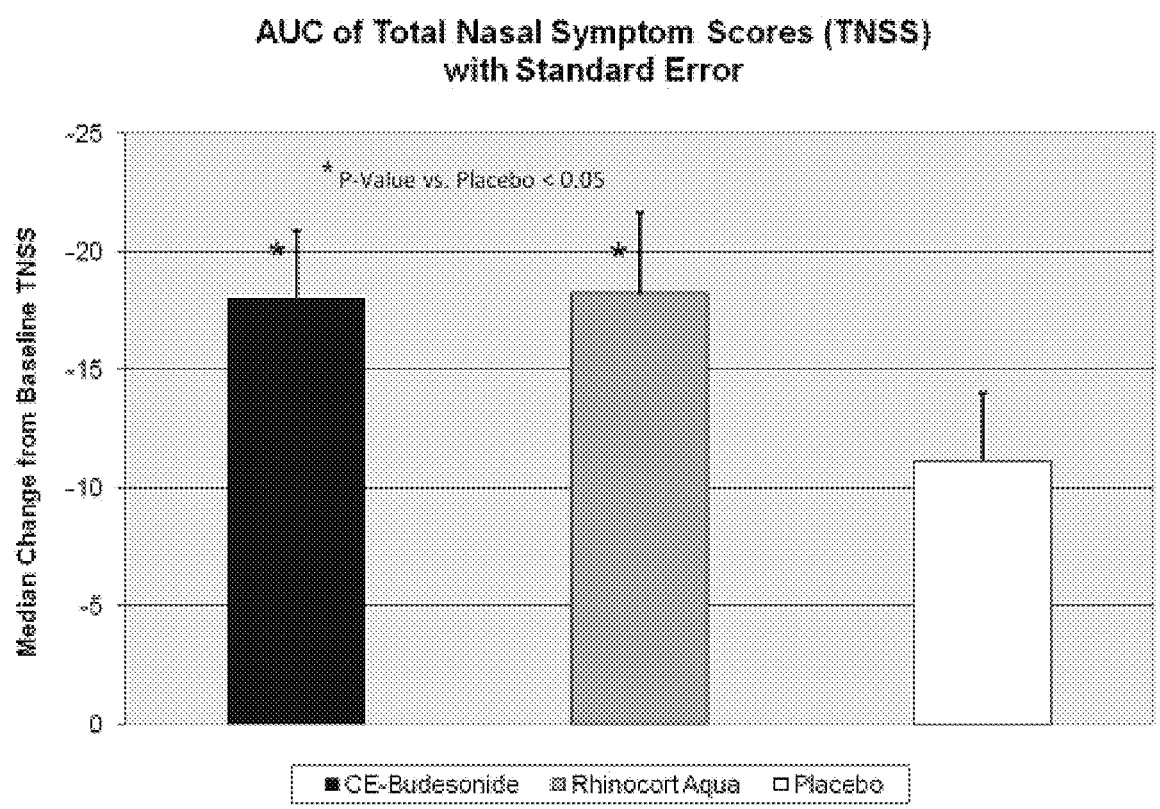
Figure 6H:
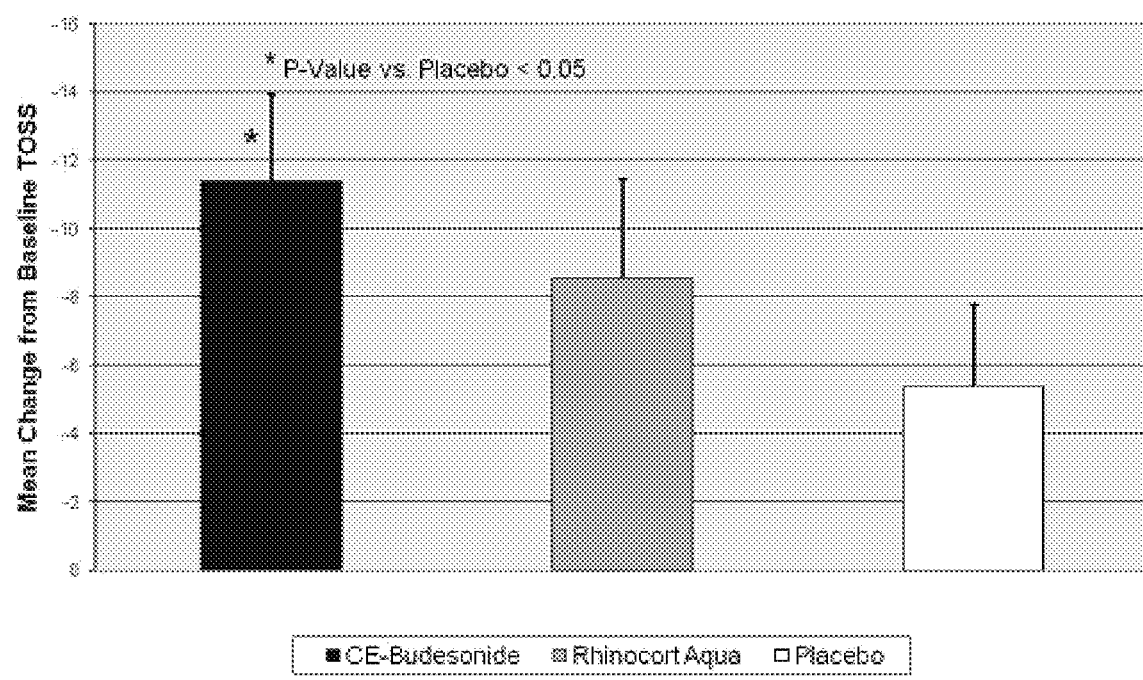
Figure 6I:
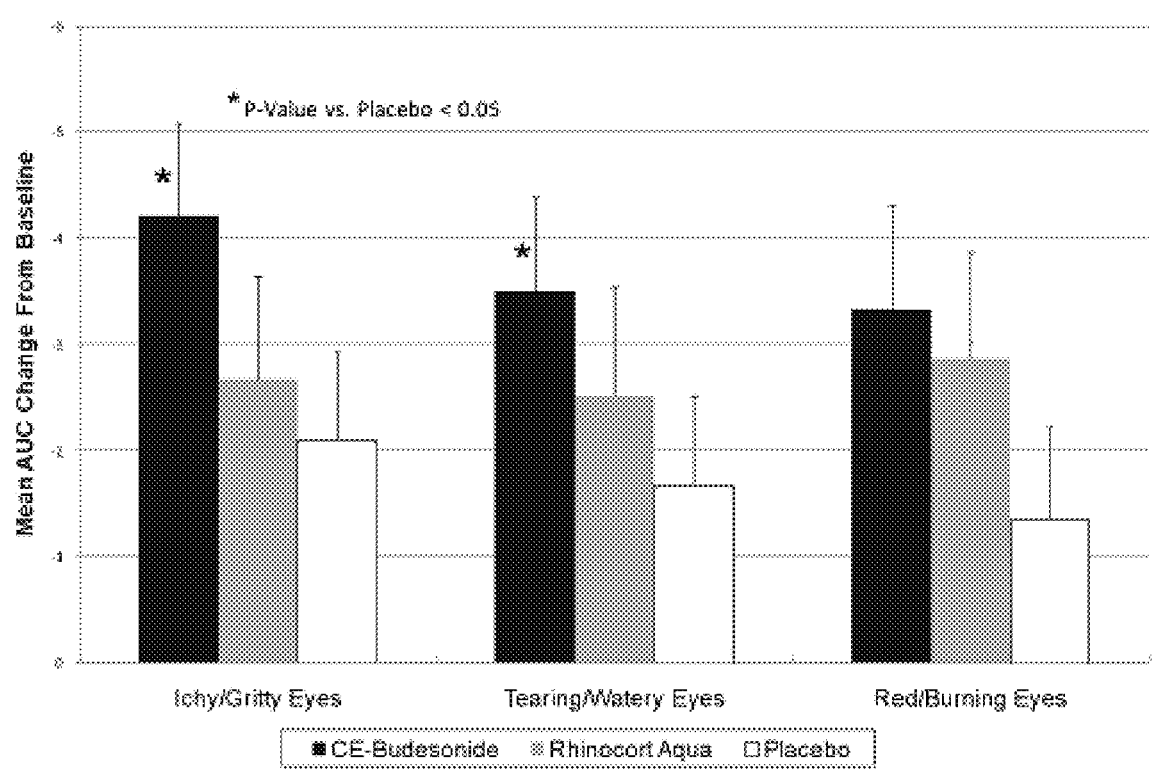

In FIG. 6F, the MCFB in TSS was greater at hours 0.25, 0.5, 0.75, 1.0, and 1.5 for CAPTISOL-ENABLED Budesonide (−2.33, −4.01, −4.30, −4.57, −4.77 and −4.86, respectively) than for RHINOCORT AQUA (−1.5, −2.34, −2.95, −3.43, −4.03, and −3.91, respectively) with an onset of action of 0.5 h compared to 4 h onset for RHINOCORT AQUA.

The mean AUC TNSS was significant for CAPTISOL-ENABLED Budesonide (−18.02±22.7) versus placebo (−11.12±23.1) (p=0.036). Likewise, AUC TNSS for RHINOCORT AQUA was −18.23±27.2 versus placebo at −11±23.1 At 0.25 h, 0.5 h and 0.75 h, the mean change from baseline TNSS was greater for CAPTISOL-ENABLED Budesonide (−1.22, −2.11, −2.27 respectively) than for RHINOCORT AQUA (−0.87, −1.44, −1.73, respectively) with an onset of action for ocular symptoms at 0.5 h. RHINOCORT AQUA had no onset of action for ocular symptoms. Overall TNNSS AUC was significant (p=0.012) for CAPTISOL-ENABLED Budesonide (mean decrease of −16.61±27.3) compared to placebo (−7.62±24.0) (p values<0.05). Of note, at 0.5 h, 0.75 h and 1 h, the changes from baseline for the CAPTISOL-ENABLED Budesonide were −1.90±2.41, −2.03±2.92 and −2.41±3.11, respectively (all p values<0.05 compared to RHINOCORT AQUA and placebo). The onset of action of CAPTISOL-ENABLED Budesonide versus RHINOCORT AQUA and placebo was significantly different at 0.5 h-1 h (p values<0.05). No deaths or clinically significant adverse events were reported in this study. The CAPTISOL-ENABLED Budesonide reduced TOSS versus placebo (−11.40±20.5 vs −5.38±19.0 p<0.05) while RHINOCORT AQUA did not (−8.57±23.1). Further, each ocular symptom of itchy/gritty eyes and tearing/watery eyes demonstrated significant efficacy of CAPTISOL-ENABLED Budesonide over placebo while RHINOCORT AQUA did not for any ocular symptom. The onset of action for CAPTISOL-ENABLED Budesonide on TOSS was 1.5 hr. The average TOSS is shown as a function of time in FIG. 6C.

The data are depicted in FIGS. 6A-6G and summarized in the table below.

| Time Point (hour) | CE-Budesonide Nasal Solution (N = 65) | | RHINOCORT AQUA (N = 65) | | Placebo (N = 65) | |
|---|---|---|---|---|---|---|
| | Mean | SE | Mean | SE | Mean | SE |
| 0 | 0 | | 0 | | 0 | |
| 0.25 | −1.22 | 0.32 | −0.87 | 0.26 | −0.85 | 0.25 |
| 0.5 | −2.11 | 0.32 | −1.44 | 0.32 | −1.33 | 0.32 |
| 0.75 | −2.27 | 0.35 | −1.73 | 0.33 | −1.72 | 0.36 |
| 1 | −2.16 | 0.36 | −2 | 0.36 | −1.84 | 0.36 |
| 1.5 | −2.37 | 0.34 | −2.25 | 0.39 | −1.78 | 0.34 |
| 2 | −2.48 | 0.34 | −2.32 | 0.41 | −1.79 | 0.39 |
| 3 | −2.14 | 0.35 | −2.43 | 0.42 | −1.67 | 0.36 |
| 4 | −2.3 | 0.37 | −2.1 | 0.4 | −1.21 | 0.36 |
| 5 | −1.81 | 0.35 | −1.94 | 0.43 | −1.22 | 0.37 |
| 6 | −1.56 | 0.34 | −1.63 | 0.41 | −0.98 | 0.33 |
| 7 | −1.65 | 0.33 | −1.73 | 0.44 | −0.93 | 0.33 |
| 8 | −1.76 | 0.35 | −1.9 | 0.45 | −0.65 | 0.3 |
| 9 | −1.59 | 0.34 | −1.62 | 0.44 | −0.62 | 0.34 |
| 10 | −1.3 | 0.35 | −1.43 | 0.41 | −0.61 | 0.32 |

The table below includes a summary of the TNNSS data for the study.

| Time Point (hour) | CE-Budesonide Nasal Solution (N = 65) | | RHINOCORT AQUA (N = 65) | | Placebo (N = 65) | |
|---|---|---|---|---|---|---|
| | Mean | SE | Mean | SE | Mean | SE |
| 0 | 0 | | 0 | | 0 | |
| 0.25 | −1.11 | 0.31 | −0.63 | 0.28 | −0.48 | 0.24 |
| 0.5 | −1.9 | 0.3 | −0.9 | 0.33 | −1.02 | 0.3 |
| 0.75 | −2.03 | 0.37 | −1.22 | 0.36 | −1.16 | 0.33 |
| 1 | −2.41 | 0.39 | −1.43 | 0.38 | −1.55 | 0.37 |
| 1.5 | −2.4 | 0.38 | −1.78 | 0.42 | −1.48 | 0.36 |
| 2 | −2.38 | 0.39 | −1.59 | 0.41 | −1.19 | 0.35 |
| 3 | −2.11 | 0.37 | −1.89 | 0.44 | −1.04 | 0.35 |
| 4 | −1.76 | 0.39 | −1.41 | 0.42 | −0.92 | 0.35 |
| 5 | −1.73 | 0.37 | −1.38 | 0.45 | −0.73 | 0.36 |
| 6 | −1.51 | 0.41 | −1.14 | 0.42 | −0.65 | 0.35 |
| 7 | −1.38 | 0.44 | −1.14 | 0.44 | −0.58 | 0.34 |
| 8 | −1.43 | 0.44 | −1.13 | 0.43 | −0.68 | 0.36 |
| 9 | −1.3 | 0.41 | −0.84 | 0.45 | −0.36 | 0.34 |
| 10 | −1.13 | 0.4 | −0.68 | 0.44 | −0.38 | 0.34 |

The efficacy, as determined from the area under the TNSS rating-time curve (AUC), for Solution A and Suspension B was better than placebo. There was little difference in efficacy between Solution A and Suspension B although the median score for Solution A was better. Also, nasal itchiness trended better for Solution A than for Suspension B or Solution C.

The efficacy, based on TNNSS AUC, shows that Solution A was better than Solution C, while Suspension B was equivalent to Solution C. Overall, Solution A was substantially better than Solution C in three out of the four non-nasal categories and trended better than Solution C in the fourth non-nasal category.

The initial reduction in TNSS was greatest for Solution A. This shows that the speed of action of Solution A was faster than either Suspension B or Solution C. Even though it was faster, the reduction in TNSS lasted as long as Suspension B.

The Onset of Action in reducing TNNSS was determined to be 0.5 hours for Solution A. Suspension B never met the previously established criterion.

Figure 8A:
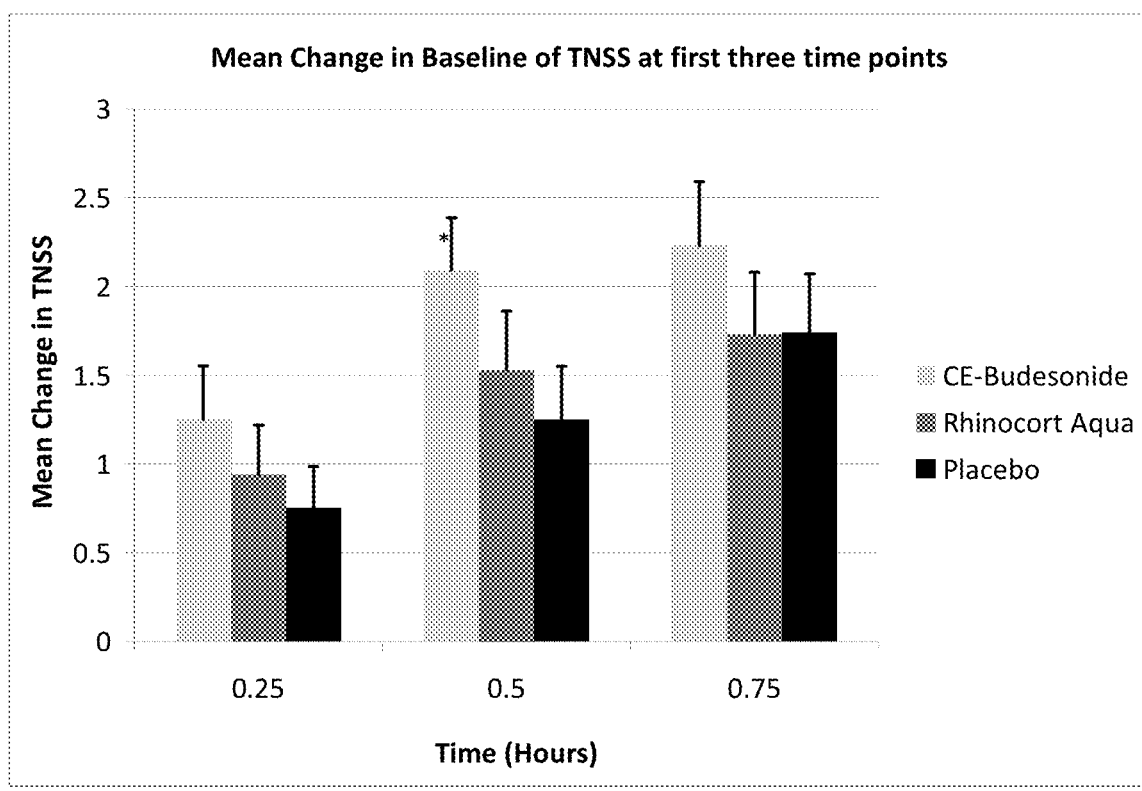
FIG. 8A depicts a chart the TNSS change from baseline with onset of action for the first three time points in the study of Example 33.
Figure 8B:
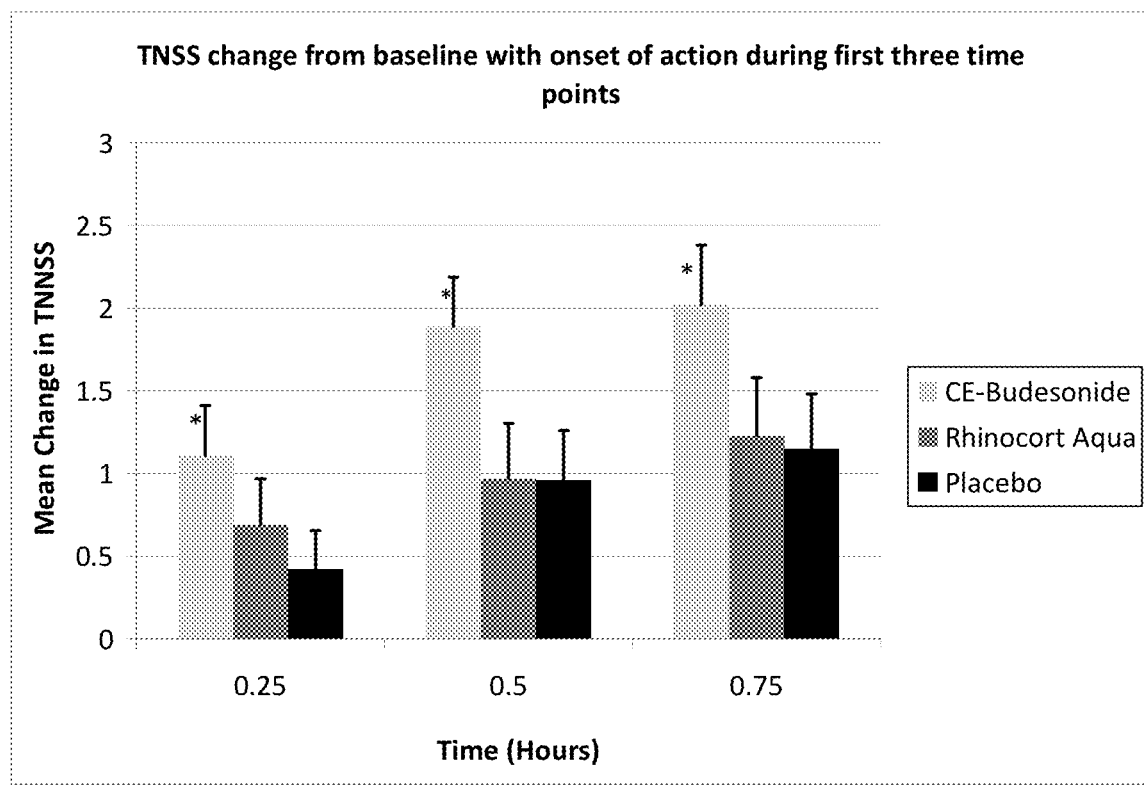
FIG. 8B depicts a chart the TNNSS change from baseline with onset of action for the first three time points in the study of Example 33.

When comparing mean change from baseline TNSS values for the first three time points (0.25 hr, 0.5 hr and 0.75 hr), the mean decrease in TNSS was greater for CAPTISOL-ENABLED Budesonide than for RHINOCORT AQUA. However, statistical significance for CAPTISOL-ENABLED Budesonide versus placebo was only achieved for the 0.5 hr time point. While CAPTISOL-ENABLED Budesonide lowered TNSS after 0.25 hours, the critical level of significance when compared to placebo was not achieved for most of the time points. See FIG. 8A. The chart for the onset of action for the first three time points for TNNSS is set forth in FIG. 8B.

CAPTISOL-ENABLED Budesonide reduced non-nasal symptom scores at 30 minutes. This effect was not observed with RHINOCORT AQUA. There was no significant difference in the efficacy of CAPTISOL-ENABLED Budesonide and RHINOCORT AQUA for the primary efficacy variable of TNSS. The mean AUC for TNSS illustrates a significant treatment effect for both CAPTISOL-ENABLED Budesonide versus placebo and RHINOCORT AQUA versus placebo. CAPTISOL-ENABLED Budesonide is a well tolerated, effective treatment for SAR.

EEC-QOLQ

Figure 9A:
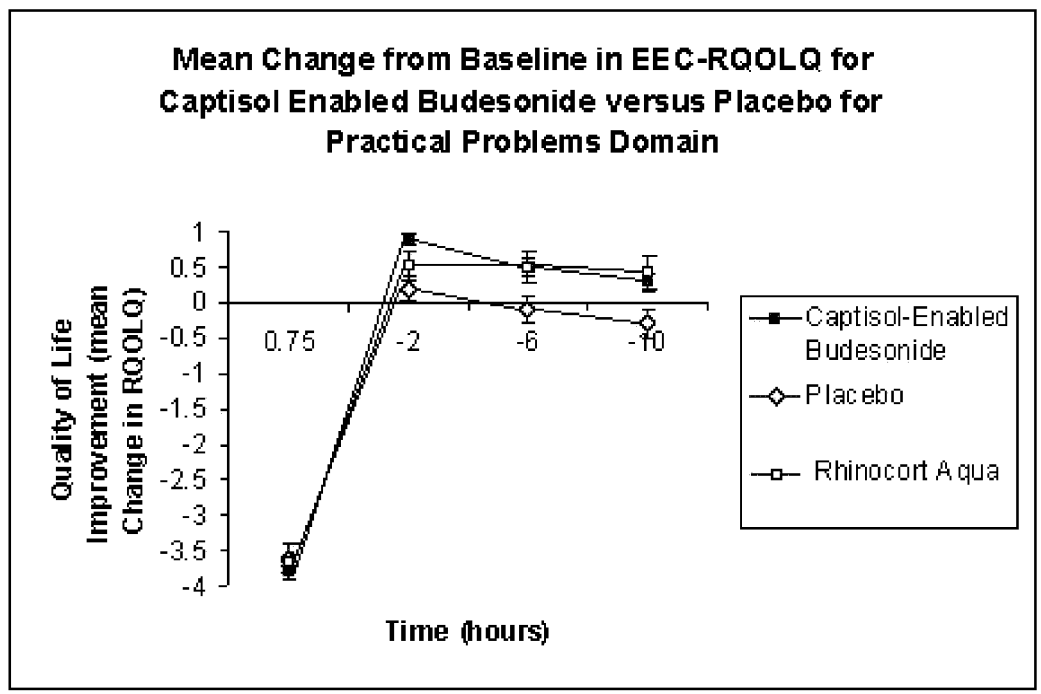
FIGS. 9A-9C depict the results of the effect that the three solutions of Example 33 have on the EEC-QOLQ as determined using the Quality of Life Questionnaire.
Figure 9B:
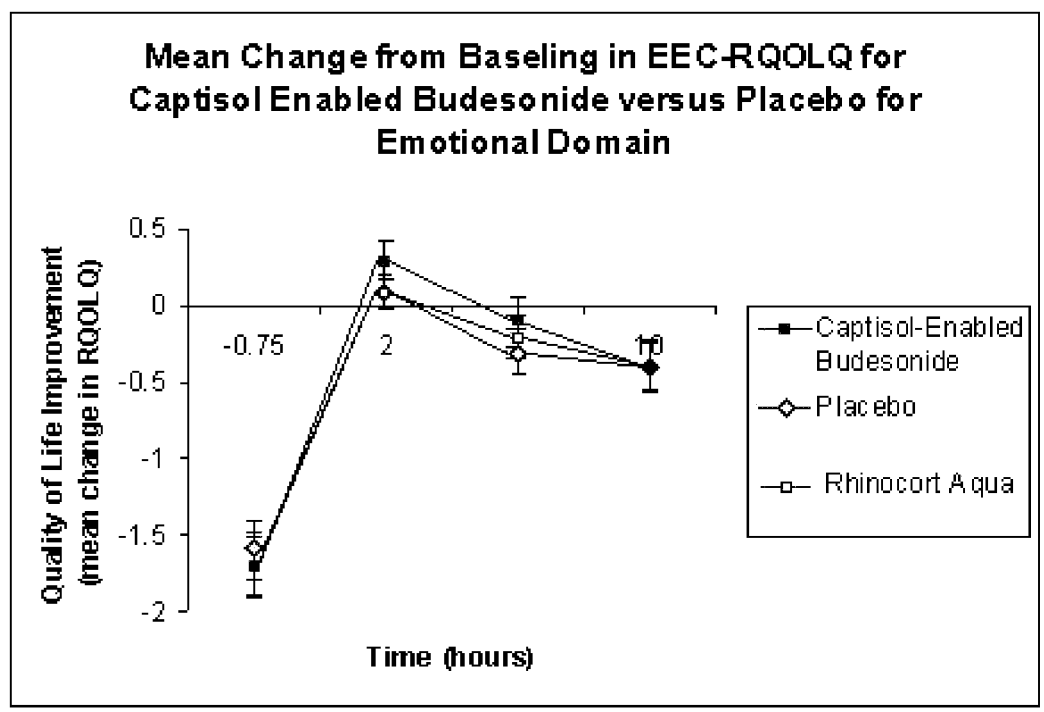
Figure 9C:
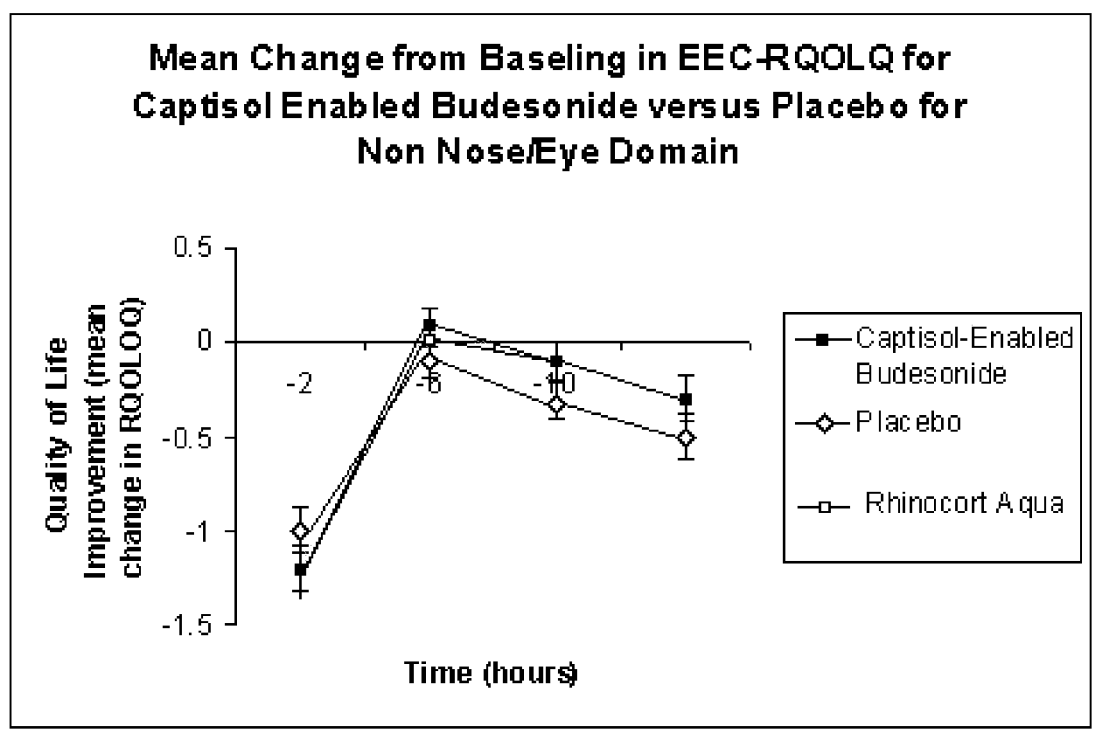

The EEC-QOLQ consisted of the following questions by way of which subjects rated their overall symptoms before and after administration of the three solutions.

using ANCOVA. The EEC-RQOLQ was administered at −0.75 hours pre-dose, and at 2, 6 and 10 hours post-dose. Quality of life was improved in patients treated with CAPTISOL-ENABLED Budesonide compared to placebo in all domains. The mean change from baseline in EEC-RQOLQ scores for CAPTISOL-ENABLED Budesonide versus placebo were, for each domain, respectively: Emotional: 2 h: −0.3; −0.1; 6 h: 0.1; 0.3; 10 h: 0.4; 0.4. Non-nose/Eye symptoms 2 h: −0.1; 0.1; 6 h: 0.1; 0.3; 10 h: 0.3; 0.5. Practical Problems: 2 h: −0.9; −0.2 (p=0.008); 6 h: −0.5; 0.1 (p=0.016), 10 h: −0.3; 0.3 (p=0.019). The effects of the three solutions on the EEC-QOLQ are summarized in FIGS. 9A to 9C. Subjects receiving CAPTISOL-ENABLED Budesonide demonstrated improved QOL in the Emotional Domain and Practical Problems Domain. There was no significant difference in RQLQ between the two treatments at ay time point.

This study demonstrates that this EEC-RQOLQ is a good indicator of QOL in the EEC. Practical Problems is an EEC-RQOL Questionnaire
How bothered by each of the following symptoms have you been during your stay in the EEC? (Circle one number per questions)

| | Not troubled | Hardly troubled | Somewhat troubled | Moderately troubled | Quite a bit troubled | Very troubled | Extremely troubled |
|---|---|---|---|---|---|---|---|
| Non-nose/eye symptoms | | | | | | | |
| 1. Lethargy, fatigue, exhaustion | 0 | 1 | 2 | 3 | 4 | 5 | 6 |
| 2. Headaches | 0 | 1 | 2 | 3 | 4 | 5 | 6 |
| 3. Nausea | 0 | 1 | 2 | 3 | 4 | 5 | 6 |
| 4. Coughing | 0 | 1 | 2 | 3 | 4 | 5 | 6 |
| 5. Thirst or dryness | 0 | 1 | 2 | 3 | 4 | 5 | 6 |
| 6. Difficulty swallowing | 0 | 1 | 2 | 3 | 4 | 5 | 6 |
| 7. Reduced productivity | 0 | 1 | 2 | 3 | 4 | 5 | 6 |
| 8. General Body Aching | 0 | 1 | 2 | 3 | 4 | 5 | 6 |
| 9. Plugged and/or popping ears | 0 | 1 | 2 | 3 | 4 | 5 | 6 |
| 10. Feeling worn out (physically) | 0 | 1 | 2 | 3 | 4 | 5 | 6 |
| Practical Problems | | | | | | | |
| 11. Need to rub eyes | 0 | 1 | 2 | 3 | 4 | 5 | 6 |
| 12. Need to blow nose repeatedly | 0 | 1 | 2 | 3 | 4 | 5 | 6 |
| Emotional | | | | | | | |
| 13. Restlessness | 0 | 1 | 2 | 3 | 4 | 5 | 6 |
| 14. Irritability | 0 | 1 | 2 | 3 | 4 | 5 | 6 |
| 15. Lack of concentration | 0 | 1 | 2 | 3 | 4 | 5 | 6 |

The EEC-RQOLQ consists of Non-nose/Eye Symptoms, Practical Problems, and Emotional domains to assess the QOL experienced by patients in the EEC. The higher the score, the worse patients feel. The Practical Problems domain is important in the EEC-RQOLQ as it assesses the need to rub nose/eyes and to blow nose repeatedly, thus having an impact on daily activity.

Baseline was defined as the QOL questionnaire administered prior to EEC entry, after exposure in the EEC and after treatment. Comparisons between treatments were completed important domain in the EEC-RQOLQ as it assesses the need to rub nose/eyes and to blow nose repeatedly, thus having an impact on daily activity. QOL scores in this domain were significantly improved in patients treated with CAPTISOL-ENABLED Budesonide compared to placebo.

Example 34

A clinical trial was conducted to evaluate the performance of a combination composition of the invention in the treatment of nasal symptoms and non-nasal symptoms caused by exposure of subjects to an allergen.

Four aqueous based formulations were made: Solution A—comprising CAPTISOL, budesonide, azelastine hydrochloride, and aqueous liquid carrier; Suspension B—comprising RHINOCORT AQUA suspension of budesonide in aqueous liquid carrier; Solution C—comprising ASTELIN solution of azelastine hydrochloride in aqueous liquid carrier, and Solution D (placebo)—comprising buffered saline. Solution A was made by mixing twenty NEBUAMPS (500 µg/mL nominal) to a bottle containing 4.71 mg CAPTISOL and 87.6 mg azelastine hydrochloride followed by mixing overnight to form a solution containing 424 µg/mL of budesonide and 100 mg/mL of CAPTISOL. A 4 mL portion of the solution was placed in a smaller bottle fitted with a spray valve. Solution B was purchased and used as is (32 µg of budesonide per spray) using a spray volume of 50 µl with the supplied valve. Solution C was purchased, poured into a smaller bottle and used with the supplied valve. Bottles containing Solutions A and D were equipped with a 70 µl Pfeiffer spray valve. Bottles were masked prior to use.

Clinical Protocol.

A Randomized, Double-Blind, Placebo-Controlled, Three-Way Cross-Over Study to Compare the Relative Efficacy of CAPTISOL-ENABLED Budesonide+Azelastine Nasal Spray (Single Solution) and RHINOCORT AQUA+ASTELIN Nasal Spray (Two Separate Solutions) against Placebo Nasal Spray Solution in the Treatment of Allergic Rhinitis in an Environmental Exposure Chamber (EEC) Model All study drugs were administered as one spray in each nostril. The test treatment (CAPTISOL-ENABLED Budesonide+Azelastine Nasal Solution) were administered along with a placebo in a blinded fashion ensuring that the CAPTISOL-ENABLED formulation is administered first. The reference treatment (RHINOCORT AQUA Nasal Spray+ASTELIN Nasal Spray) were administered in a blinded fashion ensuring that the ASTELIN Nasal Spray formulation is administered first. Two bottles were used for Treatment C (the placebo treatment). All study medications were administered intranasally using metered-dose nasal spray pumps. In this particular study, the allergic symptoms were due to allergic rhinitis and rhinoconjunctivitis. The test treatment delivered a single spray of 32 µg/spray of budesonide and 137 µg/spray of azelastine in each nostril. The reference treatment delivered separate single sprays of 32 µg/spray of budesonide and 137 µg/spray of azelastine in each nostril. The placebo was a single spray in each nostril.

Subjects enrolled in the study (108) were exposed to ragweed pollen using an EEC model. The nasal symptoms, non-nasal symptoms, and quality of life for each subject were determined.

After passing the initial Screening Visit (Visit 1), which occurred within 30 days prior to randomization (Visit 3), patients attended two 3-hour Priming Visits (Visits 2a and 2b) in the EEC. During the Priming Visits, patients were exposed to ragweed pollen at an average session concentration of approximately 3500±500 particles per $m^3$ for a total duration of approximately 3 hours. Following an initial 30-minute exposure, patients were asked to record their instantaneous nasal symptom scores (NSS) and non-nasal symptom scores (NNSS) every 30 minutes for 2.5 hours. Patients were required to meet a minimum threshold response on one Priming Visit to be eligible to be randomized on Treatment Day 1 (Visit 3). The minimum threshold is a TNSS of 6 units, including a score of at least 2 for congestion on at least one diary card on at least one priming visit.

Patients were not permitted to use rescue medications throughout the study. Use of rescue medications would result in removal from the study at the discretion of the investigator. Patients were monitored for adverse events throughout the exposure sessions.

On Treatment Day 1 (Visit 3), patients reported to the clinic approximately 1 hour prior to entry into the EEC. The patients were questioned regarding changes in their health and concomitant medications. All patients entered the EEC within an approximate 10-minute window and were exposed to ragweed pollen in the EEC for a period of 12 hours.

Over the first 1.5 hours in the EEC, the patients evaluated their nasal and non-nasal symptoms every 30 minutes to determine adequate baseline symptoms. Patients who met the predetermined minimum TNSS of 6 units, including a minimum score of 2 for congestion on at least one diary card prior to treatment, were randomized to receive one of three treatments in a double-blind manner. Patients who did not meet the predetermined TNSS were not dosed and were withdrawn from the study.

Following administration of the study drug, patients were asked to assess their nasal and ocular symptoms (TSS, TNSS and TOSS) at 10, 20, 40, 60, 90 and 120 minutes post dose, then every hour up to 10 hours post-dose. During the entire time (a total of about 12 hours) patients were in the EEC, they were exposed to ragweed pollen controlled at an average session concentration of approximately 3500±500 particles per $m^3$. An EEC-RQLQ was administered prior to entering the EEC, at −0.75 hours pre-dose, and post-dose at 2, 6 and 10 hours. At the end of the session, patients were asked to globally assess the study drug efficacy compared to how they felt prior to its administration (using a 7-point scale).

Patients were asked to return to the EEC for two priming visits prior to each of Treatment Days 2 and 3. However, patients were not required to achieve a minimum threshold response on these follow-up priming visits (Visits 4a and 4b and Visits 6a and 6b).

The procedures for Treatment Days 2 and 3 (Visits 5 and 7) was the same as for Treatment Day 1 described above, except that patients did not need to meet the predetermined minimum TNSS to proceed in the study. There was a washout period of at least 10 days between treatment periods.

The total duration of a patient's participation in this study did not exceed 75 days.

The primary objective of this study was to evaluate the relative efficacy of CAPTISOL-ENABLED Budesonide+Azelastine Nasal Spray Solution and RHINOCORT AQUA+ASTELIN Nasal Spray compared to Placebo using Total Nasal Symptom Score (TNSS) in patients with SAR exposed to controlled ragweed pollen using an EEC model.

The secondary objectives were to evaluate the relative efficacy of:
  CAPTISOL-ENABLED Budesonide+Azelastine Nasal Spray (Single Solution) and Budesonide+Azelastine Nasal Spray (Two Separate Solutions) compared to Placebo by evaluating Total Symptom Score (TSS) and Total Ocular Symptom Score (TOSS)
  The three study treatments on an EEC—Rhinoconjunctivitis Quality of Life Questionnaire (EEC-RQLQ).
  The three study treatments on the global rating score.
  The questions included in the Rhinoconjunctivitis Quality of Life Questionnaire for use in the Environmental Exposure Chamber (RQLQ-EEC) were developed using focus groups and were used in the current study as a secondary efficacy measurement. Patients were asked to complete the RQLQ-EEC 5 times at each treatment visit, once before entering the EEC, 3 times while in the EEC, and once following the completion of the final Symptom Diary Card in the EEC. The RQLQ-EEC was administered before entering the EEC and during the EEC was divided into 3 domains: non-nose/eye symptoms (10 questions), practical problems (2 questions), and emotions (3 questions). The non-nose/eye symptoms and practical problems domains were scored between 0 (not troubled) and 6 (extremely troubled), and the emotions domain were scored between 0 (none of the time) and 6 (all of the time). The mean score of the 3 domains yielded an overall quality-of-life score. The RQLQ-EEC administered at the end of the EEC session consisted of the 3 domains and an additional global assessment domain. The global assessment was scored between 0 (very much better) and 6 (very much worse).

Patients rated nasal symptoms (rhinorrhea, nasal congestion, nasal itchiness, and sneezing) and non-nasal symptoms (itchy/gritty eyes, tearing/watery eyes, red/burning eyes, itchy ears and palate).

The severity of the nasal and non-nasal symptoms of allergic rhinitis was recorded on a diary card using the severity rating scale shown below. The nasal and non-nasal symptoms are as follows: 1) nasal: runny nose (anterior rhinorrhea/postnasal drainage), itchy nose, nasal congestion (stuffy nose) and sneezing; 2) non-nasal: itchy/gritty eyes, red/burning eyes, tearing/watery eyes, itchy ear/palate; and 3) ocular: itchy/gritty eyes, red/burning eyes, tearing/watery eyes.

| Severity Rating Scale for Allergy Symptoms | |
|---|---|
| Score | Definition |
| 0 = none | Symptom is not present |
| 1 = mild | Sign/symptom is clearly present but minimal awareness; easily tolerated |
| 2 = moderate | Definite awareness of sign/symptom that is bothersome but tolerable |
| 3 = severe | Sign/symptom is hard to tolerate; causes interference with activities of daily living and/or sleep |

The TNSS, TOSS and TSS scores were then totaled. The data are set forth in FIGS. 12A-12C.

Figure 12A:
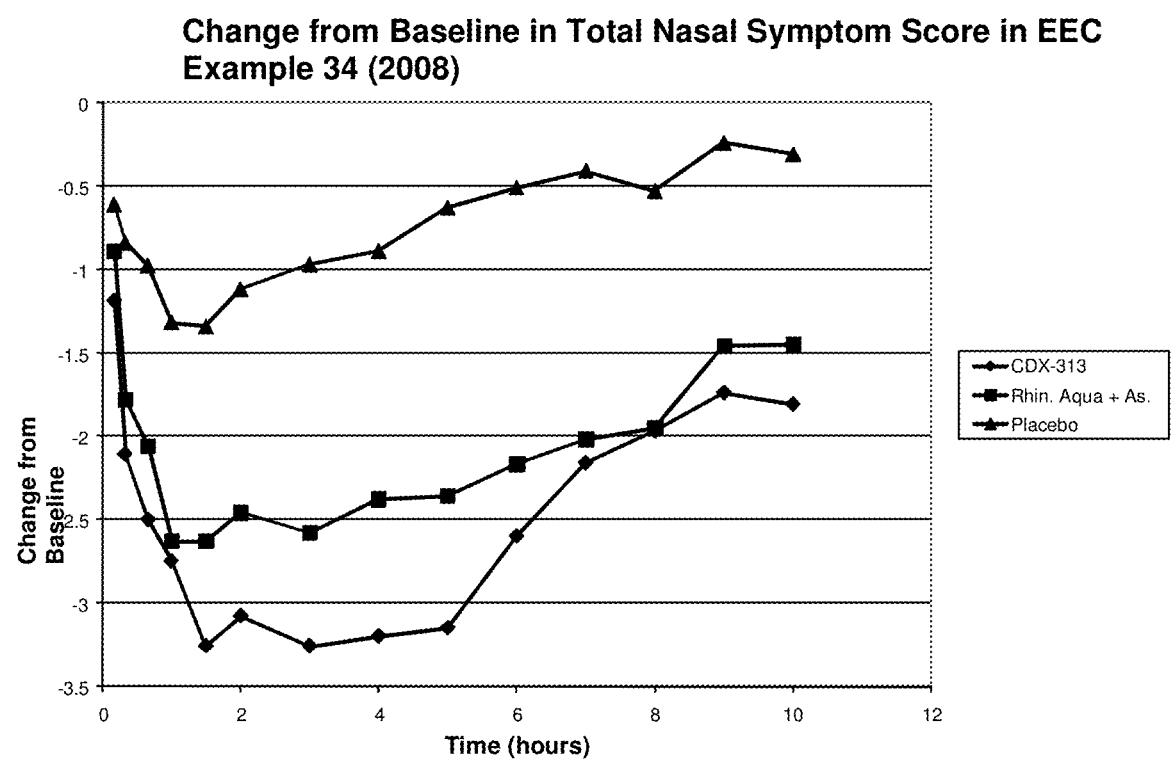
FIGS. 12A-12C depict charts for the change in baseline in the TNSS, TOSS, and TSS, respectively, in the study of Example 34 using CAPTISOL Budesonide+Azelastine solution, and budesonide and azelastine.
Figure 12B:
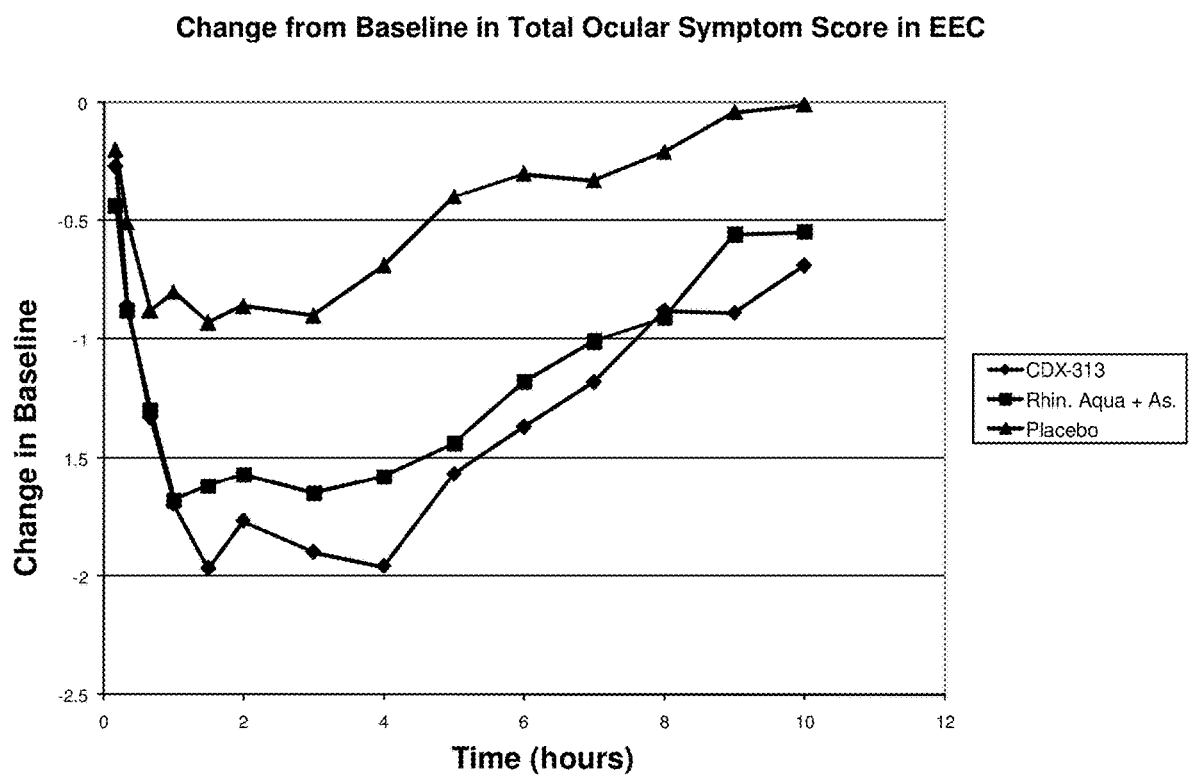
Figure 12C:
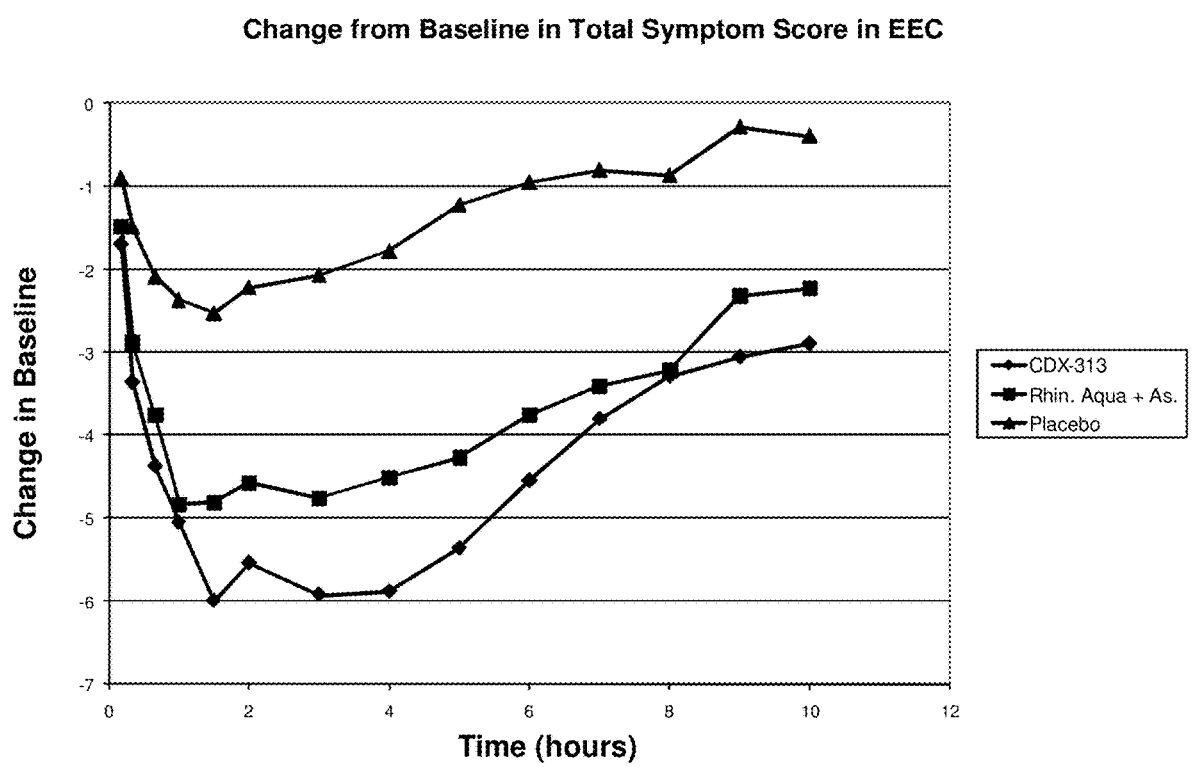
Figure 12D:
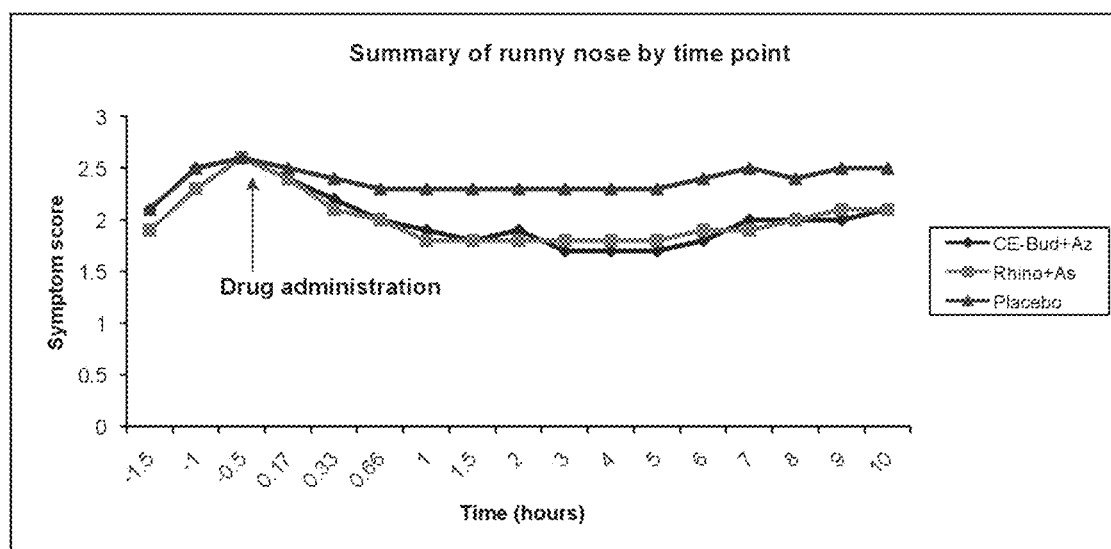
FIGS. 12D-12H depict charts of summaries for individual symptom scores as described in Example 34.
Figure 12E:
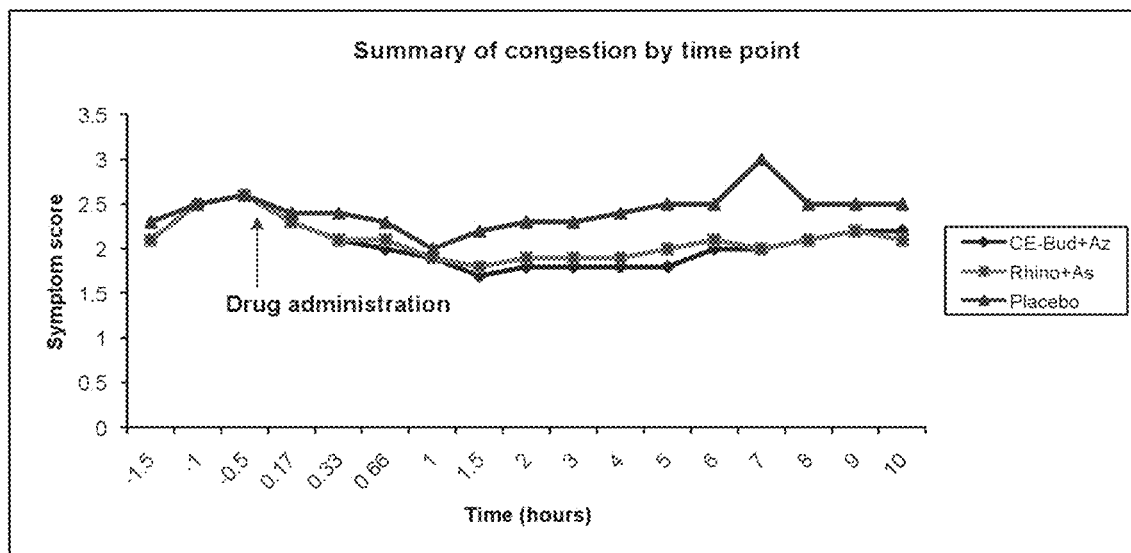
Figure 12F:
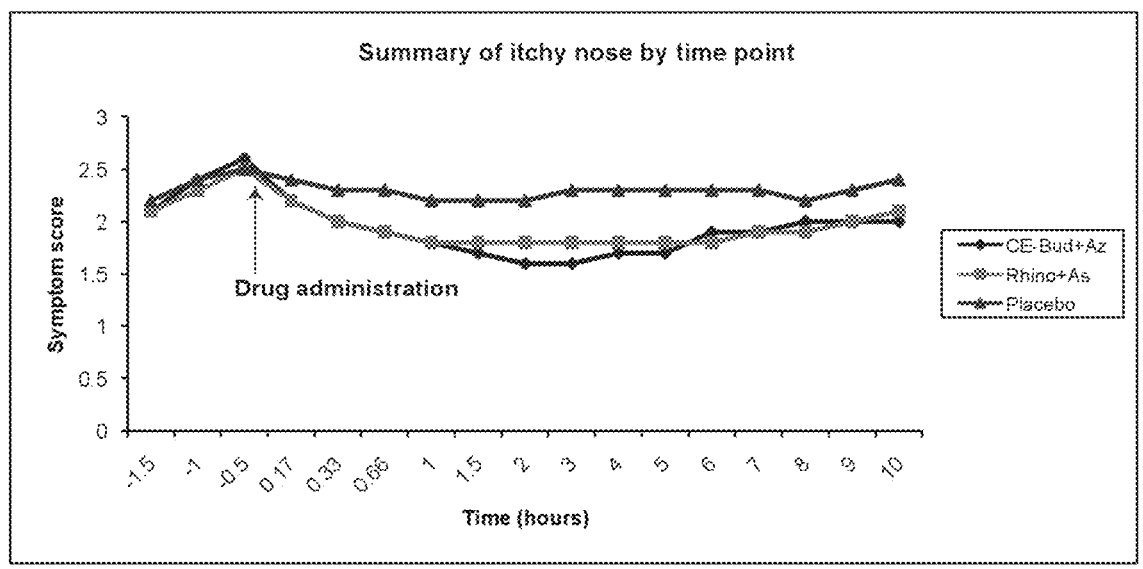
Figure 12G:
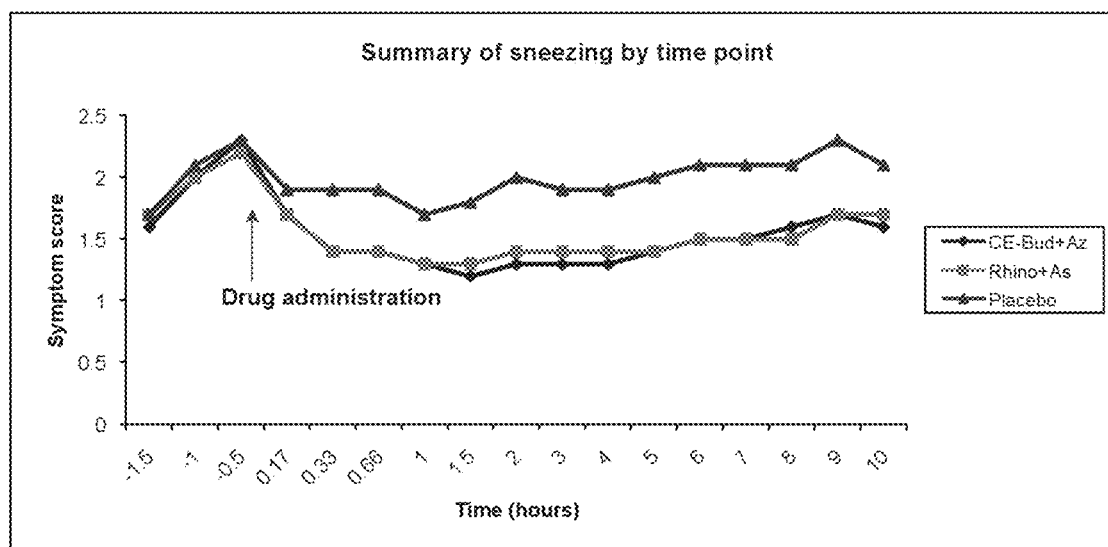
Figure 12H:
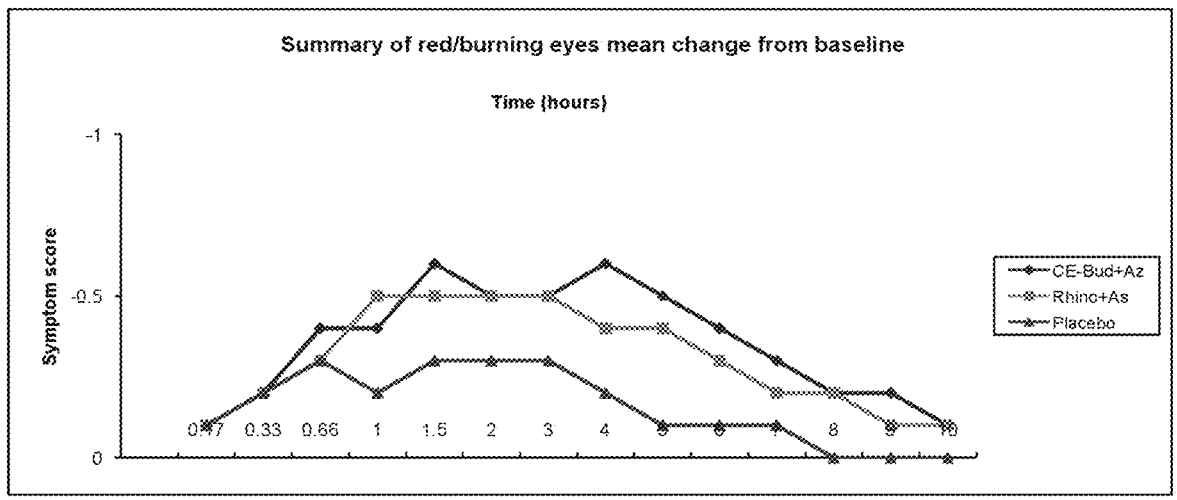
Figure 12I:
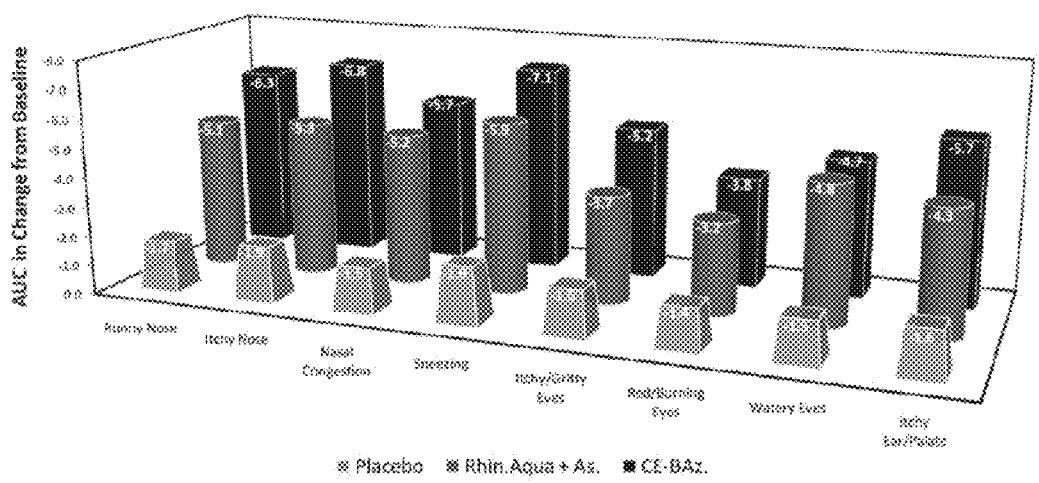
FIG. 12I depicts the AUC in change from baseline for a number of symptoms measured in the study of Example 34.
Figure 12J:
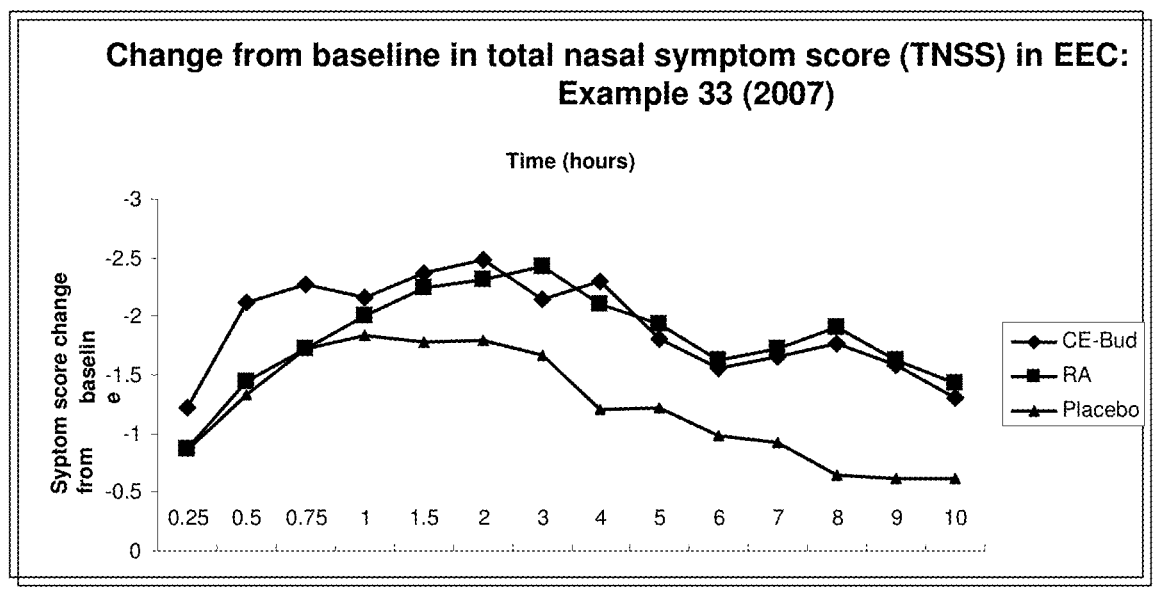
FIGS. 12J-12L depict charts relating to a meta-analysis of the clinical studies of Examples 33 and 34.

For every symptom except watery eyes, the AUC of CAPTISOL-ENABLED Budesonide+Azelastine HCl showed a rank order greater improvement than the reference treatment (see FIG. 12I).

The data demonstrate that the composition of the invention is at least as good as (provides at least the same overall relief of nasal, ocular and total symptoms as does the) combined sequential administration of the two commercial products RA and AST.

The data demonstrated the following trends as regards the performance of the CAPTISOL ENABLED Budesonide nasal solution (the combination solution, "CDX-313") compared to placebo and the separate and sequential administration of RHINOCORT AQUA and ASTELIN:

| | |
|---|---|
| Total symptom scores: | Better than placebo |
| | Combination at least as good as drugs administered separately |
| Total nasal symptom scores | Better than placebo |
| | Combination at least as good as drugs administered separately |
| Total ocular symptom scores | Better than placebo |
| | Combination comparable to drugs administered separately |
| Duration of action | Longer duration of action than placebo for relief of nasal symptoms |
| | Longer duration of action than drugs administered separately for relief of nasal symptoms |

A meta analysis was conducted to compare the clinical studies of Examples 33 (2007) and 34 (2008). Statistical analyses were first performed to ensure that the placebo arms between studies behaved similarly. An analysis of covariance (ANCOVA) was then performed on baseline adjusted Area under the Curve (AUC) for TNSS and overall mean change from baseline in TNSS (placebo arms were pooled). The model included fixed terms for sequence, period and treatment and a random effect for subject nested within sequence. Baseline TNSS was used as a covariate in the model after verifying homogeneity of slopes. All comparisons were adjusted for multiple testing.

Figure 12K:
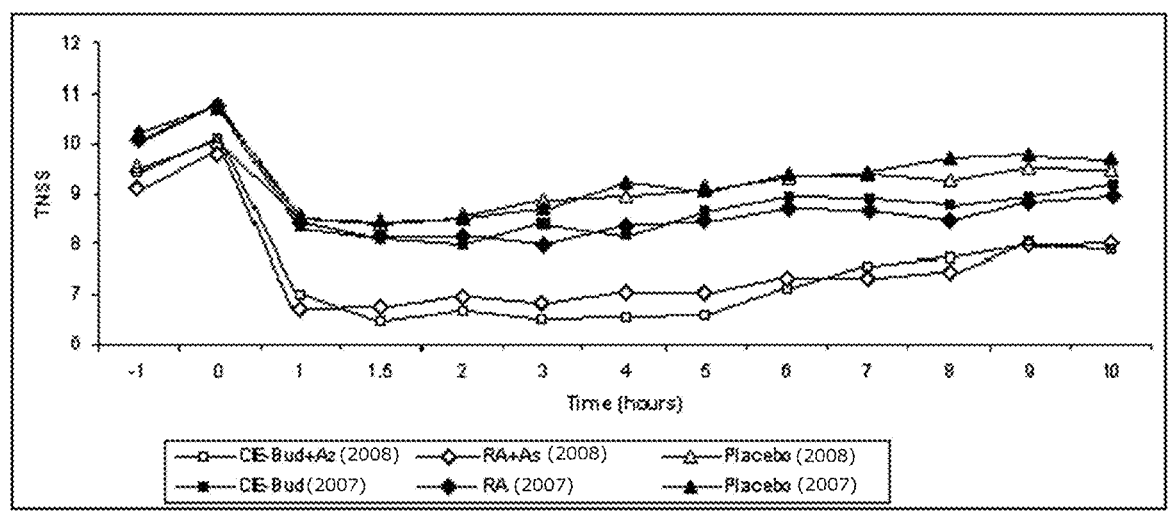
Figure 12L:
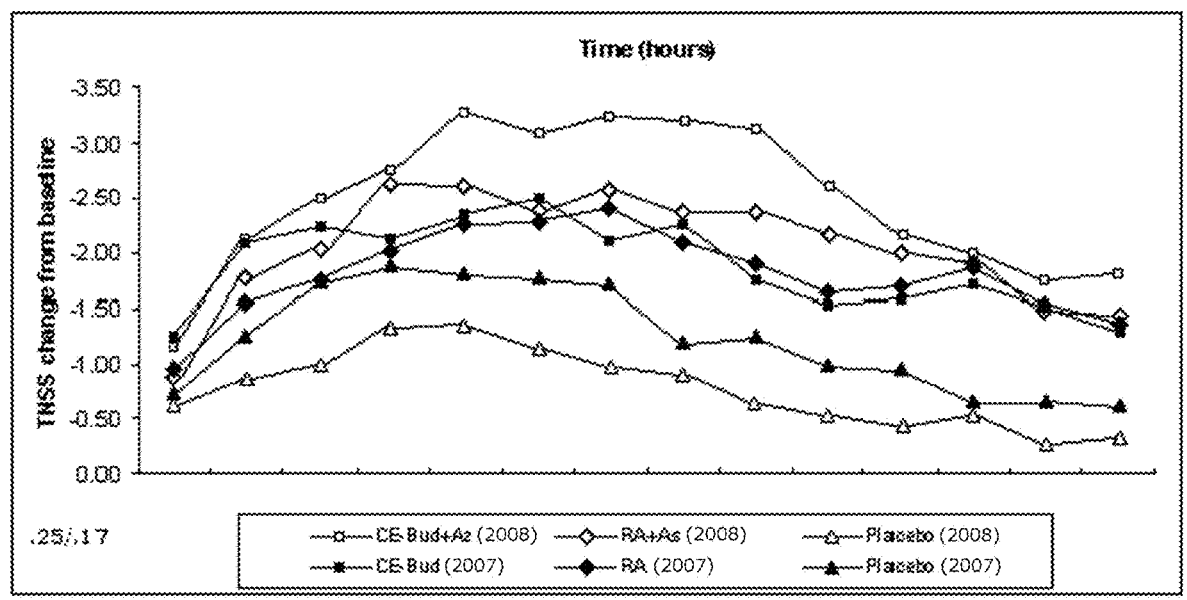
Figure 13A:
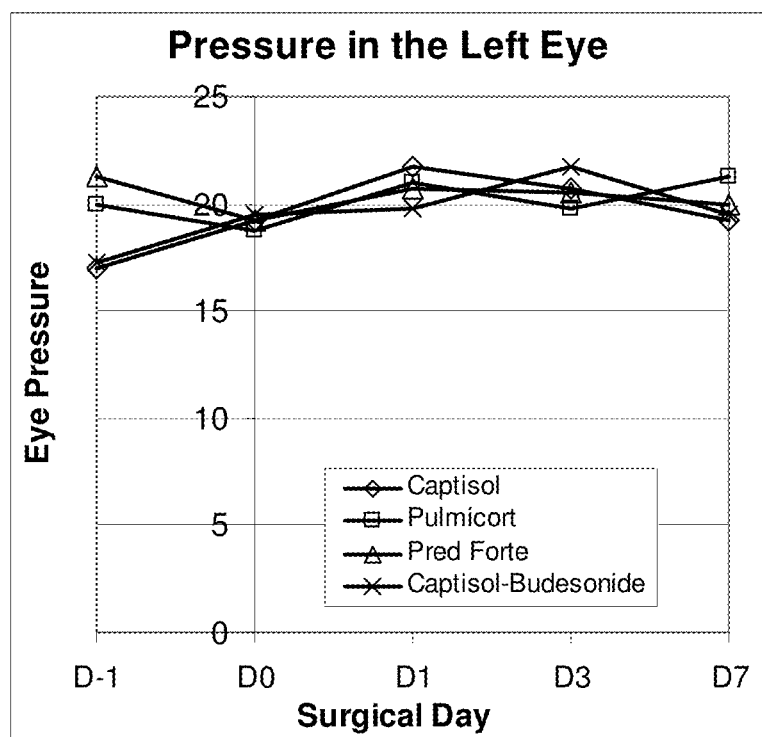
FIGS. 13A-13B depict charts detailing the changes in ocular pressure of rabbits treated according to Example 41.
Figure 13B:
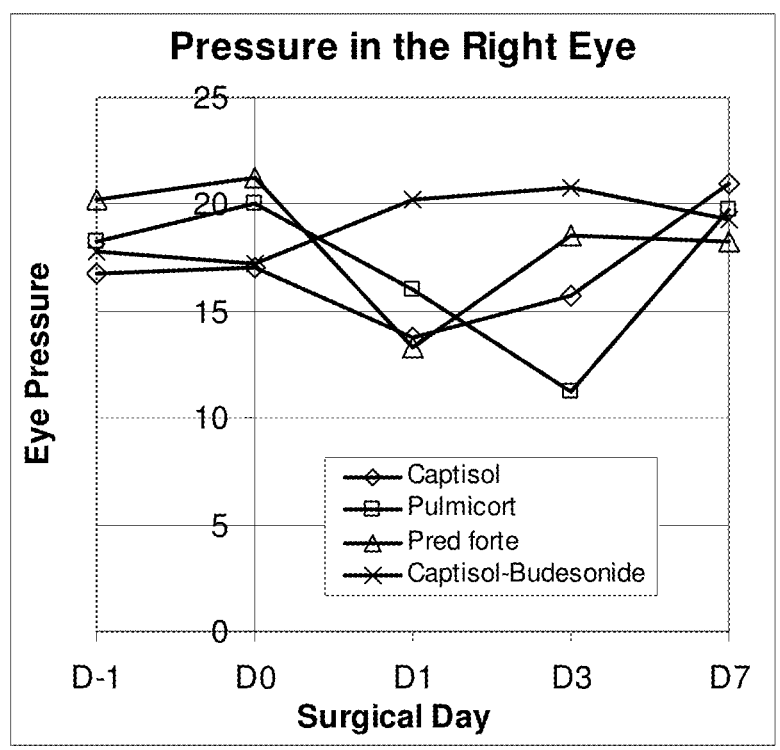

Meta analyses revealed no significant difference in the placebo effect and that placebo effects were comparable ($p=0.64$) in the two studies, thus allowing pooling of data and comparisons to be made between test products with CE and the comparators for both studies. Baseline adjusted AUC and overall mean change from baseline in TNSS showed similar trends for both studies (FIGS. 12A and 12I). Change from baseline in AUC for TNSS revealed that when CE-BUD was compared to CE-BUD+AZ there was a significantly greater relief of nasal symptoms with the combination product than CE-BUD alone ($p=0.005$) and when RA was compared with CE-BUD−AZ there was a significantly greater relief of nasal symptoms with the combination product than with RA alone ($p=0.009$) (FIGS. 12K and 12L). RA was compared to AS+RA and there was no statistically significant difference after adjustment for multiple testing ($p=0.085$) and this was also true when CE-BUD was compared with RA ($p=0.999$). A comparison of CE-BUD+AZ with AS+RA indicated no statistically significant difference in nasal relief with the solubilized product compared with each product given individually and consecutively. However, TNSS was numerically lower for CE-BUD+AZ.

In FIGS. 12D and 12E, NSS of runny nose and congestion showed similar onset and duration of action as TNSS. In FIGS. 12F and 12G, onset of action of itchy nose and sneezing were significantly faster at 10 mins for CAPTISOL-ENABLED Budesonide+Azelastine compared to RHINOCORT AQUA. RHINOCORT AQUA/ASTELIN did not show an effect until 0.33 hour. As with the other parameters, both treatments had the same duration (10 hours) for itchy nose and sneezing.

The CAPTISOL-ENABLED Budesonide+Azelastine formulation provides long-lasting relief of all allergic rhinitis symptoms similar to consecutive administration of RHINOCORT AQUA and ASTELIN. However, faster immediate relief of itchy nose and sneezing was obtained in a more convenient combination dose format.

As shown in FIG. 12H, CAPTISOL-ENABLED Budesonide+Azelastine provided the same or greater numerical TOSS relief (did not reach statistical difference) than RHINOCORT AQUA+ASTELIN for 11 of 14 time points and longer-lasting relief of red/burning eyes (7 h vs. 6 h).

Thus, CAPTISOL-ENABLED Budesonide+Azelastine provided significant long-lasting relief of all ocular symptoms. It also provided a longer duration of action for the red/burning eyes symptom compared to the RHINOCORT AQUA+ASTELIN format. Additionally, CAPTISOL-ENABLED Budesonide+Azelastine is provided in a more convenient combination single spray/dose format.

The mean AUC for TSS was significant for CAPTISOL-ENABLED Budesonide+Azelastine HCl (−45.2±45.02) vs. placebo (−13.3±35.88) (p<0.0001) but was not significantly different from the reference treatment (−37.3±47.69). The onset of action (defined as the first time point after initiation of treatment when the drug demonstrated a statistically significant greater change from baseline in the efficacy endpoint compared to placebo that proved durable from that point onward for at least three consecutive time points) of both CAPTISOL-ENABLED Budesonide+Azelastine HCl and the reference treatment was 0.33 hours. At every time point from 0.33 hours onward, both active treatments were significantly different from placebo. The reference treatment and test treatment were never significantly different from each other although the test treatment was numerically superior from 0.33 hours onward. The duration of action for each active treatment was 10 hours. The TSS maximum mean decrease from baseline was statistically significant for each of the active treatments vs. placebo (both p values<0.0001). The mean maximum change was −8.8±5.51 for CAPTISOL-ENABLED Budesonide+Azelastine HCl, −7.9±5.45 for RHINOCORT AQUA+ASTELIN, and −5.2±4.55 for placebo.

For the non-nasal symptom of itchy ear/palate, CAPTISOL-ENABLED Budesonide+Azelastine had an onset of action at the 0.33 hr time point while RHINOCORT AQUA+ASTELIN showed efficacy beginning at the 0.66 hr time point. For this symptom, both treatments maintained efficacy to the 10 hr time point. When compared to each other, no significant difference was observed between the two active treatments for itchy ear/palate at any time point.

For the Overall RQLQ, which groups all of the RQLQ domains together, a significant treatment effect was observed for CAPTISOL-ENABLED Budesonide+Azelastine at each of the 2, 6 and 10 hr time points. This treatment effect was not observed for RHINOCORT AQUA+ASTELIN at any time point. This difference between the two active treatments was also evident when comparing the two active treatments to each other at the 6 and 10 hr time points. This confirms a significant difference between the two active treatments with CAPTISOL-ENABLED Budesonide+Azelastine showing efficacy while RHINOCORT AQUA+ASTELIN did not.

CAPTISOL-ENABLED Budesonide+Azelastine HCl was demonstrated to have a rapid and durable onset of action against the nasal and ocular symptoms of ragweed allergy. The CAPTISOL-ENABLED Budesonide formulation provided a more convenient combination of a single spray/dose format than sequential RHINOCORT AQUA+ASTELIN. The single spray format offers potential advantages, such as consistent ratio of actives in every drop of the spray, increased uniformity of dosing, elimination of need to re-suspend drug before use, and ease of manufacture including aseptic filtration to allow the use of valves designed for preservative-free formulations.

Example 35

Performance of an aqueous liquid composition of the invention in a multi-dose pump nasal spray was evaluated to determine the spray content uniformity (SCU), pump delivery, spray pattern, droplet size distribution. The spray content of a delivered dose or emitted dose is the quantity of drug outside of the device that is available to a subject on a unit dose basis, i.e. after a single actuation of the pump nasal spray.

The composition comprised a corticosteroid and antihistamine, e.g., combination of budesonide (425 µg/mL), azelastine HCl (0.2%), CAPTISOL (10%). The pump nasal spray was adapted to provide a target pump delivery (the weight of composition emitted by the device) of 70 mg of composition upon each actuation.

Results from evaluation of performance of an aqueous liquid composition (budesonide (425 µg/mL), azelastine HCl (0.2%), CAPTISOL (10%) in buffer) in a pump nasal spray.

Droplet Distribution Data:

| Dv10 (µm) | Dv50 (µm) | Dv90 (µm) | Span | <10 µm (%) |
|---|---|---|---|---|
| 16.73 ± 0.28 | 32.78 ± 0.14 | 67.48 ± 0.31 | 1.55 ± 0.03 | 2.66 ± 0.13 |
| 17.11 ± 0.82 | 33.45 ± 1.63 | 69.55 ± 5.82 | 1.57 ± 0.07 | 2.47 ± 0.36 |
| 19.68 ± 0.05 | 39.18 ± 0.88 | 88.33 ± 2.04 | 1.75 ± 0.01 | 1.68 ± 0.08 |
| 19.30 ± 0.17 | 38.10 ± 0.34 | 88.36 ± 1.54 | 1.81 ± 0.04 | 1.9 ± 0.05 |
| 17.31 ± 0.5 | 36.74 ± 0.63 | 80.74 ± 3.26 | 1.73 ± 0.08 | 2.51 ± 0.21 |
| 17.39 ± 0.43 | 35.95 ± 1.25 | 77.57 ± 4.88 | 1.67 ± 0.08 | 2.48 ± 0.21 |
| 17.33 ± 0.31 | 35.74 ± 2.52 | 76.99 ± 8.21 | 1.66 ± 0.12 | 2.5 ± 0.21 |

Spray Pattern Data:

| Unit # | Dmin (mm) | Dmax (mm) | Ovality Ratio |
|---|---|---|---|
| 3 cm Distance to the Laser Beam | | | |
| SP3-COMBO1 | 20.0 | 24.5 | 1.225 |
| SP3-COMBO2 | 23.3 | 33.0 | 1.416 |
| SP3-COMBO3 | 24.7 | 29.9 | 1.211 |
| Mean | 22.7 | 29.1 | 1.284 |
| SD | 2.41 | 4.30 | 0.11 |
| % CV | 10.65 | 14.77 | 8.92 |
| 6 cm Distance to the Laser Beam | | | |
| SP6-COMBO1 | 32.8 | 57.3 | 1.747 |
| SP6-COMBO2 | 36.8 | 60.1 | 1.634 |
| SP6-COMBO3 | 33.4 | 47.7 | 1.428 |
| Mean | 34.3 | 55.0 | 1.603 |
| SD | 2.16 | 6.50 | 0.16 |
| % CV | 6.28 | 11.82 | 10.09 |

| 3 cm Distance to Laser Beam | | 6 cm Distance to Laser Beam | |
|---|---|---|---|
| Unit # | Spray Weight (mg) | Unit # | Spray Weight (mg) |
| SP3-COMBO1 | 55.5 | SP6-COMBO1 | 71.7 |
| SP3-COMBO2 | 73.0 | SP6-COMBO2 | 75.1 |
| SP3-COMBO3 | 70.4 | SP6-COMBO3 | 70.8 |
| Mean | 66.3 | Mean | 72.5 |
| SD | 9.44 | SD | 2.27 |
| % CV | 14.24 | % CV | 3.13 |

| Unit # | Spray Weight (mg) |
|---|---|
| COMBO1-DSD3 | 69.6 |
| COMBO2-DSD3 | 72.8 |
| COMBO3-DSD3 | 68.0 |
| Mean | 70.1 |
| SD | 2.44 |
| % CV | 3.48 |

The results indicate that the mean pump delivery ranged from 72.5 to 74.5 mg per actuation with a standard deviation ranging from ±0.54 to ±1.6. The plume emitted by the nasal spray was characterized by laser diffraction to determine the droplet size distribution (Dv10, Dv50, Dv90), span and percentage of droplets having a droplet size of <10 µm. The mean Dv10 ranged from 16.73 to 19.68 µm with a standard deviation ranging from ±0.05 to ±0.82 µm. The mean Dv50 ranged from 32.78 to 39.18 µm with a standard deviation ranging from ±0.14 to ±1.63 µm. The mean Dv90 ranged from 67.48 to 88.36 µm with a standard deviation ranging from ±0.31 to ±5.82 µm. The mean span ranged from 1.55 to 1.81 with a standard deviation ranging from ±0.01 to ±0.08 µm. The percentage of droplets <10 µm in size ranged from 1.68 to 2.66% with a standard deviation ranging from ±0.05 to ±0.36%.

Example 36

An ophthalmic solution comprising a corticosteroid and SAE-CD is prepared as follows.
Method A. Fluticasone Propionate
A citrate buffer solution at a pH of 4.5 was prepared by mixing various portions of 0.003M citric acid with 0.003M of trisodium citrate. A phosphate buffer solution at a pH of 6.0 was prepared by mixing various portions of 0.003M monobasic sodium phosphate with 0.003M of dibasic sodium phosphate. These stock solutions contained 10% w/v SBE-Gamma (D.S.=6.1) and 0.01% TWEEN. An excess of fluticasone propionate was added to the vials and equilibrated on a rocker for three days. The samples were then filtered using a PVDF 0.22 µm syringe filter. Aliquots of the solutions were placed into clear glass 2 mL serum vials with aluminum crimp caps and Daikyo Flurotec septums. The concentration of the pH 4.5 solution was 232 µg/mL. The concentration of the pH 6.0 solution was 238 µg/mL.
Method B. Mometasone Furoate
A 50 mL solution of 0.08M CAPTISOL with 80 µg/mL of mometasone furoate was prepared by weighing approximately 9.6 grams of CAPTISOL into a 50 mL volumetric flask and qs with a 3 mM citrate buffer pH 4.5. The approximately 4 mg of mometasone furoate was weighed into a media bottle and the CAPTISOL/buffer solution was added to the drug and the bottles were vortexed and sonicated for approximately 5 minutes. The bottles were then placed on a roller mixer (Stuart Scientific SRT2 33 rpm rise/fall 16 mm) protected from light and mixed overnight. After the overnight mixing on the roller mixer the bottles were transferred to a magnetic stirrer, set at 330 RPM, for three days. The solutions were filtered using a PVDF 0.22 µm filter and a sample was assayed from each bottle. The results from the assay were about 6% low from target so additional mometasone furoate anhydrous was added to each bottle and were placed back onto the roller mixer for another 3 days. The solutions were aseptically filtered again and 2 mLs were transferred to the 2 mL clear vials with Teflon stoppers.
Method C. Mometasone Furoate and SBE-γ-CD
A 50 mL solution of 0.08M SBE γ-CD with 400 µg/mL of mometasone furoate was prepared by weighing approximately 9.1 grams of SBE γ-CD into a 50 mL volumetric flask and qs with a 3 mM citrate buffer pH 4.5. The approximately 20 mg of mometasone furoate was weighed into a media bottle and the SBE γ-CD/buffer solution was added to the drug and the bottles were vortexed and sonicated for approximately 5 minutes. The bottles were then placed on a roller mixer (Stuart Scientific SRT2 33 rpm rise/fall 16 mm) protected from light and mixed overnight. After the overnight mixing on the roller mixer the bottles were transferred to a magnetic stirrer, set at 330 RPM, for three days. The solutions were filtered using a PVDF 0.22 µm filter and a sample was assayed from each bottle. The results from the assay were about 6% low from target so additional mometasone furoate anhydrous was added to each bottle and were placed back onto the roller mixer for another 3 days. The solutions were aseptically filtered again and 2 mLs were transferred to the 2 mL clear vials with Teflon stoppers.

Example 37

Preparation of ophthalmic budesonide solution and its placebo for in vivo-testing.
Method A
A buffered, isotonic CAPTISOL solution was prepared. 100 mL water was placed in a suitable vessel. Approximately 4.2 grams of CAPTISOL, approximately 32.3 milligrams of citric acid monohydrate, approximately 43.3 milligrams of sodium citrate dihydrate, and approximately 580 milligrams of sodium chloride were added to the vessel. The solution was mixed with a magnetic stir-bar until all solids were dissolved. The measured pH was 4.5 and the tonicity was 300 mOs.
Method B
The same procedure was followed as was in Method A, with the addition of budesonide and polysorbate-80 after the CAPTISOL, citric acid monohydrate, sodium citrate dihydrate, and sodium chloride were dissolved. Approximately 26.2 milligrams of budesonide was added to the vessel and allowed to mix for approximately 2.5 hours. Approximately 5.0 microliters of polysorbate-80 was added to the vessel and allowed to mix for an additional approximately 2.5 hours. This solution was filtered to remove undissolved excess budesonide, then assayed by HPLC to determine the final budesonide concentration, which was 251 micrograms per milliliter. The measured pH was 4.5 and the tonicity was 300 mOs.

Example 38

Preparation and use of a combination solution containing SAE-CD, budesonide, and azelastine. A solution can be made according to Example 37, except that 500 mg of azelastine is added to the vessel with the budesonide.

Example 39

Preparation and use of a combination solution containing SAE-CD, budesonide, and diclofenac.
A citrate buffer (3 mM pH 4.5) is prepared as follows. Approximately 62.5 mg of citric acid is dissolved in and brought to volume with water in one 100 mL volumetric flask. Approximately 87.7 mg of sodium citrate is dissolved in and brought to volume with water in another 100 mL volumetric flask. In a beaker the sodium citrate solution is added to the citric acid solution until the pH is approximately 4.5.
Approximately 10.4 mg of budesonide, 100 mg of diclofenac and 1247.4 mg of CAPTISOL are ground together with a mortar and pestle and transferred to a 10 mL flask. Buffer solution is added, and the mixture is vortexed, sonicated and an additional 1.4 mg budesonide added. After shaking overnight, the solution is filtered through a 0.22 µm Durapore Millex-GV Millipore syringe filter unit. The resulting budesonide concentration will be approximately 1 mg/mL and the concentration of diclofenac will be approximately 10 mg/mL.

Example 40

Preparation and use of a combination ophthalmic solution comprising CAPTISOL, ofloxacin, and mometasone furoate.

A 50 mL solution of 0.08M CAPTISOL with 80 µg/mL of mometasone furoate and 3 mg/mL ofloxacin can be prepared by weighing approximately 9.6 grams of CAPTISOL into a 50 mL volumetric flask and qs with a 3 mM citrate buffer pH 4.5. The approximately 4 mg of mometasone furoate and 150 mg ofloxacin are weighed into a media bottle and the CAPTISOL/buffer solution was added to the drug and the bottles vortexed and sonicated for approximately 5 minutes. The bottles are then placed on a roller mixer (Stuart Scientific SRT2 33 rpm rise/fall 16 mm) protected from light and mixed overnight. After the overnight mixing on the roller mixer the bottles are transferred to a magnetic stirrer, set at 330 RPM, for three days. The solutions are filtered using a PVDF 0.22 µm filter and a sample assayed from each bottle.

Example 41

In vivo evaluation of a dosage form according to the invention was conducted in rabbits as follows.

A pilot study to test the effectiveness of CE-Budesonide on ocular wound healing was conducted in rabbits. The effectiveness of CE-Budesonide (250 mcg/mL) from Example 37 was compared with commercial products—PULMICORT RESPULES (a suspension of budesonide, 250 mcg/mL) and prednisolone acetate (Pred Forte suspension, 1%) and a CAPTISOL placebo.

Treatment Protocol:

The animals were administered 40 microliter (10 µg) of test material each to both eyes of animals four times a day (6 hours apart) for 3 days prior to induction of eye injury by laser energy on Day 0 (the day of induction of eye injury). Each animal was placed in the left lateral position and thermal injury was made to the right eye with a semiconductor, diode laser. Laser energy was directed through the peripheral clear cornea to the iris surface using a hand-held fiberoptic laser probe injuring three separate sites measuring 2 mm in diameter. Laser energy treatment of the eyes resulted in inflammatory responses of the iris along with proteinaceous and cellular inflammation in the anterior chamber of the eye on Day 0. The injury was graded for inflammation based on the study Ophthalmologist's routine criteria (0: no inflammation, 1: trace flare or cells (very faint), 2: flare/cell mild but clearly visible in anterior chamber, 3: flare/cell turbity moderate in anterior chamber, 4: flare/cell severe in anterior chamber). Ocular pressure was determined using an applanation tonometer.

Slit lamp examinations revealed aqueous flare, conjunctivitis, iritis, and/or superficial keratitis of the right eye following the laser injury in all animals. Aqueous flare had resolved by Day 3 in all animals but one in the PULMICORT RESPULES group.

Decreased eye pressure in the right eye was observed in all animals following laser injury on Day 0. Eye pressure returned to normal values in the CAPTISOL-ENABLED Budesonide solution group by Day 1, and in CAPTISOL vehicle controls, PULMICORT RESPULES, and PRED FORTE by Day 3, 7, and 3, respectively. The results are summarized in the table below and in FIGS. 9a and 9b.

Eye Pressure (Mean±SD)

| | Left Eye | | | |
|---|---|---|---|---|
| Surgical day | CAPTISOL | PULMICORT RESPULES | Pred Forte | CAPTISOL-ENABLED Budesonide |
| D-1 | 17.00 ± 2.71 | 20.00 ± 1.83 | 21.25 ± 0.96 | 17.25 ± 5.12 |
| D0 | 19.25 ± 2.22 | 18.75 ± 2.22 | 19.25 ± 1.50 | 19.50 ± 1.91 |
| D1 | 21.75 ± 2.50 | 21.00 ± 3.37 | 20.75 ± 2.75 | 19.75 ± 2.50 |
| D3 | 20.75 ± 1.26 | 18.75 ± 2.22 | 20.50 ± 2.08 | 21.75 ± 1.50 |
| D7 | 19.25 ± 2.50 | 21.25 ± 2.36 | 20.00 ± 1.41 | 19.50 ± 1.73 |

| | Right Eye | | | |
|---|---|---|---|---|
| Surgical day | CAPTISOL | Pulmicort Respules | Pred Forte | CAPTISOL-ENABLED Budesonide |
| D-1 | 16.75 ± 3.69 | 18.25 ± 2.06 | 20.25 ± 2.22 | 17.75 ± 4.35 |
| D0 | 17.00 ± 2.71 | 20.00 ± 1.83 | 21.25 ± 0.96 | 17.25 ± 5.12 |
| D1 | 13.75 ± 5.62 | 16.00 ± 3.92 | 13.25 ± 2.50 | 20.25 ± 0.96 |
| D3 | 15.75 ± 3.10 | 11.25 ± 4.43 | 18.50 ± 3.00 | 20.75 ± 2.50 |
| D7 | 21.00 ± 2.16 | 19.75 ± 2.06 | 18.25 ± 3.40 | 19.25 ± 1.71 |

The results showed that CE-Budesonide solution effectively reduced inflammatory reactions following laser injury to the iris of rabbits. The resolution of laser-induced eye injury by CAPTISOL-ENABLED Budesonide occurs more rapidly than by either PULMICORT RESPULES, or PRED FORTE. Intraocular pressure returned to normal values

| Group | Treatment | Concentration | Number Of Animals M | Eye drop volume microliter | Anterior chamber flare[1] score D0 | Anterior chamber flare[1] score D1 | Anterior chamber cell[1] Score D0 | Anterior chamber cell[1] Score D1[2] |
|---|---|---|---|---|---|---|---|---|
| 1 | Vehicle Control (~4% CAPTISOL) | 0 mcg/mL | 4 | 40 | 1.75 | 1 | 1.25 | 0 |
| 2 | PUMICORT RESPULES (a suspension of budesonide) | 250 mcg/mL | 4 | 40 | 1.75 | 1 | 1.25 | 0.25 |
| 3 | prednisolone acetate (Pred Forte suspension) | 1% | 4 | 40 | 1.75 | 0.75 | 1.25 | 0.25 |
| 4 | CAPTISOL-ENABLED Budesonide | 250 mcg/mL | 4 | 40 | 2 | 0 | 1.25 | 0 |

[1]Average score of 4 animals. Day 0: the day injury was induced.
[2]Group 2 and 3 each had one animal scored as 1+, all others were 0.

Example 42

Preparation and use of a combination ophthalmic solution containing SAE-CD, budesonide and tobramycin.

An ophthalmic solution of the invention can be made to contain the following ingredients in the approximate amounts indicated per mL of solution.

| Ingredient | Amount in 1 mL of solution |
|---|---|
| Tobramycin | 0.3% (3 mg) |
| Budesonide | 0.025% (250 µg) |
| Benzalkonium chloride | 0.01% |
| SBE-γ-CD | 2% |
| Edentate disodium | 0.1% |
| Sodium chloride | 0.01% |
| Sulfuric acid and/or sodium hydroxide | To adjust pH to physiologic pH |
| Water | Qs. to 1 mL |

Example 43

Preparation and use of a combination ophthalmic solution containing SAE-CD, budesonide and azithromycin.

| Ingredient | Amount in 1 mL of solution |
|---|---|
| Azithromycin | 0.5% (5 mg) |
| Budesonide | 0.025% (250 µg) |
| Benzalkonium chloride | 0.01% |
| SBE-γ-CD | 2% |
| Edentate disodium | 0.1% |
| Sodium chloride | 0.01% |
| Sodium sulfate, sulfuric acid and/or sodium hydroxide | To adjust pH to physiologic pH |
| Water | Qs. to 1 mL |

Example 44

Preparation of ophthalmic solution of SBE γ-CD, Mometasone Furoate, and Timolol

A 50 mL solution of 0.08M SBE γ-CD with 400 µg/mL of mometasone furoate and 2.5 mg/mL of timolol can be prepared by weighing approximately 9.1 grams of SBE γ-CD into a 50 mL volumetric flask and qs with a 3 mM citrate buffer pH 4.5. The approximately 20 mg of mometasone furoate and 125 mg of timolol are weighed into a media bottle and the SBE γ-CD/buffer solution is added to the drugs. The bottles are vortexed and sonicated for approximately 5 minutes. The bottles are then placed on a roller mixer (Stuart Scientific SRT2 33 rpm rise/fall 16 mm) protected from light and mixed overnight. After the overnight mixing on the roller mixer the bottles are transferred to a magnetic stirrer, set at 330 RPM, for three days. The solutions are filtered using a PVDF 0.22 nm filter.

Example 45

The table below summarizes some solubility data for the listed corticosteroids in the absence (intrinsic solubility of corticosteroid in the aqueous test medium) and in the presence of two different SAE-CD's as determined herein.

| | [Steroid] $\times 10^5$ M | | |
|---|---|---|---|
| Steroid ID | Intrinsic Solubility ($H_2O$) | 0.04M CAPTISOL | 0.04M $(SBE)_{6.1}$ γ |
| Hydrocortisone | 92.4 | 2656.3 | 2369.3 |
| Methylprednisolone | 43.6 | 743.1 | 1215.3 |
| Prednisolone | 62.5 | 1995.3 | 2095 |
| Prednisone | 50.5 | 1832.7 | 1313.7 |
| Flunisolide | 11.3 | 261.5 | 455.1 |
| Beclomethasone Dipropionate | 0.41 | 11.6 | 46.8 |
| Budesonide | 6.6 | 254.8 | 306.6 |
| Fluticasone Propionate | 0.39 | 5.41 | 51.8 |
| Mometasone Fuorate | 1.82 | 16.4 | 41.5 |
| Triamcinolone Acetonide | 3.56 | 457 | 1059.5 |

Example 46

The table below summarizes the equilibrium binding constants (K) for some corticosteroids in the presence of CAPTISOL or SBE6.1-γ-CD (0.04 M).

| | Binding Constant- K | |
|---|---|---|
| Steroid ID | CAPTISOL | $(SBE)_{6.1}$ γ |
| Hydrocortisone | 1932 | 1430 |
| Methylprednisolone | 486 | 950 |
| Prednisolone | 1496 | 1653 |
| Prednisone | 1591 | 914 |
| Flunisolide | 590 | 1104 |
| Beclomethasone Dipropionate | 684 | 2862 |
| Budesonide | 1002 | 1229 |
| Fluticasone Propionate | 322 | 3338 |
| Mometasone Fuorate | 201 | 551 |
| Triamcinolone Acetonide | 3591 | 10075 |

Example 47

An aqueous budesonide/olopatadine solution was prepared. The target composition was budesonide 320 µg/mL, olopatadine HCl 6.6 mg/mL, and CAPTISOL 5, 7.5 and 10% w/v.

Part A

Three mM citrate buffer was prepared at pH 4.5. Approximately 0.32 grams of citric acid monohydrate and approximately 0.44 grams of sodium citrate dihydrate were dissolved with water in 500 mL volumetric flasks, respectively. Those citrate solutions were mixed to adjust the pH to 4.5. Three CAPTISOL solutions (5, 7.5 and 10% w/v) were prepared with the 3 mM citrate buffer at pH 4.5. Approximately 5.2, 7.9 and 10.5 grams of CAPTISOL were dissolved with 3 mM citrate buffer at pH 4.5 in 100 mL volumetric flasks, respectively. The solutions were transferred into 250 mL amber beakers with a magnetic stir disk. The solutions were mixed with a magnetic stir disk at 900 rpm at a temperature of 35° C.

Approximately 34 milligrams of budesonide was suspended in each CAPTISOL solution. The samples were mixed with a magnetic stir disk at 900 rpm and 35° C. After 24 hours, the samples were filtered through 0.22 µm PVDF filter. The budesonide in the aliquots was assayed by an HPLC assay method and the concentrations were ~340 µg/mL. The measured pHs were ~4.4 and the tonicities with CAPTISOL 5, 7.5 and 10% w/v were 132, 202 and 277 mOsm, respectively.

Part B

Approximately 27 milligrams of olopatadine HCl was weighed into each of three 2 drams amber vials. The olopatadine HCl was suspended to 4 mL of budesonide/CAPTISOL solutions prepared in Part A. The samples were mixed on a roller mixer at RT. After 24 hours, the samples were filtered through 0.22 µm PVDF filter. The olopatadine and budesonide in the aliquots was assayed by HPLC assay methods, respectively. All olopatadine HCl concentrations were >6.6 mg/mL and all budesonide concentrations were >320 µg/mL. The ratio of budesonide epimer B to budesonide epimer A (R/S ratio) of budesonide solution with 5% w/v CAPTISOL was 1.09 and it was decreased to 1.07 after olopatadine dissolved. The R/S ratios of other samples were 1.09. The measured pHs were ~3.8 and the tonicities with CAPTISOL 5, 7.5 and 10% w/v were 154, 224 and 297 mOsm, respectively.

Part C

Approximately 27 milligrams of olopatadine HCl were weighed into each of three 2 drams amber vials. The olopatadine HCl was suspended to 4 mL of budesonide/CAPTISOL solutions prepared in Part A. The samples were mixed on a roller mixer at RT. After 1 hour, the pH of each sample was adjusted to 4.5 with 1N NaOH. Again, the samples were mixed on a roller mixer at RT. After 23 hours, a precipitation was observed in the presence of 5% w/v CAPTISOL at pH 4.5. All samples were filtered through 0.22 µm PVDF filter. The olopatadine and budesonide in the aliquots were assayed by HPLC assay methods, respectively. The olopatadine HCl concentrations with CAPTISOL 7.5 and 10% w/v were >6.6 mg/mL, but the concentration with CAPTISOL 5% w/v was 6.5 mg/mL. The budesonide concentrations with CAPTISOL 7.5 and 10% w/v were >320 µg/mL, but the concentration with CAPTISOL 5% w/v was 210 µg/mL. The R/S ratio of budesonide solution with 5% w/v CAPTISOL from Part A was 1.09 and it was decreased to 0.6 after olopatadine dissolved. The R/S ratios of other samples were 1.09. The measured pHs were ~4.5 and the tonicities with CAPTISOL 5, 7.5 and 10% w/v were 159, 228 and 301 mOsm, respectively.

All documents cited herein are each incorporated by reference herein in its entirety. The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims.

The invention claimed is:

1. A method for treating an allergic symptom or disorder in a subject in need thereof, comprising: nasally administering by a pump sprayer to the subject a solution comprising a therapeutically effective amount of budesonide, SAE-CD, an antihistamine, and a pharmaceutically acceptable aqueous liquid carrier, wherein the molar ratio of SAE-CD to budesonide is about 47:1, wherein the budesonide is present in an amount of about 30 µg per unit dose, and wherein the antihistamine is present in an amount of about 137 µg per unit dose;
   wherein the therapeutically effective amount is administered in one unit dose per nostril;
   wherein the antihistamine is azelastine or a pharmaceutically acceptable salt thereof;
   wherein the SAE-CD is sulfobutylether β-cyclodextrin; and
   wherein the method provides more rapid relief from the allergy symptom or disorder compared to a budesonide suspension at the same unit dose.

2. The method of claim 1, wherein the allergic symptom or disorder includes a non-nasal symptom selected from the group consisting of: itchy or gritty eyes, tearing or watery eyes, red or burning eyes, itchy ears or palate, and combinations thereof.

3. The method of claim 1, wherein the allergic symptom or disorder further comprises symptoms selected from the group consisting of runny nose, itchy nose, nasal congestion, sneezing and combinations thereof.

4. The method of claim 1, wherein the solution is administered to the subject 1-2 times per day.

5. A method for treating an ocular symptom or disorder in a subject in need thereof, comprising: nasally administering by a pump sprayer to the subject a solution comprising a therapeutically effective amount of budesonide, SAE-CD, an antihistamine and a pharmaceutically acceptable aqueous liquid carrier, wherein the molar ratio of SAE-CD to budesonide is about 47:1, wherein the budesonide is present in an amount of about 30 µg per unit dose, and wherein the antihistamine is present in an amount of about 137 µg per unit dose;
   wherein the therapeutically effective amount is administered in one unit dose per nostril;
   wherein the antihistamine is azelastine or a pharmaceutically acceptable salt thereof;
   wherein the SAE-CD is sulfobutylether β-cyclodextrin;
   wherein the method provides more rapid relief from the ocular symptom or disorder compared to a budesonide suspension at the same unit dose.

6. The method of claim 5, wherein the ocular symptom or disorder includes a non-nasal symptom selected from the group consisting of itchy or gritty eyes, tearing or watery eyes, red or burning eyes, itchy ears or palate, and combinations thereof.

7. The method of claim 5, wherein the solution is administered to the subject 1-2 times per day.

8. A method for treating ocular inflammation in a subject in need thereof, comprising: ophthalmically administering to the subject a solution comprising a therapeutically effective amount of budesonide, SAE-CD, an antihistamine and a pharmaceutically acceptable aqueous liquid carrier, wherein the molar ratio of SAE-CD to budesonide is about 47:1, wherein the budesonide is present in an amount of about 30 µg per unit dose, and wherein the antihistamine is present in an amount of about 137 µg per unit dose;
   wherein the therapeutically effective amount is administered in one unit dose per nostril;
   wherein the budesonide solution provides more rapid reduction in ocular inflammation compared with a budesonide suspension at the same unit dose;
   wherein the SAE-CD is sulfobutylether β-cyclodextrin;
   wherein the antihistamine is azelastine or a pharmaceutically acceptable salt thereof.

9. The method of claim 8, wherein the solution is administered to the subject 1-2 times per day.

* * * * *